United States Patent [19]

Rasetti et al.

[11] Patent Number: 5,719,141

[45] Date of Patent: Feb. 17, 1998

[54] 2,9-DIAMINO- AND 2-AMINO-8-CARBAMOYL-4-HYDROXY-ALKANOIC ACID AMIDE DERIVATIVES

[75] Inventors: Vittorio Rasetti, Riehen; Heinrich Rüeger, Flüh, both of Switzerland; Jürgen Klaus Maibaum, Weil-Haltingen, Germany; Robert Mah, Basel; Markus Grütter, Hochwald, both of Switzerland; Nissim Claude Cohen, Village-Neuf, France

[73] Assignee: Novartis Corporation, Summit, N.J.

[21] Appl. No.: 525,254

[22] Filed: Sep. 8, 1995

[30] Foreign Application Priority Data

Sep. 15, 1994 [CH] Switzerland .............. 2816/94

[51] Int. Cl.⁶ .............. A61K 31/54; A61K 31/535; C07D 413/02; C07D 411/02
[52] U.S. Cl. .............. 514/211; 514/213; 514/221; 514/224.2; 514/230.5; 514/249; 514/259; 514/315; 514/311; 514/399; 544/52; 544/105; 544/253; 544/283; 544/355; 546/175; 546/168; 546/245; 546/246; 548/491; 548/493; 548/309.4; 548/309.7; 540/593
[58] Field of Search .............. 544/253, 105, 544/52, 283, 353, 355; 540/593; 546/175, 245, 168, 246; 548/491, 493, 309.4, 309.7; 514/211, 213, 221, 224.2, 230.5, 249, 259, 315, 311, 349

[56] References Cited

U.S. PATENT DOCUMENTS

| | | | |
|---|---|---|---|
| 4,613,676 | 9/1986 | Fuhrer et al. | 560/39 |
| 4,898,877 | 2/1990 | Meyer et al. | 514/526 |
| 5,409,925 | 4/1995 | Hanson et al. | 514/230.5 |
| 5,411,961 | 5/1995 | Hanson et al. | 514/230.5 |
| 5,411,962 | 5/1995 | Hanson et al. | 514/230.5 |
| 5,420,126 | 5/1995 | Matsumoto et al. | 514/230.5 |
| 5,440,035 | 8/1995 | Bernstein et al. | 544/51 |
| 5,496,815 | 3/1996 | Ozeki et al. | 514/224.2 |

FOREIGN PATENT DOCUMENTS 212903  3/1987  European Pat. Off. .

OTHER PUBLICATIONS

Plummer, Mark et al., Bioorganic & Medicinal Chemistry Letters, vol. 3, pp. 2119–2124 (1993).
Hanessian, Stephen et al. Bioorganic & Medicinal Chemistry Letters, vol. 4, pp. 1696–1702 (1994).
Tetrahedron Letters, vol. 30, pp. 3845–3849 (1989). Bradbury et al.
Tetrahedron Letters, vol. 31, pp. 1803–1806 (1990).
Tetrahedron Letters, vol. 32, pp. 3985–3988, (1991).
Bradbury, Robert et al., J. Med. Chem. vol. 33, pp. 2335–2342 (1990).
Journal of Organic Chemistry, vol. 51, pp. 4828–4833 (1986).

Primary Examiner—Matthew V. Grumbling
Attorney, Agent, or Firm—Marla J. Mathias; Gregory D. Ferraro

[57] ABSTRACT

Compounds of the formula I

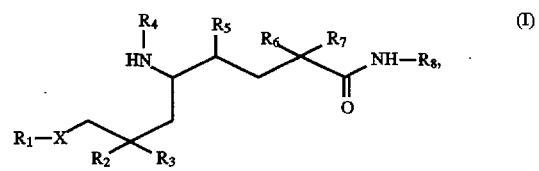

in which $R_1$ is arylamino, N-aryl-N-(lower alkoxy-lower alkyl)-amino, N-aryl-N-aryl-lower alkyl-amino or heterocyclyl bonded via a ring carbon atom, X is a carbonyl or methylene group, $R_2$ and $R_3$ independently of one another are hydrogen or lower alkyl or, together with the carbon atom with which they are bonded, are a cycloalkylidene radical, $R_4$ is hydrogen, lower alkyl, lower alkanoyl or lower alkoxycarbonyl, $R_5$ is hydroxyl, lower alkanoyloxy or lower alkoxycarbonyloxy, $R_6$ is hydrogen, lower alkyl, lower alkenyl, lower alkynyl, cycloalkyl, cycloalkyl-lower alkyl, aryl-lower alkyl or heteroaryl-lower alkyl having 5 to 7 ring atoms in the heteroaryl ring and $R_7$ is hydrogen or lower alkyl, or $R_6$ and $R_7$, together with the carbon atom with which they are bonded, are a cydoalkylidene radical and $R_8$ denotes an aliphatic, cycloaliphatic-aliphatic or heteroarylaliphatic radical, and their salts can be used as active ingredients for medicaments for treatment of high blood pressure.

14 Claims, No Drawings

2,9-DIAMINO- AND 2-AMINO-8-CARBAMOYL-4-HYDROXY-ALKANOIC ACID AMIDE DERIVATIVES

The invention relates to compounds of the formula I

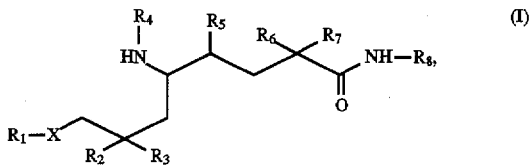

in which $R_1$ is arylamino, N-aryl-N-(lower alkoxy-lower alkyl)-amino, N-aryl-N-aryl-lower alkyl-amino or heterocyclyl bonded via a ring carbon atom, X is a carbonyl or methylene group, $R_2$ and $R_3$ independently of one another are hydrogen or lower alkyl or, together with the carbon atom with which they are bonded, are a cycloalkylidene radical, $R_4$ is hydrogen, lower alkyl, lower alkanoyl or lower alkoxycarbonyl, $R_5$ is hydroxyl, lower alkanoyloxy or lower alkoxycarbonyloxy, $R_6$ is hydrogen, lower alkyl, lower alkenyl, lower alkynyl, cycloalkyl, cycloalkyl-lower alkyl, aryl-lower alkyl or heteroaryl-lower alkyl having 5 to 7 ring atoms in the heteroaryl ring and $R_7$ is hydrogen or lower alkyl, or $R_6$ and $R_7$, together with the carbon atom with which they are bonded, are a cycloalkylidene radical and $R_8$ denotes an aliphatic, cycloaliphatic-aliphatic or heteroarylaliphatic radical, and their salts, processes for the preparation of the compounds according to the invention, pharmaceutical preparations comprising these and their use as medicament active ingredients.

The asymmetric carbon atoms substituted by $R_2$, $R_3$, $R_4$NH—, $R_5$, $R_6$ and $R_7$, and other asymmetric carbon atoms which may be present in compounds of the formula I can have the R, S or R,S configuration. The present compounds can accordingly occur as isomer mixtures or as pure isomers, in particular as diastereomer mixtures, enantiomer pairs or pure enantiomers. The same applies analogously to any asymmetric C atoms present in the radical $R_1$.

Aryl and aryl in arylamino, aryl-lower alkyl, N-aryl-N-(lower alkoxy-lower alkyl)-amino and N-aryl-N-aryl-lower alkylamino generally contains 1–14, preferably 6–10, carbon atoms and is, for example, phenyl, indenyl, for example 2- or 4-indenyl, or naphthyl, 1- or 2-naphthyl. Aryl having 6–10 carbon atoms is preferred, in particular phenyl or 1- or 2-naphthyl. The radicals mentioned can be unsubstituted or mono- or polysubstituted, for example mono- or disubstituted, for example by lower alkyl, hydroxyl, lower alkoxy, carbamoyl lower alkoxy, lower alkylcarbamoyl-lower alkoxy, di-lower alkylcarbamoyl-lower alkoxy, amino, lower alkyl- or di-lower alkylamino, carboxyl, lower alkoxycarbonyl, carbamoyl, sulfamoyl, lower alkanesulfonyl, halogen, nitro, phenyl, 5- or 6-membered heteroaryl containing, as the heteroatom, 1 nitrogen, sulfur or oxygen atom, 2N atoms, 1N atom and 1 S atom or 1N atom and 1 O atom, such as pyridyl, and/or by cyano, it being possible for the substituent to be in any position, for example in the o-, m- or p-position of the phenyl radical or in the 3- or 4-position of the 1- or 2-naphthyl radical, and it also being possible for several identical or different substituents to be present.

Arylamino is, for example, anilino or 1- or 2-naphthylamino which are unsubstituted or substituted in the phenyl or naphthyl part as defined above.

Aliphatic radicals are, for example, lower alkyl, lower alkoxy-lower alkyl, amino-lower alkyl, N-lower alkylamino-lower alkyl, N,N-di-lower alkylamino-lower alkyl, N,N-lower alkyleneamino-lower alkyl, carbamoyl-lower alkyl, N-lower alkylcarbamoyl-lower alkyl, N,N-di-lower alkylcarbamoyl-lower alkyl or cyano-lower alkyl.

Heteroarylaliphatic radicals are, for example, heteroaryl-lower alkyl radicals having 5 to 7 ring atoms in the heteroaryl ring, which contains a ring nitrogen atom and can contain a further ring heteroatom chosen from oxygen, sulfur and nitrogen.

Aryl-lower alkyl is, for example, phenyl-lower alkyl which is unsubstituted or substituted in the phenyl part as defined above.

Cycloalkyl is, for example, 3- to 8-, in particular 3- to 6-membered cycloalkyl, such as cyclopropyl, cyclobutyl, cyclopentyl or cyclohexyl.

Cycloalkylidene is, for example, 3- to 8-, in particular 3- to 6-membered cycloalkylidene, such as cyclopropylidene, cyclobutylidene, cyclopentylidene or cyclohexylidene.

Cycloalkyl-lower alkyl is, for example, 3- to 8-, in particular 3- to 6-membered cycloalkyl-lower alkyl, such as cyclopropyl-, cyclobutyl-, cyclopentyl- or cyclohexyl-lower alkyl.

Heteroaryl-lower alkyl having 5 to 7 ring atoms in the heteroaryl ring and that which contains a ring nitrogen atom and can contain a further ring heteroatom chosen from oxygen, sulfur and nitrogen is, for example, pyridyl-lower alkyl or imidazolyl-lower alkyl.

N-Aryl-N-(lower alkoxy-lower alkyl)-amino is, for example, N-phenyl- or N-naphthyl-N-(lower alkoxy-lower alkyl)-amino which are unsubstituted or substituted in the phenyl or naphthyl part as defined above.

N-Aryl-N-aryl-lower alkyl-amino is, for example, N-phenyl- or N-naphthyl-N-(phenyl-lower alkyl)-amino which are unsubstituted or substituted in the phenyl or naphthyl part as defined above.

Heterocyclyl having 4 to 8 ring atoms and bonded via a ring nitrogen atom contains, in particular, 5 to 7 ring atoms and can be fused with 1 or 2 fused-on phenyl or cycloalkyl radicals. Examples are pyrrolidino, piperidino, piperazino, morpholino, thiomorpholino, indolin-1-yl, isoindolin-2-yl, 2,3-dihydrobenzoimidazol-1-yl, 1,2,3,4-tetrahydroquinol-1-yl, 1,2,3,4-tetrahydroisoquinol-2-yl, 1,2,3,4-tetrahydro-1,3-benzodiazin-1-yl or -3-yl, 1,2,3,4-tetrahydro-1,4-benzodiazin-1-yl, 3,4-dihydro-2H-1,4-benzooxazin-4-yl, 3,4-dihydro-2H-1,4-benzothiazin-4-yl, 3,4-dihydro-2H-1,3-benzothiazin-1-yl, 3,4,5,6,7,8-hexahydro-2H-1,4-benzooxazin-4-yl, 3,4,5,6,7,8-hexahydro-2H-1,4-benzothiazin-4-yl, 2,3,4,5-tetrahydro-1H-1-benz[6,7-b]azepin-1-yl and 5,6-dihydrophenanthridin-5-yl. Preferred radicals are benzo-fused 5- to 7-membered aza-, diaza-, azoxa- and azathiacycloalkenyl radicals bonded via a nitrogen atom, in particular indolin-1-yl, 1,2,3,4-tetrahydroquinolin-1-yl, 1,2,3,4-tetrahydroisoquinolin-2-yl, 1,2,3,4-tetrahydro-1,3-benzodiazin-1-yl, 1,2,3,4-tetrahydro-1,4-benzodiazin-1-yl, 3,4-dihydro-2H-1,4-benzooxazin-4-yl, 3,4-dihydro-2H-1,4-benzothiazin-4-yl, 3,4-dihydro-2H-1,3-benzothiazin-1-yl and 2,3,4,5-tetrahydro-1H-1-benzol[6,7-b]azepin-1-yl.

The radicals mentioned can be unsubstituted or N-substituted, S,S-substituted and/or C-substituted, it being possible for a total of up to 3, in particular 1, 2 or 3, substitutents to be present.

N substituents are, for example, lower alkyl, lower alkanoyl, lower alkoxycarbonyl or lower alkanesulfonyl. S substituents are, for example, 1 or preferably 2 oxy groups. C substituents are, for example, lower alkyl, hydroxy lower alkyl, lower alkoxy-lower alkyl, lower alkenyloxy-lower alkyl, naphthoxy-lower alkyl, phenyloxy-lower alkyl, phenyl-lower alkoxy-lower alkyl, lower-alkanoyloxy lower alkyl, benzoyloxy-lower alkyl, lower alkoxycarbonyloxy-lower alkyl, phenyloxycarbonyloxy-lower alkyl, phenyl-lower alkoxycarbonyloxy-lower alkyl, amino-lower alkyl, N-lower alkylamino-lower alkyl, N,N-di-lower alkylamino-lower alkyl, carbamoyl-lower alkyl, lower alkanoylamino-lower alkyl, benzoylamino-lower alkyl, lower alkoxycarbonylamino-lower alkyl, lower alkoxycarbonyl-lower alkyl, lower alkoxy-lower alkoxy-lower alkyl, lower alkylthio-lower alkoxy-lower alkyl, N-lower alkoxyimino-lower alkyl, cycloalkoxy-lower alkyl, cycloalkyl-lower alkoxy-lower alkyl, lower alkenyl, lower alkenyloxy, lower alkoxy-lower alkenyl, lower alkynyl, lower alkynyloxy, lower alkanoyl, oxo, hydroxy, lower alkoxy, carbamoyl-lower alkoxy, N-lower alkylcarbamoyl-lower alkoxy, N-lower alkylcarbamoyloxy, N,N-di-lower alkylcarbamoyloxy, lower alkoxy-lower alkoxy, lower alkylthio-lower alkoxy, lower alkanoyloxy, benzoyloxy, N-lower alkylcarbamoyl, amino, N-lower alkylamino, N,N-di-lower alkylamino, lower alkanoylamino, benzoylamino, cycloalkylcarbonylamino, cycloalkyl-lower alkanoylamino, lower alkoxycarbonyl-lower alkylamino, lower alkenyloxycarbonylamino, lower alkoxy-lower alkoxycarbonylamino, lower alkoxy-lower alkanoylamino, N-lower alkylcarbamoylamino, N,N-di-lower alkylcarbamoylamino, N-lower alkanoyl-N-lower alkylamino, lower alkoxycarbonylamino, N-lower alkoxycarbonyl-N-lower alkylamino, N,N-lower alkyleneamino, N,N-(1-oxo-lower alkylene)amino, N,N-(1-oxo-2-oxa-lower alkylene)amino, carboxy, lower alkoxycarbonyl, phenyl-lower alkoxycarbonyl, phenyloxycarbonyl, pyrrolidinylcarbonyl, piperidinylcarbonyl, piperazinylcarbonyl, morpholinylcarbonyl, thiomorpholinylcarbonyl, S,S-dioxothiomorpholin-4-ylcarbonyl, cyano, carbamoyl, N,N-di-lower alkylcarbamoyl, N-lower alkenylcarbamoyl, N-cycloalkylcarbamoyl, N-cycloalkyl-lower alkylcarbamoyl, N-hydroxy-lower alkylcarbamoyl, N-lower alkoxy-lower alkylcarbamoyl, N-carboxy-lower alkylcarbamoyl, carbamoyl-lower alkylcarbamoyl, phenyl, dioxolan-2-yl, oxazol-2-yl, oxazolin-2-yl, oxazolidin-2-yl, nitro, sulfamoyl, lower alkanesulfonyl, phosphono, lower alkanephosphono, di-lower alkylphosphono and halogen.

Particularly preferred radicals $R_1$ are bicyclic radicals of the formula Ia

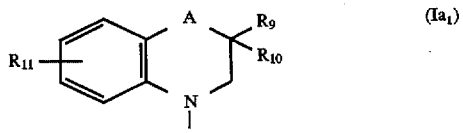

in which

A is a direct bond, methylene, ethylene, imino, oxy or thio, $R_9$ is lower alkoxy-lower alkyl, lower alkenyloxy-lower alkyl, lower alkoxy-lower alkoxy-lower alkyl, lower alkoxycarbonylamino-lower alkyl, N-lower alkoxyimino-lower alkyl, phenyl, lower alkoxycarbonyl, cyano, carbamoyl, N-lower alkylcarbamoyl, N-(lower alkoxy-lower alkyl) carbamoyl, lower alkoxy, lower alkoxy-lower alkoxy, lower alkanoyloxy, benzoyloxy, lower alkanoylamino, lower alkoxycarbonylamino, 3- to 6-membered cycloalkylcarbonylamino, N-(lower alkoxy-lower alkanoyl)amino, N-(lower alkylcarbamoyl)amino, N,N-(1-oxo-lower alkylene) amino or N,N-(1-oxo2-oxa-lower alkylene)amino $R_{10}$ is hydrogen or lower alkyl and $R_{11}$ is hydrogen or halogen.

Lower radicals and compounds above and below are to be understood as meaning, for example, those which contain up to and including 7, preferably up to and including 4, carbon atoms (C atoms).

Amino-lower alkyl is, for example, amino-$C_1$–$C_4$alkyl, such as aminomethyl, 2-aminoethyl, 3-aminopropyl or 4-aminobutyl.

Benzoylamino-lower alkyl is, for example, benzoylamino-$C_1$–$C_4$alkyl, such as benzoylaminomethyl, 2-benzoylaminoethyl, 3-benzoylaminopropyl or 4-benzoylaminobutyl.

Benzoyloxy-lower alkyl is, for example, benzoyloxy-$C_1$–$C_4$alkyl, such as benzoyloxymethyl, 2-benzoyloxyethyl, 3-benzoyloxypropyl or 4-benzoyloxybutyl, in particular benzoyloxymethyl.

Carbamoyl-lower alkoxy is, for example, carbamoyl-$C_1$–$C_4$alkoxy, such as carbamoylmethoxy, 2-carbamoylethoxy, 3-carbamoylpropyloxy or 4-carbamoylbutyloxy.

Carbamoyl-lower alkyl is, for example, carbamoyl-$C_1$–$C_4$alkyl, such as 2-(N-methylcarbamoyl)ethyl, carbamoylmethyl, 2-carbamoylethyl, 3-carbamoylpropyl or 4-carbamoylbutyl.

N-(Carbamoyl-lower alkyl)carbamoyl is, for example, N-(carbamoyl-$C_1$–$C_4$alkyl)carbamoyl, such as N-(carbamoylmethyl)carbamoyl, N-(2-carbamoylethyl) carbamoyl, N-(3-carbamoylpropyl)carbamoyl or N-(4-carbamoylbutyl)carbamoyl.

Cycloalkoxy-lower alkyl is, for example, $C_3$–$C_7$cycloalkoxy-$C_1$–$C_4$alkyl, such as cyclopropyl-$C_1$–$C_4$alkyl, cyclopentyl-$C_1$–$C_4$alkyl or cyclohexyl-$C_1$–$C_4$alkyl, in particular cyclopropylmethyl.

Cycloalkylcarbonylamino is, for example, N—$C_3$–$C_7$cycloalkylcarbonylamino, such as cyclopropylcarbonylamino, cyclopentylcarbonylamino or cyclohexylcarbonylamino, in particular N-cyclopropylcarbonylamino.

Cycloalkyl-lower alkanoylamino is, for example, N—($C_3$–$C_7$cycloalkyl-$C_1$–$C_4$alkanoyl)amino, such as cyclopropyl-$C_1$–$C_4$alkanoylamino, cyclopentyl-$C_1$–$C_4$-alkanoylamino or cyclohexyl-$C_1$–$C_4$alkanoylamino, in particular cyclopropylacetylamino.

Cycloalkyl-lower alkoxy-lower alkyl is, for example, $C_3$–$C_7$cycloalkyl-$C_1$–$C_4$alkoxy-$C_1$–$C_4$alkyl, such as cyclopropyl-$C_1$–$C_4$alkoxy-$C_1$–$C_4$alkyl, cyclopentyl-$C_1$–$C_4$alkoxy-$C_1$–$C_4$alkyl or cyclohexyl-$C_1$–$C_4$alkoxy-$C_1$–$C_4$alkyl, in particular cyclopropylmethoxymethyl.

Cycloalkyl-lower alkyl is, for example, $C_3$–$C_7$cycloalkyl-$C_1$–$C_4$alkyl, such as cyclopropyl-$C_1$–$C_4$alkyl, cyclopentyl-$C_1$C_4$alkyl or cyclohexyl-$C_1$–$C_4$alkyl, in particular cyclopropylmethyl.

Hydroxy-lower alkyl is, for example, hydroxy-$C_1$–$C_4$alkyl, such as hydroxymethyl, 2-hydroxyethyl, 3-hydroxypropyl or 4-hydroxybutyl, in particular 2-hydroxyethyl.

Imidazolyl-lower alkyl is, for example, 4-imidazolylmethyl.

Naphthyloxy-lower alkyl is, for example, naphthyloxy-$C_1$–$C_4$alkyl, in particular naphth-1-yl- or naphth-2-yl-$C_1$–$C_4$alkoxy, in which $C_1$–$C_4$alkyl is, for example, methyl, ethyl, propyl or butyl, such as naphth-1-yl- or naphth-2-yloxymethyl. Naphthyl-lower alkanoyl is, for example, naphthyl-$C_1$–$C_4$alkanoyl, such as naphth-1-yl- or naphth-2-ylacetyl.

Naphthyl-lower alkoxycarbonyl is, for example, naphthyl-$C_1$–$C_4$alkoxycarbonyl, in particular naphth-1-yl- or naphth-2-yl-$C_1$–$C_4$alkoxycarbonyl, in which $C_1$–$C_4$alkyl is, for example, methyl, ethyl, propyl or butyl, such as naphth-1-yl- or naphth-2-yloxycarbonyl.

Naphthyl-lower alkyl is, for example, naphthyl-$C_1$–$C_4$alkyl, such as naphth-1-yl- or naphth-2-ylmethyl or 1- or 2-naphthylethyl.

Lower alkanoyl is, for example, $C_1$–$C_7$alkanoyl, in particular $C_1$–$C_4$alkanoyl, such as formyl, acetyl, propionyl, butyryl or pivaloyl. Lower alkanoyl $R_4$ is, in particular, formyl, acetyl, propionyl, butyryl, isobutyryl or pivaloyl.

Lower alkanoylamino is, for example, $C_1$–$C_7$alkanoylamino, in particular $C_1$–$C_4$alkanoylamino, such as acetylamino, propionylamino, butyrylamino or pivaloylamino.

Lower alkanoylamino-lower alkyl is, for example, $C_1$–$C_7$alkanoylamino-$C_1$–$C_4$alkyl, in particular $C_1$–$C_4$alkanoylamino-$C_1$–$C_4$alkyl, such as formylaminomethyl, acetylaminomethyl, propionylaminomethyl, butyrylaminomethyl, pivaloylaminomethyl, 2-formylaminoethyl, 2-acetylaminoethyl, 2-propionylaminomethyl, 2-butyrylaminoethyl or 2-pivaloylaminoethyl.

Lower alkanoyloxy is, for example, $C_1$–$C_7$alkanoyloxy, in particular $C_1$–$C_4$-alkanoyloxy, such as acetyloxy, propionyloxy, butyryloxy or pivaloyloxy.

Lower alkanoyloxy-lower alkyl is, for example, $C_1$–$C_7$alkanoyloxy-$C_1$–$C_4$alkyl, in particular $C_1$–$C_4$alkanoyloxy-$C_1$–$C_4$alkyl, such as acetyloxy-$C_1$–$C_4$alkyl, in which $C_1$–$C_4$alkyl is, for example, methyl, ethyl, propyl or butyl, in particular propionyloxymethyl.

N-Lower alkanoyl-N-lower alkyl-amino is, for example, N—($C_1$–$C_7$alkanoyl)-N—($C_1$–$C_4$alkyl)amino, in particular N—($C_1$–$C_4$alkanoyl)-N—($C_1$–$C_4$alkyl)-amino, such as N-formyl-N-methylamino, N-acetyl-N-methylamino, N-propionyl-N-methyl-amino or N-butyryl-N-methyl-amino.

Lower alkanesulfonyl is, for example, $C_1$–$C_7$alkanesulfonyl, in particular $C_1$–$C_4$alkanesulfonyl, such as methanesulfonyl, ethanesulfonyl, propanesulfonyl, propane-2-sulfonyl, butanesulfonyl, 2-methylpropanesulfonyl, butane-2-sulfonyl or 2,2-dimethylethanesulfonyl. Lower alkanesulfonyl $R_4$ is, in particular, methane-, ethane-, propane-, 2-methylpropane, butane-2,2,2-dimethylethane-, n-butane-, n-pentane-, isopentane-, neopentane-, tert- pentane-, n-hexane-, isohexane- or n-heptanesulfonyl.

Lower alkenyl is, for example, $C_2$–$C_7$alkenyl, in particular $C_3$–$C_5$alkenyl, such as allyl. N-Lower alkenylcarbamoyl is, for example, N—$C_2$–$C_7$alkenylcarbamoyl, in particular N—$C_3$–$C_5$alkenylcarbamoyl, such as allylcarbamoyl.

Lower alkenyloxy is, for example, $C_2$–$C_7$alkenyloxy, in particular $C_3$–$C_5$alkenyloxy, such as allyloxy or methallyloxy.

N-Lower alkenylcarbamoyl is, for example, N—$C_2$–$C_7$alkenylcarbamoyl, in particular N—$C_3$–$C_5$alkenylcarbamoyl, such as N-allylcarbamoyl or N-methallylcarbamoyl.

Lower alkenyloxycarbonylamino is, for example, $C_2$–$C_7$alkenyloxycarbonylamino, in particular $C_3$–$C_5$alkenyloxycarbonylamino, such as allyloxycarbonylamino or methallyloxycarbonylamino.

Lower alkenyloxy-lower alkyl is, for example, $C_2$–$C_7$alkenyloxy-$C_1$–$C_4$alkyl, in particular $C_3$–$C_5$alkenyloxy-$C_1$–$C_4$alkyl, such as allyloxy-$C_1$–$C_4$alkyl, in particular allyloxymethyl.

Lower alkynyl is, for example, $C_3$–$C_7$alkynyl, in particular $C_3$–$C_5$alkynyl, such as propargyl.

Lower alkynyloxy is, for example, $C_3$–$C_7$alkynyloxy, in particular $C_3$–$C_5$alkynyloxy, such as propargyloxy.

Lower alkoxy is, for example, $C_1$–$C_7$alkoxy, in particular $C_1$–$C_4$alkoxy, such as methoxy, ethoxy, propyloxy, isopropyloxy, butyloxy, isobutyloxy, sec-butyloxy or tert-butyloxy, but can also be a $C_5$–$C_7$alkoxy group, such as a pentyloxy, hexyloxy or heptyloxy group.

Lower alkoxycarbonyl is, for example, $C_1$–$C_7$alkoxycarbonyl, in particular $C_1$–$C_4$alkoxycarbonyl, such as methoxycarbonyl, ethoxycarbonyl, propyloxycarbonyl, isopropyloxycarbonyl, butyloxycarbonyl, isobutyloxycarbonyl, sec-butyloxycarbonyl or tert-butyloxycarbonyl.

Lower alkoxycarbonylamino is, for example, $C_1$–$C_7$alkoxycarbonylamino, in particular $C_1$–$C_4$alkoxycarbonylamino, such as methoxycarbonylamino, ethoxycarbonylamino, propyloxycarbonylamino, isopropyloxycarbonylamino or butyloxycarbonylamino.

Lower alkoxycarbonylamino-lower alkyl is, for example, $C_1$–$C_7$-alkoxycarbonylamino-$C_1$–$C_4$alkyl, in particular $C_1$–$C_4$alkoxycarbonylamino-$C_1$–$C_4$alkyl, such as methoxycarbonylamino-$C_1$–$C_4$alkyl, ethoxycarbonylamino-$C_1$–$C_4$alkyl, propyloxycarbonylamino-$C_1$–$C_4$alkyl, isopropyloxycarbonylamino-$C_1$–$C_4$alkyl, butyloxycarbonylamino-$C_1$–$C_4$alkyl, isobutyloxycarbonylamino-$C_1$–$C_4$alkyl, sec-butyloxycarbonylamino-$C_1$–$C_4$alkyl or tert-butyloxycarbonylamino-$C_1$–$C_4$alkyl, in which $C_1$–$C_4$alkyl is, for example, methyl, ethyl, propyl or butyl, such as ethoxycarbonylaminomethyl.

Lower alkoxycarbonyl-lower alkyl is, for example, $C_1$–$C_7$alkoxycarbonyl-$C_1$–$C_4$alkyl, in particular $C_1$–$C_4$alkoxycarbonyl-$C_1$–$C_4$alkyl, such as methoxycarbonyl-$C_1$–$C_4$alkyl, ethoxycarbonyl-$C_1$–$C_4$alkyl, propyloxycarbonyl-$C_1$–$C_4$alkyl, isopropyloxycarbonyl-$C_1$–$C_4$alkyl, butyloxycarbonyl-$C_1$–$C_4$alkyl, isobutyloxycarbonyl-$C_1$–$C_4$alkyl, sec-butyloxycarbonyl-$C_1$–$C_4$alkyl or tert-butyloxycarbonyl-$C_1$–$C_4$alkyl, in which $C_1$–$C_4$alkyl is, for example, methyl, ethyl, propyl or butyl, for example methoxycarbonylmethyl or ethoxycarbonylmethyl.

Lower alkoxycarbonyl-lower alkylamino is, for example, $C_1$–$C_7$alkoxycarbonyl-$C_1$–$C_4$alkylamino, in particular $C_1$–$C_4$alkoxycarbonyl-$C_1$–$C_4$alkylamino, such as methoxycarbonyl-$C_1$–$C_4$alkylamino, ethoxycarbonyl-$C_1$–$C_4$alkylamino, propyloxycarbonyl-$C_1$–$C_4$alkylamino, isopropyloxycarbonyl-$C_1$–$C_4$alkylamino, butyloxycarbonyl-$C_1$–$C_4$alkylamino, isobutyloxycarbonyl-$C_1$–$C_4$alkylamino, sec-butyloxycarbonyl-$C_1$–$C_4$-alkylamino or tert-butyloxycarbonyl-$C_1$–$C_4$alkylamino, in which $C_1$–$C_4$alkyl is, for example, methyl, ethyl, propyl or butyl.

N-(Lower alkoxycarbonyl-lower alkyl)carbamoyl is, for example, N—($C_1$–$C_7$alkoxycarbonyl-$C_1$–$C_4$alkyl)carbamoyl, in particular N—($C_1$–$C_4$alkoxycarbonyl-$C_1$–$C_4$alkyl)carbamoyl, such as N-(methoxycarbonyl-$C_1$–$C_4$alkyl)carbamoyl, N-(ethoxycarbonyl-$C_1$–$C_4$alkyl)carbamoyl, N-(propyloxycarbonyl-$C_1$–$C_4$alkyl)carbamoyl, N-(isopropyloxycarbonyl-$C_1$–$C_4$alkyl)carbamoyl, N-(butyloxycarbonyl-$C_1$–$C_4$alkyl)carbamoyl or N-(tert-butyloxycarbonyl-$C_1$–$C_4$alkyl)carbamoyl, in which $C_1$–$C_4$alkyl is, for example, methyl, ethyl, propyl or butyl, in particular N-(methoxy- or ethoxycarbonylmethyl) carbamoyl.

Lower alkoxycarbonyloxy-lower alkyl is, for example, $C_1$–$C_7$alkoxycarbonyloxy-$C_1$–$C_4$alkyl, in particular $C_1$–$C_4$alkoxycarbonyloxy-$C_1$–$C_4$alkyl, such as methoxycarbonyloxy-$C_1$–$C_4$alkyl, ethoxycarbonyloxy-$C_1$–$C_4$alkyl, propyloxycarbonyloxy-$C_1$–$C_4$alkyl, isopropyloxycarbonyloxy-$C_1$–$C_4$alkyl, butyloxycarbonyloxy-$C_1$–$C_4$alkyl or tert-butyloxycarbonyloxy-$C_1$–$C_4$alkyl, in which $C_1$–$C_4$alkyl is, for example, methyl, ethyl, propyl or butyl, in particular propyloxycarbonyloxymethyl.

N-Lower alkoxycarbonyl-N-lower alkyl-amino is, for example, $C_1$–$C_7$alkoxycarbonyl-N—$C_1$–$C_4$alkyl-amino, in particular $C_1$–$C_4$alkoxycarbonyl-N—$C_1$–$C_4$alkylamino, such as methoxycarbonyl-N—$C_1$–$C_4$alkyl-amino, ethoxycarbonyl-N—$C_1$–$C_4$alkyl-amino, propyloxycarbonyl-N—$C_1$–$C_4$alkyl-amino, isopropyloxycarbonyl-N—$C_1$–$C_4$alkyl-amino, butyloxycarbonyl-N—$C_1$–$C_4$alkyl-amino or tert-butyloxycarbonyl-N—$C_1$–$C_4$alkylamino, in which $C_1$–$C_4$alkyl is, for example, methyl, ethyl, propyl or butyl, in particular N-(methoxy- or ethoxycarbonyl)-N-amino.

Lower alkoxyimino-lower alkyl is, for example, $C_1$–$C_4$alkoxyimino-$C_1$–$C_4$alkyl, such as methoxyimino-$C_1$–$C_4$alkyl, ethoxyimino-$C_1$–$C_4$alkyl, propoxyimino-$C_1$–$C_4$alkyl or butoxyimino-$C_1$–$C_4$alkyl, in which $C_1$–$C_4$alkyl is, for example, methyl or ethyl, in particular methoxyiminomethyl, ethoxyiminomethyl or propoxyiminomethyl, Lower alkoxy-lower alkanoylamino is, for example, $C_1$–$C_4$alkoxy-$C_1$–$C_4$alkanoylamino, such as methoxy-$C_1$–$C_4$alkanoylamino, ethoxy-$C_1$–$C_4$alkanoylamino, propyloxy-$C_1$–$C_4$alkanoylamino, isopropyloxy-$C_1$–$C_4$alkanoylamino or butyloxy-$C_1$–$C_4$alkanoylamino, in which $C_1$–$C_4$alkanoyl is, for example, acetyl, propionyl or butyryl.

Lower alkoxy-lower alkenyl is, for example, $C_1$–$C_4$alkoxy-$C_3$–$C_5$alkenyl, such as methoxy-$C_3$–$C_5$alkenyl, ethoxy-$C_3$–$C_5$alkenyl, propyloxy-$C_3$–$C_5$alkenyl, isopropyloxy-$C_3$–$C_5$alkenyl or butyloxy-$C_3$–$C_5$alkenyl, in which $C_3$–$C_5$alkenyl is, for example, allyl or methallyl, in particular 3-ethoxyallyl.

Lower alkoxy-lower alkoxy is, for example, $C_1$–$C_7$alkoxy-$C_1$–$C_4$alkoxy, in particular $C_1$–$C_4$alkoxy-$C_1$–$C_4$alkoxy, such as methoxy-$C_1$–$C_4$alkoxy, ethoxy-$C_1$–$C_4$alkoxy, propyloxy-$C_1$–$C_4$alkoxy, isopropyloxy-$C_1$–$C_4$alkoxy, butyloxy-$C_1$–$C_4$alkoxy, isobutyloxy-$C_1$–$C_4$alkoxy, sec-butyloxy-$C_1$–$C_4$alkoxy or tert-butyloxy-$C_1$–$C_4$alkoxy, in which $C_1$–$C_4$alkoxy is, for example, methoxy, ethoxy, propyloxy or butyloxy, in particular methoxy- or ethoxymethoxy or 2-(methoxy)- or 2-(ethoxy) ethoxy.

Lower alkoxy-lower alkoxycarbonylamino is, for example, $C_1$–$C_7$alkoxy-$C_1$–$C_4$alkoxycarbonylamino, in particular $C_1$–$C_4$alkoxy-$C_1$–$C_4$alkoxycarbonylamino, such as methoxy-$C_1$–$C_4$alkoxycarbonylamino, ethoxy-$C_1$–$C_4$alkoxycarbonylamino, propyloxy-$C_1$–$C_4$alkoxycarbonylamino, isopropyloxy-$C_1$–$C_4$alkoxycarbonylamino, butyloxy-$C_1$–$C_4$alkoxycarbonylamino, isobutyloxy-$C_1$–$C_4$alkoxycarbonylamino, sec-butyloxy-$C_1$–$C_4$alkoxycarbonylamino or tert-butyloxy-$C_1$–$C_4$alkoxycarbonylamino, in which $C_1$–$C_4$alkoxy is, for example, methoxy, ethoxy, propyloxy or butyloxy, in particular N-(2-ethoxyethoxycarbonyl)amino.

Lower alkoxy-lower alkoxy-lower alkyl is, for example, $C_1$–$C_7$alkoxy-$C_1$–$C_4$alkoxy-$C_1$–$C_4$alkyl, in particular $C_1$–$C_4$alkoxy-$C_1$–$C_4$alkoxy-$C_1$–$C_4$alkyl, such as methoxy-$C_1$–$C_4$alkoxy-$C_1$–$C_4$alkyl, ethoxy-$C_1$–$C_4$alkoxy-$C_1$–$C_4$alkyl, propyloxy-$C_1$–$C_4$alkoxy-$C_1$–$C_4$alkyl, isopropyloxy-$C_1$–$C_4$alkoxy-$C_1$–$C_4$alkyl or butyloxy-$C_1$–$C_4$alkoxy-$C_1$–$C_4$alkyl, in which $C_1$–$C_4$alkoxy is, for example, methoxy, ethoxy, propyloxy or butyloxy and $C_1$–$C_4$alkyl is, for example, methyl, ethyl, propyl or butyl, in particular 2-methoxyethoxymethyl.

Lower alkoxy-lower alkyl is, for example, $C_1$–$C_7$alkoxy-$C_1$–$C_4$alkyl, in particular $C_1$–$C_4$alkoxy-$C_1$–$C_4$alkyl, such as methoxy-$C_1$–$C_4$alkyl, ethoxy-$C_1$–$C_4$alkyl, propyloxy-$C_1$–$C_4$alkyl, isopropyloxy-$C_1$–$C_4$alkyl, butyloxy-$C_1$–$C_4$alkyl, isobutyloxy-$C_1$–$C_4$alkyl, sec-butyloxy-$C_1$–$C_4$alkyl or tert-butyloxy-$C_1$–$C_4$alkyl, in which $C_1$–$C_4$alkyl is, for example, methyl, ethyl, propyl or butyl, in particular ethoxymethyl.

Lower alkoxy-lower alkyl is, for example, $C_1$–$C_7$alkoxy-$C_1$–$C_4$alkyl, in particular $C_1$–$C_4$alkoxy-$C_1$–$C_4$alkyl, such as methoxy-$C_1$–$C_4$alkyl, ethoxy-$C_1$–$C_4$alkyl, propyloxy-$C_1$–$C_4$alkyl, isopropyloxy-$C_1$–$C_4$alkyl, butyloxy-$C_1$–$C_4$alkyl, isobutyloxy-$C_1$–$C_4$alkyl, sec-butyloxy-$C_1$–$C_4$alkyl or tert-butyloxy-$C_1$–$C_4$alkyl, in which $C_1$–$C_4$alkyl is, for example, methyl, ethyl, propyl or butyl.

N-Lower alkoxy-lower alkylcarbamoyl is, for example, N—$C_1$–$C_7$alkoxy-$C_1$–$C_4$alkylcarbamoyl, in particular $C_1$–$C_4$alkoxy-$C_1$–$C_4$alkylcarbamoyl, such as methoxy-$C_1$–$C_4$alkylcarbamoyl, ethoxy-$C_1$–$C_4$alkylcarbamoyl, propyloxy-$C_1$–$C_4$alkylcarbamoyl, isopropyloxy-$C_1$–$C_4$alkylcarbamoyl butyloxy-$C_1$–$C_4$alkylcarbamoyl, isobutyloxy-$C_1$–$C_4$alkylcarbamoyl, sec-butyloxy-$C_1$–$C_4$alkyl or tert-butyloxy-$C_1$–$C_4$alkylcarbamoyl, in which $C_1$–$C_4$alkyl is, for example, methyl, ethyl, propyl or butyl, in particular N-(2-propyloxyethoyl)carbamoyl.

Lower alkyl is branched or unbranched and is, for example, $C_1$–$C_7$alkyl, in particular $C_1$–$C_4$alkyl, such as methyl, ethyl, n-propyl, isopropyl, n-butyl, isobutyl, sec-butyl, tert-butyl, n-pentyl, isopentyl, neopentyl, tert-pentyl, n-hexyl, isohexyl or n-heptyl. Lower alkyl $R_2$ and $R_3$ is preferably methyl, ethyl or propyl.

N-Lower alkylamino is, for example, N—$C_1$–$C_7$akylamino, in particular $C_1$–$C_4$alkylamino, such as methylamino, ethylamino, propylamino, butylamino, isobutylamino, sec-butylamino or tert-butylamino.

N,N-Di-lower alkylamino is, for example, N,N-di-$C_1$–$C_4$alkylamino, such as N,N-dimethylamino, N,N-diethylamino, N,N-dipropylamino, N-methyl-N-ethylamino or N-methyl-N-propylamino.

N-Lower alkylamino-lower alkyl is, for example, N—$C_1$–$C_4$alkylamino-$C_1$–$C_4$alkyl, such as N-methylamino-$C_1$–$C_4$alkyl, N-ethylamino-$C_1$–$C_4$alkyl, N-propylamino-$C_1$–$C_4$alkyl or N-butylamino-$C_1$–$C_4$alkyl, in which $C_1$–$C_4$alkyl is, for example, methyl or ethyl, in particular N-methylaminomethyl, N-ethylaminomethyl or N-propylaminomethyl.

N-Lower alkylcarbamoyl is, for example, N—$C_1$–$C_4$alkylcarbamoyl, such as N-methylcarbamoyl, N-ethylcarbamoyl, N-propylcarbamoyl or N-butylcarbamoyl.

N-Lower alkylcarbamoylamino is, for example, N—$C_1$–$C_4$alkylcarbamoylamino, such as N-methylcarbamoylamino, N-ethylcarbamoylamino, N-propylcarbamoylamino or N-butylcarbamoylamino.

N-Lower alkylcarbamoyl-lower alkoxy is, for example, N—$C_1$–$C_4$alkylcarbamoyl-$C_1$–$C_4$alkoxy, such as N-methylcarbamoyl-$C_1$–$C_4$alkoxy, N-ethylcarbamoyl-$C_1$–$C_4$alkoxy, N-propylcarbamoyl-$C_1$–$C_4$alkoxy or N-butylcarbamoyl-$C_1$–$C_4$alkoxy, in which $C_1$–$C_4$alkoxy is, for example, methoxy or ethoxy, in particular N-methylcarbamoylmethoxy, N-ethylcarbamoylmethoxy, 2-(N-methylcarbamoyl)ethoxy or N-propylcarbamoylmethoxy.

N-Lower alkylcarbamoyloxy is, for example, N—$C_1$–$C_4$alkylcarbamoyloxy, such as N-methylcarbamoyloxy, N-ethylcarbamoyloxy, N-propylcarbamoyloxy or N-butylcarbamoyloxy.

N-Phenyl-N-(lower alkoxy-lower alkyl)amino is, is for example, N-phenyl-N—($C_1$–$C_4$alkoxy-$C_1$–$C_4$alkyl)amino, such as N-phenyl-N-(methoxy-$C_1$–$C_4$alkyl)amino, N-phenyl-N-(ethoxy-$C_1$–$C_4$alkyl)amino, N-phenyl-N-(propyloxy-$C_1$–$C_4$alkyl)amino, N-phenyl-N-(isopropyloxy-$C_1$–$C_4$alkyl)amino or N-phenyl-N-(butyloxy-$C_1$–$C_4$alkyl) amino, in which $C_1$–$C_4$alkyl is, for example, methyl, ethyl, propyl or butyl, in particular N-phenyl-N-(ethoxymethyl) amino.

N-Phenyl-N-lower alkyl-amino is, for example, N-phenyl-N—$C_1$–$C_4$alkyl-amino, such as N-phenyl-N-methyl-amino, N-phenyl-N-ethyl-amino, N-phenyl-N-propyl-amino, N-phenyl-N-isopropyl-amino or N-phenyl-N-butyl-amino, in particular N-phenyl-N-methyl-amino.

N-Phenyl-N-(phenyl-lower alkyl)-amino is, for example, N-phenyl-N-(phenyl-$C_1$–$C_4$alkyl)amino, such as N-phenyl-N-benzyl-amino, N-phenyl-N-(2-phenylethyl)-amino, N-phenyl-N-(3-phenylpropyl)-amino or N-phenyl-N-(4-phenylbutyl)-amino, in particular N-phenyl-N-(2-phenylethyl)-amino.

Lower alkanephosphono is, for example, $C_1$–$C_7$alkanephosphono, in particular $C_1$–$C_4$alkanephosphono, such as methanephosphono, ethanephosphono, propanephosphono, propane-2-phosphono, butanephosphono, 2-methylpropanephosphono, butane-2-phosphono or 2,2-dimethylethanephosphono.

Lower alkylthio-lower alkoxy is, for example, $C_1$–$C_7$alkylthio-$C_1$–$C_4$alkoxy, in particular $C_1$–$C_4$alkylthio-$C_1$–$C_4$alkoxy, such as methylthio-$C_1$–$C_4$alkoxy, ethylthio-$C_1$–$C_4$alkoxy, propylthio-$C_1$–$C_4$alkoxy, isopropylthio-$C_1$–$C_4$alkoxy, butylylthio-$C_1$–$C_4$alkoxy, isobutylylthio-$C_1$–$C_4$alkoxy, sec-butylylthio-$C_1$–$C_4$alkoxy or tert-butylylthio-$C_1$–$C_4$alkoxy, in which $C_1$–$C_4$alkoxy is, for example, methoxy, ethoxy, propyloxy or butyloxy, in particular methylthio- or ethylthiomethoxy or 2-(methylthio)- or 2-(methylthio)ethoxy.

Lower alkylthio-lower alkoxy-lower alkyl is, for example, $C_1$–$C_7$alkylthio-$C_1$–$C_4$alkoxy-$C_1$–$C_4$alkyl, in particular $C_1$–$C_4$alkylthio-$C_1$–$C_4$alkoxy-$C_1$–$C_4$alkyl, such as methylthio-$C_1$–$C_4$alkoxy-$C_1$–$C_4$alkyl, ethylthio-$C_1$–$C_4$alkoxy-$C_1$–$C_4$alkyl, propylylthio-$C_1$–$C_4$alkoxy-$C_1$–$C_4$alkyl, isopropylylthio-$C_1$–$C_4$alkoxy-$C_1$–$C_4$alkyl or butylylthio-$C_1$–$C_4$alkoxy-$C_1$–$C_4$alkyl, in which $C_1$–$C_4$alkoxy is, for example, methoxy, ethoxy, propyloxy or butyloxy and $C_1$–$C_4$alkyl is, for example, methyl, ethyl, propyl or butyl, in particular 2-methylthioethoxymethyl.

N,N-Di-lower alkylamino is, for example, N,N-di-$C_1$–$C_4$alkylamino, such as N,N-dimethylamino, N,N-diethylamino, N,N-dipropylamino, N-methyl-N-ethyl-amino or N-methyl-N-propylamino.

N,N-Di-lower alkylamino-lower alkyl is, for example, N,N-di-$C_1$–$C_4$alkylamino-$C_1$–$C_4$alkyl, such as N,N-dimethylamino-$C_1$–$C_4$alkyl, N,N-diethylamino-$C_1$–$C_4$alkyl, N,N-dipropylamino-$C_1$–$C_4$alkyl, N-methyl-N-ethyl-amino or N-methyl-N-propylamino.

N,N-Di-lower alkylcarbamoyl is, for example, N,N-di-$C_1$–$C_4$alkylcarbamoyl, such as N,N-dimethylcarbamoyl, N,N-diethylcarbamoyl, N,N-dipropylcarbamoyl, N-methyl-N-ethylcarbamoyl or N-methyl-N-propyl-carbamoyl.

N,N-Di-lower alkylcarbamoylamino is, for example, N,N-di-$C_1$–$C_4$alkylcarbamoylamino, such as N,N-dimethylcarbamoylamino, N,N-diethylcarbamoylamino, N,N-dipropylcarbamoylamino, N-methyl-N-ethyl-carbamoylamino or N-methyl-N-propyl-carbamoylamino.

N,N-Di-lower alkylcarbamoyloxy is, for example, N,N-di-$C_1$–$C_4$alkylcarbamoyloxy, such as N,N-dimethylcarbamoyloxy, N,N-diethylcarbamoyloxy, N,N-dipropylcarbamoyloxy, N-methyl-N-ethyl-carbamoyloxy or N-methyl-N-propyl-carbamoyloxy.

N,N-Di-lower alkylcarbamoyl-lower alkoxy is, for example, N,N-dimethylcarbamoyl-$C_1$–$C_4$alkoxy, N,N-diethylcarbamoyl-$C_1$–$C_4$alkoxy, N,N-dipropylcarbamoyl-$C_1$–$C_4$alkoxy, N-methyl-N-ethyl-carbamoyl-$C_1$–$C_4$alkoxy or N-methyl-N-propyl-carbamoyl-$C_1$–$C_4$alkoxy, in which $C_1$–$C_4$alkoxy is, for example, methoxy, ethoxy, propyloxy or butyloxy, in particular N,N-dimethylcarbamoylmethoxy.

N,N-Lower alkyleneamino has, for example, 3 to 8, in particular 5 to 7, ring members and is, for example, 5- or 6-membered N,N-lower alkyleneamino, such as pyrrolidino, piperidino or hexahydroazepino.

N,N-Lower alkyleneamino-lower alkyl has, for example, 3 to 8, in particular 5 to 7, ring members and is, for example, pyrrolidino-$C_1$–$C_4$alkyl or piperidino-$C_1$–$C_4$alkyl, in which $C_1$–$C_4$alkyl is, for example, methyl, ethyl, propyl or butyl, in particular piperidinomethylmethyl.

N,N-(1-Oxo-lower alkylene)amino has, for example, 3 to 8, in particular 5 to 7, ring members and is, for example, 5- to 6-membered N,N-(1-oxo-lower alkylene)amino, such as 2-oxo-pyrrolidin-1-yl.

N,N-(1-Oxo-2-oxa-lower alkylene)amino has, for example, 3 to 8, in particular 5 to 7, ring members and is, for example, 5- or 6-membered N,N-(1-oxo-2-oxa-lower alkylene)amino, such as 2-oxo-oxazolidin-3-yl.

N,N-(Aza-lower alkylene)amino has, for example, 3 to 8, in particular 5 to 7, ring members and is, for example, 5- or 6-membered N,N-(aza-lower alkylene)amino, such as piperazino, N'—($C_1$–$C_4$alkyl)piperazino, such as N'-methylpiperazino, or N'—($C_1$–$C_4$alkanoyl)piperazino, such as N'-acetylpiperazino.

N,N-(Aza-lower alkyleneamino)-lower alkyl has, for example, 3 to 8, in particular 5 to 7, ring members and is, for example, 5- or 6-membered N,N-(aza-lower alkyleneamino)-lower alkyl, such as piperazino-$C_1$–$C_4$alkyl, N'—($C_1$–$C_4$alkyl)piperazino-$C_1$–$C_4$alkyl, such as N'-methylpiperazino-$C_1$–$C_4$alkyl, or N'—($C_1$–$C_4$alkanoyl)piperazino-$C_1$–$C_4$alkyl, such as N'-acetylpiperazino-$C_1$–$C_4$alkyl, in which $C_1$–$C_4$alkyl is, for example, methyl, ethyl, propyl or butyl, in particular N'-methylpiperazinomethyl.

N,N-(Oxa-lower alkylene)amino has, for example, 3 to 8, in particular 5 to 7, ring members and is, for example, 5- or 6-membered N,N-(oxa-lower alkylene)amino, such as morpholino.

N,N-(Oxa-lower alkyleneamino)-lower alkyl has, for example, 3 to 8, in particular 5 to 7, ring members and is 5- or 6-membered N,N-(oxa-lower alkyleneamino)-lower alkyl, such as morpholino-$C_1$–$C_4$alkyl, in which $C_1$–$C_4$alkyl is, for example, methyl, ethyl, propyl or butyl, in particular morpholinomethyl.

N,N-(Thia-lower alkylene)amino has, for example, 3 to 8, in particular 5 to 7, ring members and is, for example, 5- or 6-membered N,N-(thia-lower alkylene)amino, such as thiomorpholino or S,S-dioxythiomorpholino.

N,N-(Thia-lower alkyleneamino)-lower alkyl has, for example, 3 to 8, in particular 5 to 7, ring members and is, for example, 5- or 6-membered N,N-(thia-lower alkyleneamino)-lower alkyl, such as thiomorpholino-$C_1$-$C_4$alkyl or S,S-dioxythiomorpholino-$C_1$-$C_4$alkyl, in which $C_1$-$C_4$alkyl is, for example, methyl, ethyl, propyl or butyl, in particular thiomorpholinomethyl.

N,N-(2-Oxo-lower alkylene)amino has, for example, 3 to 8, in particular 5 to 7, ring members and is, for example, 2-oxopyrrolidino.

N-Carboxy-lower alkylcarbamoyl is, for example, N-carboxy-$C_1$-$C_4$alkylcarbamoyl, such as N-carboxymethylcarbamoyl, N-(2-carboxyethyl)carbamoyl or N-(3-carboxypropyl)carbamoyl.

N-Cycloalkylcarbamoyl is, for example, N—$C_3$-$C_7$cycloalkylcarbamoyl, such as cyclopropyl-, cyclopentyl- or cyclohexylcarbamoyl, in particular N-cyclopropylcarbamoyl.

N-Cycloalkyl-lower alkylcarbamoyl is, for example, N—($C_3$-$C_7$cycloalkyl-$C_1$-$C_4$alkyl)carbamoyl, such as N-(cyclopropyl-$C_1$-$C_4$alkyl)carbamoyl, N-(cyclopentyl-$C_1$-$C_4$alkyl)carbamoyl or N-(cyclohexyl-$C_1$-$C_4$-alkyl) carbamoyl, in particular N-(cyclopropylmethyl)carbamoyl.

N-Hydroxy-lower alkylcarbamoyl is, for example, N-hydroxy-$C_1$-$C_4$alkylcarbamoyl, such as N-hydroxymethylcarbamoyl, N-(2-hydroxyethyl) carbamoyl, N-(3-hydroxypropyl)carbamoyl or N-(4-hydroxybutyl)carbamoyl, in particular N-(2-hydroxyethyl) carbamoyl.

Phenyl-lower alkoxycarbonyl is, for example, phenyl-$C_1$-$C_7$alkoxycarbonyl, in particular phenyl-$C_1$-$C_4$alkoxycarbonyl, in which $C_1$-$C_4$alkyl is, for example, methyl, ethyl, propyl or butyl, such as benzyloxycarbonyl.

Phenyl-lower alkoxycarbonyl $R_4$ is, in particular, benzyloxycarbonyl, 1- or 2-naphthylmethoxycarbonyl or 9-fluorenylmethoxycarbonyl.

Phenyl-lower alkoxycarbonyloxy-lower alkyl is, for example, phenyl-$C_1$-$C_7$alkoxycarbonyloxy-$C_1$-$C_4$alkyl, in particular phenyl-$C_1$-$C_4$alkoxycarbonyloxy-$C_1$-$C_4$alkyl, in which $C_1$-$C_4$alkyl is in each case, for example, methyl, ethyl, propyl or butyl, such as benzyloxycarbonyloxymethyl.

Phenyl-lower alkanoyl is, for example, phenyl-$C_1$-$C_4$alkanoyl, in which $C_1$-$C_4$alkanoyl is, for example, acetyl, in particular phenylacetyl.

Phenyl-lower alkyl is, for example, phenyl-$C_1$-$C_7$alkyl, in particular phenyl-$C_1$-$C_4$alkyl, in which $C_1$-$C_4$alkyl is, for example, methyl, in particular benzyl or 2-phenethyl.

Phenyloxy-lower alkyl is, for example, phenyloxy-$C_1$-$C_7$alkyl, in particular phenyloxy-$C_1$-$C_4$alkyl, in which $C_1$-$C_4$alkyl is, for example, methyl, in particular benzyloxy or 2-phenethoxy.

Pyridyl-lower alkyl is, for example, pyridyl-$C_1$-$C_4$alkyl, in particular pyrid-2-yl-$C_1$-$C_4$alkyl, in which $C_1$-$C_4$alkyl is, for example, methyl, in particular pyrid-2-ylmethyl or 2-(pyrid-2-yl)ethyl.

Salts of compounds with salt-forming groups are, in particular, acid addition salts, salts with bases or, if several salt-forming groups are present, if desired mixed salts or inert salts.

Salts are, in particular, the pharmaceutically acceptable or non-toxic salts of compounds of the formula I.

Such salts are formed, for example, by compounds of the formula I having an acid group, for example a carboxyl or sulfo group, and are, for example, salts thereof with suitable bases, such as non-toxic metal salts derived from metals of group Ia, Ib, IIa and IIb of the periodic table of the element, for example alkali metal salts, in particular lithium, sodium, or potassium salts, alkaline earth metal salts, for example magnesium or calcium salts, and furthermore zinc salts, or ammonium salts, and also those salts which are formed with organic amines, such as mono-, di- or trialkylamines which are unsubstituted or substituted by hydroxyl, in particular mono-, di- or tri-lower alkylamines, or with quaternary ammonium bases, for example methyl-, ethyl-, diethyl- or triethylamine, mono-, bis- or tris-(2-hydroxy-lower alkyl) amines, such as ethanol-, diethanol- or triethanolamine, tris-(hydroxymethyl)methylamine or 2-hydroxytert-butylamine, N,N-di-lower alkyl-N-(hydroxy-lower alkyl) amines, such as N,N-dimethyl-N-(2-hydroxyethyl)amine, or N-methyl-D-glucamine, or quaternary ammonium hydroxides, such as tetrabutylammonium hydroxide. The compounds of the formula I with a basic group, for example an amino group, can form acid addition salts, for example with suitable inorganic acids, for example hydrogenhalide acid, such as hydrochloric acid or hydrobromic acid, sulfuric acid, with replacement of one or both protons, phosphoric acid, with replacement of one or more protons, for example ortho-phosphoric acid or meta-phosphoric acid, or pyrophosphoric acid, with replacement of one or more protons, or with organic carboxylic, sulfonic, sulfo or phosphonic acids or N-substituted sulfamic acids, for example acetic acid, propionic acid, glycolic acid, succinic acid, maleic acid, hydroxymaleic acid, methylmaleic acid, fumaric acid, mallic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and furthermore amino acids, for example the abovementioned α-amino acids, as well as methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose-6-phosphate or N-cyclohexylsulfamic acid (to form cyclamates), or with other acid organic compounds, such as ascorbic acid. Compounds of the formula I with acid and basic groups can also form inner salts.

Pharmaceutically unsuitable salts can also be used for isolation and purification.

The compounds of the present invention have enzyme-inhibiting properties. In particular, they inhibit the action of the natural enzyme renin. The latter enters the blood from the kidneys and causes cleavage of angiotensinogen there, releasing the decapeptide angiotensin I, which then undergoes cleavage in the lung, the kidneys and other organs to give the octapeptide angiotensin II. The octapeptide increases blood pressure both directly by arterial vasoconstriction and indirectly by release of the hormone aldosterone, which retains sodium ions, from the adrenals, which is associated with an increase in the volume of extracellular fluid. This increase is to be attributed to the action of angiotensin II. Inhibitors of the enzymatic activity of renin has the effect of reducing the formation of angiotensin I. As a consequence, a smaller amount of angiotensin II is formed. The reduced concentration of this active peptide hormone is the direct cause for the hypotensive action of renin inhibitors.

The action of renin inhibitors is detected, inter alia, experimentally by means of in vitro tests, the reduction in the formation of angiotensin I being measured in various systems (human plasma, purified human renin together with synthetic or natural renin substrate). The following in vitro test, inter alia, is used: an extract of human renin from the kidney (0.5 mGu [milli-Goldblatt units]/ml) is incubated for one hour at 37° C. and pH 7.2 in 1 molar aqueous 2-N-(trishydroxymethylmethyl)amino-ethanesulfonic acid buffer solution with 23 µg/ml of synthetic resin substrate, the tetradecapeptide H-Asp-Arg-Val-Tyr-Ile-His-ProPhe-His-Leu-Leu-Val-Tyr-Ser-OH. The amount of angiotensin I formed is determined in a radio-immunoassay. The inhibitors according to the invention are each added to the incubation mixture in different concentrations. That concentration of the particular inhibitor which reduces the formation of angiotensin I by 50% is called the $IC_{50}$. The compounds of the present invention show inhibiting actions at minimum concentrations of about $10^{-6}$ to about $10^{-10}$ mol/l in the in vitro systems.

Renin inhibitors cause a drop in blood pressure in salt-deficient animals. Human renin differs from renin from other species. Primates (marmosets, Callithrix jacchus) are used to test inhibitors of human renin, because human renin and primate renin are largely homologous in the enzymatically active range. The following in vivo test, inter alia, is employed: the test compounds are tested on normotensive marmosets of both sexes which have a bodyweight of about 300 g and are conscious. The blood pressure and heart rate are measured with a catheter in the femoral artery. The endogenous release of renin is stimulated by intravenous injection of furosemide (5-(aminosulfonyl)-4-chloro-2-[(2-furanylmethyl)amino]benzoic acid) (5 mg/kg). 30 minutes after the injection of furosemide, the test substances are either administered via a catheter in the lateral tail vein or by a continuous infusion or pumped into the stomach as a suspension or solution via a tube, and their action on the blood pressure and heart rate is evaluated. The compounds of the present invention are active in the in vivo test described at doses of about 0.1 to about 1.0 mg/kg i.v. and at doses of about 3 to about 30 mg/kg p.o.

The compounds of the present invention also have the property of being able to regulate, in particular lower, intraocular pressure.

The compounds of the present invention can be used as antihypertensives, and furthermore for the treatment of cardiac insufficiency or congestive heart diseases, or else for the treatment of increased intraocular pressure and glaucoma.

The invention relates to, for example, compounds of the formula I in which $R_1$ is arylamino, N-aryl-N-(lower alkoxy-lower alkyl)amino, N-aryl-N-aryl-lower alkyl-amino or heterocyclyl bonded via a ring nitrogen atom, it being possible for the heterocyclyl mentioned to contain, in addition to the ring nitrogen atom via which it is bonded, further ring heteroatoms chosen from the group consisting of oxygen, nitrogen, nitrogen substituted by lower alkyl, lower alkanoyl, lower alkanesulfonyl or lower alkoxycarbonyl, sulfur and sulfur linked with 1 or 2 oxygen atoms, X is a carbonyl or methylene group, $R_2$ and $R_3$ independently of one another are hydrogen or lower alkyl or, together with the carbon atom with which they are bonded, are a cycloalkylidene radical, $R_4$ is hydrogen, lower alkyl, lower alkanoyl or lower alkoxycarbonyl, $R_5$ is hydroxyl, lower alkanoyloxy or lower alkoxycarbonyloxy, $R_6$ is hydrogen, lower alkyl, lower alkenyl, lower alkynyl, cycloalkyl, cycloalkyl-lower alkyl, aryl-lower alkyl or heteroaryl-lower alkyl having 5 to 7 ring atoms in the heteroaryl ring and $R_7$ is hydrogen or lower alkyl, or $R_6$ and $R_7$, together with the carbon atom with which they are bonded, are a cycloalkylidene radical and $R_8$ is lower alkyl, lower alkoxy-lower alkyl, amino-lower alkyl, N-lower alkylamino-lower alkyl, N,N-di-lower alkylamino-lower alkyl, N,N-lower alkyleneamino-lower alkyl, N,N-(aza-lower alkyleneamino)-lower alkyl, N,N-(oxa-lower alkyleneamino)-lower alkyl, N,N-(thia-lower alkyleneamino)-lower alkyl, carbamoyl-lower alkyl, N-lower alkylcarbamoyl-lower alkyl, N,N-di-lower alkylcarbamoyl-lower alkyl, cyano-lower alkyl or heteroaryl-lower alkyl having 5 to 7 ring atoms in the heteroaryl ring, which contains a ring nitrogen atom and can contain a further ring heteroatom chosen from oxygen, sulfur and nitrogen, and their salts.

The invention relates in particular to compounds of the formula I in which $R_1$ is anilino or naphthylamino which are unsubstituted or substituted in the phenyl or naphthyl part as defined below, N-phenyl- or N-naphthyl-N-(lower alkoxy-lower alkyl)-amino which are unsubstituted or substituted in the phenyl or naphthyl part as defined below, N-phenyl or N-naphthyl-N-(phenyl-lower alkyl)-amino which are unsubstituted or substituted in the phenyl or naphthyl part as defined below, or 5- to 8-membered heterocyclyl which is bonded via a ring nitrogen atom, may be fused with 1 or 2 fused-on phenyl or cycloalkyl radicals and can contain 1 or 2 further ring heteroatoms chosen from oxygen, nitrogen and free or oxidized sulfur, X is a carbonyl or methylene group, $R_2$ and $R_3$ independently of one another are hydrogen or lower alkyl or, together with the carbon atom with which they are bonded, are 3- to 8-membered cycloalkylidene, $R_4$ is hydrogen, lower alkyl, lower alkanoyl or lower alkoxycarbonyl, $R_5$ is hydroxyl, lower alkanoyloxy or lower alkoxycarbonyloxy, $R_6$ is hydrogen, lower alkyl, 3- to 8-membered cycloalkyl, 3- to 8-membered cycloalkyl-lower alkyl, lower alkenyl, lower alkynyl, phenyl which is unsubstituted or substituted as defined below, indenyl, naphthyl, phenyl- or naphthyl-lower alkyl which are unsubstituted or substituted in the phenyl or naphthyl part as defined below, pyridyl-lower alkyl or imidazolyl-lower alkyl, $R_7$ is hydrogen or lower alkyl or $R_6$ and $R_7$, together with the carbon atom with which they are bonded, are 3- to 8-membered cycloalkylidene and $R_8$ is lower alky, lower alkoxy-lower alkyl, amino-lower alkyl, N-lower alkylamino-lower alkyl, N,N-di-lower alkylamino-lower alkyl, N,N-lower alkyleneamino-lower alkyl N,N-(aza-lower alkyleneamino)-lower alkyl, N,N-(oxa-lower alkyleneamino)-lower alkyl, N,N-(thia-lower alkyleneamino)-lower alkyl or heteroaryl-lower alkyl having 5 to 7 ring atoms in the heteraryl ring, which contains a ring nitrogen atom and can contain a further ring heteroatom chosen from oxygen, sulfur and nitrogen, in which phenyl, naphthyl, and phenyl and naphthyl radicals as a constituent of naphthylamino, N-phenyl- or N-naphthyl)-N-(lower alkoxy-lower alkyl)-amino, N-phenyl- or N-naphthyl)-N-lower alkyl-amino, indenyl, phenyl- or naphthyl-lower alkyl and N-phenyl-N-(phenyl-lower alkyl)-amino can be mono- or polysubstituted, for example mono- or disubstituted, by lower alkyl, hydroxyl, lower alkoxy, carbamoyl-lower alkyl, N-lower alkylcarbamoyl-lower alkoxy, N-lower alkylcarbamoyl, N,N-di-lower alkylcarbamoyl-lower alkoxy, amino, N-lower alkyl- or N,N-di-lower alkylamino, carboxyl, lower alkoxycarbonyl, carbamoyl, sulfamoyl, lower alkanesulfonyl, halogen, nitro, phenyl, 5- or 6-membered heteroaryl containing, as the heteroatom, 1 nitrogen, sulfur or oxygen atom, 2N atoms, 1N atom and 1 S atom or 1N atom and 1 O atom, such as pyridyl, and/or by cyano, and radicals $R_1$ can be N-subsituted by lower alkyl, lower alkanoyl, lower alkoxycarbonyl or lower alkanesulfonyl, S-mono- or S,S-disubstituted by oxy and/or mono- or di-C-substituted by lower alkyl, hydroxy-lower alkyl, lower alkoxy-lower alkyl, lower alkenyloxy-lower alkyl, naphthoxy-lower alkyl, phenyloxy-lower alkyl, phenyl-lower alkoxy-lower alkyl, lower alkanoyloxy-lower alkyl, benzoyloxy-lower alkyl, lower alkoxycarbonyloxy-lower alkyl, phenyloxycarbonyloxy-lower alkyl, phenyl-lower alkoxycarbonyloxy-lower alkyl, amino-lower alkyl, N-lower alkylamino-lower alkyl, N,N-di-lower alkylamino-lower alkyl, carbamoyl-lower alkyl, lower alkanoylamino-lower alkyl, benzoylamino-lower alkyl, lower alkoxycarbonylamino-lower alkyl, lower alkoxycarbonyl-lower alkyl, lower alkoxy-lower alkoxy-lower alkyl, lower alkylthio-lower alkoxy-lower alkyl, N-lower alkoxyimino-lower alkyl, cycloalkoxy-lower alkyl, cycloalkyl-lower alkoxy-lower alkyl, lower alkenyl, lower alkenyloxy, lower alkoxy-lower alkenyl, lower alkynyl, lower alkynyloxy, lower alkanoyl, oxo, hydroxyl, lower alkoxy, carbamoyl-lower alkoxy, N-lower alkylcarbamoyl-lower alkoxy, N-lower alkylcarbamoyloxy, N,N-di-lower alkylcarbamoyloxy, lower alkoxy-lower alkoxy, lower alkylthio-lower alkoxy, lower alkanoyloxy, benzoyloxy, N-lower alkylcarbamoyl, amino, N-lower alkylamino, N,N-di-lower alkylamino, lower alkanoylamino, benzoylamino, cycloalkylcarbonylamino, cycloalkyl-lower alkanoylamino, lower alkoxycarbonyl-lower alkylamino, lower alkenyloxycarbonylamino, lower alkoxy-lower alkoxycarbonylamino, lower alkoxy-lower alkanoylamino, N-lower alkylcarbamoylamino, N,N-di-lower alkylcarbamoylamino, N-lower alkanoyl-N-lower alkylamino, lower alkoxycarbonylamino, N-lower alkoxycarbonyl-N-lower alkyl-amino, N,N-lower alkyleneamino, N,N-(1-oxo-lower alkylene)amino, N,N-(1-oxo2-oxa-lower alkylene)amino, carboxyl, lower alkoxycarbonyl, phenyl-lower alkoxycarbonyl, phenyloxycarbonyl, pyrrolidinylcarbonyl, piperidinylcarbonyl, piperazinylcarbonyl, morpholinylcarbonyl, thiomorpholinylcarbonyl, S,S-dioxothiomorpholin-4-ylcarbonyl, cyano, carbamoyl, N,N-di-lower alkylcarbamoyl, N-lower alkenylcarbamoyl, N-cycloalkylcarbamoyl, N-cycloalkyl-lower alkylcarbamoyl, N-hydroxy-lower alkylcarbamoyl, N-lower alkoxy-lower alkylcarbamoyl, N-carboxy-lower alkylcarbamoyl, carbamoyl-lower alkylcarbamoyl, lower alkoxycarbonyl-lower alkylcarbamoyl, phenyl, dioxolan-2-yl, oxazol-2-yl, oxazolin-2-yl, oxazolidin-2-yl, nitro, sulfamoyl, lower alkanesulfonyl, phosphono, lower alkanephosphono, di-lower alkylphosphono and/or halogen and their salts, in particular their pharmaceutically acceptable salts.

The invention relates above all to compounds of the formula I in which $R_1$ is anilino, naphthylamino, N-phenyl-N—($C_1$–$C_4$alkoxy-$C_1$–$C_4$alkyl)-amino, such as N-phenyl-N-(ethoxymethyl)amino, or N-phenyl-N-(phenyl-$C_1$–$C_4$alkyl)-amino, such as N-phenyl-N-(2-phenylethyl)-amino, which are unsubstituted or mono- or disubstituted in the phenyl or naphthyl part by $C_1$–$C_4$alkoxy, such as methoxy, $C_1$–$C_4$alkoxycarbonyl, such as methoxy-, ethoxy-, isopropyloxy or tert-butyloxycarbonyl, carbamoyl-$C_1$–$C_4$alkoxy, such as carbamoylmethoxy, $C_1$–$C_4$alkanoylamino-$C_1$–$C_4$alkyl, such as formylaminomethyl, $C_1$–$C_4$alkoxycarbonylamino-$C_1$–$C_4$alkyl, such as methoxycarbonylaminomethyl, halogen and/or pyridyl which may be N-oxidized, such as pyrid-3-yl or 1-oxidopyrid-3-yl, or pyrrolidino, piperidino, piperazino, morpholino or thiomorpholino which are in each case mono-, di- or trisubstituted by $C_1$–$C_4$alkyl, such as methyl, hydroxy-$C_1$–$C_4$alkyl, such as hydroxymethyl, $C_1$–$C_4$alkoxy-$C_1$–$C_4$alkyl, such as methoxymethyl or propyloxymethyl, $C_3$–$C_5$alkenyloxy-$C_1$–$C_4$alkyl, such as allyloxymethyl, $C_1$–$C_4$alkoxy-$C_1$–$C_4$alkoxy-$C_1$–$C_4$alkyl, such as methoxymethoxymethyl or 2-methoxyethoxymethyl, $C_1$–$C_4$alkoxycarbonylamino-$C_1$–$C_4$alkyl, such as methoxy- or ethoxycarbonylaminomethyl, $C_1$–$C_4$alkoxyimino-$C_1$–$C_4$alkyl, such as methoxyiminomethyl, ethoxyiminomethyl or propoxyiminomethyl, carboxy, $C_1$–$C_7$alkoxycarbonyl, such as methoxy-, ethoxy-, isopropyloxy- or tert-butyloxycarbonyl, cyano, carbamoyl, N—$C_7$alkylcarbamoyl, such as N-methyl- or N-butylcarbamoyl, N,N-di-$C_1$–$C_4$carbamoyl, such as N,N-dimethylcarbamoyl, $C_1$–$C_4$alkoxy-$C_1$–$C_4$alkylcarbamoyl, such as N-(2-propyloxyethyl)carbamoyl, N-carboxy-$C_1$–$C_4$alkylcarbamoyl, such as N-carboxymethylcarbamoyl, morpholinocarbonyl, $C_1$–$C_4$alkoxy, such as propyloxy, $C_1$–$C_4$alkoxy-$C_1$–$C_4$alkoxy, such as methoxymethoxy or 2-methoxyethoxy, $C_1$–$C_7$alkanoyloxy, such as acetoxy, benzoyloxy, $C_1$–$C_4$alkanoylamino, such as acetylamino, $C_1$–$C_7$alkoxycarbonylamino, such as methoxycarbonylamino, 3- to 6-membered cycloalkylcarbonylamino, such as cyclopropylcarbonylamino, N—$C_1$–$C_4$alkoxy-$C_1$–$C_4$alkanoylamino, such as methoxyacetylamino, N—$C_1$–$C_4$alkylcarbamoylamino, such as methylcarbamoylamino. 5- or 6-membered N,N-(1-oxo-lower alkylene)amino or N,N-(1-oxo2-oxa-lower alkylene)amino, such as 2-oxopyrrolidin-1-yl or 2-oxo-oxazolidin-3-yl, $C_1$–$C_7$alkanoyl, such as acetyl, oxo, nitro, $C_1$–$C_4$alkanesulfonyl, such as methan- or ethanesulfonyl, and/or halogen, indolin-1-yl, isoindolin-2-yl, 2,3-dihydrobenzimidazol-1-yl, 1,2,3,4-tetrahydroquinol-1-yl, 1,2,3,4-tetrahydroisoquinol-2-yl, 1,2,3,4-tetrahydro-1,3-benzodiazin-1-yl, 1,2,3,4-tetrahydro-1,4-benzodiazin-1-yl, 3,4-dihydro-2H-1,4-benzooxazin-4-yl, 3,4-dihydro-2H-1,3-benzothiazin-1-yl, which may be S,S-dioxidized, 3,4,5,6,7,8-hexahydro-2H-1,4-benzoxazin-4-yl, 3,4,5,6,7,8-hexahydro-2H-1,4-benzothiazin-4-yl, 2,3,4,5-tetrahydro-1H-1-benz[6,7-b]azepin-1-yl or 5,6-dihydrophenanthridin-5-yl, X is a carbonyl group, $R_2$ and $R_3$ independently of one another are hydrogen or $C_1$–$C_4$alkyl, such as methyl, or, together with the carbon atom with which they are bonded, are 3- to 8-membered cycloalkylidene, such as cyclopropylidene, $R_4$ is hydrogen or $C_1$–$C_4$alkanoyl, such as formyl, $R_5$ is hydroxyl, $R_6$ is hydrogen, $C_1$–$C_4$alkyl, such as methyl, ethyl, propyl, isopropyl, butyl or isobutyl, 3- to 8-membered cycloalkyl, such as cyclopropyl, or phenyl-$C_1$–$C_4$alkyl, such as benzyl or 2-phenethyl, and $R_7$ is hydrogen, or $R_6$ and $R_7$, together with the carbon atom with which they are bonded, are 3- to 8-membered cycloalkylidene, such as cyclopropylidene, and $R_8$ is $C_1$–$C_7$alkyl, such as butyl, $C_1$–$C_4$alkoxy-$C_1$–$C_4$alkyl, such as 2-methoxyethyl, amino-$C_1$–$C_4$alkyl, such as 3-aminopropyl, N—$C_1$–$C_4$alkylamino-$C_1$–$C_4$alkyl, such as 2-(N-methylamino)ethyl, N,N-di-$C_1$–$C_4$alkylamino-$C_1$–$C_4$alkyl, such as 2-(N-methylamino)ethyl, 2-(N,N-dimethylamino)ethyl or 3-(N,N-dimethyl)propyl, 5- or 6-membered N,N-lower alkyleneamino-$C_1$–$C_4$alkyl or N,N-(aza)-, N,N-(oxa)-or N,N-(thia)-lower alkyleneamino-$C_1$–$C_4$alkyl, such as 2-morpholinoethyl or 3-morpholinopropyl, carbamoyl-$C_1$–$C_4$alkyl, such as 2-(N-methylcarbamoyl)ethyl, carbamoylmethyl, 2-carbamoylethyl, 3-carbamoylpropyl or 4-carbamoylbutyl, N—$C_1$–$C_4$akylcarbamoyl, such as N-methylcarbamoyl, N-ethylcarbamoyl, N-propylcarbamoyl or N-butylcarbamoyl, N,N-di-$C_1$–$C_4$alkylcarbamoyl, such as N,N-dimethylcarbamoyl, N,N-diethylcarbamoyl, N,N-dipropylcarbamoyl, N-methyl-N-ethyl-carbamoyl or N-methyl-N-propyl-carbamoyl, cyano-$C_1$–$C_4$alkyl, such as cyanomethyl, 2-cyanoethyl, 3-cyanopropyl or 4-cyanobutyl, or pyridyl-$C_1$–$C_4$alkyl, such as 2-pyrid-2-ylethyl, and their salts, in particular their pharmaceutically acceptable salts.

The invention particularly relates to compounds of the formula I in which $R_1$ is a group of the formula Ia or Ib

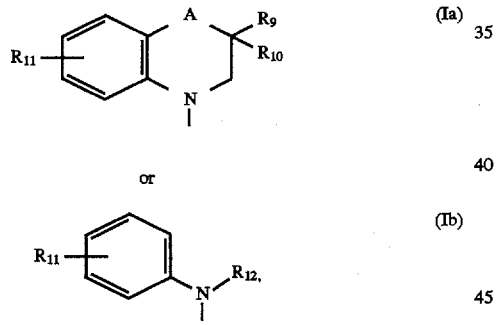

in which

A is a direct bond, methylene, ethylene, imino, oxy or thio, $R_9$ is $C_1$–$C_4$alkoxy-$C_1$–$C_4$alkyl, such as methoxy- or propyloxymethyl, $C_3$–$C_5$alkenyloxy-$C_1$–$C_4$alkyl, such as allyloxymethyl, $C_1$–$C_4$alkoxy-$C_1$–$C_4$alkoxy-$C_1$–$C_4$alkyl, such as methoxymethoxymethyl or 2-methoxyethoxymethyl, $C_1$–$C_4$alkoxycarbonylamino-$C_1$–$C_4$alkyl, such as methoxy- or ethoxycarbonylaminomethyl, $C_1$–$C_4$alkoxyimino-$C_1$–$C_4$alkyl, such as methoxyiminomethyl, phenyl, $C_1$–$C_4$alkoxycarbonyl, such as methoxycarbonyl, ethoxycarbonyl or isopropyloxycarbonyl, cyano, carbamoyl, N—$C_1$–$C_4$alkylcarbamoyl, such as N-methylcarbamoyl, N-ethylcarbamoyl or N-butylcarbamoyl, $C_1$–$C_4$alkoxy-$C_1$–$C_4$-alkylcarbamoyl, such as N-(2-methoxyethyl) carbamoyl, $C_1$–$C_4$alkoxy, such as propyloxy, $C_1$–$C_4$alkoxy-$C_1$–$C_4$alkoxy, such as methoxymethoxy or 2-methoxyethoxy, $C_1$–$C_7$alkanoyloxy, such as acetoxy, benzoyloxy, N—$C_1$–$C_4$alkylcarbamoylamino, such as N-methylcarbamoylamino, $C_1$–$C_4$alkanoylamino, such as acetylamino, $C_1$–$C_7$alkoxycarbonylamino, such as methoxycarbonylamino, 3- to 6-membered cycloalkylcarbonylamino, such as cyclopropylcarbonylamino, $C_1$–$C_4$alkoxy-$C_1$–$C_4$alkanoylamino, such as methoxyacetylamino, or 5- or 6-membered N,N-(1-oxo-lower alkylene)amino or N,N-(1-oxo2-oxa-lower alkylene)amino, such as 2-oxopyrrolidin-1-yl or 2-oxo-oxazolidin-3-yl, N—$C_1$–$C_4$alkylcarbamoylamino, such as methylcarbamoylamino, $R_{10}$ is hydrogen, but can also be $C_1$–$C_4$alkyl, such as methyl, $R_{11}$ is hydrogen or halogen and $R_{12}$ is $C_1$–$C_4$alkoxy-$C_1$–$C_4$alkyl, such as methoxy-$C_1$–$C_4$alkyl, ethoxy-$C_1$–$C_4$alkyl, propyloxy-$C_1$–$C_4$alkyl, isopropyloxy-$C_1$–$C_4$alkyl, butyloxy-$C_1$–$C_4$alkyl, isobutyloxy-$C_1$–$C_4$alkyl, sec-butyl-oxy-$C_1$–$C_4$alkyl or tert-butyloxy-$C_1$–$C_4$alkyl, in which $C_1$–$C_4$alkyl is, for example, ethyl, propyl or butyl, and in particular 3-methoxypropyl, X is a carbonyl group, $R_2$ and $R_3$ independently of one another are hydrogen or $C_1$–$C_4$alkyl, such as methyl, or, together with the carbon atom with which they are bonded, are 3- to 8-membered cycoalkylidene, such as cyclopropylidene, $R_4$ is hydrogen or $C_1$–$C_4$alkanoyl, such as formyl, $R_5$ is hydroxyl, $R_6$ is hydrogen, $C_1$–$C_4$alkyl, such as methyl, ethyl, propyl, isopropyl, butyl or isobutyl, 3- to 8-membered cycloalkyl, such as cyclopropyl, or phenyl-$C_1$–$C_4$alkyl, such as benzyl or 2-phenethyl, $R_7$ is hydrogen and $R_8$ is $C_1$–$C_7$-alkyl, such as butyl, $C_1$–$C_4$alkoxy-$C_1$–$C_4$alkyl, such as 2-methoxyethyl, amino-$C_1$–$C_4$alkyl, such as 3-aminopropyl, N—$C_1$–$C_4$alkylamino-$C_1$–$C_4$alkyl, such as 2-(N-methylamino)ethyl, N,N-di-$C_1$–$C_4$alkylamino-$C_1$–$C_4$alkyl, such as 2-(N-methylamino)ethyl, 2-(N,N-dimethylamino)ethyl or 3-(N,N-dimethyl)propyl, 5- or 6-membered N,N-lower alkyleneamino-$C_1$–$C_4$-alkyl or N,N-(aza)-, N,N-(oxa)- or N,N-(thia)-lower alkyleneamino-$C_1$–$C_4$alkyl, such as 2-morpholinoethyl or 3-morpholinopropyl, or pyridyl-$C_1$–$C_4$alkyl, such as 2-pyrid-2-ylethyl, and their salts, in particular their pharmaceutically acceptable salts.

Compounds of the formula I which are particularly active are in each case those having the stereotaxy of the main chain shown in the formula

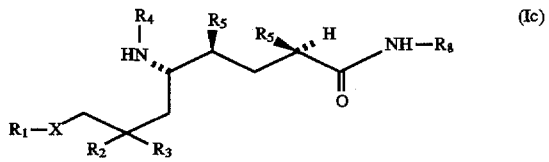

The invention preferably relates in each case to the stereoisomers of compounds of the formula I having the stereotaxy of the main chain shown in the formula Ia, in which the variables are as defined above, and their salts, in particular their pharmaceutically acceptable salts.

The invention preferably relates to compounds of the formula Ib in which $R_1$, $R_2$, $R_3$, $R_4$, $R_5$, $R_6$, $R_7$, $R_8$, $R_9$, $R_{10}$ and $R_{11}$ are as defined above, and their salts, in particular their pharmaceutically acceptable salts.

The invention relates especially to the compounds of the formula I mentioned in the examples and their salts, in particular their pharmaceutically acceptable salts.

The invention relates above all to compounds of the formula Id

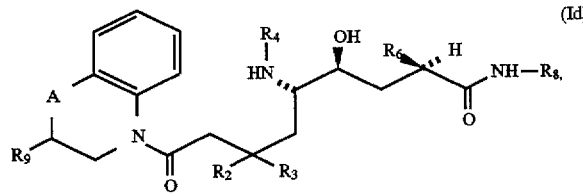

in which

A is a methylene, oxy or thio, $R_2$ and $R_3$ are $C_1$–$C_4$alkyl, such as methyl, $R_4$ is hydrogen or $C_1$–$C_4$alkanoyl, such as formyl, $R_6$ is $C_1$–$C_4$alkyl, such as methyl, ethyl, isopropyl, butyl or isobutyl, or phenyl-$C_1$–$C_4$alkyl, such as benzyl, $R_8$ is $C_1$–$C_7$alkyl, such as butyl, and $R_9$ is $C_1$–$C_4$alkoxycarbonylamino, such as methoxycarbonylamino, ethoxycarbonylamino, propyloxycarbonylamino, isopropyloxycarbonylamino or butyloxycarbonylamino, $C_1$–$C_4$alkoxy-$C_1$–$C_4$alkoxy-$C_1$–$C_4$alkyl, such as methoxy-$C_1$–$C_4$alkoxy-$C_1$–$C_4$alkyl, ethoxy-$C_1$–$C_4$alkoxy-$C_1$–$C_4$alkyl, propyloxy-$C_1$–$C_4$alkoxy-$C_1$–$C_4$alkyl, isopropyloxy-$C_1$–$C_4$alkoxy-$C_1$–$C_4$alkyl or butyloxy-$C_1$–$C_4$alkoxy-$C_1$–$C_4$alkyl, in which $C_1$–$C_4$alkoxy is, for example, methoxy, ethoxy, propyloxy or butyloxy and —$C_1$–$C_4$alkyl is, for example, methyl, ethyl, propyl or butyl, in particular methoxymethoxymethyl, 2-methoxyethoxymethyl or 3-methoxypropyl, $C_1$–$C_4$alkoxy-$C_1$–$C_4$alkyl, such as methoxy-$C_1$–$C_4$alkyl, ethoxy-$C_1$–$C_4$alkyl, propyloxy-$C_1$–$C_4$alkyl, isopropyloxy-$C_1$–$C_4$alkyl, butyloxy-$C_1$–$C_4$alkyl, isobutyloxy-$C_1$–$C_4$alkyl, sec-butyloxy-$C_1$–$C_4$alkyl or tert-butyloxy-$C_1$–$C_4$alkyl, in which $C_1$–$C_4$alkyl is, for example, methyl, ethyl, propyl or butyl in particular ethoxymethyl or 2-methoxyethyl, or N—$C_1$–$C_4$alkylcarbamoyl, in which N-methylcarbamoyl, N-ethylcarbamoyl, N-propylcarbamoyl or N-butylcarbamoyl, and their salts, in particular their pharmaceutically acceptable salts.

The compounds of the formula I according to the invention and salts of such compounds having at least one salt-forming group are obtained by processes known per se, for example by a) subjecting a compound of the formula II

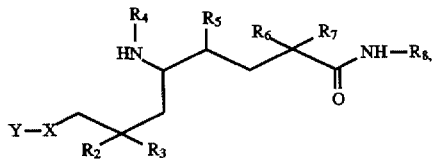

in which Y is free or reactive functionally modified hydroxyl and X, $R_2$, $R_3$, $R_4$, $R_5$, $R_6$, $R_7$ and $R_8$ are as defined above, or a salt thereof, to a condensation reaction with a compound of the formula $R_1$—H (III), in which $R_1$ is as defined, to form an amine or amide bond, free functional groups present in the reaction components, with the exception of the groups participating in the reaction, being in protected form, and splitting off the protective groups present, or b) subjecting a carboxylic acid of the formula IV

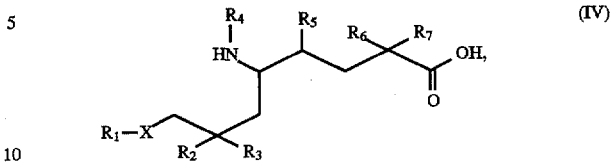

in which $R_1$, X, $R_2$, $R_3$, $R_4$, $R_5$, $R_6$ and $R_7$ are as defined, or a salt or a reactive acid derivative thereof, to a condensation reaction with a compound of the formula H—N(H)—$R_8$ (V) or a reactive derivative thereof with a reactive amino group, in which $R_8$ is as defined, to form an amide bond, free functional groups present in the reaction components, with the exception of the groups participating in the reaction, being in protected form, and splitting off the protective groups present, or c) to prepare a compound of the formula I wherein $R_5$ is hydroxyl and the other substituents are as defined, in a compound of the formula VI

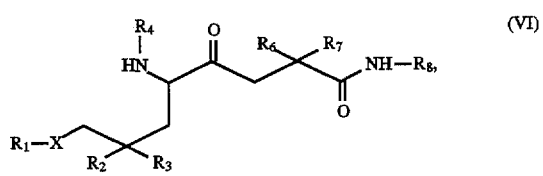

in which $R_1$, X, $R_2$, $R_3$, $R_4$, $R_6$, $R_7$ and $R_8$ are as defined and free functional groups, with the exception of the keto group participating in the reaction, are in protected form, or in a salt thereof, reducing the keto group to hydroxymethylene and splitting off any protective groups present, or d) to prepare a compound of the formula I wherein $R_6$ is alkyl, arylalkyl or heteroaralkyl, in particular methyl, and $R_7$ is hydrogen and the other substituents are as defined, in a compound of the formula VII

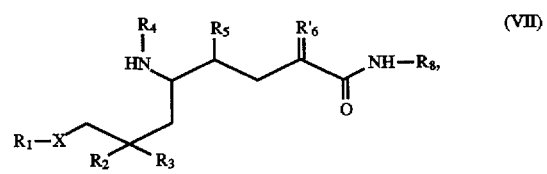

in which $R_6$ is alkylidene, arylalkylidene or heteroaralkylidene, in particular methylene, and $R_1$, X, $R_2$, $R_3$, $R_4$, $R_5$ and $R_8$ are as defined, free functional groups being in protected form if desired, or a salt thereof, reducing the group $R_6$ to the desired group $R_6$, or e) to prepare a compound of the formula I in which $R_4$ is hydrogen and the other substituents are as defined, in a compound of the formula VIII

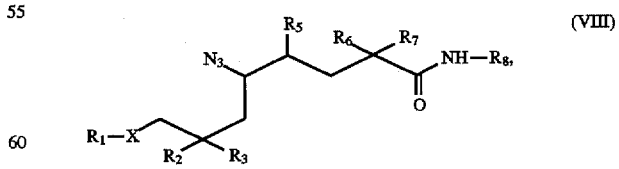

in which the substituents $R_1$, X, $R_2$, $R_3$, $R_5$, $R_6$, $R_7$ and $R_8$ are as defined and free functional groups are in protected form, if appropriate, or a salt thereof, reducing the azido group to amino and splitting off the protective groups present, and in each case if desired, converting a compound of the formula I obtainable by one of the abovementioned processes a) to e) and having at least one salt-forming group into its salt or converting a salt obtainable into the free compound or into another salt, and/or, if appropriate, separating isomer mixtures obtainable, and/or converting a compound of the formula I according to the invention into another compound of the formula I according to the invention.

The reactions in the processes are carried out and the novel starting substances or intermediates are prepared by reaction and formation methods analogous to those of known starting substances and intermediates. The particular customary auxiliaries, such as catalysts, condensing agents and solvolysing agents and/or solvents or diluents, and reaction conditions, such as temperature and pressure conditions, and also inert gases, if appropriate, are used here, even if not expressely mentioned below.

The starting substances of the formula II for process variant a) contain a terminal carboxyl or hydroxymethyl group or are reactive functional derivatives thereof, for example activated esters or anhydrides derived from acids of the formula II (Y=hydroxyl; X=carbonyl), or furthermore reactive cyclic amides, or reactive esters derived from alcohols of the formula II (Y=hydroxyl; X=methylene), in which the reactive functionally modified hydroxyl group is, in particular, hydroxyl esterified with a strong inorganic acid, a mineral acid, for example a hydrohalic acid, such as hydrochloric, hydrobromic or hydriodic acid, with a strong organic sulfonic acid or with hydrazoic acid. The reactive acid and alcohol derivatives can also be formed in situ.

Activated esters of the formula II are, in particular, esters which are unsaturated on the linking carbon atom of the esterifying radical, for example of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolinium or Woodward method) or 1-lower alkoxy vinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, in particular phenyl esters suitably substituted by electron-withdrawing substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensing agent, such as N,N'-dicyclohexylcarbodiimide; activated aryl ester method), cyanomethyl esters (obtainable, for example, by treatment of the corresponding acid with chloroacetonitrile in the presence of a base; cyanomethyl ester method), thioesters, in particular phenylthioesters which are unsubstituted or substituted, for example by nitro (obtainable, for example, by treatment of the corresponding acid with thiophenols which are unsubstituted or substituted, for example by nitro, inter alia with the aid of the anhydride or carbodiimide method; activated thiol ester method), or, in particular, amino or amido esters (obtainable, for example, by treatment of the corresponding acid with an N-hydroxyimino or N-hyroxyamido compound, for example N-hydroxysuccinimide, N-hydroxypiperidine, N-hydroxyphthalimide, N-hydroxy-5-norbornene-2,3-dicarboxylic acid imide, 1-hydroxybenzotriazole or 3-hydroxy-3,4-dihydro-1,2,3-benzotriazin-4-one, for example by the anhydride or carbodiimide method; activated N-hydroxy ester method). Inner esters, for example γ-lactones, can also be employed.

Anhydrides of the formula II of acids can be symmetric or, preferably, mixed anhydrides of these acids, for example anhydrides with inorganic acids, such as acid halides, in particular acid chlorides (obtainable, for example, by treatment of the corresponding acid with thionyl chloride, phosphorus pentachloride, oxalyl chloride or 1-chloro-N,N,2-trimethyl-propenylamine; acid chloride method), azides (obtainable, for example, from a corresponding acid ester via the corresponding hydrazide and treatment thereof with nitrous acid; azide method), anhydrides with carbonic acid half-esters, for example carbonic acid lower alkyl half-esters (obtainable, for example, by treatment of the corresponding acid with chloroformic acid lower alkyl esters or with a 1-lower alkoxycarbonyl-2-lower alkoxy-1,2-dihydroquinoline; mixed O-alkylcarbonic acid anhydride method), or anhydrides with dihalogenated, in particular dichlorinated, phosphoric acid (obtainable, for example, by treatment of the corresponding acid with phosphorus oxychloride; phosphorous oxychloride method), anhydrides with other phosphoric acid derivatives (for example those which can be obtained with phenyl N-phenyl-phosphoroamidochloridate or bis(2-oxo-3-oxazolidinyl) phosphinic acid chloride) or with phosphorous acid derivatives, or anhydrides with organic acids, such as mixed anhydrides with organic carboxylic acids (obtainable, for example, by treatment of the corresponding acid with an optionally substituted lower alkane- or phenyl-lower alkanecarboxylic acid halide, for example phenylacetyl, pivalyl or trifluoroacetyl chloride; mixed carboxylic acid anhydride method) or with organic sulfonic acids (obtainable, for example, by treatment of a salt, such as an alkali metal salt, of the corresponding acid with a suitable organic sulfonic acid halide, such as lower alkane- or aryl-, for example methane- or p-toluenesulfonyl chloride; mixed sulfonic acid anhydride method), and symmetric anhydrides (obtainable, for example, by condensation of the corresponding acid in the presence of a carbodiimide or of 1-diethylaminopropyne; (symmetric anhydride method).

Suitable reactive cyclic amides are, in particular, amides with five-membered diazacyclic radicals of aromatic character, such as amides with imidazoles, for example imidazole (obtainable, for example, by treatment of the corresponding acid with N,N'-carbonyldiimidazole; imidazole method), or pyrazole, for example, 3,5-dimethylpyrazole (obtainable, for example, by the acid hydrazide by treatment with acetylacetone; pyrazolide method).

Reactive esters derived from alcohols of the formula II (Y=hydroxyl; X=methylene) are, for example, esters thereof with a strong inorganic acid, such as with a mineral acid, for example a hydrohalic acid, such as hydrochloric, hydrobromic or hydriodic acid, and furthermore sulfuric acid or halosulfuric acid, for example fluorosulfuric acid, or with a strong organic sulfonic acid, such as a lower alkanesulfonic acid which is unsubstituted or substituted, for example by halogen, such as fluorine, or an aromatic sulfonic acid, for example a benzenesulfonic acid which is unsubstituted or substituted by lower alkyl, such as methyl, halogen, such as bromine, and/or nitro, for example a methanesulfonic, trifluoromethanesulfonic or p-toluenesulfonic acid, or with hydrazoic acid.

As mentioned, derivatives of carboxylic acids and alcohols of the formula II can also be formed in situ. Thus, for example, N,N'-disubstituted amidino esters can be formed in situ by reacting the mixture of a carboxylic acid of the formula II and the amine component of the formula III in the presence of a suitable N,N'-disubstituted carbodiimide, for example N,N'-cyclohexyldiimide. Amino or amido esters of acids of the formula II furthermore can be formed in the presence of the starting material of the formula III to be acylated by reacting a mixture of the corresponding acid and amino starting substances in the presence of an N,N-disubstituted carbodiimide, for example N,N'-dicyclohexylcarbodiimide, and an N-hydroxyamine or N-hydroxyamide, for example N-hydroxysuccinimide, in the presence or absence of a suitable base, for example 4-dimethylaminopyridine.

Reactive functional derivatives of alcohols of the formula II can likewise be obtained in situ by reaction of these with a halogenating agent, such as a hydrohalic acid or thionyl chloride or bromide, a di-lower alkyl sulfate or a sulfonylating agent, such as fluorosulfonyl chloride or a halide derived from a strong organic sulfonic acid, such as a lower alkanesulfonic acid which is unsubstituted or substituted, for example by halogen, such as fluorine, or an aromatic sulfonic acid, for example a benzenesulfonic acid which is unsubstituted or substituted by lower alkyl, such as methyl, halogen, such as bromine and/or nitro, for example a methanesulfonic, trifluoromethanesulfonic or p-toluenesulfonic acid.

The condensation of compounds of the formulae II and III can be carried out in a manner known per se. Procedures for the preparation of an amide bond are described, for example in standard works, such as "Houben-Weyl, Methoden der organischen Chemie (Houben-Weyl, Methods of Organic Chemistry)", 4th edition, Volume 15/II (1974), Volume IX (1955) Volume E 11 (1985), Georg Thieme Verlag, Stuttgart, "The Peptides" (E. Gross and J. Meienhofer, Hg.), Volume 1 and 2, Academic Press, London und New York, 1979/1980, or M. Bodansky, "Principles of Peptide Synthesis", Springer-Verlag, Berlin 1984.

The condensation of free carboxylic acids or alcohols of the formulae II (Y=hydroxyl) with the amine of the formula III can preferably be carried out in the presence of one of the customary condensing agents. Customary condensing agents are, for example, carbodiimides, for example diethyl-, dipropyl- or N-ethyl-N'-(3-dimethylaminopropyl)-carbodiimide or, in particular, dicyclohexylcarbodiimide, and furthermore suitable carbonyl compounds, for example carbonyldiimidazole, 1,2-oxazolium compounds, for example 2-ethyl-5-phenyl-1,2-oxazolium 3'-sulfonate and 2-tert-butyl-5-methyl-isoxazolium perchlorate, or a suitable acylamino compound, for example 2-ethoxy-1-ethoxycarbonyl-1,2-dihydroquinoline, and furthermore activated phosphoric acid derivatives, for example diphenylphosphorylazide, diethylphosphorylcyanide, phenyl-N-phenylphosphoroamidochloridate, bis(2-oxo-3-oxazolidinyl)-phosphinic acid chloride or 1-benzotriazolyloxytris(dimethylamino)-phosphonium hexafluorophosphate.

If desired, an organic base is added, for example a tri-lower alkylamine with bulky radicals, for example N-ethyl-N,N-diisopropyl-amine, and/or a heterocyclic base, for example pyridine, N-methylmorpholine or, preferably, 4-dimethylaminopyridine.

The condensation of activated esters, reactive anhydrides or reactive cyclic amides of acids of the formula II or reactive esters of alcohols of the formula II with the corresponding amines is usually carried out in the presence of an organic base, for example simple tri-lower alkylamines, for example triethylamine or tributylamine, or one of the abovementioned organic bases. If desired, a condensing agent is also additionally used, as is described for free carboxylic acids.

The condensation of acid anhydrides with amines can be carried out, for example, in the presence of inorganic carbonates, for example ammonium of alkali metal carbonates or bicarbonates, such as sodium carbonate or bicarbonate or potassium carbonate or bicarbonate (usually together with a sulfate).

Carboxylic acid chlorides, for example the chlorocarbonic acid derivatives derived from the acid of the formula II, are preferably subjected to a condensation reaction with the corresponding amines in the presence of an organic amine, for example the abovementioned tri-lower alkylamines or heterocyclic bases, in particular 4-dimethylaminopyridine, in the presence or absence of a hydrogensulfate. This condensation is preferably carried out in an inert, aprotic, preferably anhydrous solvent or solvent mixture, for example in a carboxylic acid amide, for example dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, if appropriate under reduced or elevated temperature, for example in a temperature range from about −40° C. to about +100° C., preferably from about −10° C. to about +50° C., and if arylsulfonyl esters are used, also at about +100° C. to +200° C., and if appropriate under an inert gas atmosphere, for example a nitrogen or argon atmosphere. Aqueous, for example alcoholic solvents, for example ethanol, or aromatic solvents, for example benzene or toluene, are also possible. If alkali metal hydroxides are present as bases, acetone can also be added if appropriate. The condensation can also be carried out by the technique known as solid phase synthesis, which is attributed to R. Merrifield and is described, for example, in Angew. Chem. 97, 801–812 (1985), Naturwissenschaften 71, 252–258 (1984) or in R. A. Houghten, Proc. Natl. Acad. Sci. USA 82, 5131–5135 (1985).

Functional groups in starting materials of which reaction is to be avoided, in particular carboxyl, amino, hydroxyl and mercapto groups, can be protected by conventional protecting groups which are usually used in the synthesis of peptide compounds, and also of cephalosporins and penicillins as well as nucleic acid derivatives and sugars. These protective groups can already be present in the precursors and are intended to protect the functional groups in question from undesirable side reactions, such as acylations, etherifications, esterifications, oxidations, solvolysis and the like. In certain cases, the protecting groups furthermore can cause a selective, for example stereoselective, course of reactions. It is characteristic of protecting groups that they can easily be split off, i.e. without undesirable side reactions, for example solvolytically, reductively, photolyrically or also enzymatically, for example under physiological conditions. However, protecting groups can also be present in the end products. Compounds of the formula I with protected functional groups can have a higher metabolic stability or pharmacodynamic properties improved in other ways compared with the corresponding compounds with free functional groups.

The protection of functional groups by such protecting groups, the protecting groups reactions themselves, and their elimination are described, for example, in standard works, such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides"; Volume 3 (E. Gross and J. Meienhofer, editors), Academic Press, London and New York 1981, in "Methoden der organischen Chemie" (Methods of Organic Chemistry), HoubenWeyl, 4th Edition, Volume 15/I, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974.

A carboxyl group is protected, for example, as an ester group which can be split selectively under mild conditions. A carboxyl group protected in esterified form is esterified in particular by a lower alkyl group, which is preferably branched in the 1-position of the lower alkyl group or is substituted by suitable substituents in the 1- or 2-position of the lower alkyl group, for example methoxycarbonyl or ethoxycarbonyl, tert-lower alkoxycarbonyl, for example tert-butyloxycarbonyl, arylmethoxycarbonyl having one or two aryl radicals, in which aryl is phenyl which is unsubstituted or mono-, di- or trisubstituted, for example by lower alkyl, for example tert-lower alkyl, such as tert-butyl, lower alkoxy, for example methoxy, hydroxyl, halogen, for example chlorine, and/or nitro, for example benzyloxycarbonyl, benzyloxy-carbonyl which is substituted by the substituents mentioned, for example 4-nitrobenzyloxycarbonyl or 4-methoxybenzyloxycarbonyl, diphenylmethoxycarbonyl which is substituted by the substituents mentioned, for example di-(4-methoxyphenyl)-methoxycarbonyl, 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxycarbonyl, for example 1-methylthiomethoxycarbonyl or 1-ethylthioethoxycarbonyl, aroylmethoxycarbonyl, in which the aroyl group is benzoyl which is unsubstituted or substituted, for example by halogen, such as bromine, for example phenacyloxycarbonyl, 2-halogeno-lower alkoxycarbonyl, for example 2,2,2-trichloroethoxycarbonyl, 2-bromoethoxycarbonyl or 2-iodoethoxycarbonyl, 2-tri-lower alkylsilyl-lower alkoxycarbonyl, such as 2-tri-lower alkylsilylethoxycarbonyl, for example 2-trimethylsilylethoxycarbonyl or 2-(di-n-butyl-methyl-silyl)-ethoxycarbonyl, or 2-triarylsilylethoxycarbonyl, such as triphenylsilylethoxycarbonyl.

A carboxyl group can also be protected as a tri-lower alkylsilyloxycarbonyl group, for example trimethylsilyloxycarbonyl.

A protected carboxyl group is preferably tert-lower alkoxycarbonyl, for example tert-butoxycarbonyl, benzyloxycarbonyl, 4-nitrobenzyloxycarbonyl, 9-fluoroenylmethoxycarbonyl or diphenylmethoxycarbonyl.

A protected amino group can be, for example, in the form of an acylamino, arylmethylamino, etherified mercaptoamino, 2-acyl-lower alk-1-enylamino or silylamino group, or in the form of an azido group.

In a corresponding acylamino group, acyl is, for example, the acyl radical of an organic carboxylic acid having, for example, up to 18 carbon atoms, in particular a lower alkanecarboxylic acid which is unsubstituted or substituted, for example by halogen or aryl, or a benzoic acid which is unsubstituted or substituted, for example by halogen, lower alkoxy or nitro, or, preferably, a carbonic acid half-ester. Such acyl groups are, for example, lower alkanoyl, such as formyl, acetyl, propionyl or pivaloyl, halogeno-lower alkanoyl, for example 2-halogenoacetyl, such as 2-chloro-, 2-bromo-, 2-iodo-, 2,2,2-trifluoro- or 2,2,2-trichloroacetyl, benzoyl which is unsubstituted or substituted by halogen, lower alkoxy or nitro, for example benzoyl, 4-chlorobenzoyl, 4-methoxybenzoyl or 4-nitrobenzoyl, or lower alkoxycarbonyl which is branched in the 1-position of the lower alkyl radical or suitably substituted in the 1- or 2-position, for example tert-lower alkoxycarbonyl, such as tert-butoxycarbonyl, arylmethoxycarbonyl having one or two aryl radicals, which are phenyl which is unsubstituted or mono- or polysubstituted, for example by lower alkyl, for example tert-lower alkyl, such as tert-butyl, lower alkoxy, such as methoxy, hydroxyl, halogen, such as chlorine, and/or nitro, for example benzyloxycarbonyl, substituted benzyloxycarbonyl, such as 4-nitrobenzyloxycarbonyl, diphenylmethoxycarbonyl, fluorenylmethoxycarbonyl or substituted diphenylmethoxycarbonyl, such as di(4-methoxyphenyl)methoxycarbonyl, aroylmethoxycarbonyl, in which the aroyl group is preferably benzoyl which is unsubstituted or substituted, for example by halogen, such as bromine, for example phenacyloxycarbonyl, 2-halogeno-lower alkoxycarbonyl, for example 2,2,2-trichloroethoxycarbonyl, 2-bromoethoxycarbonyl or 2-iodoethoxycarbonyl, 2-(trisubstituted silyl))-lower alkoxycarbonyl, for example 2-tri-lower alkylsilyl-lower alkoxycarbonyl, for example 2-trimethylsilylethoxycarbonyl or 2-(di-n-butyl-methyl-silyl)-ethoxycarbonyl, or triarylsilyl-lower alkoxycarbonyl, for example 2-triphenylsilylethoxycarbonyl.

In an arylmethylamino group which is, for example, a mono-, di- or, in particular, triarylmethylamino group, the aryl radicals are, in particular, substituted or unsubstituted phenyl radicals. Such groups are, for example, benzyl-, diphenylmethyl- or, in particular, tritylamino.

In a 2-acyl-lower alk-1-enyl radical which can be used as an amino-protecting group, acyl is, for example, the corresponding radical of a lower alkanecarboxylic acid, a benzoic acid which is unsubstituted or substituted, for example by lower alkyl, such as methyl or tert-butyl, lower alkoxy, such as methoxy, halogen, such as chlorine, and/or nitro, or, in particular, a carbonic acid half-ester, such as carbonic acid lower alkyl half-ester. Corresponding protecting groups are, in particular, 1-lower alkanoyl-prop-1-en-2-yl, for example 1-acetyl-prop-1-en-2-yl, or lower alkoxycarbonyl-prop-1-en-2-yl, for example 1-ethoxycarbonyl-prop-1-en-2-yl.

A silylamino group is, for example, a tri-lower alkylsilylamino group, for example trimethylsilylamino. The silicon atom of the silylamino group can also be substituted only by two lower alkyl groups, for example methyl groups, and the amino group or carboxyl group of a second molecule of the formula I. Compounds with such protecting groups can be prepared, for example, with dimethylchlorosilane as the silylating agent.

An amino group can also be protected by conversion into the protonated form; corresponding anions are, in particular, those of strong inorganic acids, such as of sulfuric acid, phosphoric acid or hydrogenhalide acids, for example the chlorine or bromine anion, or of organic sulfonic acids, such as p-toluenesulfonic acid.

Preferred amino-protecting groups are acyl radicals of carbonic acid half-esters, in particular tert-butoxycarbonyl or fluorenylmethoxycarbonyl, substituted or unsubstituted benzyloxycarbonyl, for example 4-nitrobenzyloxycarbonyl, diphenylmethoxycarbonyl, 2-halogeno-lower alkoxycarbonyl, for example 2,2,2-trichloroethoxycarbonyl, and furthermore trityl or formyl.

A hydroxyl group can be protected, for example, by an acyl group, for example by halogen, such as chlorine, substituted lower alkanoyl, for example 2,2-dichloroacetyl, or, in particular, by an acyl radical of a carbonic acid half-ester mentioned for protected amino groups. A preferred hydroxyl-protecting group is, for example, 2,2,2-trichloroethoxycarbonyl, 4-nitrobenzyloxycarbonyl, diphenylmethoxycarbonyl or trityl. A hydroxyl group can furthermore be protected by tri-lower alkylsilyl, for example trimethylsilyl, triisopropylsilyl or dimethyl-tert-butylsilyl, an etherifying group which can easily be split off, for example an alkyl group, such as tert-lower alkyl, for example tert-butyl, an oxa- or a thia-aliphatic or -cycloaliphatic, in particular 2-oxa- or 2-thia-aliphatic or -cycloaliphatic, hydrocarbon radical, for example 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thiacycloalkyl having 5-7 ring atoms, for example 2-tetrahydrofuryl or 2-tetrahydropyranyl, or a corresponding thia analogue, as well as by 1-phenyl-lower alkyl, for example benzyl, diphenylmethyl or trityl, where the phenyl radicals can be substituted, for example by halogen, for example chlorine, lower alkoxy, for example methoxy, and/or nitro.

Two hydroxy groups occurring in one molecule, in particular adjacent hydroxyl groups, or an adjacent hydroxyl and amino group can be protected, for example, by bivalent protective groups, such as a methylene group, which is preferably substituted, for example by one or two alkyl radicals. Compounds of the formula II which are intermediately protected by a bivalent protecting group on the adjacent hydroxyl and amino group are preferably those of the formula II'

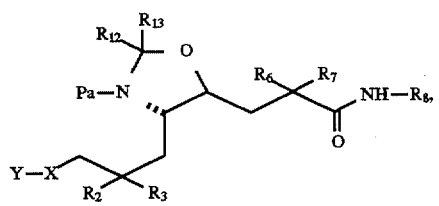

(II')

in which Y, X, $R_2$, $R_3$, $R_4$, $R_5$, $R_6$, $R_7$ and $R_8$ are as defined above, Pa is an amino-protecting group as defined above and the group $>C(R_{12})(R_{13})$ is carbonyl or, in particular, unsubstituted or substituted alkylidene, such as lower alkylidene, for example isopropylidene, cycloalkylidene, for example cyclohexylidene, a carbonyl group or benzylidene.

The starting materials for carrying out process a) can be prepared by processes known per se.

Thus, compounds of the formula II can be prepared by reducing, in a compound of the formula IIa

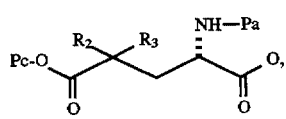

(IIa)

in which Pc is a carboxyl-protecting group and Pa is a univalent amino-protecting group and $R_2$ and $R_3$ are as defined, the free carboxyl group to hydroxymethyl, reacting the resulting compound of the formula IIb

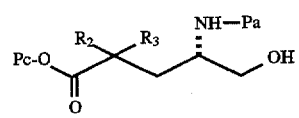

(IIb)

with a reagent as defined above which introduces a bivalent protecting group, to give a compound of the formula IIc

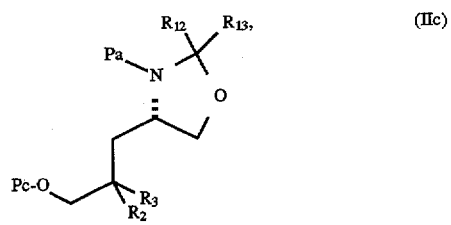

(IIc)

in which $R_{12}$ and $R_{13}$ independently of one another are hydrogen or alkyl, in particular lower alkyl, for example methyl, or together are oxo, in the compound thus obtainable, if $R_2$ and $R_3$ are hydrogen, if desired replacing hydrogen by the radicals $R_2$ and/or $R_3$ defined above, excluding hydrogen, reducing the protected carboxyl group while splitting off the protecting group Pc to give hydroxymethyl, oxidizing the compound thus obtainable, of the formula IId

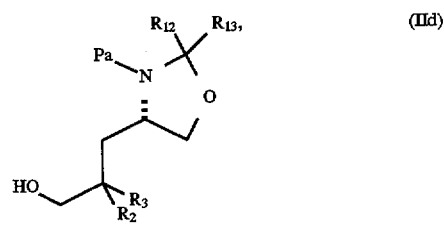

(IId)

in which the radicals are as defined, to give the corresponding aldehyde, reacting this with a reagent which replaces the oxygen of the aldehyde group by a methylene group, hydrating the compound thus obtainable, of the formula IIe

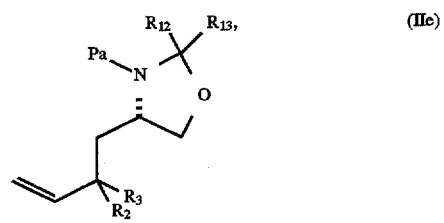

(IIe)

in which the radicals are as defined, against the Markovnikov rule, reacting the compound thus obtainable, of the formula IIf

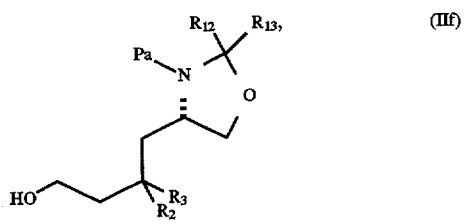

(IIf)

in which the radicals are as defined, with a reagent which introduces a hydroxyl-protecting group Po, splitting off the bivalent protecting group which bridges the vicinal hydroxyl and amino functions, oxidizing the compound thus obtainable, of the formula IIg

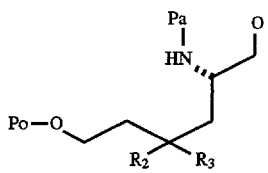

in which the radicals are as defined, to give the corresponding aldehyde, reacting the aldehyde of the formula IIh

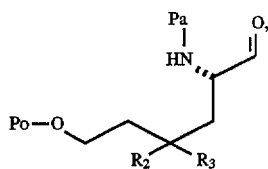

in which the substituents are as defined, with a compound of the formula IIi

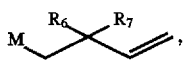

in which M is a metallic radical, for example a halogenomagnesium group, to give the corresponding compound of the formula IIj

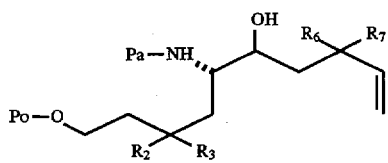

protecting this by a bivalent protecting group of the formula >C(R$_{12}$)(R$_{13}$), oxidizing the terminal vinyl group, for example by means of Ru(III) chloride/potassium metaperiodate or potassium permanganate, to carboxyl, to give an acid of the formula IIk

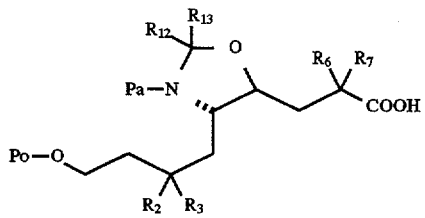

which is then converted, by reaction with an amine V, into the corresponding intermediate of the formula IIm.

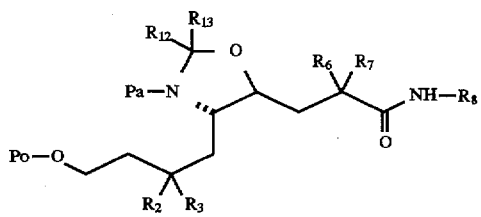

This stage also offers a good possibility for reversal of the configuration on the C atom of the main chain carrying the oxy function. For this, the bivalent protecting group of the formula >C(R$_{12}$)(R$_{13}$) and the amino-protecting group Pa are removed, the resulting compound of the formula II'm

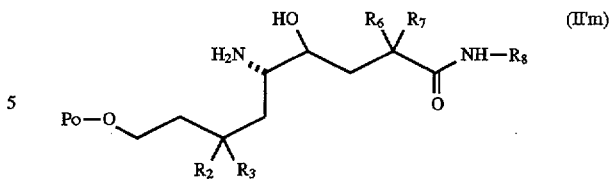

is first N-substituted on the amino group by an acyl group derived from a half-ester of carbonic acid, for example benzyloxycarbonyl, and then cyclized under conditions which convert the hydroxyl group intermediately into a nucleofugic leaving group, such as chlorine, for example in the presence of thionyl chloride, with reversal of the configuration on the C atom carrying the hydroxyl group before to give the corresponding oxazolidinone compound of the formula II"m

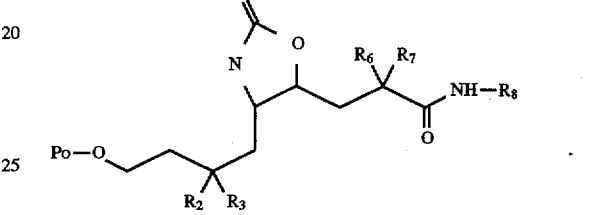

and an amino-protecting group Pa is then introduced again, to form the intermediate IIm having the desired stereotaxy.

To obtain starting substances of the formula II' in which Y is free or reactive functionally modified hydroxyl and X is methylene, the protecting groups Po in the intermediate product IIm are split off and, if desired, the terminal hydroxyl group liberated is functionally modified reactively. If possible according to the nature of Y, the corresponding compound of the formula II can be obtained by subsequent splitting off of the bivalent protecting group >C(R$_{12}$)(R$_{13}$) and of the amino-protecting group Pa.

To obtain starting substances of the formula II in which the fragment Y—X— is free or functionally modified carboxyl, the protecting group Po in the intermediate product YYM is first split off, the hydroxyl compound liberated is oxidized to give carboxyl, and if desired the carboxyl group is functionally modified. If possible from the nature of Y, the corresponding compound of the formula II can be obtained by subsequent splitting off of the bivalent protecting group >C(R$_{12}$)(R$_{13}$) and of the amino-protecting group Pa.

If desired, in each case a radical R$_4$ other than hydrogen can then be introduced, in each case by reaction with a corresponding compound of the formula R$_4$—S, in which S is a leaving group or a hydroxyl function, and/or hydroxyl R$_5$ can be acylated with an acylating reagent.

Some advantageous methods of formation are available for key compounds of the reaction sequence described above.

Thus, to prepare compounds of the formula IIm in which R$_6$ is alkyl or cycloalkyl and R$_7$ is hydrogen, and the other substituents are as defined, the aldehyde of the formula IIh can be reacted with an amide of the formula IIn

in which R'$_6$ is alkylidene or cycloalkylidene and R$_8$ is as defined, and the resulting compound of the formula IIo

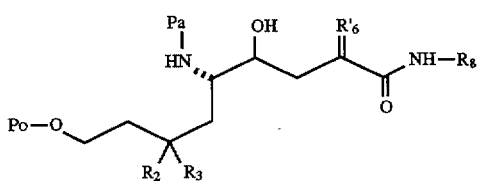 (IIo)

can be separated, if desired, into the stereoisomers with respect to the C atom carrying the hydroxyl group, the group of the formula >C=R'$_6$ can then be reduced to the desired group of the formula >CH—R$_6$, the reduction advantageously being carried out stereoselectively with respect to the C atom carrying the group of the formula >CH—R$_6$, and the hydroxyl and amino group can then be protected by a bivalent protecting group of the formula >C(R$_{12}$)(R$_{13}$), the corresponding compound of the formula II'm in which the radicals are as defined being obtained.

Intermediates of the formula IIh in which at least one of the radicals R$_2$ and R$_3$ is other than hydrogen can likewise also advantageously be prepared starting from corresponding compounds of the formula IIp

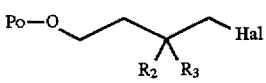 (IIp)

by reaction with a chiral or achiral nucleophilic synthesis unit usually used for building up protected amino acid derivatives, for example with a compound of the formula IIq

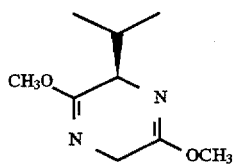 (IIq)

in the presence of a metal base, for example butyllithium, advantageously in tetrahydrofuran, hydrolysis of the resulting compound of the formula IIr

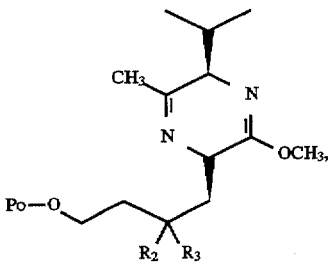 (IIr)

followed by introduction of the univalent amino-protecting group Pa, and reduction of the methoxycarbonyl group formed in an intermediate thus obtainable, of the formula IIs

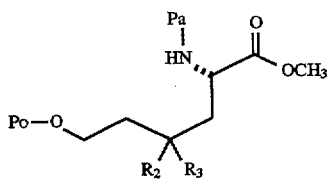 (IIs)

to give formyl.

The carboxyl-protecting group Pc used in compounds of the formula IIa is, in particular, one of the lower alkoxy groups defined above, for example methoxy, ethoxy or tert-butyloxy. An amino-protecting group Pa is introduced as described above, in particular by reaction with a lower alkoxycarbonyl compound, such as a di-lower alkoxy dicarbonate, for example di-tert-butyl dicarbonate, preferably in aqueous solution, to which water-soluble organic solvents, such as cyclic ethers, for example dioxane, and a base, for example a weak base, such as an alkali metal bicarbonate, for example sodium bicarbonate, are added if appropriate, at temperatures from 0° to 100° C., preferably at about room temperature. The reduction to give compounds of the formula IIc is carried out in inert organic solvents, for example ethers, such as tetrahydrofuran, if appropriate after activation of the carboxyl group to be reduced, as described under process a), for example as carboxylic acid hydrazide, such as carboxylic acid chloride, with a suitable reducing agent, for example complex hydrides, such as lithium borohydride, at temperatures from −50° to 50° C., preferably −30° to 20° C.

The reaction of compounds of the formula IIb or IIj for introduction of bivalent protecting groups to give compounds of the formula IIc or IIk is carried out as described above for introduction of the corresponding protecting groups, preferably in inert solvents, such as halogenoalkanes, for example methylene chloride, using suitable reagents, in particular enol ethers, such as lower alkyloxy-lower alkenes, for example isopropenyl methyl ether, at temperatures from −50° to 50° C., in particular from −10° to 40° C.

The reaction of compounds of the formula IIc for introduction of radicals R$_2$ and/or R$_3$, apart from hydrogen, is carried out in the presence of reagents which can split off the hydrogen atoms R$_2$ and R$_3$ as protons to form a carbanion, such as strong bases, for example hexa-lower alkyl-, such as hexamethyldisilazane, and/or lower alkyl-, such as butyllithium, in organic solvents, such as ethers, for example tetrahydrofuran, and/or hydrocarbons, such as hexane, with introduction of the radicals R$_2$ and R$_3$ as compounds with good leaving groups, in particular halides, for example lower alkyl halides, such as methyl iodide, at temperatures between −100° and 50° C., preferably between −80° and 20° C.

The reduction of the carboxyl group protected by Pc with splitting off of the protecting groups to give compounds of the formula IId is carried out with suitable reducing agents, in particular with hydrogenating agents, such as complex hydrides, for example lithium aluminium hydride, in inert solvents, such as ethers, for example tetrahydrofuran, at temperatures from −50° C. to 50° C., in particular from −20° to 30° C.

The oxidation of the hydroxymethyl group in compounds of the formula IId to give formyl is carried out, for example, by reaction with mild oxidizing agents which allow conversion of the hydroxyl function into an aldehyde function, for example after conversion of the hydroxyl function into a halide, for example chloride, for example by means of an acid halide, such as oxalyl chloride, with di-lower alkyl sulfoxides, for example dimethyl sulfoxide, in inert solvents, for example methylene chloride, at temperatures from −100° to 50° C., preferably −80° to 20° C.

To convert the formyl group into vinyl for preparation of the intermediate IIe, reagents which can split off, from the corresponding compounds which can introduce the methylene group, protons to form a corresponding ylide, for example a methyltriarylphosphonium salt, such as methyltriphenylphosphonium salt, for example strong bases, for example hexa-lower alkyl- such as hexamethyldisilazane, and/or lower alkyl-, such as butyllithium, are employed in organic solvents, such as ethers, for example tetrahydrofuran, and/or hydrocarbons, such as hexane, at temperatures from −80° to 100° C., in particular from −50° to 50° C.

The hydration of compounds of the formula IIe against the Markovnikov rule is carried out, in particular, by hydroboronation, for example with diborane, which is produced in situ, or preferably with the borane-dimethyl sulfide complex, in organic solvents, such as ethers, for example tetrahydrofuran, at temperatures between −20° and 30° C., and subsequent hydrolysis of the corresponding boron compound by addition of an aqueous solution of an organic solvent, such as an ether, for example tetrahydrofuran in water, if appropriate with addition of a base, such as an alkali, for example an alkali metal hydroxide, such as sodium hydroxide, and hydrogen peroxide at temperatures from −20° to 50° C., preferably −10° to 30° C.

The introduction of a hydroxyl-protecting group into compounds of the formula IIf is carried out as described above, in particular by benzylation, for example with benzyl bromide, or using a tri-lower alkylchlorosilane, such as triisopropylchlorosilane, in inert solvents, for example methylene chloride, in the presence of bases, for example imidazole, and/or catalysts, such as dimethylaminopyridine, at temperatures from about −20° to 50° C., The bivalent protecting group is split off from compounds of the formula IIf, for example, by one of the methods described below for splitting off protecting groups, in particular in the presence of salts of organic bases and acids, such as pyridinium p-toluenesulfonate, in polar organic solvents, such as alcohols, for example methanol, at temperatures from 0° to 60° C.

The free hydroxyl group in compounds of the formula IIg is oxidized, for example, as described above for compounds of the formula IId.

The preparation of compounds of the formula IIo by reaction of compounds of the formula IIh and IIn is carried out, in particular, in the presence of strong bases, such as metal alkyls, for example lower alkyl-alkali metal compounds, for example butyllithium, in the presence of suitable Lewis acids, for example chlorotitanium triisopropyloxide, and in organic solvents, such as hydrocarbons, for example hexane, at temperatures from −100° to 50° C., the compound of the formula IIn being deprotonated.

The reduction of the intermediate IIo is then carried out, in particular by hydrogenolysis, preferably with catalytically excited hydrogen in the presence of a metal catalyst, for example a noble metal catalyst, such as a palladium catalyst, for example palladium-on-charcoal, in inert solvents, for example ethers, such as tetrahydrofuran, at temperatures from −50° to 50° C., if appropriate under increased pressure. The hydrogenolysis can advantageously be carried out stereoselectively in the presence of a suitable optically active noble metal-ligand complex. Such catalysts are, in particular, complexes of ruthenium or ruthenium salts, such as Ru-II halides, such as $RuCl_2$, $Ru_2Cl_4$ or RuHCl, non-halogenated or halogenated Ru-II-lower alkanoylates, such as $Ru(OAc)_2$ or $Ru(OOC-CF_3)_2$, with (S)-bis(2,2'-diphenylphosphino)-1,1'-binaphthyl (S-BINAP) or derivatives thereof which contain substituted phenyl radicals, such as p-tolyl or p-methoxyphenyl, instead of phenyl, and also ruthenium complexes with (S)-bis(2,2'-diphenylphosphino) 5,5'-dimethyl-diphenyl and the like. Hydrogenation with complexes of this type is preferably carried out in alcohols, such as lower alkanols, or alkyl halides, such as methylene chloride, in the pressure range from about 1 to 100, preferably 20 to 30 bar, and in the temperature range from about 10° to 80° C., preferably 15° to 25° C. An example is bis[(S)-(−)-2,2'-bis(diphenylphosphino)-1,1'-binaphthyl] (triethylamino)diruthenium tetrachloride.

The reaction of compounds of the formula IIo with a reagent for introduction of a bivalent protecting group is carried out analogously to the reaction of compounds of the formula IIc or preferably using di-lower alkylketals of di-lower alkyl ketones, such as acetones, for example dimethoxypropane, in inert solvents, such as methylene chloride, in the presence of acids, such as p-toluenesulfonic acid, at temperatures from 0° to 50° C. The hydroxyl-protecting group Po is split off. for example, under the conditions defined above, preferably using ammonium fluoride derivatives, such as tetra-lower alkylammonium fluorides, for example tetrabutylammonium fluoride, in inert solvents, for example methylene chloride, at temperatures from 0° to 50° C., or by hydrogenation.

Compounds of the formula III are known or can be prepared by processes known per se.

For example, the compounds of the formula III which contain heterocyclyl $R_1$ can be prepared by partly or completely saturating unsaturated non-fused or fused, heterocyclyl radicals, which are unsubstituted or substituted as defined above, by reaction with the reducing agents, such as hydrogen in the presence of hydrogenation catalysts, the partly or completely saturated heterocyclic radicals being protected or being in protected form on the nitrogen atom which is to react with radicals of the formula II during the condensation to give compounds of the formula I and if appropriate on further functional groups by reaction with reagents which introduce protecting groups, and reacting the compounds obtainable, if these contain carboxyl groups as substituents, with reagents which a) esterify the carboxyl groups to give the corresponding carboxylic acid esters; and/or b) amidate them to give the corresponding unsubstituted or substituted carbamoyl groups; and/or c) reduce them to give the formyl groups or to give hydroxymethyl groups, which, if appropriate, are converted into formyl groups by oxidizing reagents, after which the compounds obtainable with formyl groups are alkylated by metal alkyls and the hydroxyalkyl compounds formed are reduced and then oxidized to give the corresponding carboxyalkyl compounds, or are oxidized directly to give the corresponding carboxyalkyl compounds, and then, if appropriate, reduced on the double bond.

The condensation of compounds of the formula IV with compounds of the formula V according to process variant b) and the pre- and after-treatment are carried out in the manner described under a) with compounds analogous to the reactive carboxylic acid derivatives described there which can be used as acylating agents, the condensation described there for preparation of the amide bond and the protecting groups and, if these are not a constituent of the desired end product of the formula I, processes for splitting off the protecting groups described there.

A particular variant of this process is used to prepare those compounds of the formula I in which $R_5$ is hydroxyl and the other radicals are as defined above.

Activated esters which are reacted here are the inner esters (γ-lactones) of the compounds of the formula IV with the formula IVa

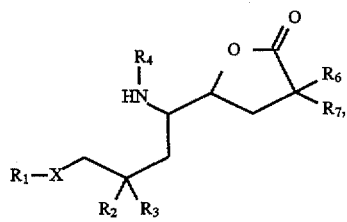
(IVa)

with the compounds of the formula V, free functional groups present in the reaction components, with the exception of the groups participating in the reaction, being in the protected form if appropriate, as described, and the protecting groups present being split off as described above. The condensation to form the amide bond is carried out under suitable conditions in accordance with process variant a). In particular, a γ-lactone of the formula IVa can be reacted with a primary amine of the formula V without a solvent or in the presence of a polar solvent, for example a lower alcohol, such as methanol or ethanol, a polar ether, such as tetrahydrofuran or dioxane, a nitrile, such as acetonitrile, an amide, such as dimethylformamide, N,N-dimethylacetamide, N-methylpyrrolidone or hexamethylphosphoric acid triamide, a urea, for example N,N'-dimethyl-N,N'-propylenylurea, a lower alkoxy-lower alkanol, for example diethylene glycol monomethyl ether, in dimethyl sulfoxide or a mixture of the solvents mentioned or a mixture of one or more of the solvents mentioned with water, at temperatures from −30° to 100° C., preferably from 20° to 80° C., the above statements applying to the protecting groups.

The starting materials for process variant b) can be prepared by methods known per se, for example analogously to the formation methods of compounds of the formula II described above, for example by reacting an aldehyde of the formula IIh

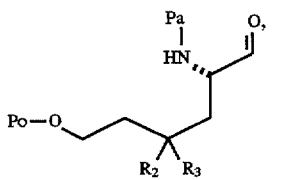
(IIh)

in which the substituents are as defined, with an organometallic compound of the formula IVb

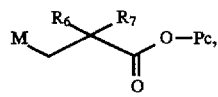
(IVb)

in which M is a metallic radical, for example a halogenozinc group, and Pc is a carboxyl-protecting group as defined under process variant a), in the presence of a suitable Lewis acid to give the corresponding compound of the formula IVc

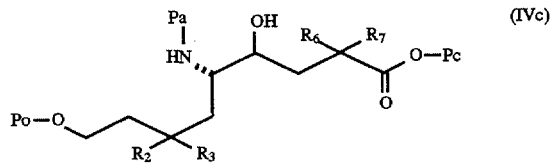
(IVc)

protecting this by a bivalent protecting group as described under process variant a), converting the group Po—O—CH$_2$— into a radical of the formula R$_1$—X— and splitting off the protecting groups >C(R$_{12}$)(R$_{13}$) and Pc from the resulting compound of the formula IVd.

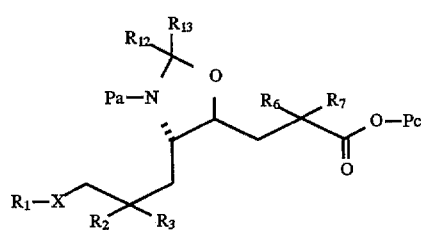
(IVd)

The preferred starting substances of the formula IVa can be prepared as intermediates of the formula IVc by intramolecular condensation with splitting off of the protecting group Pc, for example by treatment with acid, for example with glacial acetic acid in toluene, However, the reaction of the aldehyde of the formula IIh with an organometallic compound of the formula IVe

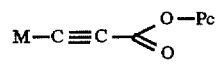
(IVe)

in which M is a metallic radical, for example lithium, and Pc is a carboxyl-protecting group as defined under process variant a), if necessary in the presence of a Lewis acid, such as zinc chloride, to give the corresponding compound of the formula IVf

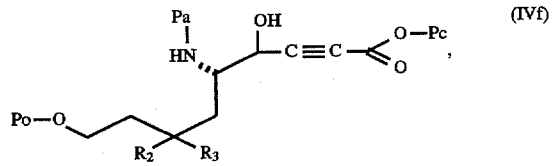
(IVf)

which is cyclized by complete hydrogenation of the triple bond in the presence of a suitable catalyst, for example platinum-on-charcoal, for example under normal pressure at room temperature, and subsequent splitting off of the Pc-protecting group, in particular as described above, with intramolecular condensation to give the corresponding compound of the formula IVa (R$_6$=R$_7$=H) is preferred. Into this compound, a radical R$_6$ and, if appropriate, R$_7$, other than hydrogen can then be introduced by reaction with a compound of the formula R"$_6$—Y$_1$ (IVg) and if desired with a compound of the formula R"$_7$—Y$_1$(IVh), in which R"$_6$ is a radical R$_6$ other than hydrogen and, if appropriate, R"$_7$ is a radical R$_7$ other than hydrogen and Y$_1$ is reactive functionally modified hydroxyl as described under process variant a), for example halogen or sulfonyloxy, such as lower alkanesulfonyloxy, or substituted or unsubstituted benzenesulfonyloxy, advantageously in the presence of a base, such as an alkali metal disilazide, for example sodium hexamethyldisilazide.

In a starting material of the formula VI for process variant c), functional groups, with the exception of the keto group to be reduced, are protected, if appropriate, by a protecting group defined under process a).

Suitable reducing agents for reduction of the keto group in such a compound of the formula VI are those which reduce an isolated keto group under the reaction conditions of the process selectively or faster than the amide groups present in compounds of the formula VI.

Suitable borohydrides, such as alkali metal borohydrides, in particular sodium borohydride, lithium borohydride or sodium cyanoborohydride, or suitable aluminium hydrides, such as alkali metal lower alkyl-aluminium hydrides with bulky radicals, for example lithium tris-tert-butylaluminium hydride, are particular reducing agents.

The reduction can also be carried out with hydrogen in the presence of suitable heavy metal catalysts, for example Raney nickel or platinum catalysts or palladium catalysts, for example platinum- or palladium-on-active charcoal, or by the Meerwein-Ponndorf-Verley method with the aid of aluminium alcoholates, preferably aluminium 2-propanolate or -ethanolate.

The reduction can preferably be carried out with stoichiometric amounts or an appropriately measured excess of the reducing agent in an inert solvent at temperatures between −80° C. and the boiling point of the solvent, preferably between 20° and 100° C., if necessary under an inert gas, for example nitrogen or argon. An excess of the reducing agent is necessary in particular if this also reacts with the solvent, for example the protons of a protic solvent.

If sodium borohydride is used, polar, aprotic solvents, for example methanol, ethanol or isopropanol, are suitable; if the other reducing agents are used, the polar, protic solvents mentioned under process a), for example tetrahydrofuran, are suitable.

Those reducing agents or reduction processes which reduce the keto group to form the preferred (S) configuration on the C atom bonded to the hydroxyl group formed are preferred.

The keto group can also be reduced enzymatically by treatment with suitable microorganisms, for example with bacteria, yeasts or fungi, preferably in the temperature range from about 15° to about 50° C., for example at about 15° to about 25° C., in aqueous or aqueous/organic solution, for example in aqueous ethanol.

The 4-keto-amides of the formula VI to be used as starting materials for process c) can be obtained, for example, by mild oxidation of corresponding hydroxyamide compounds of the formula I. This process variant is particularly suitable for the preparation of compounds of the formula I having a specific stereotaxy on the C atom carrying the hydroxyl group formed in respect of the possibility mentioned of stereoselective reduction of the keto-amides.

In a starting material of the formula VII for process variant d), functional groups which are not to participate in the reaction are protected by suitable protecting groups defined under a).

Suitable hydrogenating agents for hydrogenation of the olefinic double bond in a compound of the formula VII are those which, under the reaction conditions of the process, reduce the double bond selectively or faster than the amide bonds present in compounds of the formula VII.

Hydrogenating agents such as hydrogen in the presence of suitable catalysts are particularly suitable.

Catalysts which are suitable for the hydrogenation are metals, such as, for example, nickel, iron, cobalt or ruthenium, or noble metals or oxides thereof, such as palladium or rhodium or oxides thereof, if appropriate adsorbed on a suitable support material, such as barium sulfate, aluminium oxide or active charcoal, or in the form of skeleton catalysts, for example Raney nickel, but in particular homogeneous or heterogeneous optically active metal- or noble metal-ligand complexes, in particular those which bring about the particular desired configuration of the C atom carrying the group $R_6$. Catalysts which are particularly suitable for this are optically active noble metal-ligand complexes, for example those mentioned above, in particular bis[(S)-(−)-2,2'-bis(diphenylphosphino)-1,1'-binaphthyl](triethylamino)diruthenium tetrachloride.

Customary solvents for the catalytic hydrogenation are polar organic or inorganic solvents, for example water, alcohols, esters, dioxanes, glacial acetic acid or mixtures of these solvents. The hydrogenation is carried out at temperatures from 0° C. to 250° C., preferably from room temperature to about 100° C., and under hydrogen pressures from 1 to 200 bar.

The starting materials for process d) can be prepared by processes known per se, for example by separating a compound of the formula IIo

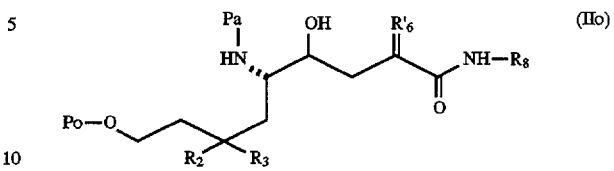

the preparation of which is described under process variant a), if desired, into the stereoisomers with respect to the C atom carrying the hydroxyl group, protecting the hydroxyl and amino group by a divalent protective group of the formula >C($R_{12}$)($R_{13}$), reacting the compound obtainable, of the formula VIIa

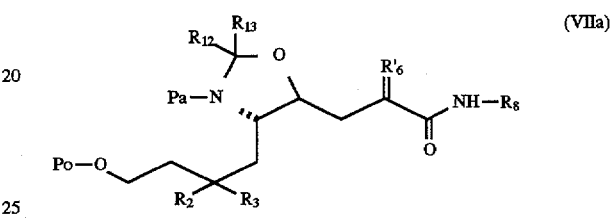

with a reagent which splits off the hydroxyl-protecting group Po, oxidizing the hydroxyl compound liberated on the free hydroxyl group to give the corresponding carboxylic acid of the formula VIIb

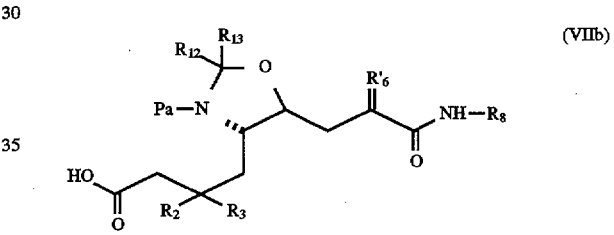

in which $R_2$, $R_3$, $R_6$ and $R_8$ are as defined, amidating this as described under process variant a) to give the corresponding diamide compound of the formula VIIc

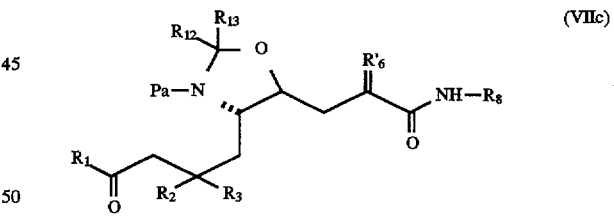

splitting off the divalent protective group of the formula >C($R_{12}$)($R_{13}$) and the amino-protecting group Pa and, if desired, in each case introducing a radical $R_4$ other than hydrogen and/or acylating $R_5$ with an acylating reagent, by reaction with a compound of the formula $R_4$—S, in which S is a leaving group or a hydroxyl function.

In starting materials of the formula VIII for process variant e), functional groups which are not to participate in the reaction are protected by one of the protecting groups mentioned under process a).

Reducing agents which are suitable for reduction of the azido group in such a compound of the formula VIII are those which, under the reaction conditions of the process, reduce a keto or azido group selectively or faster than the amide groups present in the compounds of the formula VIII.

Suitable borohydrides, such as alkali metal borohydrides, in particular sodium borohydride, lithium borohydride or sodium cyanoborohydride, or suitable aluminium hydrides, such as alkali metal aluminium hydrides, for example lithium aluminium hydride, or alkali metal lower alkoxyaluminium hydrides having bulky radicals, for example lithium tris-tert-butylaluminium hydride, are particular compounds.

The reduction can also be carried out with hydrogen in the presence of suitable heavy metal catalysts, for example Raney nickel or platinum catalysts or palladium catalysts, for example platinum- or palladium-on-active charcoal.

The reduction can preferably be carried out with stoichiometric amounts or an appropriately measured excess of the reducing agent in an inert solvent at temperatures between −80° C. and the boiling point of the solvent, preferably between −20° and 100° C., if necessary under an inert gas, for example nitrogen or argon. An excess of the reducing agent is necessary, in particular, if this also reacts with the solvent, for example the protons of a protic solvent.

If sodium borohydride is used, polar protic solvents, for example methanol, ethanol or isopropanol, are suitable; if the other reducing agents are used, the polar, aprotic solvents mentioned under process a), for example tetrahydrofuran or diethyl ether, are suitable.

Intermediates of the formula VIII can be prepared, for example, by reacting a compound of the formula VIIIa

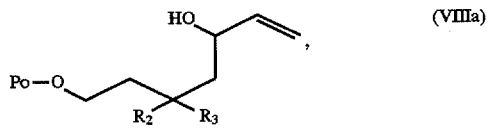

in which Po is a hydroxyl-protecting group and $R_2$ and $R_3$ are as defined, with a thionyl halide, such as thionyl bromide, to give the corresponding compound of the formula VIIIb

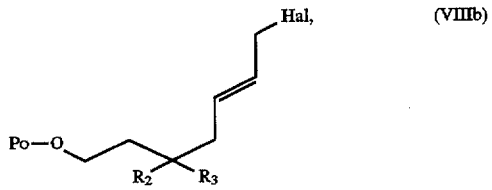

n which Hal is halogen, such as bromine, subjecting this to a condensation reaction with a substituted malonic ester of the formula VIIIc

in which R is, for example, lower alkyl, halolactonizing the alkanoic acid compound subsequently obtained by hydrolysis and decarboxylation, of the formula VIIId

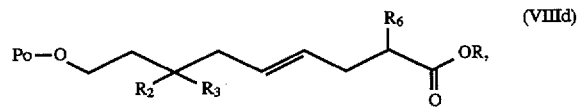

if appropriate after introduction of a radical $R_7$ other than hydrogen and/or cleavage into the enantiomers with respect to the chain C atom in the α-position relative to the ROOC group by intermediate conversion into a chiral amide and separation into the diastereomers, in the customary manner to give the corresponding compound of the formula VIIIe

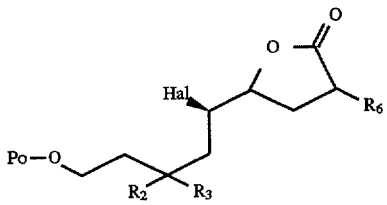

reacting this with an alkali metal azide, such as sodium azide, to give the corresponding azide of the formula VIIIf

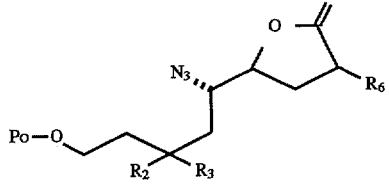

splitting off the protecting group Po in the customary manner, for example as described for compounds of the formula Im under process variant a), oxidizing the terminal hydroxymethyl group formed to give carboxyl, and reacting the resulting acid with an amine of the formula H—N(H)—$R_1$ (III) and then with an amine of the formula H—N(H)—$R_8$ (V).

Splitting off of the protective groups which are not a constituent of the desired end product of the formula I, for example the carboxyl-, amino- and/or hydroxyl-protecting groups, is carried out in a manner known per se, for example by means of solvolysis, in particular hydrolysis, alcoholysis or acidolysis, or by means of reduction, in particular hydrogenolysis or chemical reduction, as well as photolysis, if appropriate stepwise or simultaneously, it also be being possible to use enzymatic methods. Splitting off the protecting groups is described, for example, in the standard works mentioned above in the section on "protecting groups".

Thus, for example, protected carboxyl, for example tert-lower alkoxycarbonyl, lower alkoxycarbonyl which is substituted in the 2-position by a trisubstituted silyl group or in the 1-position by lower alkoxy or lower alkylthio, or unsubstituted or substituted diphenylmethoxycarbonyl, can be converted into free carboxyl by treatment with a suitable acid, such as formic acid or trifluoroacetic acid, if appropriate with the addition of a nucleophilic compound, such as phenol or anisole. Substituted or unsubstituted benzyloxycarbonyl can be liberated, for example, by means of hydrogenolysis, i.e. by treatment with hydrogen in the presence of a metallic hydrogenation catalyst, such as a palladium catalyst. Furthermore, suitably substituted benzyloxycarbonyl, such as 4-nitrobenzyloxycarbonyl, can also be converted into free carboxyl by reduction, for example by treatment with an alkali metal dithionite such as sodium dithionite, or with a reducing metal, for example zinc, or a reducing metal salt, such as a chromium(II) salt, for example chromium(II) chloride, usually in the presence of an agent which donates hydrogen and which can produce nascent hydrogen together with the metal, such as an acid, in particular a suitable carboxylic acid, such as a lower alkanecarboxylic acid which is unsubstituted or substituted, for example by hydroxyl, for example acetic acid, formic acid, glycolic acid, diphenylglycolic acid, lactic acid, mandelic acid, 4-chloromandelic acid or tartaric acid, or an alcohol or thiol, water preferably being added. 2-Halo-lower alkoxycarbonyl (if appropriate after conversion of a 2-bromo-lower alkoxycarbonyl group into a corresponding 2-iodo-lower alkoxycarbonyl group) or aroylmethoxycarbonyl, can also be converted into free carboxyl by treatment with a reducing metal or metal salt, as described above. Aroylmethoxycarbonyl can likewise be split by treatment with a nucleophilic, preferably salt-forming reagent, such as sodium thiophenolate or sodium iodide. 2-(trisubstituted silyl)-lower alkoxycarbonyl, such as 2-tri-lower alkylsilyl-lower alkoxycarbonyl, can also be converted into free carboxyl by treatment with a salt of hydrofluoric acid which donates the fluoride anion, such as an alkali metal fluoride, for example sodium fluoride or potassium fluoride, if appropriate in the presence of a macrocyclic polyether ("crown ether"), or with a fluoride of an organic quaternary base, such as tetra-lower alkylammonium fluoride or N,N,N-tri-lower alkyl-N-aryl-ammonium fluoride, for example tetraethylammonium fluoride or tetrabutylammonium fluoride, in the presence of an aprotic polar solvent, such as dimethyl sulfoxide or N,N-dimethylacetamide. Carboxyl protected as organic silyloxycarbonyl, such as tri-lower alkylsilyloxycarbonyl, for example trimethylsilyloxycarbonyl, can be liberated in the customary manner solvolytically, for example by treatment with water, an alcohol or an acid, or furthermore fluoride, as described above. Esterified carboxyl can also be liberated enzymatically, for example by esterases or suitable peptidases.

A protected amino group is liberated in a manner which is known per se and is diverse, depending on the nature of the protecting groups, preferably by means of solvolysis or reduction.

2-Halo-lower alkoxycarbonylamino (if appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be split, for example, by treatment with a suitable reducing agent, such as zinc in the presence of a suitable carboxylic acid, such as aqueous acetic acid. Aroylmethoxycarbonylamino can also be split by treatment with a nucleophilic, preferably salt-forming reagent, such as sodium thiophenolate, and 4-nitrobenzyloxycarbonylamino can also be split by treatment with an alkali metal, for example sodium dithionite. Substituted or unsubstituted diphenylmethoxycarbonylamino, tert-lower alkoxycarbonylamino or 2-(trisubstituted silyl)-lower alkoxycarbonylamino, such as 2-tri-lower alkylsilyl-lower alkoxycarbonylamino, can be liberated by treatment with a suitable acid, for example formic or trifluoroacetic acid, substituted or unsubstituted benzyloxycarbonylamino can be liberated, for example, by means of hydrogenolysis, i.e. by treatment with hydrogen in the presence of a suitable hydrogenation catalyst, such as a palladium catalyst, substituted or unsubstituted triarylmethylamino or formylamino can be liberated, for example, by treatment with an acid, such as mineral acid, for example hydrochloric acid, or an organic acid, for example formic, acetic or trifluoroacetic acid, in the presence or absence of water, and an amino group protected as silylamino can be liberated, for example by means of hydrolysis or alcoholysis. An amino group protected by 2-halogenoacetyl, for example 2-chloroacetyl, can be liberated by treatment with thiourea in the presence of a base, or with a thiolate salt, such as an alkali metal thiolate of the thiourea, and subsequent solvolysis, such as alcoholysis or hydrolysis, of the condensation product formed. An amino group protected by 2-(trisubstituted silyl)-lower alkoxycarbonyl, such as 2-lower alkylsilyl-lower alkoxycarbonyl, can also be converted into the free amino group by treatment with a salt of hydrofluoric acid which donates fluoride anions, as described above in connection with the liberation of a corresponding protected carboxyl group. Silyl bonded directly to a heteroatom, such as nitrogen, can likewise be split off by means of fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, by reduction by means of mercapto compounds, such as dithiothreitol or mercaptoethanol, or also by treatment with zinc in the presence of an acid, such as acetic acid. The catalytic hydrogenation is preferably carried out in an inert solvent, such as a halogenated hydrocarbon, for example methylene chloride, or also in water or a mixture of water and an organic solvent, such as an alcohol or dioxane, at about 20° to 25° C., or also with cooling or heating.

A hydroxyl or mercapto group protected by a suitable acyl or by a tri-lower alkylsilyl group or by substituted or unsubstituted 1-phenyl-lower alkyl is liberated analoguously to a correspondingly protected amino group. A hydroxyl or mercapto group protected by 2,2-dichloroacetyl is liberated, for example, by basic hydrolysis, a hydroxyl or mercapto group protected by tert-lower alkyl or by a 2-oxa- or 2-thia-aliphatic or -cycloaliphatic hydrocarbon radical is liberated by acidolysis, for example by treatment with a mineral acid or a strong carboxylic acid, for example trifluoroacetic acid. Mercapto protected by pyridyldiphenylmethyl can be liberated, for example, by mercury(II) salts at pH 2–6 or by zinc/acetic acid or electrolytic reduction, acetamidomethyl and iso-butrylamidomethyl can be liberated, for example, by reaction with mercury(II) salts at pH 2–6, 2-chloroacetamidomethyl can be liberated, for example, by 1-piperidinothiocarboxamide, and S-ethylthio, S-tert-butylthio and S-sulfo can be liberated, for example, by thiolysis with thiophenol, thioglycolic acid, sodium thiophenolate or 1,4-dithiothreitol. Two hydroxyl groups or an adjacent amino and hydroxyl group which are protected together by means of a bivalent protecting group, preferably, for example, a methylene group mono- or disubstituted by alkyl, such as by lower alkylidene, for example isopropylidene, cycloalkylidene, for example cyclohexylidene, or benzylidene, can be liberated by acid solvolysis, in particular in the presence of a mineral acid or a strong organic acid. 2-Halo-lower alkoxycarbonyl is also removed by the reducing agents mentioned above, for example reducing metal, such as zinc, reducing metal salts, such as chromium(II) salts, or by sulfur compounds, for example sodium dithionite or, preferably, sodium sulfide and carbon disulfide.

If several protected functional groups are present, the protecting groups can be chosen, if desired, such that more than one such group can be split off simultaneously, for example acidolytically, such as by treatment with trifluoroacetic acid, or with hydrogen and a hydrogenation catalyst, such as a palladium-on-charcoal catalyst. Conversely, the groups can also be chosen such that they are not all split off simultaneously but are split off in a desired sequence or only partly.

In each of the abovementioned processes, the starting compounds can also be used as salts if the reaction conditions allow this.

Possible secondary measures are, in particular, the conversion of compounds obtainable by the process by modification of the variables $R_1$, $R_2$, $R_3$, $R_4$, $R_5$, $R_6$, $R_7$ and/or NH-$R_8$ into other compounds of the formula I, the separation of mixtures of stereoisomers obtainable by the process into the individual stereoisomers and the conversion of free salt-forming compounds obtainable by the process into their salts or the conversion of salts obtainable by the process into the free compounds.

Thus, for example, a carboxyl group present in the free or in a reactive form in a compound of the formula I obtainable can be esterified or amidated, or an esterified or amidated carboxyl group can be converted into a free carboxyl group.

For esterification or amidation of a carboxyl group in a compound of the formula I, the free acid can be used, if desired, or the free acid can be converted into one of the above-mentioned reactive derivatives and this can be reacted with an alcohol, ammonia or a primary or secondary amine, or for esterification, the free acid or a reactive salt, for example the caesium salt, can be reacted with a reactive derivative of an alcohol. For example, the caesium salt of a carboxylic acid can be reacted with a halide or sulfonic acid ester corresponding to the alcohol. The esterification of the carboxyl group can also be carried out with other customary alkylating agents, for example with diazomethane, Meerwein salts or 1-substituted 3-aryltriazenes.

For conversion of an esterified or amidated carboxyl group into the free carboxyl group, one of the methods described above for splitting off the carboxyl-protecting groups, or if desired, alkaline hydrolysis under the reaction conditions mentioned in Organikum, 17th Edition, VEB Deutscher Verlag der Wissenschaften. Berlin 1988, can be used.

An esterified carboxyl group in a compound of the formula I can be converted into a substituted or unsubstituted carboxamide group by aminolysis with ammonia or a primary or secondary amine. The aminolysis can be carried out under the reaction conditions mentioned for such reactions in Organikum, 15th Edition, VEB Deutscher Verlag der Wissenschaften, Berlin (East) 1976.

A free amino group present in a compound of the formula I can be acylated to alkanoylamino or alkoxycarbonylamino $R_4$ or alkylated to mono- or dialkylamino dialkylamino $R_4$. The acylation and the alkylation can be carried out by one of the methods mentioned for protecting groups or by the process described in Organikum, 17th Edition, VEB Deutscher Verlag der Wissenschaften, Berlin (East) 1988.

A free hydroxyl group present in a compound of the formula I can be acylated, for example for introduction of a radical $R_5$ other than hydroxyl. The acylation can be carried out with acylating reagents by one of the methods mentioned for protecting groups or by a process described in Organikum, 17th Edition, VEB Deutscher Verlag der Wissenschaften, Berlin (East) 1988.

In a compound of the formula I obtainable, the corresponding sulfoxide or sulfone can be prepared from a sulfide.

The oxidation to give the sulfonyl group can be carried out with most of the customary oxidizing agents. Those oxidizing agents which oxidize the thio group or the sulfide sulfur selectively in the presence of other functional groups of the particular compound of the formula I, for example amino or hydroxyl groups, for example aromatic or aliphatic peroxycarboxylic acids, for example peroxybenzoic acid, monoperphthalic acid, m-chloroperbenzoic acid, peracetic acid, performic acid or trifluoroperacetic acid, are particularly preferably used. The oxidation with peroxycarboxylic acids is carried out in the customary solvents suitable for this oxidation, for example chlorohydrocarbons, for example methylene chloride or chloroform, ethers, such as diethyl ether, or esters, such as ethylacetate or the like, at temperatures between −78° C. and room temperature, for example between −20° C. and +10° C., preferably about 0° C. The peroxycarboxylic acid can also be formed in situ, for example with hydrogen peroxide in acetic acid or formic acid, which may contain acetic anhydride, for example with 30% or 90% hydrogen peroxide in acetic acid/acetic anhydride. Other peroxy compounds, for example potassium peroxymonosulfate, in lower alkanol/water mixtures, for example methanol/water or ethanol/water, or in aqueous acetic acid at temperatures between −70° C. and +30° C., for example between −20° C. and room temperature, and furthermore sodium metaperiodate in methanol or methanol/water mixtures at temperatures between 0° C. and 50° C., for example at about room temperature, are also suitable. If stoichiometric amounts of the oxidizing agents mentioned are employed, the corresponding sulfoxides can also be obtained.

Stereoisomer mixtures, i.e. mixtures of diastereomers and/or enantiomers, such as, for example, racemic mixtures, can be separated into the corresponding isomers by suitable separation processes in a manner known per se. Thus, diastereomer mixtures can be separated into the individual diastereomers by fractional crystallization, chromatography, solvent distribution and the like. Racemates can be separated from one another, after conversion of the optical antipodes into diastereomers, for example by reaction with optically active compounds, for example optically active acids or bases, by chromatography on column materials charged with optically active compounds or by enzymatic methods, for example by selective reaction of only one of the two enantiomers. This separation can be carried out either at the stage of one of the starting substances or on the compounds of the formula I themselves.

The configuration on individual chirality centres in a compound of the formula I can be reversed in a controlled manner. For example, the configuration of asymmetric carbon atoms which carry nucleophilic substituents, such as amino or hydroxyl, can be reversed by nucleophilic substitution of the second order, if appropriate after conversion of the bonded nucleophilic substituents into a suitable nucleofugic leaving group and reaction with a reagent which introduces the original substituents, or the configuration on carbon atoms with hydroxyl groups, such as the carbon atom of the formula I carrying $R_5$ can be reversed by oxidation and reduction by a process analogous to that in European Patent Application EP-A-0 236 734.

Reactively functional modification of the hydroxyl group $R_5$ and subsequent replacement thereof by hydroxyl or acyloxy $R_5$ with reversal of the configuration on the C atom carrying the hydroxyl group is also advantageous. Thus, a compound of the formula I in which $R_4$ is amino and $R_5$ is hydroxyl can first be protected on the amino group by an amino-protective group Pa, for example benzyloxycarbonyl, and then be cyclized under conditions which convert the hydroxyl group $R_5$ intermediately into a leaving group $X_1$, such as chlorine, for example in the presence of thionyl chloride, with reversal of the configuration on the C atom originally carrying the hydroxyl group $R_5$, to give the corresponding oxazolidinone compound of the formula IX

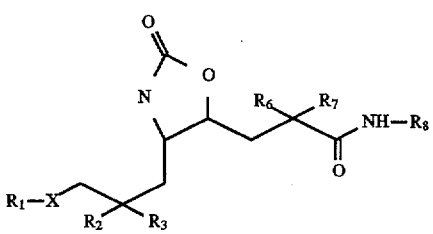 (IX)

The corresponding compound of the formula I can then be liberated from the reactive intermediate of the formula IX in the customary manner, in particular hydrolytically.

Salts of compounds of the formula I having at least one salt-forming group can be prepared in a manner known per se. Thus, salts of compounds of the formula I with acid groups can be formed, for example, by treatment with metal compounds, such as alkali metal salts of suitable organic carboxylic acids, for example the sodium salt of 2-ethylhexanoic acid, or with organic alkali metal or alkaline earth metal compounds, such as the corresponding hydroxides, carbonates or bicarbonates, such as sodium hydroxide, carbonate or bicarbonate and potassium hydroxide, carbonate or bicarbonate, with corresponding calcium compounds or with ammonia or a suitable organic amine, stoichiometric amounts or only a small excess of the salt-forming agent preferably being used. Acid addition salts of compounds of the formula I are obtained in the customary manner, for example by treatment with an acid or a suitable anion exchanger reagent. Inner salts of compounds of the formula I which contain acid and basic salt-forming groups, for example a free carboxyl group and a free amino group, can be formed, for example, by neutralization of salts, such as acid addition salts, to the isoelectric point, for example with weak bases, or by treatment with ion exchangers.

Salts can be converted into the free compounds in the customary manner; metal and ammonium salts can be converted, for example, by treatment with suitable acids, and acid addition salts can be converted, for example, by treatment with a suitable basic agent.

The invention also relates to those embodiments of the process in which a compound obtainable as an intermediate at any stage is used as the starting substance and the missing steps are carried out, or the process is interrupted at any stage or a starting substance is formed under the reaction conditions or used in the form of a reactive derivative or salt, or a compound obtainable by the process according to the invention is produced under the process conditions and further used in situ. Those starting substances which lead to the compounds defined above as very preferred or especially preferred are preferably used here.

The present invention also relates to novel starting materials and/or intermediates and to processes for their preparation. Those starting substances are used and those reaction conditions are chosen which lead to the compounds listed as especially preferred. In particular, if functional groups are present, all the starting compounds mentioned can be protected in a suitable manner by protecting groups, and protecting groups can be removed or introduced, if appropriate, at the various reaction stages.

The invention also relates to pharmaceutical preparations comprising compounds of the formula I.

The pharmacologically acceptable compounds of the present invention can be used, for example, for the preparation of pharmaceutical preparations which comprise an active amount of the active ingredient, together or as a mixture with a significant amount of inorganic or organic, solid or liquid pharmaceutically acceptable carriers.

The pharmaceutical preparations according to the invention are those for enteral, such as nasal, rectal or oral, or parenteral, such as intramuscular or intravenous, administration to warm-blooded animals (humans and animals) which comprise an effective dose of the pharmacological active ingredient by itself or together with a significant amount of a pharmaceutically acceptable carrier. The dosage of the active ingredient depends on the species of warm-blooded animal, the bodyweight, the age and the individual state, individual pharmacokinetic circumstances, the disease to be treated and the mode of administration.

The pharmaceutical preparations contain from about 1% to about 95%, preferably from about 20% to about 90% of active ingredient. Pharmaceutical preparations according to the invention can be present, for example, in dosage unit form, such as ampoules, vials, suppositories, plain or coated tablets, or capsules.

The pharmaceutical preparations of the present invention are prepared in a manner known per se, for example by means of conventional dissolving, lyophilizing, mixing, granulating or tablet coating processes.

Solutions of the active ingredient are preferably used, and in addition also suspensions, and in particular isotonic aqueous solutions or suspensions, it being possible for these to be prepared before use, for example in the case of lyophilized preparations which comprise the active substance by itself or together with a carrier, for example mannitol. The pharmaceutical preparations can be sterilized and/or comprise auxiliaries, for example preservatives, stabilizers, wetting agents and/or emulsifying agents, solubilizing agents, salts for regulating the osmotic pressure and/or buffers, and are prepared in a manner known per se, for example by means of conventional dissolving or lyophilizing processes. The solutions or suspensions mentioned can comprise viscosity-increasing substances, such as sodium carboxymethylcellulose, carboxylmethylcellulose, dextran, polyvinylpyrrolidone or gelatin.

Suspensions in oil comprise, as oily components, the vegetable, synthetic or semi-synthetic oils customary for injection purposes. Such oils are, in particular, liquid fatty acid esters which contain, as the acid component, a long-chain fatty acid having 8–22, in particular 12–22, carbon atoms, for example lauric acid, tridecylic acid, myristic acid, pentadecylic acid, palmitic acid, margaric acid, stearic acid, arachidic acid or behenic acid, or corresponding unsaturated acids, such as, for example oleic acid, elaidic acid, erucic acid, brasidic acid or linoleic acid, if appropriate with the addition of antioxidants, such as, for example, vitamin E, β-carotene or 3,5-di-tert-butyl-4-hydroxytoluene. The alcohol component of these fatty acid esters has not more than 6 carbon atoms and is a mono- or polyhydric, for example mono-, di- or trihydric alcohol, for example methanol, ethanol, propanol, butanol or pentanol or isomers thereof, but above all glycol and glycerol. Fatty acid esters are therefore, for example: ethyloleate, isopropylmyristate, isopropylpalmitate, "Labrafil® M 2375" (polyoxyethyleneglyceroltrioleate from Gattefossé, Paris), "Myglyol® 812" (triglyceride of saturated fatty acids of chain length $C_8$ to $C_{12}$ from Chemische Werke Witten/Ruhr, Germany), but in particular vegetable oils, such as cotton seed oil, almond oil, olive oil, castor oil, sesame oil, soyabean oil and above all peanut oil.

The preparation of the injection preparations is carried out in the customary manner under sterile conditions, as is the transfer to ampoules or vials and the closing of the containers.

Pharmaceutical preparations for oral use can be obtained by combining the active ingredient with solid carriers, if appropriate granulating a resulting mixture, and, if desired or necessary, after addition of suitable auxiliaries, processing the mixture to tablets, sugar coated tablet cores or capsules. They can also be incorporated into a carrier of plastic which releases the active ingredients or allows them to diffuse in metered form.

Suitable carriers are, in particular, fillers, such as sugars, for example lactose, sucrose, mannitol or sorbitol, cellulose preparations and/or calcium phosphates, for example tricalcium phosphate or calcium hydrogen phosphate, and furthermore binders, such as starch mucilage, using, for example, maize, wheat, rice or potato starch, gelatin, tragacanth, methylcellulose, hydroxypropylmethylcellulose, sodium carboxylmethylcellulose and/or polyvinylpyrrolidone, and/or, if desired, disintegrating agents, such as the abovementioned starches, and furthermore carboxymethylstarch, crosslinked polyvinylpyrrolidone, agar, alginic acid or a salt thereof, such as sodium alginate. Auxiliaries are, in particular, flow regulators and lubricants, for example silicic acid, talc, stearic acid or salts thereof, such as magnesium stearate or calcium stearate, and/or polyethylene glycol. Sugar coated tablet cores are provided with suitable enteric coatings, if appropriate, it being possible to use, inter alia, concentrated sugar solutions, which comprise, if appropriate, gum arabic, talc, polyvinylpyrrolidine, polyethylene glycol and/or titanium dioxide, coating solutions in suitable organic solvents or, for the preparation of enteric coatings, solutions of suitable cellulose preparations, such as ethylcellulose phthalate or hydroxypropylmethylcellulose phthalate. Capsules are hard gelatin capsules as well as soft, closed capsules of gelatin and a plasticizer, such as glycerol or sorbitol. The hard gelatin capsules can contain the active ingredient in the form of granules, for example with fillers, such as lactose, binders, such as starches, and/or lubricants, such as talc or magnesium stearate, and if appropriate with stabilizers. In soft capsules, the active ingredient is preferably dissolved or suspended in suitable oily excipients, such as fatty oils, paraffin oil or liquid polyethylene glycols, it also being possible for stabilizers and/or antibacterial agents to be added. Dyes or pigments can be added to the tablets or tablet coatings and the capsule shells, for example for identification or for coding of different active ingredient doses.

The invention also relates to the use of compounds of the formula I for the treatment of high blood pressure and/or glaucoma, in particular in warm-blooded animals requiring such treatment because they are suffering from high blood pressure or glaucoma.

The dose quantities to be administered to warm-blooded animals, for example humans, of, for example, about 70 kg bodyweight, in particular the doses active for inhibition of the enzyme renin, for lowering blood pressure and/or for improving glaucoma symptoms, are between about 3 mg and about 3 g, preferably between about 10 mg and about 1 g, for example approximately 300 mg per person and day, distributed over preferably 1 to 4 individual doses, which can be, for example, of equal size. Children are usually given about half the dose of adults. The individual dosage needed can be monitored and adjusted to the optimum, for example, by measuring the serum concentration of the active ingredient.

The following examples serve to illustrate the invention; temperatures are stated in degrees Celsius and pressures in mbar. The following abbreviations also apply:

Mobile phase systems used in the thin layer and flash column chromatography:

| | |
|---|---|
| A | Ethyl acetate-n-hexane 1:1 |
| B | Ethyl acetate-n-hexane 1:2 |
| C | Ethyl acetate-n-hexane 1:3 |
| D | Ethyl acetate-n-hexane 1:4 |
| E | Ethyl acetate-n-hexane 1:5 |
| F | Ethyl acetate-n-hexane 1:6 |
| G | Ethyl acetate-n-hexane 1:10 |
| H | Ethyl acetate-n-hexane 3:1 |
| I | Methylene chloride-methanol 98.5:1.5 |
| J | Methylene chloride-methanol 98:2 |
| K | Methylene chloride-methanol 97:3 |
| L | Methylene chloride-methanol 95:5 |
| M | Methylene chloride-methanol 92.5:7.5 |
| N | Methylene chloride-methanol 20:1 |
| O | Methylene chloride-methanol 10:1 |
| P | Methylene chloride-methanol 9:1 |
| Q | Methylene chloride-methanol 4:1 |
| R | Methylene chloride-methanol-concentrated ammonia 200:10:1 |
| S | Methylene chloride-methanol-concentrated ammonia 90:10:1 |
| T | Methylene chloride-methanol-concentrated ammonia 65:10:1 |
| U | Methylene chloride-methanol-concentrated ammonia 40:10:1 |
| V | Methylene chloride-methanol-water-glacial acetic acid 170:26:3:1 |
| W | Methylene chloride-methanol-water-glacial acetic acid 150:54:10:1 |
| X | Ethyl acetate-glacial acetic acid 100:1 |
| Y | Methylene chloride-diethyl ether 1:1 |
| Z | Methylene chloride-diethyl ether 9:1 |

HPLC gradients on $C_{18}$-Nucleosil® (5 μm); column: 4.6×250 mm

| | |
|---|---|
| I | 90% water/10% acetonitrile/0.1% trifluoroacetic acid to 0% Wasser/100% acetonitrile/0.1% trifluoroacetic acid in 30 minutes; |
| II | 50% water/50% acetonitrile/0.1% trifluoroacetic acid to 0% water/100% acetonitrile/0.1 % trifluoroacetic acid in 30 minutes; |
| III | 100% water/0% acetonitrile/0.1% trifluoroacetic acid to 0% water/100% acetonitrile/0.1% trifluoroacetic acid in 60 minutes; |
| IV | 100% water/0% acetonitrile/0.1% trifluoroacetic acid to 10% water/90% acetonitrile/0.1% trifluoroacetic acid in 60 minutes; |
| V | 70% water/30% acetonitrile/0.1% trifluoroacetic acid to 10% water/90% acetonitrile/0.1% trifluoroacetic acid in 60 minutes |

The abbreviation "$R_f(A)$" means, for example, that the $R_f$ value is determined in solvent system A. The ratio of the amounts of solvents with respect to one another is always stated in contents by volume.

For designation of the mobile phase systems, the same abbreviations are used for flash chromatography and medium pressure chromatography.

The short designations and abbreviations used have the following meanings:

| | |
|---|---|
| atm | Pressure in atmospheric units |
| bar | Pressure in bar |
| c | Concentration for measurement of the optical rotation |
| $C_{18}$-Nucleosil® | Tradename for "Reversed Phase" column material for HPLC charged with octadecyl radicals (Nucleosil® 5$C_{18}$, Macherey & Nagel, FRG) |
| Chiralcel® | CA-1 tradename for triacetylcellulose (Daicel, Japan) |
| TLC | Thin layer chromatography |
| DMAP | 4-Dimethylaminopyridine |
| DMF | Dimethylformamide |
| Ethyl acetate | Acetic acid ethyl ester |
| FAB-MS | "Fast Atom Bombardment Mass Spectroscopy" |
| FC | "Flash Chromatography" |
| h | Hour(s) |
| HPLC | High performance liquid chromatography |
| Hyflo® | Tradename for filter aid (Fluka, Buchs, Switzerland) |
| IR | Infrared spectroscopy |
| bp | Boiling point at the pressure stated in mmHg |
| ml | Milliliter |
| min | Minute(s) |
| MS | Mass spectroscopy |

| $R_f$ | Ratio of the migration zone of a substance to the distance of the mobile phase front from the startpoint in TLC |
| --- | --- |
| $R_t$ | Retention time of a substance in HPLC (in min) |
| mp | Melting point (temperature) |

The values for IR spectra are stated in cm$^{-1}$, and the particular solvent is given in round brackets. In addition, s means a strong, m a moderate and w a weak intensity of the particular band.

Mass spectroscopy measurement values are obtained either by conventional MS or by the "Fast Atom Bombardment" (FAB-MS) method. The mass data relate in the first case to the non-protonated molecular ion (M)$^+$ or to the protonated molecular ion (M+H)$^+$.

The measurement value for the optical rotation is the specific rotational angle $[\alpha]^D$, and the concentration of the substance to be analysed in g/ml and the solvent in question are given in parentheses.

In the case of the elemental analysis, in each case the percentage weight contents of the atoms in question calculated from the empirical formula are stated first (anal. calc.), followed by the measurement values actually found (found).

EXAMPLE 1

5(S)-Amino-4(S)-hydroxy-2(R),7,7-trimethyl-8-[3(R,S)-methoxycarbonyl-1,2,3,4-tetrahydroquinolin-1-ylcarbonyl]-octanoic acid (N-butyl)amide 95 mg of (4O,5N-isopropylidene)-5(S)-tert-butoxycarbonylamino-4(S)-hydroxy-2(R),7,7-trimethyl-8-[3(R,S)-methoxycarbonyl-1,2,3,4-tetrahydroquinolin-1-ylcarbonyl]-octanoic acid (N-butyl)amide are dissolved in 95% trifluoroacetic acid at room temperature. After 20 min, the solution is concentrated under a water pump vacuum. The crude product is purified by FC over 10 g of silica gel (mobile phase O). The title compound is obtained as a diastereomer mixture: $R_f(V)$=0.31; $R_t(I)$=19.0 and 19.8 min; FAB-MS (M+H)$^+$=490.

The starting materials are prepared as follows a) (4O,5N-Isopropylidene)-5(S)-tert-butoxycarbonylamino-4(S)-hydroxy-2(R),7,7-trimethyl-8-[3(R,S)-methoxycarbonyl-1,2,3,4-tetrahydroquinolin-1-ylcarbonyl]-octanoic acid (N-butyl)amide 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide are dissolved in 5 ml of methylene chloride, and 0.07 ml of 1-chloro-N,N,2-trimethylpropenylamine are added at 5° C. After 1 hour, 96 mg of 3(R,S)-methoxycarbonyl-1,2,3,4-tetrahydroquinoline (Example 1r), 0.09 ml of diisopropylethylamine and 3 mg of 4-DMAP, dissolved in 1 ml of methylene chloride, are added dropwise and the mixture is stirred at 25° C. for 1 hour. The reaction mixture is concentrated and the crude product is purified by means of FC (10 g of silica gel, mobile phase B). The title compound is obtained as a diastereomer mixture: $R_f(A)$=0.55; $R_t(II)$=21.0 min.

b) 3-[N-Tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide 2.9 g of 3-[3-tert-butoxycarbonyl-4(S)-(4-hydroxy-2,2-dimethylbutyl)-2,2-dimethyloxazolidin-5(S)-yl]-2(R)-methyl-propionic acid (N-butyl)amide are dissolved in 45 ml of acetonitrile and 45 ml of carbon tetrachloride and the solution is added to a solution of 8.56 g of sodium periodate and 150 mg of ruthenium(III) chloride hydrate in 85 ml of water. After 5 h, the crude product is isolated by extraction with methylene chloride. The crude product is then dissolved in 200 ml of diethyl ether and the solution is stirred with 10 g of Hyflo® and, after 30 min, filtered over Hyflo®. The filtrate is concentrated and the residue is purified by FC (100 g of silica gel, mobile phase S). The title compound is obtained: $R_f(S)$=0.35; $R_t(II)$=11.4 min; FABMS: (M+H)$^+$=457.

c) 3-[3-Tert-butoxycarbonyl-4(S)-(4-hydroxy-2,2-dimethylbutyl)-2,2-dimethyl-1,3-oxazolidin-5(S)-yl]-2(R)-methyl-propionic acid (N-butyl)amide 7.2 g of 3-[3-tert-butoxycarbonyl-4(S)-(2,2-dimethyl-4-triisopropylsilyloxybutyloxy-2,2-dimethyl-1,3-oxazolidin-5(S)-yl]-2-(R,S)-methyl-propionic acid (N-butyl)amide are dissolved in 70 ml of tetrahydrofuran, and 25 ml of a 1M tetrabutylammonium fluoride solution in tetrahydrofuran are added at room temperature. After 2 h, the reaction mixture is evaporated. The diastereomer mixture is separated by means of FC (500 g of silica gel, mobile phase A/ethyl acetate). This gives the title compound (diastereomer I): $R_f$(ethyl acetate) 0.39; FABMS: (M+H)$^+$=443; and diastereomer II: $R_f$(ethyl acetate)=0.33; FABMS: (M+H)$^+$=443.

d) 3-[3-Tert-butoxycarbonyl-4(S)-(2,2-dimethyl-4-triisopropylsilyloxybutyl)-2,2-dimethyl-1,3-oxazolidin-5(S)-yl]-2-(R,S)-methyl-propionic acid (N-butyl)amide 13 g of 5(S)-tert-butoxycarbonylamino-4(S)-hydroxy-9-triisopropylsilyloxy-2(R,S),7,7-trimethyl-nonanoic acid butylamide and 20 ml of 2,2-dimethoxypropane are dissolved in 40 ml of methylene chloride, and 0.3 g of p-toluenesulfonic acid hydrate is added at room temperature. After 2 h, 1 ml of triethylamine is added. The reaction mixture is concentrated and the crude product is purified by means of FC (500 g of silica gel, mobile phase D). The title compound is isolated as a diastereomer mixture: $R_f(D)$=0.27/0.22.

e) 5(S)-Tert-butoxycarbonylamino-4(S)-hydroxy-9-triisopropylsilyoxy-2(R,S),7,7-trimethylnonanoic acid (N-butyl)amide is obtained by hydrogenation of 13.3 g of 5(S)-tert-butoxycarbonylamino-4(S)-hydroxy-9-triisopropylsilyloxy-7,7-dimethyl-2-methylene-nonanoic acid (N-butyl)amide in the presence of 10 g of palladium-on-charcoal (10% of Pd) in 200 ml of tetrahydrofuran at room temperature under normal pressure over a period of 4 h and subsequent filtration of the reaction mixture of Hyflo® and concentration of the filtrate. The title compound is a mixture of the two 2(R) and 2(S) diastereomers in the ratio of about (5:4): $R_f(A)$=0.26; $R_t(II)$=34.0 and 34.4 min; FAB-MS: (M+H)$^+$=559.

f) 5(S)-Tert-butoxycarbonylamino-4(S)-hydroxy-9-triisopropylsilyloxy-7,7-dimethyl-2-methylene-nonanoic acid (N-butyl)amide 14.6 g of methacrylic acid butylamide are dissolved in 400 ml of tetrahydrofuran, and the solution is deprotonated at −75° C. with 130 ml of a 1.6M n-butyllithium solution in hexane. The reaction mixture is then stirred at 0° C. for 30 minutes. 160 ml of a 1.0M chlorotriisopropyloxytitanium solution in hexane are added to this solution at −75° C. in the course of 30 minutes. After 15 minutes, a solution of 18.7 g of 2(S)-tert-butoxycarbonylamino-6-triisopropylsilyloxy-4,4-dimethyl-hexanal in 100 ml of absolute tetrahydrofuran is added dropwise at −70° C. The reaction mixture is stirred at −70° C. for 15 min and then allowed to warm slowly to 0° C., and after 40 min 200 ml of a saturated ammonium chloride solution are added at −15° C. The suspension is filtered over Hyflo® and the product is extracted with diethyl ether. The diastereomer mixture is separated by means of FC (600 g of silica gel, mobile phase B). This gives the title compound (diastereomer I): $R_f(A)=0.44$; $R_f(II)=36.0$ min; and diastereomer II: $R_f(A)=0.36$; $R_f(II)=35.3$ min.

g) 2(S)-Tert-butoxycarbonylamino-6-triisopropylsilyloxy-4,4-dimethyl-hexanal 14.7 ml of dimethylsulfoxide in 200 ml of methylene chloride are added dropwise to a solution of 13.4 ml of oxalyl chloride in 200 ml of methylene chloride at −60° C. After 15 min, a solution of 43.2 g of 2(S)-tert-butoxycarbonylamino-6-triisopropylsilyloxy-4,4-dimethyl-hexan-1-ol in 320 ml of methylene chloride is added dropwise at −60° C. in the course of 40 min, while stirring vigorously. 58 ml of triethylamine are then added and the reaction mixture is stirred at −60° C. for 90 min. It is allowed to warm to −10° C., 200 ml of a 20% potassium hydrogen sulfate solution are added, the mixture is subsequently stirred briefly and the product is extracted with methylene chloride. This gives 43 g of the title compound, which is reacted further without additional purification: $R_f(A)=0.62$, $R_f(D)=0.3$; $R_f(II)=34.8$ min.

h) 2(S)-Tert-butoxycarbonylamino-6-triisopropylsilyloxy-4,4-dimethyl-hexan-1-ol 5.7 g of 3-tert-butoxycarbonyl-4(S)-(4-triisopropylsilyloxy-2,2-dimethylbutyl)-2,2-dimethyl-1,3-oxazolidine are dissolved in 100 ml of methanol, and 180 mg of pyridinium p-toluenesulfonate are added. After the mixture has been stirred at room temperature for 72 hours, it is concentrated and the crude product is purified by means of FC (300 g of silica gel, mobile phases G and B). This gives the title compound: $R_f(B)=0.42$; IR(CH$_2$Cl$_2$): 3600 w, 3440 m, 1705 s (cm$^{-1}$).

i) 3-Tert-butoxycarbonyl-4(S)-(4-triisopropylsililoxy-2,2-dimethylbutyloxy-2,2-dimethyl-1,3-oxazolidine 5.6 g of 3-tert-butoxycarbonyl-4(S)-(4-hydroxy-2,2-dimethylbutyloxy-2,2-dimethyl-1,3-oxazolidine are dissolved in 50 ml of methylene chloride, and 1.6 g of imidazole, 4.3 g of triisopropylchlorosilane and 20 mg of 4-DMAP are added in succession at room temperature. The mixture is stirred at 20° C. for 16 h, the salt which has precipitated out is filtered off and the concentrated residue is purified by means of FC over 500 g of silica gel with a 1:20 mixture of ethyl acetate and hexane as the mobile phase. This gives the pure title compound: $R_f(G)=0.45$; IR (CH$_2$Cl$_2$): 1690 s (cm$^{-1}$).

j) 3-Tert-butoxycarbonyl-4(S)-(4-hydroxy-2,2-dimethylbutyloxy-2,2-dimethyl-1,3-oxazolidine 68.6 g of 3-tert-butoxycarbonyl-2,2-dimethyl-4(S)-(2,2-dimethylbut-3-enyl)-1,3-oxazolidine are dissolved in 500 ml of tetrahydrofuran, and 10 ml of borane/dimethylsulfide complex are added dropwise at 0° C. The reaction mixture is stirred at 0° C. for 1 h and at room temperature for 2 h. 60 ml of a 3:1 mixture of tetrahydrofuran and water (v/v) and then 61 ml of a 2N sodium hydroxide solution, at room temperature, and finally 35 ml of a 30% hydrogen peroxide solution, at 0° C., are subsequently slowly added dropwise. The reaction mixture is stirred at room temperature for 1 h and then diluted with 200 ml of saturated potassium carbonate solution. The product is extracted with ethyl acetate and the title compound is obtained in a pure form by FC (600 g of silica gel, mobile phase B): $R_f(A)=0.47$; FAB-MS: (M+H)$^+$=302.

k) 3-Tert-butoxycarbonyl-2,2-dimethyl-4(S)-(2,2-dimethylbut-3-enyl)-1,3-oxazolidine 255 ml of a 1.6M butyllithium solution in hexane are added to a solution of 85 ml of hexamethyldisilazane in 800 ml of tetrahydrofuran at −40° C. After 15 min, 140 g of methyltriphenylphosphonium bromide are added at 0° C. and the reaction mixture is stirred at 30° C. for 30 min. 77 g of 3-tert-butoxycarbonyl-2,2-dimethyl-4(S)-(2-formyl-2-methylpropyl)-1,3-oxazolidine, dissolved in 200 ml of tetrahydrofuran, are then added to the reaction solution at −30° C. The reaction mixture is stirred at room temperature for 1 h, and 600 ml of hexane are then added at 0° C. The triphenylphosphinoxide which has precipitated out is filtered off and, after dilution with 400 ml of saturated ammonium chloride solution, the filtrate is extracted with diethyl ether. The crude product is purified by means of FC (400 g of silica gel, mobile phase G): $R_f(D)=0.55$, $R_f$(ethyl acetate)=0.44; $[\alpha]^D=+4.2$ (c=1.25 in CHCl$_3$); MS: (M)$^+$=283.

l) 3-Tert-butoxycarbonyl-1-2,2-dimethyl-4(S)-(2-formyl-2-methylpropyl)-1,3-oxazolidine 58 ml of of dimethylsulfoxide are added dropwise to a solution of 37.4 ml of oxalyl chloride in 750 ml of methylene chloride at −60° C. After 5 min, a solution of 77.8 g of 3-tert-butoxycarbonyl-2,2-dimethyl-4(S)-(3-hydroxy-2,2-dimethylpropyl)-1,3-oxazolidine in 250 ml of methylene chloride is added dropwise at −60° C. The reaction mixture is stirred at −30° C. for 30 min. 133 ml of triethylamine are then added at −60° C. and the mixture is warmed to 0° C. for 30 min. The reaction mixture is then washed several times with water and subsequently evaporated. The product is dissolved in 200 ml of toluene and the solution is dried over sodium sulfate, filtered and concentrated again. This gives the title compound: $R_f(A)=0.70$, $R_f(D)=0.35$; $[\alpha]^D=+20.7$ (c=1.25 in CHCl$_3$); FAB-MS: (M+H)$^+$=286.

m) 3-Tert-butoxycarbonyl-2,2-dimethyl-4(S)-(3-hydroxy-2,2-dimethylpropyl)-1,3-oxazolidine A solution of 85.5 g of methyl 3-[3-tert-butoxycarbonyl-2,2-dimethyl-1,3-oxazolidine-4(S)-yl]-2,2-dimethyl-propionate in 300 ml of tetrahydrofuran is added to a suspension of 22 g of lithium aluminium hydride in 700 ml of tetrahydrofuran at −10° C. and the mixture is then stirred at 0° C. for 30 min. Thereafter, 22 ml of water, 22 ml of a 5N sodium hydroxide solution and 66 ml of water are added dropwise in succession at 0° C. and the mixture is subsequently stirred for 30 min. The suspension is filtered over Hyflo® and evaporated. After drying with sodium sulfate in methylene chloride, the title compound is obtained in the pure form: white crystals; mp. 45°–6° C.; $R_f(A)=0.53$, $R_f(D)=0.18$; $[\alpha]^D=+52.8$ (c=0.91 in CHCl$_3$); FAB-MS: (M+H)$^+$=288; anal. calc. for C$_{15}$H$_{29}$NO$_4$: C 62.69%, H 10.17%, N 4.87%; found C 62.88%, H 10.11%, N 4.86%.

n) Methyl 3-[3-tert-butoxycarbonyl-2,2-dimethyl-1,3-oxazolidin-4(S)-yl]-2,2-dimethylpropionate 500 ml of a 1.6M n-butyllithium solution in hexane are added to a solution of 168 ml of hexamethyldilsilazane in 800 ml of tetrahydrofuran at −40 ° C. After 20 min, 50 ml methyliodide and then a solution of 86.2 g of methyl 3-[3-tert-butoxycarbonyl-2,2-dimethyl-1,3-oxazolidin-4(S)-yl]-propionate in 400 ml of tetrahydrofuran are added dropwise at −70° C. to −75° C. The reaction mixture is stirred at −70° C. for 15 min and then warmed to 0° C. in the course of 1 h, and after 30 min, 300 ml of saturated ammonium chloride solution and 400 ml of water are added. The title compound is obtained by extraction with diethyl ether and subsequent vacuum distillation: bp$_{0.003}$=95°–8° C.; $[\alpha]^D$=+23.7 (c=1.0 in CHCl$_3$); $R_f(D)=0.42$; FAB-MS: (M+H)$^+$=316; anal. calc. for C$_{16}$H$_{29}$NO$_5$: C 60.93%, H 9.27%, N 4.44%; found C 61.10%, H 9.14%, N 4.66%.

o) Methyl 3-[3-tert-butoxycarbonyl-2,2-dimethyl-1,3-oxazolidin-4(S)-yl]-propionate 120 ml of isopropenyl methyl ether are added to a solution of 159.5 g of methyl 4(S)-tert-butoxycarbonylamino-5- hydroxyvalerate and 3 g of p-toluenesulfonic acid hydrate in 500 ml of methylene chloride at 0° C. The reaction mixture is stirred at 0° C. for 2 h and at room temperature for 3 h. The reaction solution is washed with 100 ml of saturated sodium bicarbonate solution and evaporated. The title compound is obtained by FC (800 g of silica gel, mobile phase E): $[\alpha]^D=+20.5$ (c=0.8 in $CHCl_3$); $R_f(D)=0.24$; MS: $(M)^+=287$.

p) Methyl 4(S)-tert-butoxycarbonylamino-5-hydroxyvalerate 130.5 g of 5-methyl 2(S)-tert-butoxycarbonylglutamate and 76.7 ml of triethylamine are dissolved in 500 ml of tetrahydrofuran, and 76 ml of methyl chloroformate are added dropwise at −20° C. under argon. After the mixture has been stirred at −15° C. for 20 min, 10 g of lithium borohydride are added in portions over 30 min. The reaction mixture is stirred at −20° C. for 15 min and then acidified to pH 3 with 2N sulfuric acid and subsequently extracted with ethyl acetate. The crude product is purified by means of crystallization from ethyl acetate/hexane. The title compound is obtained: mp 48°–9° C.; $R_f(O)=0.58$, $R_f(V)=0.46$; $[\alpha]^D=-11.5$ (c=0.96 in $CHCl_3$); FAB-MS: $(M+H)^+=248$; anal. calc. for $C_{11}H_{21}NO_5$: C 53.43%, H 8.56%, N 5.66%; found C 53.22%, H 8.64%, N 5.67%.

q) 5-Methyl 2(S)-tert-butoxycarbonylglutamate 100 g of: 5-methyl (S)-glutamate and 52.1 g of sodium bicarbonate are dissolved in 300 ml of water and 300 ml of dioxane. 150 g of di-tert-butyldicarbonate are added to this solution at room temperature. After 3 h, the reaction mixture is diluted with 370 ml of a 2M potassium hydrogen sulfate solution and the product is extracted with ethyl acetate. The title compound is obtained by crystallization from diethyl ether/hexane: mp 75°–6° C.; $[\alpha]^D=-10.8$ (c=1.0 in acetic acid); $R_f(D)=0.43$.

r) 3(R,S)-Methoxycarbonyl-1,2,3,4-tetrahydroquinoline is obtained by hydrogenation of 495 mg of N-benzyloxycarbonyl-3(R,S)-methoxycarbonyl-1,2,3,4-tetrahydroquinoline in the presence of 100 mg of palladium-on-charcoal (10% of Pd) in 20 ml of methanol at room temperature under normal pressure for 4 h. The reaction mixture is filtered over Hyflo® and concentrated. The title compound is obtained as a pure oil: $R_f(D)=0.28$; $R_t(II)=3.5$ min; FAB-MS: $(M)^+=191$.

s) N-Benzyloxycarbonyl-3(R,S)-methoxycarbonyl-1,2,3,4-tetrahydroquinoline 1.87 g of N-benzyloxycarbonyl-1,2,3,4-tetrahydroquinoline-3(R,S)-carboxylic acid and 5 ml of N,N-dimethylformamide dimethyl acetal are heated at 80° C. in 20 ml of toluene for 4 h. The reaction mixture is concentrated and the residue is purified by means of FC (50 g of silica gel, mobile phase D): $R_f(D)=0.29$; MS: $(M)^+=325$.

t) N-Benzyloxycarbonyl-1,2,3,4-tetrahydroquinoline-3(R,S)-carboxylic acid 5 g of quinoline-3-carboxylic acid are hydrogenated in the presence of 5 g of Raney nickel at room temperature in 100 ml of 1N sodium hydroxide solution for 16 h under 5.1 bar (5 atm). The reaction mixture is filtered over Hyflo® and 100 ml of tetrahydrofuran and 6 g of benzyl chloroformate are added at 0°–5° C. After 1 h, the reaction mixture is concentrated to half and extracted with diethyl ether. The aqueous phase is then acidified to pH 2.5 and extracted with methylene chloride. The title compound is obtained in a pure form by recrystallization from diethyl ether/hexane: mp 113° C.; $R_f(X)=0.43$; MS: $(M)^+=311$; anal. calc. for $C_{11}H_{17}NO_4$: C 69.44%, H 5.50%, N 4.50%; found C 69.27%, H 5.68%, N 4.49%.

EXAMPLE 2

4(S)-Amino-3(S)-hydroxy-1(R),6,6-trimethyl-heptanedicarboxylic acid 1-(N-butyl)amide 7-(N-naphth-1-yl)amide The title compound is prepared in a manner analogous to that described in Example 1) starting from 195 mg of (3O,4N-isopropylidene)-4(S)-tert-butoxycarbonylamino-3(S)-hydroxy-1(R),6,6-trimethyl-heptanedicarboxylic acid 1-(N-butyl)amide 7-(N-naphth-1-yl)amide and is purified by FC over 50 g of silica gel (mobile phase S). This gives the pure title compound: $R_f(S)=0.22$; $R_f(Y)=0.43$; FAB-MS: $(M+H)^+=442$.

The starting material is prepared, for example, as follows:
a) (3O,4N-Isopropylidene)4(S)-tert-butoxycarbonylamino-3(S)-hydroxy-1(R),6,6-trimethyl-heptanedicarboxylic acid 1-(N-butyl)amide 7-(N-naphth-1-yl)amide The title compound is obtained by stirring 370 mg of 3-[N-tert-butoxycarbonyl-4(S)-(3-carboxy-2,2-dimethylpropyloxy-2,2-dimethyl-1,3-oxazolidine-5(S)-yl]-2(R)-methyl-propionic acid (N-butyl)amide, 0.56 ml of ethyl diisopropylamine, 413 mg of bis(2-oxo-3-oxazolidinyl)phosphinic acid chloride, 350 mg of 1-naphthylamine and 10 mg of 4-DMAP in 5 ml of methylene chloride at room temperature for 24 h. The crude product is purified by means of FC over 70 g of silica gel (mobile phases Z and Y). This gives the pure title compound: $R_f(Y)=0.50$.

EXAMPLE 3

5(S)-Amino-4(S)-hydroxy-2(R),7,7-trimethyl-8-(1,2,3,4-tetrahydroquinolin-1-yl-carbonyl)-octanoic acid N,N-butyl)amide In an analogous manner to that described in Examples 2 and 2a) for the corresponding reaction stages, the title compound is obtained starting from 150 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 0.25 ml of 1,2,3,4-tetrahydroquinoline via (4O,5N-isopropylidene)-5(S)-tert-butoxycarbonylamino-4(S)-hydroxy-2(R),7,7-trimethyl-8-(1,2,3,4-tetrahydroquinolin-1-ylcarbonyl]-octanoic acid (N-butyl)amide $(R_f(Y)=0.36)$: $R_f(S)=0.32$; FAB-MS: $(M+H)^+=432$.

EXAMPLE 4

5(S)-Amino-4(S)-hydroxy-2(R),7,7-trimethyl-8-(2,3-dihydroindol1-ylcarbonyl)octanoic acid (N-butyl)amide In an analogous manner to that described in Examples 2 and 2a) for the corresponding reaction stages, the title compound is obtained starting from 80 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 0.120 ml of indoline via (4O,5N-isopropylidene)-5(S)-tert-butoxycarbonylamino-4(S)-hydroxy-2(R),7,7-trimethyl-8-(2,3-dihydroindol1-ylcarbonyl)-octanoic acid (N-butyl)amide $(R_f(Y)=0.71)$: $R_f(S)=0.33$; $R_f(T)=0.38$; FAB-MS: $(M+H)^+=418$.

EXAMPLE 5

4(S)-Amino-3(S)-hydroxy-1(R),6,6-trimethyl-heptanedicarboxylic acid 1-(N-butyl)amide 7-(N-phenyl)amide In an analogous manner to that described in Examples 2 and 2a) for the corresponding reaction stages, the title compound is obtained starting from 80 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 0.1 ml aniline via (3O,4N-isopropylidene)-4(S)-N-tert-butoxycarbonylamino-3(S)-

EXAMPLE 6

4(S)-Amino-3(S)-hydroxy-1(R),6,6-trimethyl-heptanedicarboxylic acid 1-(N-butyl)-amide 7-[N-[2-(methoxycarbonylaminomethyl)phenyl]]amide In an analogous manner to that described in Examples 2 and 2a) for the corresponding reaction stages, the title compound is obtained starting from 300 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amid and 473 mg of 2-(methoxycarbonylamino-methyl)aniline via (3O,4N-isopropylidene)-4(S)-tert-butoxycarbonylamino-3(S)-hydroxy-1(R),6,6-trimethyl-heptanedicarboxylic acid 1-(N-butyl)amide 7-[N-[2-(methoxycarbonylaminomethyl)phenyl]]amide ($R_f(B)$=0.35) and purification over silica gel (mobile phase S): $R_f(S)$=0.24; FAB-MS: (M+H)$^+$=479.

The amine component employed is obtained starting from 2.0 g of 2-(aminomethyl)aniline, dissolved in 30 ml of methylene chloride, by reaction with 1.3 ml of methyl chloroformate in the presence of 3.1 ml of diisopropylethylamine at 5° C. After purification over 80 g of silica gel (mobile phase A), 2-(methoxycarbonylaminomethyl)aniline is obtained: $R_f(A)$=0.23; $R_f(Z)$=0.31.

EXAMPLE 7

4(S)-Amino-3(S)-hydroxy-1(R),6,6-trimethyl-heptanedicarboxylic acid 1-(N-butyl)amide 7-[N-(4-bromnaphth-1-yl)]amide In an analogous manner to that described in Examples 2 and 2a) for the corresponding reaction stages, the title compound is obtained starting from 80 mg of 3-[N-tert-butoxycarbonyl-4(S)-3-carboxy-2,2-dimethylpropyloxy-2,2-dimethyl-1,3-oxazolidin-5(S)-yl]-2(R)-methyl-propionic acid (N-butyl)amide and 233 mg of 4-bromonaphthylamine via (3O,4N-isopropylidene)-4(S)-tert-butoxycarbonylamino-3(S)-hydroxy-1(R),6,6-trimethyl-heptanedicarboxylic acid 1-(N-butyl)amide 7-[N-(4-bromonaphth-1-yl)]amide ($R_f(Y)$=0.61): $R_f(S)$=0.20; $R_f(T)$=0.28; FAB-MS: (M+H)$^+$=520.

EXAMPLE 8

5(S)-Amino-4(S)-hydroxy-2(R),7,7-trimethyl-8-(5,6-dihydrophenanthridinocarbonyl)-octanoic acid (N-butyl) amide In an analogous manner to that described in Examples 2 and 2a) for the corresponding reaction stages, the title compound is obtained starting from 80 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 190 mg of dihydrophenanthridine via (4O,5N-isopropylidene)-5(S)-tert-butoxycarbonylamino-4(S)-hydroxy-2(R),7,7-trimethyl-8-(5,6-di-hydrophenanthridinocarbonyl)-octanoic acid (N-butyl)amide ($R_f(Y)$=0.61): $R_f(S)$=0.36; FAB-MS: (M+H)$^+$=480.

The 5,6-dihydrophenanthridine employed as the starting material is prepared, for example, as follows:

5.0 g of 6(5H)-phenanthridinone are reduced in 50 ml of tetrahydrofuran with the addition of 1.46 g of lithium aluminium hydride at room temperature for 26 h. The crude product is purified by FC over 250 g of silica gel with methylene chloride: $R_f$(1:1 mixture of methylene chloride and hexane)=0.25.

EXAMPLE 9

5(S)-Amino-4(S)-hydroxy-2(R),7,7-trimethyl-8-(1,2,3,4-tetrahydroisoquinolin-2-ylcarbonyl)-octanoic acid (N-butyl) amide In an analogous manner to that described in Examples 2 and 2a) for the corresponding reaction stages, the title compound is obtained starting from 80 mg of 3-[N-tert-butoxycarbonyl-4(S)-3-carboxy-2,2-dimethylpropyloxy-2,2-dimethyl-1,3-oxazolidin-5(S)-yl]-2(R)-methyl-propionic acid (N-butyl)amide and 0.14 ml of 1,2,3,4-tetrahydroisoquinoline via (4O,5N-isopropylidene)-5(S)-tert-butoxycarbonylamino-4(S)-hydroxy-2(R),7,7-trimethyl-8-(1,2,3,4-tetrahydroisoquinolin2-ylcarbonyl)-octanoic acid (N-butyl)amide ($R_f(Y)$=0.49) and purification over 30 g of silica gel (mobile phase N): $R_f(S)$=0.28; $R_f(T)$=0.44; FAB-MS: (M+H)$^+$=432.

EXAMPLE 10

4(S)-Amino-3(S)-hydroxy-1(R),6,6-trimethyl-heptanedicarboxylic acid 1-(N-butyl)amide 7-[N-[2-(formylaminomethyl)phenyl]]amide In an analagous manner to that described for the corresponding reaction stages in Examples 2 and 2a), the title compound is obtained starting from 300 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 394 mg of 2-(formylaminomethyl)aniline via (3O,4N-isopropylidene)-4(S)-tert-butoxycarbonylamino-3(S)-hydroxy-1(R),6,6-trimethyl-heptanedicarboxylic acid 1-(N-butyl)amide 7-[N-[2-(formylaminomethyl)phenyl]]amide ($R_f(O)$=0.46): $R_f(T)$=0.38; FAB-MS: (M+H)$^+$=449.

The amine component employed is prepared by reaction of 2.6 g of 2.6 g of 2-(aminomethyl)aniline, dissolved in 50 ml of methylene chloride, with 3.91 g of 4-nitrophenyl formate at room temperature for 4 h. Purification over 250 g of silica gel (mobile phase N) gives 2-(formylaminomethyl)aniline: $R_f(N)$=0.22.

EXAMPLE 11

4(S)-Formylamino-3(S)-hydroxy-1(R),6,6-trimethyl-heptanedicarboxylic acid 1-(N-butyl)amide 7-(N-phenyl) amide 28 mg of 4(S)-Amino-3(S)-hydroxy-1(R),6,6-trimethyl-heptanedicarboxylic acid 1-(N-butyl)amide 7-(N-phenyl)amide (Example 5) 16 mg of 4-nitrophenyl formate are stirred in 2 ml of methylene chloride for 2 h. The concentrated crude product is then purified over 10 g of silica gel (mobile phase O): $R_f(T)$=0.42; FAB-MS: (M+H)$^+$=420.

EXAMPLE 12

5(S)-Amino-4(S)-hydroxy-2(R),7,7-trimethyl-8-[3(R)- or 3(S)-ethoxycarbonylpiperidin-1-ylcarbonyl]-octanoic acid (N-butyl)amide In an analogous manner to that described in Examples 1 and 1a) for the corresponding reaction stages, the title compound is obtained starting from 30 mg of (4O,5N-isopropylidene)-5(S)-tert-butoxycarbonylamino-4(S)-hydroxy-2(R),7,7-trimethyl-8-[3(R)- or 3(S)-ethoxycarbonylpiperidin-1-ylcarbonyl)-octanoic acid (N-butyl)amide (diastereomer I; Example 13) and purification by means of FC (5 g of silica gel, mobile phases O and U) as the pure stereoisomer: $R_f(U)$=0.71; $R_f(II)$=3.8 min; FAB-MS: $(M+H)^+$=456.

EXAMPLE 13

5(S)-Amino-4(S)-hydroxy-2(R),7,7-trimethyl-8-[3(R)- or 3(S)-ethoxycarbonylpiperidin-1-ylcarbonyl]-octanoic acid (N-butyl)amide In an analogous manner to that described in Examples 1 and 1a) for the corresponding reaction stages, the title compound is obtained starting from 30 mg of (4O,5N-isopropylidene)-5(S)-tert-butoxycarbonylamino-4(S)-hydroxy-2(R),7,7-trimethyl-8-[3(R)- or 3(S)-ethoxycarbonylpiperidin-1-ylcarbonyl)-octanoic acid (N-butyl)amide (diastereomer II) and purification by means of FC (5 g of silica gel, mobile phases O and U): $R_f(U)$=0.75; $R_f(II)$=4.2 min; FAB-MS: $(M+H)^+$=456.

The (4O,5N-isopropylidene)-5(S)-tert-butoxycarbonylamino-4(S)-hydroxy-2(R),7,7-trimethyl-8-[3(R)- or 3(S)-ethoxycarbonylpiperidin-1-ylcarbonyl)-octanoic acid (N-butyl)amide employed in the preceding Examples 12 and 13) as a starting material in the form of the pure 3(R) or 3(S) stereoisomers is prepared starting from 60 mg of 3-[N-tert-butoxycarbonyl-4(S)-(3-carboxy-2,2-dimethylpropyloxy-2,2-dimethyl-1,3-oxazolidin-5(S)-yl]-2(R)-methylpropionic acid (N-butyl)amide and 0.05 ml of ethyl piperidine-3(R,S)-carboxylate. The resulting diastereomer mixture is separated by FC over 10 g of silica gel (mobile phase A and ethyl acetate). This gives diastereomer I: $R_f(A)$=0.20; and diastereomer II: $R_f(A)$=0.13.

EXAMPLE 14

5(S)-Amino-4(S)-hydroxy-2(R),7,7-trimethyl-9-(1,2,3,4-tetrahydroquinolin-1 yl)nonanoic acid (N-butyl)amide In an analogous manner to that described in Examples 1 and 1a) for the corresponding reaction stages, the title compound is obtained starting from 90 mg of (4O,5N-isopropylidene)-5(S)-tert-butoxycarbonylamino-4(S)-hydroxy-2(R),7,7-trimethyl-9-(1,2,3,4-tetrahydroquinolin-1-yl)nonanoic acid (N-butyl)amide: $R_f(S)$=0.44; FAB-MS: $(M+H)^+$=418.

The starting materials are prepared, for example, as follows:

a) (4O,5N-Isopropylidene)-5(S)-tert-butoxycarbonylamino-4(S)-hydroxy-2(R),7,7-trimethyl-9-(1,2,3,4-tetrahydroquinolin-1-yl)nonanoic acid (N-butyl)amide 174 mg of 3-[3-tert-butoxycarbonyl-4(S)-(4-iodo-2,2-dimethylbutyl)-2,2-dimethyl-1,3-oxazolidin-5(S)-yl]-2(R)-methyl-propionic acid (N-butyl)amide are stirred in 2 ml of 1,2,3,4-tetrahydroquinoline at 100° C. for 6 h. The reaction mixture is concentrated under a high vacuum and the resulting crude product is purified over 65 g of silica gel with a 20:1 mixture of methylene chloride and diethyl ether. The title compound is obtained as a yellowish oil: $R_f$(20:1 mixture of methylene chloride and diethyl ether)=0.21.

b) 3-[3-Tert-butoxycarbonyl-4(S)-(4-iodo-2,2-dimethylbutyl)-2,2-dimethyl-1,3-oxazolidin-5(S)-yl]-2(R)-methyl-propionic acid (N-butyl)amide 168 mg of N-iodosuccinamide and 196 mg of triphenylphosphine are added to a solution of 300 mg of 3-[3-tert-butoxycarbonyl-4(S)-(4-hydroxy-2,2-dimethylbutyl)-2,2-dimethyl-1,3-oxazolidin-5(S)-yl]-2(R)-methyl-propionic acid (N-butyl)amide (Example 1c)) in 5 ml of methylene chloride at 0° C. and the reaction mixture is stirred for 7 h. The crude product is purified, after customary working up, over 65 g of silica gel (mobile phase B) to give the title compound: $R_f(B)$=0.55.

EXAMPLE 15

5(S)-Amino-4(S)-hydroxy-2(R),7,7-trimethyl-8-[3(R,S)-carboxy-1,2,3,4-tetrahydroquinolin-1-ylcarbonyl]-octanoic acid (N-butyl)amide 49 mg of 5(S)-amino-4(S)-hydroxy-2(R),7,7-trimethyl-8-[3(R,S)-carboxy-1,2,3,4-tetrahydroquinolin-1-ylcarbonyl]-octanoic acid (N-butyl)amide (from Example 1) are stirred in 1 ml of 1N sodium hydroxide solution and 2 ml of dioxane at 25° C. for 1 h. The reaction mixture is acidified with 1.05 ml of a 2N hydrochloric acid solution and concentrated and the crude product is purified by means of FC (10 g of silica gel, mobile phases V and W). This gives the title compound as a diastereomer mixture: $R_f(V)$=0.09; $R_f(I)$=17.0/18.0 min; FAB-MS: $(M+H)^+$=476.

EXAMPLE 16

5(S)-Amino-4(S)-hydroxy-2(R),7,7-trimethyl-8-[2(R,S)-ethoxycarbonyl-3,4-dihydro-2H-1,4-benzoxazin-4-ylcarbonyl]-octanoic acid (N-butyl)amide:

In an analogous manner to that described in Examples 2 and 2a) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 213 mg of 2(R,S)-ethoxycarbonyl-3,4-dihydro-2H-1,4-benzoxazine (prepared by the process described by H. Bartsch and O. Schwarz in Arch. Pharm. 315, 538 (1982)) via (4O,5N-isopropylidene)-5(S)-tert-butoxy-carbonylamino-4(S)-hydroxy-2(R),7,7-trimethyl-8-[2(R,S)-ethoxycarbonyl-3,4-dihydro-2H-1,4-benzoxazin-4-ylcarbonyl]-octanoic acid (N-butyl)amide ($R_f(Y)$=0.51) as a diastereomer mixture: $R_f(S)$=0.34; $R_f(T)$=0.39; FAB-MS: $(M+H)^+$=506.

EXAMPLE 17

5(S)-Formylamino-4(S)-hydroxy-2(R),7,7-trimethyl-8-[2(R,S)-ethoxycarbonyl-4-dihydro-2H-1,4-benzoxazin-4-ylcarbonyl]-octanoic acid (N-butyl)amide 25 mg of 5(S)-Amino-4(S)-hydroxy-2(R),7,7-trimethyl-8-[2(R,S)-ethoxycarbonyl-3,4-dihydro-2H-1,4-benzoxazin-4-ylcarbonyl]-octanoic acid (N-butyl)amide are stirred with 10 mg of 4-nitrophenyl formate in 2 ml of methylene chloride at room temperature for 26 h. The crude product is then purified by means of FC (mobile phase S) over 20 g of silica gel. This gives the pure title compound: $R_f(S)$=0.49; FAB-MS: $(M+H)^+$=534.

EXAMPLE 18

5(S)-Amino-4(S)-hydroxy-2(R),7,7-trimethyl-8-2(R,S)-methoxycarbonyl-3,4-dihydro-2H-1,4-benzothiazin-4-ylcarbonyl]-octanoic acid (N-butyl)amide In an analogous manner to that described in Examples 2 and 2a) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 267 mg of 2(R,S)-methoxycarbonyl-3,4-dihydro-2H-1,4-benzothiazine (prepared by the process described by R.C.M. Butleretal. in J. Heterocyclic Chem.22, 177(1985)) via (4O,5N-isopropylidene)-5(S)-tert-butoxy-carbonylamino-4(S)-hydroxy-2(R),7,7-trimethyl-8-[2(R,S)-methoxycarbonyl-3, 4-dihydro-2H-1,4-benzothiazin-4-ylcarbonyl]-octanoic acid (N-butyl)amide ($R_f(Y)$=0.44) and purification by FC over 50 g of silica gel (mobile phase S) as a diastereomer mixture: $R_f(S)$=0.36; $R_f(T)$=0.40; FAB-MS: $(M+H)^+$=508.

EXAMPLE 19

5(S)-Amino-4(S)-hydroxy-2(R),7,7-trimethyl-8-[3(R,S)-ethoxycarbonyl-3,4-dihydro-2H-1,4-benzooxazin-4-ylcarbonyl-octanoic acid N-butyl)amide In an analogous manner to that described in Examples 2 and 2a) for the corresponding reaction stages, the title compound is obtained starting from 80 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 218 mg of 3(R,S)ethoxycarbonyl-3,4-dihydro-2H-1,4-benzooxazine (prepared by the process described by H. Bartsch and O. Schwarz in Arch. Pharm. 315, 538 (1982)) via (4O,5N-isopropylidene)-5(S)-tert-butoxycarbonylamino-4(S)-hydroxy-2(R),7,7-trimethyl-8-[3(R,S)-ethoxycarbonyl-3,4-dihydro-2H-1,4-benzooxazin-4-ylcarbonyl]-octanoic acid (N-butyl)amide ($R_f(Y)$=0.80) as a mixture of diastereomers: $R_f(S)$=0.38; $R_f(T)$=0.47; FAB-MS: $(M+H)^+$=506.

EXAMPLE 20

5(S)-Amino-4(S)-hydroxy-2(R),7,7-trimethyl-8-[3-(R,S)-tert-butoxycarbonyl-1,2,3,4-tetrahydroquinolin-1-ylcarbonyl]-octanoic acid N(-butyl)amide 28 mg of 5(S)-tert-butoxycarbonylamino-4(S)-hydroxy-2(R),7,7-trimethyl-8-[3(R,S)-tert-butoxycarbonyl-1,2,3,4-tetrahydroquinolin-1-ylcarbonyl]-octanoic acid (N-butyl) amide are dissolved in 2 ml of 4N hydrochloric acid in dioxane and the solution is stirred at 20° C. for 30 min. The reaction mixture is diluted with dioxane and lyophilized. The crude product is purified by means of FC (5 g of silica gel, mobile phases N and O). This gives the title compound as a diastereomer mixture: $R_f(O)$=0.32; $R_f(I)$=23.8 min; FAB-MS: $(M+H)^+$=532.

The starting materials are prepared, for example, as follows:

a) 5(S)-Tert-butoxycarbonylamino-4(S)-hydroxy-2(R),7,7-trimethyl-8-[3(R,S)-tert-butoxycarbonyl-1,2,3,4-tetrahydroquinolin-1-ylcarbonyl]-octanoic acid N-(butyl)amide A mixture of 41 mg of (4O,5N-isopropylidene)-5(S)-tert-butoxycarbonylamino-4(S)-hydroxy-2(R),7,7-trimethyl-8-[3(R,S)-tert-butoxycarbonyl-1,2,3,4-tetrahydroquinolin-1-ylcarbonyl]-octanoic acid (N-butyl)amide, 4 mg of p-toluenesulfonic acid hydrate and 3 ml of methanol is stirred at room temperature. When the reaction has ended (TLC monitoring), 1 ml of toluene is added and the reaction mixture is then concentrated. The crude product thus obtained is purified by means of FC (10 g of silica gel, ethyl acetate as the mobile phase). This gives the title compound: $R_f(A)$=0.10.

b) 4O,5N-Isopropylidene-5(S)-tert-butoxycarbonylamino-4(S)-hydroxy-2(R),7,7-trimethyl-8-[3(R,S)-tert-butoxycarbonyl-1,2,3,4-tetrahydroquinolin-1-ylcarbonyl]-octanoic acid (N-butyl)amide The title compound is obtained starting from 57 mg of 3-[N-tert-butoxycarbonyl-4(S)-(3-carboxy-2,2-dimethylpropyloxy-2,2-dimethyl-1,3-oxazolidine-5(S)-yl]-2(R)-methyl-propionic acid (N-butyl)amide, 66 mg of bis(2-oxo-3-oxazolidinyl)phosphinic acid chloride, 58 mg of 3(R,S)-tert-butoxycarbonyl-1,2,3,4-tetrahydroquinoline and 0.08 ml of triethylamine analogously to Example 2a) and is purified by FC (20 g of silica gel, mobile phase B). The title compound is obtained as a diastereomer mixture: $R_f(A)$= 0.31/0.34; $R_f(II)$=26.3/26.6 min.

c) 3(R,S)-Tert-butoxycarbonyl-1,2,3,4-tetrahydroquinoline

The title compound is prepared analogously to Example 1r) starting from 367 mg of N-benzyloxycarbonyl-3(R,S)-tert-butoxycarbonyl-1,2,3,4-tetrahydroquinoline: $R_f(A)$= 0.62; MS: $(M)^+$=233.

d) N-Benzyloxycarbonyl-3(R,S)-tert-butoxycarbonyl-1,2,3,4-tetrahydroquinoline

The title compound is prepared analogously to Example 1s) starting from 622 mg of N-benzyloxycarbonyl-1,2,3,4-tetrahydroquinoline-3(R,S)-carboxylic acid and 2.2 ml of N,N-dimethylformamide di-tert-butyl acetal and is purified by means of FC (50 g of silica gel, mobile phases G and E): $R_f(D)$=0.48; MS: $(M)^+$=367.

EXAMPLE 21

5(S)-Amino-4(S)-hydroxy-2(R),7,7-trimethyl-8-[3(R)- or 3(S)-methoxycarbonyl-1,2,3,4-tetrahydroquinolin-1-ylcarbonyl]-octanoic acid N-butyl)amide The title compound is prepared analogously to Example 20) starting from 88 mg of 5(S)-tert-butoxycarbonylamino-4(S)-hydroxy-2(R),7,7-trimethyl-8-[3(R)- or 3(S)-methoxycarbonyl-1,2,3,4-tetrahydroquinolin-1-ylcarbonyl]-octanoic acid (N-butyl)amide and 1 ml of 4N-hydrochloric acid in dioxane and is purified by means of FC (10 g of silica gel, mobile phase N and O). The title compound is obtained as a pure stereoisomer: $R_f(O)$=0.25; $R_f(I)$=19.7 min.

The starting materials are prepared, for example, as follows:

a) 5(S)-Tert-butoxycarbonylamino-4(S)-hydroxy-2(R),7,7-trimethyl-8-[3(R)- or -3(S)-methoxycarbonyl-1,2,3,4-tetrahydroquinolin-1-ylcarbonyl]-octanoic acid (N-butyl) amide The title compound is obtained analogously to Example 20a) starting from 150 mg of (4O,5N-isopropylidene)-5(S)-tert-butoxycarbonylamino-4(S)-hydroxy-2(R),7,7-trimethyl-8-[3(R)- or 3(S)-methoxycarbonyl-1,2,3,4-tetrahydroquinolin-1-ylcarbonyl]-octanoic acid (N-butyl) amide and 5 mg of p-toluene sulfonic acid hydrate and is purified by means of FC (10 g of silica gel, mobile phase A): $R_f(X)$=0.45; $R_f(O)$=0.74; $R_f(II)$=26.4 min.

b) (4O,5N-Isopropylidene)-5(S)-tert-butoxycarbonylamino-4(S)-hydroxy-2(R),7,7-trimethyl-8-[3(R)- or 3(S)-methoxycarbonyl-1,2,3,4-tetrahydroquinolin-1-ylcarbonyl]-octanoic acid (N-butyl)amide The title compound is obtained starting from 183 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 115 mg of 3(R)- or 3(S)-methoxycarbonyl-1,2,3,4-tetrahydroquinoline in a manner analogous to that described in Example 1a) and is purified by means of FC (10 g of silica gel, mobile phase A): $R_f(A)$=0.32.

c) 3(R)- or 3(S)-Methoxycarbonyl-1,2,3,4-tetrahydroquinoline

The title compound is prepared analogously to Example 1r) starting from 495 mg of N-benzyloxycarbonyl-3(R)- or 3(S)-methoxycarbonyl-1,2,3,4-tetrahydroquinoline: $R_f(II)$= 3.5 min; $[\alpha]^D$ =−25.6 (c=0.7 in ethanol).

d) N-Benzyloxycarbonyl-3(R)- or 3(S)-methoxycarbonyl-1,2,3,4-tetrahydroquinoline The title compound is obtained starting from 1.5 g of N-benzyloxycarbonyl-3(R,S)-methoxycarbonyl-1,2,3,4-tetrahydroquinoline (Example 1s) by means of medium pressure chromatography over a Chiralcel® CA-1 column with 95% of ethanol as the eluting agent: $[\alpha]^D = -5.4$ (c=1.0 in chloroform).

EXAMPLE 22

(S)-Amino-4(S)-hydroxy-2(R),7,7-trimethyl-8-[3(R)- or 3(S)-methoxycarbonyl-1,2,3,4-tetrahydroquinolin-1-ylcarbonyl]-octanoic acid (N-butyl)amide In a manner analogous to that described in Example 21), the title compound is obtained starting from 59 mg of 5(S)-tert-butoxycarbonylamino-4(S)-hydroxy-2(R),7,7-trimethyl-8-[3(R)- or 3(S)-methoxycarbonyl-1,2,3,4-tetrahydroquinolin-1-ylcarbonyl]-octanoic acid (N-butyl) amide as the pure stereoisomer: $R_f(O)=0.25$; $R_t(I)=19.8$ min; FAB-MS: $(M+H)^+=490$.

The starting materials are prepared as follows:
a) 5(S)-Tert-butoxycarbonylamino-4(S)-hydroxy-2(R),7,7-trimethyl-8-[3(R)- or -3(S)-methoxycarbonyl-1,2,3,4-tetrahydroquinolin-1-ylcarbonyl]-octanoic acid (N-butyl)amide The title compound is prepared in a manner analogous to that described in Example 20a), starting from 126 mg of (4O,5N-isopropylidene)-5(S)-tert-butoxycarbonylamino-4(S)-hydroxy-2(R),7,7-trimethyl-8-[3(R)- oder 3(S)-methoxycarbonyl-1,2,3,4-tetrahydroquinolin-1-ylcarbonyl]-octanoic acid (N-butyl)amide and 5 mg of p-toluenesulfonic acid hydrate: $R_f(X)=0.44$; $R_f(O)=0.74$; $R_f(II)=26.5$ min.

b) (4O,5N-Isopropylidene)-5(S)-tert-butoxycarbonylamino-4(S)-hydroxy-2(R),7,7-trimethyl-8-[3[(R)- or 3(S)-methoxycarbonyl-1,2,3,4-tetrahydroquinolin-1-ylcarbonyl]-octanoic acid (N-butyl)amide The title compound is prepared in a manner analogous to that described in Example 1a), starting from 183 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 115 mg of 3(R)- or 3(S)-methoxycarbonyl-1,2,3,4-tetrahydroquinoline: $R_f(A)=0.32$.

c) 3(R)- or 3(S)-Methoxycarbonyl-1,2,3,4-tetrahydroquinoline

The title compound is prepared analogously to Example 1r) starting from 495 mg of N-benzyloxycarbonyl-3(R)- or 3(S)-methoxycarbonyl-1,2,3,4-tetrahydroquinoline: $R_f(II)=3.5$ min; $[\alpha]^D=+25.1$ (c=0.66 in ethanol).

d) N-Benzyloxycarbonyl-3(R)- or 3(S)-methoxycarbonyl-1,2,3,4-tetrahydroquinoline The title compound is obtained starting from 1.5 g of N-benzyloxycarbonyl-3(R,S)-methoxycarbonyl-1,2,3,4-tetrahydroquinoline (Example 1s) by means of medium pressure chromatography over a Chiralcel CA-1 column with 95% of ethanol as the eluting agent: $[\alpha]^D=+5.5$ (c=0.9 in chloroform).

Example 23
5(S)-Amino-4(S)-hydroxy-2(R),7,7-trimethyl-8-[3(R,S)-dimethylaminocarbonyl-1,2,3,4-tetrahydroquinolin-1-ylcarbonyl]-octanoic acid (N-butyl)amide In a manner analogous to that described in Example 21), the title compound is obtained starting from 29 mg of 5(S)-tert-butoxycarbonylamino-4(S)-hydroxy-2(R),7,7-trimethyl-8-[3(R,S)-dimethylaminocarbonyl-1,2,3,4-tetrahydroquinolin-1-ylcarbonyl]-octanoic acid (N-butyl) amide and 2 ml of 4N-hydrochloric acid in dioxane and is purified by means of FC (5 g of silica gel, mobile phase N and O): $R_f(O)=0.11$; $R_t(I)=18.2$ min; FAB-MS: $(M+H)^+=503$.

The starting materials are prepared, for example, as follows:
a) 5(S)-Tert-butoxycarbonylamino-4(S)-hydroxy-2(R),7,7-trimethyl-8-[3(R,S)-dimethylaminocarbonyl-1,2,3,4-tetrahydroquinolin-1-ylcarbonyl]-octanoic acid (N-butyl)amide The title compound is prepared in a manner analogous to that described in Example 20a) starting from 40 mg of (4O,5N-isopropylidene)-5(S)-tert-butoxycarbonylamino-4(S)-hydroxy-2(R),7,7-trimethyl-8-[3(R,S)-dimethylaminocarbonyl-1,2,3,4-tetrahydroquinolin-1-ylcarbonyl]-octanoic acid (N-butyl)amide with purification by means of FC (10 g of silica gel, mobile phase N), as a diastereomer mixture: $R_f(O)=0.30/0.33$.

b) (4O,5N-Isopropylidene)-5(S)-tert-butoxycarbonylamino-4(S)-hydroxy-2(R),7,7-trimethyl-8-[3(R,S)-dimethylaminocarbonyl-1,2,3,4-tetrahydroquinolin-1-ylcarbonyl]-octanoic acid (N-butyl)amide The title compound is prepared starting from 92 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 123 mg of 1,2,3,4-tetrahydroquinoline-3(R,S)-carboxylic acid (N,N-dimethyl)amide in a manner analogous to that in Example 2a), with purification by FC over 30 g of silica gel with a mobile phase gradient of A to ethyl acetate, as a mixture of stereoisomers: $R_f(A)=0.11/0.13$; $R_f(II)=17.2/17.4$ min.

c) 1,2,3,4-Tetrahydroquinoline-3(R,S)-carboxylic acid (N,N-dimethyl)amide

The title compound is prepared analogously to Example 1r) starting from 620 mg of N-benzyloxycarbonyl-1,2,3,4-tetrahydroquinoline-3(R,S)-carboxylic acid (N,N-dimethyl)amide and purified by recrystallization from diethyl ether/hexane: mp 130° C.

d) N-Benzyloxycarbonyl-1,2,3,4-tetrahydroquinoline-3(R,S)-carboxylic acid (N,N-dimethyl)amide The title compound is obtained in a manner analogous to that described in Example 1a) starting from 0.6 g of N-benzyloxycarbonyl-1,2,3,4-tetrahydroquinoline-3(R,S)-carboxylic acid, 0.55 ml of 1-chloro-N,N,2-trimethylpropenylamine and 0.3 ml of dimethylamine and is purified by means of FC (50 g of silica gel, mobile phase gradient from A to ethyl acetate): $R_f(A)=0.15$; MS: $(M)^+=338$.

EXAMPLE 24

5(S)-Amino-4(S)-hydroxy-2(R),7,7-trimethyl-8-[2(R,S)-butylaminocarbonyl-3,4-dihydro-2H-1,4-benzoxazin-4-ylcarbonyl]-octanoic acid (N-butyl)amide In an analogous manner to that described in Examples 2 and 2a) for the corresponding reaction stages, the title compound is obtained starting from 100 mg 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 205 mg of 2(R,S)-butylaminocarbonyl-3,4-dihydro-2H-1,4-benzoxazine via (4O,5N-isopropylidene)-5(S)-tert-butoxycarbonylamino-4(S)-hydroxy-2(R),7,7-trimethyl-8-[2(R,S)-butylaminocarbonyl-3,4-dihydro-2H-1,4-benzoxazin-4-ylcarbonyl]-octanoic acid (N-butyl)amide($R_f(Y)=0.33$) as a diastereomer mixture: $R_f(S)=0.27$; FAB-MS: $(M+H)^+=533$.

The amine component employed as the starting material is prepared, for example, as follows:

A mixture of 600 mg of 2(R,S)-ethoxycarbonyl-3,4-dihydro-2H-1,4-benzoxazine (Example 16)) and 1.2 ml of butylamine is stirred at 60° C. for 1 h. The reaction mixture is concentrated and the residue is purified directly by means of FC over 50 g of silica gel with a 20:1 mixture of methylene chloride and diethyl ether as the mobile phase. 2(R,S)-Butylaminocarbonyl-3,4-dihydro-2H-1,4-benzoxazine is obtained: $R_f$(20:1-mixture of methylene chloride and diethyl ether)=0.32.

EXAMPLE 25

5(S)-Amino-4(S)-hydroxy-2(R),7,7-trimethyl-8-[3(R,S)-butylaminocarbonyl-1,2,3,4-tetrahydroquinolin-1-ylcarbonyl]-octanoic acid (N-butyl)amide In an analogous manner to that described in Examples 2 and 2a) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 204 mg of 3(R,S)-butylaminocarbonyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)-butylaminocarbonyl-1,2,3,4-tetrahydroquinolin-1-yl-carbonyl]-octanoic acid (N-butyl)amide ($R_f(Y)$=0.18) as diastereomer mixture: $R_f(S)$=0.16; FAB-MS: $(M+H)^+$=531.

The amine component employed as the starting material is prepared, for example as follows:

A mixture of 500 mg of 3(R,S)-methoxycarbonyl-1,2,3,4-tetrahydroquinoline (Example 1r) and 1 ml of n-butylamine is stirred at 60° C. for 1 h. Purification of the crude product by means of FC over 50 g of silica gel (mobile phase Z) gives 3(R,S)-butylaminocarbonyl-1,2,3,4-tetrahydroquinoline: $R_f(Z)$=0.21.

EXAMPLE 26

5(S)-Amino-4(S)-hydroxy-2(R),7,7-trimethyl-8-[3(R,S)-morpholinocarbonyl-1,2,3,4-tetrahydroquinolin-1-ylcarbonyl-octanoic acid (N-butyl)amide In an analogous manner to that described in Examples 2 and 2a) for the corresponding reaction stages, the title compound is obtained starting from 183 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 195 mg of 1,2,3,4-tetrahydroquinoline-3(R,S)-carboxylic acid morpholinamide via (4O,5N-isopropylidene)-5(S)-tert-butoxycarbonylamino-4(S)-hydroxy-2(R),7,7-trimethyl-8-[3(R,S)-morpholinocarbonyl-1,2,3,4-tetrahydroquinolin-1-ylcarbonyl]-octanoic acid (N-butyl)amide ($R_f$(ethyl acetate)=0.22; $R_f$(II)=17.1/16.8 min) with FC purification over 5 g of silica gel (mobile phases N and O) as a diastereomer mixture: $R_f(O)$=0.08; $R_f(I)$=18.1 min; FAB-MS: $(M+H)^+$=545.

The amine component employed as the starting material is prepared, for example, as follows:

1.2 g of N-benzyloxycarbonyl-1,2,3,4-tetrahydroquinoline-3(R,S)-carboxylic acid, 1.1 ml of 1-chloro-N,N,2-trimethylpropenylamine and 0.67 ml of morpholine are reacted in a manner analogous to that described in Example 1a). Purification of the crude product by means of FC (50 g of silica gel, mobile phase gradient from A to ethyl acetate) gives N-benzyloxycarbonyl-1,2,3,4-tetrahydroquinoline-3(R,S)-carboxylic acid morpholine amide: $R_f(A)$=0.24; MS: $(M)^+$=380. 1.52 g of N-benzyloxycarbonyl-1,2,3,4-tetrahydroquinoline3(R,S)-carboxylic acid morpholine amide are reacted analogously to Example 1r). Recrystallization from methylene chloride/hexane gives 1,2,3,4-tetrahydroquinoline-3(R,S)-carboxylic acid morpholine amide: mp 155° C.; $R_f(O)$=0.78.

EXAMPLE 27

5(S)-Amino-4(S)-hydroxy-2(R),7,7-trimethyl-8-[2(R,S)-methylaminocarbonyl-3,4-dihydro-2H-1,4-benzothiazin-4-ylcarbonyl]-octanoic acid (N-butyl)amide 92 mg of 5(S)-Amino-4(S)-hydroxy-2(R),7,7-trimethyl-8-[2(R,S)-methoxycarbonyl-3,4-dihydro-2H-1,4-benzothiazin-4-ylcarbonyl]-octanoic acid (N-butyl)amide (Example 18)) are dissolved in 3 ml of a 5N methylamine solution in dimethylformamide and the solution is left to stand at room temperature for 26 h. After purification of the concentrated crude product by means of FC (mobile phase T) over 50 g of silica gel, the title compound is obtained as a diastereomer mixture: $R_f(T)$=0.26/0.31; FAB-MS: $(M+H)^+$=507.

EXAMPLE 28

5(S)-Amino-4(S)-hydroxy-2(R),7,7-trimethyl-8-[2(R,S)-methylaminocarbonyl-3,4-dihydro-2H-1,4-benzoxazin-4-ylcarbonyl]-octanoic acid (N-butyl)amide The title compound is obtained analogously to Example 27) starting from 30 mg of 5(S)-amino-4(S)-hydroxy-2(R),7,7-trimethyl-8-[2(R,S)-ethoxycarbonyl-3,4-dihydro-2H-1,4-benzoxazin-4-ylcarbonyl]-octanoic acid (N-butyl)amide (Example 16)) and 2 ml of a 5N methylamine solution in dimethylformamide: $R_f(S)$=0.14; FAB-MS: $(M+H)^+$=491.

EXAMPLE 29

5(S)-Amino-4(S)-hydroxy-2(R),7,7-trimethyl-8-[3(R,S)-acetyl-1,2,3,4-tetrahydroquinolin-4-ylcarbonyl]-octanoic acid (N-butyl)amide In an analogous manner to that described in Examples 2 and 2a) for the corresponding reaction stages, the title compound is obtained starting from 80 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 123 mg of 3(R,S)-acetyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)acetyl-1,2,3,4-tetrahydroquinolin-4-ylcarbonyl]-octanoic acid (N-butyl)amide ($R_f(Y)$=0.39) and purification by FC over 30 g of silica gel (mobile phase T) as a diastereomer mixture: $R_f(T)$=0.39; FAB-MS: $(M+H)^+$=474.

The starting materials are prepared, for example, as follows:

a) 3(R,S)-Acetyl-1,2,3,4-tetrahydroquinoline 868 mg of 1-benzyl-3(R,S)-acetyl-1,2,3,4-tetrahydroquinoline are hydrogenated to saturation in 100 ml of tetrahydrofuran in the presence of 100 mg of palladium-on-charcoal (10% of Pd) under normal pressure at room temperature. The reaction mixture is filtered and the concentrated filtrate is purified by means of FC over 50 g of silica gel (mobile phase B). This gives the title compound: $R_f(A)$=0.29; $R_f(D)$=0.08.

b) 1-Benzyl-3(R,S)-acetyl-1,2,3,4-tetrahydroquinoline 0.78 ml of oxalyl chloride is dissolved in 15 ml of methylene chloride and the solution is cooled to −65° C. First 0.85 ml of dimethyl sulfoxide and then a solution 1.6 g of 1-benzyl-3(R,S)-(1-hydroxyethyl)-1,2,3,4-tetrahydroquinoline and 3.3 ml of triethylamine in 25 ml of methylene chloride are added dropwise at this temperature. After 3 h, 10 ml of a 20% potassium hydrogen sulfate solution are added. The crude product is extracted with methylene chloride and purified by means of FC over 500 g of silica gel (mobile phase D): $R_f(D)$=0.27.

c) 1-Benzyl-3(R,S)-1hydroxyethyl-1,2,3,4-tetrahydroquinoline 1.12 ml of methyliodide are added dropwise to 0.435 g of magnesium powder, suspended in 50 ml of diethyl ether, in the course of 10 min. After the mixture has been subsequently stirred for 0.5 h, 1.5 g of 1-benzyl-3(R,S)-formyl- 1,2,3,4-tetrahydroquinoline, dissolved in 10 ml of diethyl ether, are added dropwise. The mixture is subsequently stirred for 0.5 h and then poured onto ice-water. The crude product extracted with methylene chloride is purified by means of FC over 150 g of silica gel (mobile phase B): $R_f(B)=0.31$; $R_f(D)=0.15$.

d) 1-Benzyl-3(R,S)-formyl-1,2,3,4-tetrahydroquinoline 5.4 g of 1-benzyl-3(R,S)-hydroxymethyl-1,2,3,4-tetrahydroquinoline are reacted with 2.8 ml oxalyl chloride, 3.0 ml dimethylsulfoxide and 12 ml triethylamine analogously to Example 29b). Purification by means of FC is carried out over 500 g of silica gel (mobile phase D): $R_f(D)=0.26$; $R_f(B)=0.41$.

e) 1-Benzyl-3(R,S)-hydroxymethyl-1,2,3,4-tetrahydroquinoline 6.24 g of 1-benzyl-3(R,S)-benzyloxycarbonyl-1,2,3,4-tetrahydroquinoline are dissolved in 60 ml of tetrahydrofuran, 920 mg of lithium borohydride are added and the mixture is stirred at room temperature for 4 h. 120 ml of methanol are then added dropwise, while cooling with ice, the reaction mixture is evaporated to dryness and the product is purified by means of FC over 250 g of silica gel (mobile phase Z): $R_f(Z)=0.36$.

f) 1-Benzyl-3(R,S)-benzyloxycarbonyl-1,2,3,4-tetrahydroquinoline 5.6 g of 1,2,3,4-tetrahydroquinoline-3(R,S)-carboxylic acid (Example 1t)) are stirred in 100 ml of dimethylformamide, with the addition of 12.7 ml of benzyl bromide and 25.1 g of caesium carbonate, at room temperature for 24 h. The concentrated crude product is then purified by means of FC over 250 g of silica gel with a 1:1 mixture of methylene chloride and hexane as the mobile phase. The title compound is obtained: $R_f(1:1$ mixture of methylene chloride and hexane$)=0.31$.

EXAMPLE 30

5(S)-Amino-4(S)-hydroxy-2(R),7,7-trimethyl-8-[2(R,S)-glycinylcarbonyl-3,4-dihydro-2H-1,4-benzoxazin-4-ylcarbonyl]-octanoic acid (N-butyl)amide In an analogous manner to that described in Examples 2 and 2a) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 384 mg of 2(R,S)-(tert-butoxycarbonylmethyl-aminocarbonyl)-3,4-dihydro-2H-1,4-benzoxazine via (4O,5N-isopropylidene)-5(S)-tert-butoxycarbonylamino-4(S)-hydroxy-2(R),7,7-trimethyl-8-[2(R,S)-(tert-butoxycarbonylmethylaminocarbonyl-3,4-dihydro-2H-1,4-benzoxazin-4-ylcarbonyl]-octanoic acid (N-butyl)amide ($R_f(Y)=0.45$), with purification by FC over 30 g of silica gel (mobile phase U), as a mixture of diastereomers: $R_f(U)=0.26$; $R_f(V)=0.52$; FAB-MS: $(M+H)^+=535$.

The amine component employed as the starting material is prepared, for example as follows:

1.0 g of 2(R,S)-ethoxycarbonyl-3,4-dihydro-2H-1,4-benzoxazine and 1.2 g of glycine-tert-butyl ester are heated at 80° C. in 10 ml of toluene. After 5 h, the mixture is evaporated and pure 2(R,S)-(tert-butoxycarbonylmethylaminocarbonyl)-3,4-dihydro-2H-1,4-benzoxazine is isolated by means of FC over 100 g of silica gel (mobile phase Z): $R_f(Z)=0.38$.

EXAMPLE 31

5(S)-Amino-4(S)-hydroxy-2(R),7,7-trimethyl-8-[3(R,S)-ethoxycarbonyl-1,2,3,4-tetrahydroquinolin-1-ylcarbonyl]-octanoic acid (N-butyl)amide In an analogous manner to that described in Examples 20 and 20a) for the corresponding reaction stages, the title compound is obtained starting from 58 mg of (4O,5N-isopropylidene)-5(S)-tert-butoxycarbonylamino-4(S)-hydroxy-2(R),7,7-trimethyl-8-[3(R,S)-ethoxycarbonyl-1,2,3,4-tetrahydroquinolin-1-ylcarbonyl]-octanoic acid (N-butyl)amide via 5(S)-tert-butoxycarbonylamino-4(S)-hydroxy-2(R),7,7-trimethyl-8-[3(R,S)-ethoxycarbonyl-1,2,3,4-tetrahydroquinolin-1-ylcarbonyl]-octanoic acid (N-butyl)amide ($R_f(A)=0.10$) with purification by means of FC (5 g of silica gel, mobile phase N): $R_f(O)=0.20$; $R_f(I)=20.8$ min; FAB-MS: $(M+H)^+=504$.

The starting materials are prepared, for example, as follows:

a) (4O,5N-Isopropylidene)-5(S)-tert-butoxycarbonylamino-4(S)-hydroxy-2(R),7,7-trimethyl-8-[3(R,S)-ethoxycarbonyl-1,2,3,4-tetrahydroquinolin-1-ylcarbonyl]-octanoic acid (N-butyl)amide The title compound is obtained starting from 69 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide, 0.01 ml of oxalyl chloride, 45 mg of 3(R,S)-ethoxycarbonyl-1,2,3,4-tetrahydroquinoline, 0.08 ml of diisopropylethylamine and 3 mg of 4-DMAP in a manner analogous to that described in Example 1a) and is purified by FC (20 g of silica gel, mobile phase B). The title compound is obtained as a diastereomer mixture: $R_f(A)=0.30$.

b) 3(R,S)-Ethoxycarbonyl-1,2,3,4-tetrahydroquinoline

The title compound is prepared analogously to Example 1r) starting from 1.55 g of N-benzyloxycarbonyl-3(R,S)-ethoxycarbonyl-1,2,3,4-tetrahydroquinoline. This gives the title compound: $R_f(A)=0.62$; $R_f(II)=4.7$ min.

c) N-Benzyloxycarbonyl-3(R,S)-ethoxycarbonyl-1,2,3,4-tetrahydroquinoline

The title compound is prepared analogously to Example 1s) starting from 1.5 g of N-benzyloxycarbonyl-1,2,3,4-tetrahydroquinoline-3(R,S)-carboxylic acid and 3.7 ml of N,N-dimethylformamide diethyl acetal and is purified by means of FC (100 g of silica gel, mobile phases D and B). This gives the title compound: $R_f(A)=0.75$; MS: $(M)^+=339$.

EXAMPLE 32

5(S)-Amino-4(S)-hydroxy-2(R),7,7-trimethyl-8-[3(R,S)-isopropoxycarbonyl-1,2,3,4-tetrahydroquinolin-1-ylcarbonyl]-octanoic acid (N-butyl)amide In an analogous manner to that described in Examples 20 and 20a) for the corresponding reaction stages, the title compound is obtained starting from 41 mg of (4O,5N-isopropylidene)-5(S)-tert-butoxycarbonylamino-4(S)-hydroxy-2(R),7,7-trimethyl-8-[3(R,S)-isopropoxycarbonyl-1,2,3,4-tetrahydroquinolin-1-ylcarbonyl]-octanoic acid (N-butyl)amide via 5(S)-tert-butoxycarbonylamino-4(S)-hydroxy-2(R),7,7-trimethyl-8-[3(R,S)-isopropoxycarbonyl-1,2,3,4-tetrahydroquinolin-1-ylcarbonyl]-octanoic acid (N-butyl)amide ($R_f(A)=0.15$; $R_f(II)=17.7$ min): $R_f(O)=0.28$; $R_f(I)=21.7$ min; FAB-MS: $(M+H)^+=518$.

The starting materials are prepared, for example, as follows:

a) (4O,5N-Isopropyliden)-5(S)-tert-butoxycarbonylamino-4(S)-hydroxy-2(R),7,7-trimethyl-8-[3(R,S)-isopropoxycarbonyl-1,2,3,4-tetrahydroquinolin-1-ylcarbonyl]-octanoic acid (N-butyl)amide The title compound is obtained starting from 69 mg of 3-[N-tert-butoxycarbonyl-4(S)-(3-carboxy-2,2-dimethylpropyloxy-2,2-dimethyl-1,3-oxazolidin-5(S)-yl]-2

(R)-methyl-propionic acid (N-butyl)amide and 88 mg of 3(R,S)-isopropoxycarbonyl-1,2,3,4-tetrahydroquinoline analogously to Example 31a) as a diastereomer mixture and is purified by FC (20 g of silica gel, mobile phase B): $R_f(A)=0.34$; $R_f(II)=32.7/32.8$ min.

b) 3(R,S)-Isopropoxycarbonyl-1,2,3,4-tetrahydrochinoline

The title compound is prepared analogously to Example 1r) starting from 2.19 g of N-benzyloxycarbonyl-3(R,S)-isopropoxycarbonyl-1,2,3,4-tetrahydroquinoline: $R_f(D)=0.37$; MS: $(M)^+=219$.

c) N-Benzyloxycarbonyl-3(R,S)-isopropoxycarbonyl-1,2,3,4-tetrahydroquinoline

The title compound is prepared analogously to Example 1s) starting from 1.87 g of N-benzyloxycarbonyl-1,2,3,4-tetrahydroquinoline-3(R,S)-carboxylic acid and 5.1 ml of N,N-dimethylformamide diisopropyl acetal $R_f(A)=0.78$; MS: $(M)^+=353$.

EXAMPLE 33

5(S)-Amino-4(S)-hydroxy-2(R),7,7-trimethyl-8-(6-bromo-1,2,3,4-tetrahydroquinolin-1ylcarybonyl)-octanoic acid N-butyl)amide In an analogous manner to that described in Examples 20 and 20a) for the corresponding reaction stages, the title compound is obtained starting from 74 mg of (4O,5N-isopropylidene)-5(S)-tert-butoxycarbonylamino-4(S)-hydroxy-2(R),7,7-trimethyl-8-(6-bromo-1,2,3,4-tetrahydroquinolin-1-ylcarbonyl)-octanoic acid (N-butyl) amide via 5(S)-tert-butoxycarbonylamino-4(S)-hydroxy-2(R),7,7-trimethyl-8-(6-bromo-1,2,3,4-tetrahydroquinolin-1-ylcarbonyl]-octanoic acid (N-butyl)amide ($R_f(A)=0.29$): $R_f(O)=0.20$; $R_f(I)=21.8$ min; FAB-MS: $(M+H)^+=510$.

The starting materials are prepared, for example, as follows:

a) (4O,5N-Isopropylidene)-5(S)-tert-butoxycarbonylamino-4(S)-hydroxy-2(R),7,7-trimethyl-8-(6-bromo-1,2,3,4-tetrahydroquinolin-1-ylcarbonyl)-octanoic acid (N-butyl)amide The title compound is obtained starting from 69 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 85 mg of 6-bromo-1,2,3,4-tetrahydroquinoline as described in Example 31a) and is purified by FC (20 g of silica gel, mobile phase B): $R_f(A)=0.50$.

b) 6-Bromo-12 3 4-tetrahydroquinoline is prepared starting from 6.7 g of 1,2,3,4-tetrahydroquinoline and 2.7 ml of bromine by a process analogous to that described by Z. Hoffman and W. Königs in Chemische Berichte, 16, 727 (1883).

EXAMPLE 34

5(S)-Amino-4(S)-hydroxy-2(R),7,7-trimethyl-8-[6-bromo-3(R,S)-ethoxycarbonyl-1,2,3,4-tetrahydroquinolin-1-ylcarbonyl]-octanoic acid (N-butyl)amide In an analogous manner to that described in Examples 20 and 20a) for the corresponding reaction stages, the title compound is obtained starting from 320 mg of (4O,5N-isopropylidene)-5(S)-tert-butoxycarbonylamino-4(S)-hydroxy-2(R),7,7-trimethyl-8-[6-bromo-3(R,S)-ethoxycarbonyl-1,2,3,4-tetrahydroquinolin-1-ylcarbonyl]-octanoic acid (N-butyl)amide ($R_f(A)=0.31$; $R_f(I)=29.6$ min), which is obtained analogously to the process in Example 1a) starting from 228 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl) amide and 240 mg of 6-bromo-3(R,S)-ethoxycarbonyl-1,2,3,4-tetrahydroquinoline, via 5(S)-tert-butoxycarbonyl-amino-4(S)-hydroxy-2(R),7,7-trimethyl-8-[6-bromo-3(R,S)-ethoxycarbonyl-1,2,3,4-tetrahydroquinolin-1-ylcarbonyl]-octanoic acid (N-butyl)amide ($R_f(X)=0.50$; $R_f(II)=26.9/27.1$ min) as a mixture of diastereomers: $R_f(O)=0.21$; $R_f(I)=22.7$ min; FAB-MS: $(M+H)^+=582$.

The amine component employed as the starting material is prepared, for example, as follows:

Analogously to Example 33b), starting from 410 mg of 3(R,S)-ethoxycarbonyl-1,2,3,4-tetrahydroquinoline and 0.11 ml of bromine, 6-bromo-3(R,S)-ethoxycarbonyl-1,2,3, 4-tetrahydroquinoline is obtained: $R_f(D)=0.15$; MS: $(M)^+=285$.

EXAMPLE 35

5(S)-Amino-4(S)-hydroxy-7,7-dimethyl-8-[2(R,S)-methoxycarbonyl-3,4-dihydro-2H-1,4-benzothiazin-4-ylcarbonyl]-octanoic acid (N-butyl)amide In an analogous manner to that described in Examples 2 and 2a) for the corresponding reaction stages, the title compound is obtained starting from 205 mg of 3-[N-tert-butoxycarbonyl-4(S)-(3-carboxy-2,2-dimethylpropyloxy-2,2-dimethyl-1,3-oxazolidin-5(S)-yl]-propionic acid (N-butyl)amide and 581 mg of 2(R,S)-methoxycarbonyl-3,4-dihydro-2H-1,4-benzothiazine (Example 18) via (4O,5N-isopropylidene)-5(S)-tert-butoxycarbonylamino-4(S)-hydroxy-7,7-dimethyl-8-[2(R,S)-methoxycarbonyl-3,4-dihydro-2H-1,4-benzothiazin-4-yl-carbonyl]-octanoic acid (N-butyl)amide (purification over 80 g of silica get with a 20:1 mixture of methylene chloride and diethyl ether to a 1:1 mixture as the mobile phase gradient; $R_f(1:1$ mixture of methylene chloride and diethyl ether$)=0.43$), with purification by FC over 30 g of silica gel (mobile phase S): $R_f(S)=0.32$; FAB-MS: $(M+H)^{3O}=494$. The starting materials are prepared, for example, as follows:

a) 3-[N-Tert-butoxycarbonyl-4(S)-(3-carboxy-2,2-dimethylpropyl)-2,2-dimethyl-1,3-oxazolidin-5(S)-yl]-propionic acid (N-butyl)amide The title compound is obtained by oxidation analogously to Example 1b) starting from 268 mg of 3-[N-tert-butoxycarbonyl-4(S)-(4-hydroxy-2,2-dimethylbutyl)-2,2-dimethyl-1,3-oxazolidin-5(S)-yl]-propionic acid (N-butyl) amide, 802 mg of sodium periodidate, 17 mg of ruthenium (III) chloride hydrate in 5 ml of acetonitrile, 5 ml of carbon tetrachloride and 10 ml of water. Purification is carried out over 50 g of silica gel (mobile phase U): $R_f(U)=0.33$.

b) 3-[N-Tert-butoxycarbonyl-4(S)-(4-hydroxy-2,2-dimethylbutyl)-2,2-dimethyl-1,3-oxazolidin-5(S)-yl]-propionic acid (N-butyl)amide The title compound is obtained analogously to Example 1c) starting from 490 mg of 3-[N-tert-butoxycarbonyl-4(S)-(2,2-dimethyl-4-triisopropylsilyoxybutyl)-2,2-dimethyl-1,3-oxazolidin-5(S)-yl]-propionic acid (N-butyl)amide and 396 mg of tetrabutylammonium fluoride trihydrate. Purification is carried out over 80 g of silica gel (ethyl acetate as the mobile phase): $R_f$(ethyl acetate)$=0.40$.

c) 3-[N-Tert-butoxycarbonyl-4(S)-(2,2-dimethyl-4-triisopropylsilyloxybutyl)-2,2-dimethyl-1,3-oxazolidin-5(S)-yl]-propionic acid {(N-butyl)amide The title compound is obtained by reacting 500 mg of 3-[N-tert-butoxycarbonyl-2,2-dimethyl-4(S)-(2,2-dimethyl-4-triisopropylsilyloxybutyl)-1,3-oxazolidin-5(S)-yl]-propionic acid in 15 ml of tetrahydrofuran with 0.2 ml of N-methylmorpholine and 0.26 ml of isobutyl chloroformate at −40° C. and, after 1 h at 0° C., adding 0.75 ml of n-butylamine to the reaction mixture. After 1 h at room temperature, this mixture is poured onto 1N hydrochloric acid and the amide is extracted with methylene chloride. Purification is carried out over 50 g of silica gel (mobile phase B). This gives the title compound: $R_f(B)=0.28$; $R_f(T)=0.60$.

d) 3-[N-Tert-butoxycarbonyl-2,2-dimethyl-4(S)-(2,2-dimethyl-4-triisopropylsilyloxybutyl)-1,3-oxazolidin-5(S)-yl]-propionic acid 1.48 g of 4-[N-tert-butoxycarbonyl-2,2-dimethyl-4(S)-(2,2-dimethyl-4-triisopropylsilyloxybutyl)-1,3-oxazolidin-5(S)-yl]-but-1-ene are oxidized with 78 mg of ruthenium(III) chloride hydrate and 3.71 g of sodium periodate in a mixture of 21 ml of acetonitrile, 21 ml of carbon tetrachloride and 39 ml of water. The crude product is purified over 250 g of silica gel (mobile phase: first T, then U). The title compound is obtained as a brownish oil: $R_f(T)=0.25$.

e) 4-[N-Tert-butoxycarbonyl-2,2-dimethyl-4(S)-(2,2-dimethyl-4-triisopropylsilyloxybutyl)-1,3-oxazolidin-5(S)-yl]-but-1-ene 1.80 g of 6(S)-tert-butoxycarbonylamino-8,8-dimethyl-5(S)-hydroxy-10-triisopropylsilyloxydec1-ene are stirred in 10 ml each of methylene chloride and dimethoxypropane with 50 mg of p-toluenesulfonic acid hydrate at room temperature for 2 h. After the mixture has been concentrated, the residue is purified over 250 g of silica gel with a 1:20 mixture of ethyl acetate and hexane as the mobile phase: $R_f(1:20$ mixture of ethyl acetate and hexane$)=0.40$.

f) 6(S)-Tert-butoxycarbonylamino-8,8-dimethyl-5(S)-hydroxy-10-triisopropylsilyloxydec-1-ene The Grignard reagent is prepared from 3.70 ml of 4-bromo-1-butene and 880 mg of magnesium powder in 50 ml of tetrahydrofuran at 55° C. This solution is then added dropwise to a solution of 3.0 g of 2(S)-tert-butoxycarbonylamino-6-triisopropylsilyloxy-4,4-dimethyl-hexanal (Example 1g)) in 25 ml of tetrahydrofuran at 5°–10° C. 1 h after the end of the addition, the mixture is poured onto a 0.1N hydrochloric acid solution, extracted with methylene chloride and concentrated. The crude product contains the two 5(S):5(R) diastereomers in a ratio of about 5:1. The title compound (non-polar diastereomer) is obtained by purification over 250 g of silica gel (mobile phase E): $R_f(E)=0.30$.

EXAMPLE 36

5(S)-Amino-4(S)-hydroxy-2(R),7,7-trimethyl-8-[3,3-bis(methoxycarbonyl)-1,2,3,4-tetrahydroquinolin-1-ylcarbonyl]-octanoic acid (N-butyl)amide In an analogous manner to that described in Examples 2 and 2a) for the corresponding reaction stages, the title compound is obtained starting from 80 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 380 mg of 3,3-bis(methoxycarbonyl)-1,2,3,4-tetrahydroquinoline via (4O,5N-isopropylidene)-5(S)-tert-butoxycarbonylamino-4(S)-hydroxy-2(R),7,7-trimethyl-8-[3,3-bis(methoxycarbonyl)-1,2,3,4-tetrahydroquinolin-1-ylcarbonyl]-octanoic acid (N-butyl)amide ($R_f(A)=0.22$): $R_f(S)=0.18$; FAB-MS: (M+H)$^+$=548.

The amine component employed as the starting material is prepared, for example, as follows:

1.00 g of N-benzyloxycarbonyl-3(R,S)-methoxycarbonyl-1,2,3,4-tetrahydroquinoline (Example 1s)) are deprotonated in 10 ml of tetrahydrofuran with excess lithium diisopropylamide (1.5 equivalents) under customary reaction conditions, and 0.80 ml of methyl chloroformate is then added at −70° C. After 30 min, the mixture is poured onto 0.1N hydrochloric acid and extracted with methylene chloride. The crude product obtained after customary further working up is dissolved in 30 ml of tetrahydrofuran and hydrogenated in the presence of 1.00 g of palladium-on-charcoal (10% of Pd) until the reaction has ended. After purification of the product over 100 g of silica gel (mobile phase B), 3,3-bis(methoxycarbonyl)-1,2,3,4-tetrahydroquinoline is obtained: $R_f(B)=0.50$.

EXAMPLE 37

5(S)-Amino-4(S)-hydroxy-2(R,S)-isopropyl-7,7-dimethyl-8-[2(R,S)-methoxycarbonyl-3,4-dihydro-2H-1,4-benzothiazin-4-ylcarbonyl]-octanoic acid (N-butyl)amide In an analogous manner to that described in Examples 2 and 2a) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R,S)-isopropyl-propionic acid (N-butyl)amide and 215 mg of 2(R,S)-methoxycarbonyl-3,4-dihydro-2H-1,4-benzothiazine via (4O,5N-isopropylidene)-5(S)-tert-butoxycarbonylamino-4(S)-hydroxy-2(R,S)-isopropyl-7,7-dimethyl-8-[2(R,S)-methoxycarbonyl-3,4-dihydro-2H-1,4-benzothiazin-4-ylcarbonyl]-octanoic acid (N-butyl)amide (purification over 30 g of silica gel (mobile phase Z); $R_f(B)=0.33$), with purification by FC over 30 g of silica gel (mobile phase S), as a diastereomer mixture: $R_f(S)=0.35$; FAB-MS: (M+H)$^+$=536.

The starting materials are prepared, for example, as follows:

a) 3-[N-Tert-butoxycarbonyl-4(S)-(3-carboxy-2,2-dimethylpropyloxy-2,2-dimethyl-1,3-oxazolidin-5(S)-yl]-2(R,S)-isopropyl-propionic acid (N-butyl)amide 970 mg of 3-[N-tert-butoxycarbonyl-4(S)-(4-hydroxy-2,2-dimethylbutyloxy-2,2-dimethyl-1,3-oxazolidin-5(S)-yl]-2(R,S)-isopropyl-propionic acid (N-butyl)amide are oxidized with 2.6 g of sodium periodate and 55 mg of ruthenium(III) chloride hydrate analogously to Example 1b). Purification over 165 g of silica gel (mobile phase S) gives the pure title compound as a diastereomer mixture: $R_f(S)=0.44$.

b) 3-[N-Tert-butoxycarbonyl-4(S)-(4-hydroxy-2,2-dimethylbutyloxy-2,2-dimethyl-1,3-oxazolidin-5(S)-yl]-2(R,S)-isopropyl-propionic acid (N-butyl)amide 1.43 g of 3-[N-tert-butoxycarbonyl-4(S)-(4-triisopropylsilyloxy-2,2-dimethylbutyloxy-2,2-dimethyl-1,3-oxazolidin-5(S)-yl]-2(R,S)-isopropyl-propionic acid (N-butyl)amide are treated with 1.1 g of tetrabutylammonium fluoride trihydrate in 25 ml of tetrahydrofuran analogously to Example 1c). Purification by FC over 150 g of silica gel (mobile phase A) gives the title compound as a diastereomer mixture: $R_f(A)=0.40$.

c) 3-[N-Tert-butoxycarbonyl-4(S)-(4-triisopropylsilyoxy-2,2-dimethylbutyloxy-2,2-dimethyl-1,3-oxazolidin-5(S)-yl]-2(R,S)-isopropyl-propionic acid (N-butyl)amide 0.98 g of 3-[N-tert-butoxycarbonyl-2,2-dimethyl-4(S)-(4-triisopropylsilyloxy-2,2-dimethylbutyl)-1,3-oxazolidin-5(S)-yl]-2(R,S)-isopropyl-propionic acid is reacted with 0.4 ml of N-methylmorpholine, 0.5 ml of isobutyl chloroformate and 1.5 ml of n-butylamine analogously to Example 35c). Purification by FC (mobile phase D) over 250 g of silica gel gives the mixture of two diastereomers: $R_f(D)=0.40/0.31$.

d) 3-[N-Tert-butoxycarbonyl-2,2-dimethyl-4(S)-(4-triisopropylsilyloxy-2,2-dimethylbutyl)-1,3-oxazolidin-5(S)-yl]-2(R,S)-isopropyl-propionic acid 3.6 g of 4-[N-tert-butoxycarbonyl-2,2-dimethyl-4(S)-(4-triisopropylsilyloxy-2,2-dimethylbutyl)-1,3-oxazolidin-5(S)

-yl]-3(R,S)-isopropylbut-1-ene are oxidized with 8.3 g of sodium periodidate and 176 mg of ruthenium(III) chloride hydrate analogously to Example 35d).

Purification by FC (mobile phase T) over 500 g of silica gel gives the title compound: $R_f(T)=0.36$.

e) 4-[N-Tert-butoxycarbonyl-2,2-dimethyl-4(S)-(4-triisopropylsilyloxy-2,2-dimethylbutyl)-1,3-oxazolidin-5(S)-yl]-3(R,S)-isopropylbut-1-ene 4.4 g of 6(S)-tert-butoxycarbonylamino-8,8-dimethyl-5(S)-hydroxy-3(R,S)-isopropyl-10-triisopropylsilyloxydec-1-ene and 134 mg of p-toluenesulfonic acid hydrate are stirred in 25 ml of methylene chloride and dimethoxypropane at room temperature for 2 h. After the reaction mixture has been concentrated, the residue is purified over 500 g of silica gel by means of FC (mobile phase D): $R_f(D)=0.61$.

f) 6(S)-Tert-butoxycarbonylamino-5(S)-hydroxy-3(R,S)-isopropyl-10-triisopropylsilyloxy-8,8-dimethyldec-1-ene The title compound is prepared in a manner analogous to that described in Example 35f) starting from 23.9 g of 1-bromo-2(R,S)-isopropyl-3-butene (preparation according to D. Mesnard et al., C.R. Acad. Sci. Paris, t. 277, Series C-567), 3.3 g of magnesium powder and 11.25 g of 2(S)-tert-butoxycarbonylamino-6-triisopropylsilyloxy-4,4-dimethyl-hexanal (Example 1g). The crude product is purified by FC over 900 g of silica gel (mobile phase E) to give the title compound as a diastereomer mixture: $R_f(E)=0.31$.

EXAMPLE 38

5(S)-Amino-4(S)-hydroxy-2(R,S)-isopropyl-7,7-dimethyl-8-[(R,S)-methoxycarbonyl-3,4-dihydro-2H-1,4-benzoxazin-4-ylcarbonyl]-octanoic acid (N-butyl)amide In an analogous manner to that described in Examples 2 and 2a) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R,S)-isopropyl-propionic acid (N-butyl)amide (Example 37a) and 213 mg of 2(R,S)-methoxycarbonyl-3,4-dihydro-2H-1,4-benzoxazine (Arch. Pharmacol. 315, 538 (1982)) via (4O,5N-isopropylidene)-5(S)-tert-butoxycarbonylamino-4(S)-hydroxy-2(R,S)-isopropyl-7,7-dimethyl-8-[2(R,S)-methoxycarbonyl-3,4-dihydro-2H-1,4-benzoxazin-4-ylcarbonyl]-octanoic acid (N-butyl)amide ($R_f(Z)=0.30$) as a mixture of diasteromers: $R_f(S)=0.34$; FAB-MS: $(M+H)^+=520$.

EXAMPLE 39

5(S)-Tert-butoxycarbonylamino-4(S)-hydroxy-2(S)-isopropyl-7,7dimethyl-8-[2(R,S)-methylaminocarbonyl-3,4-dihydro-2H-1,4-benzothiazin-4-ylcarbonyl]-octanoic acid (N-butyl)amide In a manner analogous to that described in Example 20a), starting from 535 mg of (4O,5N-isopropylidene)-5(S)-tert-butoxycarbonylamino-4(S)-hydroxy-2(S)-isopropyl-7,7-dimethyl-8-[2(R,S)-methylaminocarbonyl-3,4-dihydro-2H-1,4-benzothiazin-4-ylcarbonyl]-octanoic acid (N-butyl)amide ($R_f(D)=0.44$), which is prepared from 500 mg of 3-[N-tert-butoxycarbonyl-4(S)-(3-carboxy-2,2-dimethylpropyloxy-2,2-dimethyl-1,3-oxazolidin-5(S)-yl]-2(S)isopropyl-propionic acid (N-butyl)amide and 859 mg of 2(R,S)-methylaminocarbonyl-3,4-dihydro-2H-1,4-benzothiazine in an analogous manner to that described in Example 1a) and is purified by FC over 150 g of silica gel with a mobile phase gradient from D to ethyl acetate, with purification by means of FC over 30 g of silica gel (mobile phase D), as a diastereomer mixture: $R_f(D)=0.22/0.33$; $R_f$(ethyl acetate)=0.39/0.50; FAB-MS: $(M+H)^+=635$.

The 2(R,S)-methylaminocarbonyl-3,4-dihydro-2H-1,4-benzothiazine employed as the starting material is prepared, for example, as follows:

880 mg of 2(R,S)-methoxycarbonyl-3,4-dihydro-2H-1,4-benzothiazine (Example 18) are dissolved in 8 ml of a 3N methylamine solution in dimethylformamide and the solution is left to stand at room temperature for 20 h. The concentrated reaction mixture is then purified by means of FC over 80 g of silica gel (mobile phase D) to give the title compound: $R_f(D)=0.38$.

The diastereomerically pure 3-[N-tert-butoxycarbonyl-4(S)-(3-carboxy-2,2-dimethylpropyloxy-2,2-dimethyl-1,3-oxazolidin-5(S)-yl]-2(S)-isopropyl-propionic acid (N-butyl) amide employed as the starting material is obtained, for example, as follows:

a) Oxidation of 7.0 g of 3-[N-tert-butoxycarbonyl-4(S)-(4-hydroxy-2,2-dimethylbutyloxy-2,2-dimethyl-1,3-oxazolidin-5(S)-yl]-2(S)-isopropyl-propionic acid (N-butyl) amide with 12.8 g of sodium periodate and 140 mg of ruthenium(III) chloride hydrate analogously to Example 1b) and purification over 300 g of silica gel (mobile phase S) gives the title compound: $R_f(S)=0.44$; $R_f(O)=0.62$.

b) 3-[N-Tert-butoxycarbonyl-4(S)-(4-hydroxy-2,2-dimethylbutyloxy-2,2-dimethyl-1,3-oxazolidin-5(S)-yl]-2(S)-isopropyl-propionic acid (N-butyl)amide The title compound is prepared by hydrogenation of 10.0 g of 3-[N-tert-butoxycarbonyl-4(S)-(4-benzyloxy-2,2-dimethylbutyloxy-2,2-dimethyl-1,3-oxazolidin-5(S)-yl]-2(S)-isopropyl-propionic acid (N-butyl)amide in the presence of 2.0 g of palladium-on-charcoal (5% of Pd, Degussa) in 200 ml of tetrahydrofuran at room temperature under normal pressure for 3 h. The reaction mixture is filtered over Hyflo® and concentrated. Purification is carried out by FC over 300 g of silica gel (mobile phase A and ethyl acetate). The pure title compound is obtained as white crystals: mp 132°–3° C.; $R_f(A)=0.22$; $[\alpha]^D=46.5$ (c=1.0 in chloroform); FAB-MS: $(M+H)^+=471$; anal. calc. for $C_{26}H_{50}N_2O_5$: C 66.35%, H 10.71%, N 5.95%; found. C 66.23%, H 10.86%, N 5.93%.

c) 3-[N-Tert-butoxycarbonyl-4(S)-(4-benzyloxy-2,2-dimethylbutyloxy-2,2-dimethyl-1,3-oxazolidin-5(S)-yl]-2(S)-isopropyl-propionic acid (N-butyl)amide 27.5 g of 3-[N-butoxycarbonyl-4(S)(4-benzyloxy-2,2-dimethylbutyloxy-2,2-dimethyl-1,3-oxazolidin-5(S)-yl]-2-(R,S)-isopropyl-propionic acid are reacted with 11.4 ml of 1-chloro-N,N,2-trimethylpropenylamine and 10.7 ml of n-butylamine analogously to Example 1a). The diastereomer mixture is separated by means of FC over 800 g of silica gel with a mobile phase gradient (from a 10:1 mixture to a 3:1 mixture) of toluene and ethyl acetate. This gives the pure title compound (diastereomer I): $R_f$ (3:1 mixture of toluene and ethyl acetate)=0.36; FAB-MS: $(M+H)^+=461$; and diastereomer II: $R_f$(3:1 mixture of toluene and ethyl acetate)= 0.28; FAB-MS: $(M+H)^+=461$.

d) 3-[N-Tert-butoxycarbonyl-4(S)(4-benzyloxy-2,2-dimethylbutyloxy-2,2-dimethyl-1,3-oxazolidin-5(S)-yl]-2-(R,S)-isopropyl-propionic acid 30 g of 4-[3-tert-butoxycarbonyl-4(S)(4-benzyloxy-2,2-dimethylbutyloxy-2,2-dimethyl-1,3-oxazolidin-5(S)-yl]-3-(R,S)-isopropylbut-1-ene are oxidized with 52.8 g of sodium periodate and 600 mg of ruthenium(III) chloride hydrate analogously to Example 37d). Purification of the title compound is carried out by FC (mobile phases B and D) over 900 g of silica gel: $R_f(A)=0.22$.

e) 4-[N-Tert-butoxycarbonyl-4(S)(4-benzyloxy-2,2-dimethylbutyloxy-2,2-dimethyl-1,3-oxazolidin-5(S)-yl]-3-(R,S)-isopropylbut-1-ene 44.8 g of 10-benzyloxy-6(S)-tert-butoxycarbonylamino-5(S)-hydroxy-3(R,S)-isopropyl-8,8-dimethyldec-1-ene and 1.2 g of p-toluenesulfonic acid hydrate are stirred in 150 ml of methylene chloride and 60 ml of dimethoxypropane at room temperature for 20 h. After the reaction mixture has been concentrated, the residue is purified directly over 900 g of silica gel by means of FC (mobile phase G): $R_f(D)=0.56$; FAB-MS: $(M+H)^+=488$.

f) 10-Benzyloxy-6(S)-tert-butoxycarbonylamino-5(S)-hydroxy-3(R,S)-isopropyl-8,8-dimethyldec-1-ene 88.5 g of 1-bromo-2(R,S)-isopropyl-3-butene, 13 g of magnesium powder and 41.9 g of 6-benzyloxy-2(S)-tert-butoxycarbonylamino-4,4-dimethyl-hexanal are reacted in a manner analogous to that described in Example 37f). Purification is carried out by FC over 1 kg of silica gel (mobile phases G and E): $R_f(3:1$ mixture of toluene and ethyl acetate)=0.47; $R_f(I)=33.8/34.2$ min; FAB-MS: $(M+H)^+=520$.

g) 6-Benzyloxy-2(S)-tert-butoxycarbonylamino-4,4-dimethyl-hexanal

The title compound is prepared starting from 28.1 g of 6-benzyloxy-2(S)-tert-butoxycarbonylamino-4,4-dimethyl-hexan-1-ol, 10.5 ml of oxalyl chloride, 11.4 ml of dimethyl sulfoxide and 45 ml of triethylamine analogously to Example 1g): $R_f(A)=0.62$; $R_f(I)=28.1$ min; FAB-MS: $(M+H)^+=350$.

h) 6-Benzyloxy-2(S)-tert-butoxycarbonylamino-4,4-dimethyl-hexan-1-ol

The title compound is prepared starting from 75.2 g of 4(S)-(4-benzyloxy-2,2-dimethylbutyl)-3-tert-butoxycarbonyl-2,2-dimethyl-1,3-oxazolidine and 2.0 g of p-toluenesulfonic acid hydrate in 500 ml of methanol analogously to Example 20a): $R_f(A)=0.31$; FAB-MS: $(M+H)^+=352$; anal. calc. for $C_{20}H_{33}NO_4$: C68.34%, H9.46%, N3.99%; found C68.14%, H9.37%, N3.98%.

i) 4(S)-(4-Benzyloxy-2,2-dimethylbutyl)-3-tert-butoxycarbonyl-2,2-dimethyl-1,3-oxazolidine A solution of 55 g of 3-tert-butoxycarbonyl-4(S)-(4-hydroxy-2,2-dimethylbutyloxy-2,2-dimethyl-1,3-oxazolidine (Example 1j), dissolved in 150 ml of tetrahydrofuran, is added to a suspension of 10 g of potassium hydride in 300 ml of tetrahydrofuran at 0° C. After the mixture has been stirred at 25° C. for 1 h and cooled to 0° C., 23 ml of benzylbromide are added dropwise and the mixture is then stirred at room temperature for 1 h. The reaction mixture is diluted cautiously with 400 ml of water and extracted with diethyl ether. The crude product is purified by means of FC (500 g of silica gel, mobile phase F): $R_f(D)=0.47$; $[\alpha]^D=+27.8$ (c=1.0 in chloroform); FAB-MS: $(M+H)^+=392$; anal. calc. for $C_{23}H_{37}NO_4$: C70.55%, H9.52%, N3.58%; found C70.74%, H9.59%, N3.64%.

EXAMPLE 40

5(S)-Amino-4(S)-hydroxy-2(S)-isopropyl-7,7-dimethyl-8-[2(R,S)-methylaminocarbonyl-3,4-dihydro-2H-1,4-ylcarbonyl]octanoic acid (N-butyl)amide The title compound is obtained starting from 294 mg of 5(S)-tert-butoxycarbonylamino-4(S)-hydroxy-2(S)-isopropyl-7,7-dimethyl-8-[2(R,S)-methylaminocarbonyl-3,4-dihydro-2H-1,4-benzothiazin-4-ylcarbonyl]-octanoic acid (N-butyl)amide (Example 39) in a manner analogous to that described in Example 1) as a diastereomer mixture: $R_f(S)=0.36$ (double spot); FAB-MS: $(M+H)^+=535$.

EXAMPLE 41

5(S)-Amino-4(S)-hydroxy-2(R,S)-isopropyl-7,7-dimethyl-8-(1,2,3,4-tetrahydroquinolin-1-ylcarbonyl)-octanoic acid (N-butyl)amide In an analogous manner to that described in Examples 1 and 1a) for the corresponding reaction stages, the title compound is obtained starting from 200 mg of 3-[N-tert-butoxycarbonyl-4(S)-(3-carboxy-2,2-dimethylpropyloxy-2,2-dimethyl-1,3-oxazolidin-5(S)-yl]-2(R,S)-isopropyl-propionic acid (N-butyl)amide (Example 37a)) and 0.2 ml of 1.2.3,4-tetrahydroquinoline via (4O,5N-isopropylidene)-5(S)-tert-butoxycarbonylamino-4(S)-hydroxy-2(R,S)-isopropyl-7,7-dimethyl-8-(1,2.3,4-tetrahydroquinolin-1-yl) carbonyl]-octanoic acid (N-butyl)amide (purification of 50 g of silica gel with a mobile phase gradient from a 20:1 to a 9:1 mixture of methylene chloride and diethyl ether; $R_f(9:1$ mixture of methylene chloride and diethyl ether)=0.30) as a diastereomer mixture: $R_f(S)=0.34$; FAB-MS: $(M+H)^+=461$.

EXAMPLE 42

5(S)-Amino-4(S)-hydroxy-2(R,S)-isopropyl-7,7-dimethyl-8-[2(R,S)-carbamoyl-3,4-dihydro-2H-1,4-benzothiazin-4-ylcarbonyl]-octanoic acid (N-butyl)amide In an analogous manner to that described in Examples 1 and 1a) for the corresponding reaction stages, the title compound is obtained starting from 100 mg of 3-[N-tert-butoxycarbonyl-4(S)-(3-carboxy-2,2-dimethylpropyloxy-2, 2-dimethyl-1,3-oxazolidin-5(S)-yl]-2(R,S)-isopropyl-propionic acid (N-butyl)amide (Example 37a)) and 160 mg of 2(R,S)-carbamoyl-3,4-dihydro-2H-1,4-benzothiazine via (4O,5N-isopropylidene)-5(S)-tert-butoxycarbonylamino-4 (S)-hydroxy-2(R,S)-isopropyl-7,7-dimethyl-8-[2(R,S)-carbamoyl-3,4-dihydro-2H-1,4-benzothiazin-4-ylcarbonyl]-octanoic acid (N-butyl)amide $(R_f(Y)=0.42)$ as a diastereomer mixture: $R_f(S)=0.37$; FAB-MS: $(M+H)^+=521$.

The amine component employed is prepared, for example, as follows:

580 mg of 2(R,S)-methoxycarbonyl-3,4-dihydro-2H-1,4-benzothiazine are dissolved in 3 ml of a 6N ammonia solution in methanol and the solution is stirred at 50° C. for 16 h. Purification by chromatography over 50 g of silica gel gives 2(R,S)-carbamoyl-3,4-dihydro-2H-1,4-benzothiazine: $R_f(Y)=0.19$.

EXAMPLE 43

5(S)-Amino-4(S)-hydroxy-2(R),7,7-trimethyl-8-[2(R,S)-methoxycarbonyl-3,4-dihydro-2H-1,4-benzoxazin-4-ylcarbonyl]-octanoic acid (N-butyl)amide In an analogous manner to that described in Examples 1 and 1a) for the corresponding reaction stages, the title compound is obtained starting from 400 mg of 3-[N-tert-butoxycarbonyl-4(S)-(3-carboxy-2,2-dimethylpropyloxy-2, 2-dimethyl-1,3-oxazolidin-5(S)-yl]-2(R)-methyl-propionic acid (N-butyl)amide and 1.02 g of 2(R,S)-methoxycarbonyl-3,4-dihydro-2H-1,4-benzoxazine via (4O,5N-isopropylidene)-5(S)-tert-butoxycarbonylamino-4(S)-hydroxy-2(R),7,7-trimethyl-8-[2(R,S)-methoxycarbonyl-3, 4-dihydro-2H-1,4-benzoxazin-4-ylcarbonyl]-octanoic acid (N-butyl)amide $(R_f(Y)=0.55)$ as a diastereomer mixture: $R_f(T)=0.40$; FAB-MS: $(M+H)^+=492$.

EXAMPLE 44

5(S)-Amino-4(S)-hydroxy-2(R),7,7-trimethyl-8-[3(R,S)-hydroxymethyl-1,2,3,4-tetrahydroquinolin-1-ylcarbonyl]-octanoic acid (N-butyl)amide 137 mg of tetrabutylammonium fluoride are added to a solution of 165 mg of (4O,5N-isopropylidene)-5(S)-tert-butoxycarbonylamino-4(S)-hydroxy-2(R),7,7-trimethyl-8-[3(R,S)-(tert-butyldimethylsilyloxymethyl)-1,2,3,4- tetrahydroquinolin-1-ylcarbonyl]-octanoic acid (N-butyl) amide in 3 ml of tetrahydrofuran and the mixture is stirred at room temperature for 1 h. The reaction mixture is concentrated and the residue is then reacted directly in 5 ml of 95% trifluoroacetic acid analogously to Example 1). Purification by means of FC over 30 g of silica gel (mobile phase S) gives the title compound as a diastereomer mixture: $R_f(T)=0.30$; FAB-MS: $(M+H)^+=462$.

The starting materials are obtained, for example, as follows:

a) (4O,5N-Isopropylidene)-5(S)-tert-butoxycarbonylamino-4(S)-hydroxy-2(R),7,7-trimethyl-8-[3(R,S)-(tert-butyldimethylsilyloxymethyl)-1,2,3,4-tetrahydroquinolin-1-ylcarbonyl]-octanoic acid (N-butyl)amide The title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2 (R)-methyl-propionic acid (N-butyl)amide and 303 mg of 3(R,S)-(tert-butyldimethylsilyloxymethyl)-1,2,3,4-tetrahydroquinoline: $R_f(Z)=0.30$.

b) 3(R,S)-(Tert-butyldimethylsilyloxymethyl)-1,2,3,4-tetrahydroquinoline 25.2 g of 1-benzyl-3(R,S)-(tert-butyldimethylsilyloxymethyl)-1,2,3,4-tetrahydroquinoline in 250 ml of tetrahydrofuran are hydrogenated in the presence of 2.0 g of 10% palladium-on-charcoal under customary reaction conditions. Purification of the crude product over 500 g of silica gel with a 1:1 mixture of methylene chloride and hexane as the solvent gives 7.6 g of the title compound: $R_f$(1:1 mixture of methylene chloride and hexane)=0.19.

c) 1-Benzyl-3(R,S)-(tert-butyldimethylsilyloxymethyl)-1,2,3,4-tetrahydroquinoline 11.6 g of 1-benzyl-3(R,S)-hydroxymethyl-1,2,3,4-tetrahydroquinoline (Example 29e), 8.54 g of tert-butyldimethylchlorosilane and 4.05 g of imidazole are stirred in 120 ml of methylene chloride at room temperature for 20 h. The precipitate is then filtered off and the crude product obtained after concentration of the filtrate is purified over 900 g of silica gel (mobile phase Z). 16 g of the title compound are obtained as a yellowish oil: $R_f(Z)=0.66$.

EXAMPLE 45

4(S)-Amino-3(S)-hydroxy-1(R),6,6-trimethyl-heptanedicarboxylic acid 1-(N-butyl)amide 7-[N-[2-(3-pyridyl)phenyl]]amide 2 ml of a 25% solution of trifluoroacetic acid in methylene chloride are added to 30 mg of 4(S)-tert-butoxycarbonylamino-3(S)-hydroxy-1(R),6,6-trimethyl-heptanedicarboxylic acid 1-(N-butyl)amide 7-[N-[2-(3-pyridyl)phenyl]]amide while cooling with ice. The mixture is stirred at 0° C. for 2 h. After addition of 2 ml of toluene, the reaction mixture is concentrated and the residue is purified by FC over 15 g of silica gel with a mobile phase gradient of methylene chloride and methanol (from the 90:10 mixture to the 80:20 mixture). This gives the title compound: $R_f(S)=0.22$; $R_f(IV)=27.4$ min; FAB-MS: $(M+M)^+=469$.

The starting materials are prepared, for example, as follows:

a) 4(S)-Tert-butoxycarbonylamino-3(S)-hydroxy-1(R),6,6-trimethyl-heptanedicarboxylic acid 1-(N-butyl)amide 7-[N-[2-(3-pyridyl)phenyl]]amide The title compound is prepared starting from 143 mg of (3O,4N-isopropylidene)-4(S)-tert-butoxycarbonylamino-3(S)-hydroxy-1(R),6,6-trimethyl-heptanedicarboxylic acid 1-(N-butyl)amide 7-[N-[2-(3-pyridyl)phenyl]]amide analogously to 20a) and is purified by FC over 15 g of silica gel with a mobile phase gradient of methylene chloride and methanol (from the 97:3 mixture to the 94:6 mixture): $R_f(P)=0.42$.

b) (3O,4N-Isopropylidene)4(S)-tert-butoxycarbonylamino-3(S)-hydroxy-1(R),6,6-trimethyl-heptanedicarboxylic acid 1-(N-butyl)amide 7-[N-[2-(3-pyridyl)phenyl]]amide 0.06 ml of 1-chloro-N,N,2-trimethylpropenylamine is added to a solution of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl) amide in 3 ml of methylene chloride at 0° C. After 30 min, a solution of 2-(3-pyridyl)aniline in 1 ml of methylene chloride und 3 mg of 4-DMAP is added and the reaction mixture is stirred at room temperature for 4 h. The reaction mixture is concentrated and the residue is chromatographed by means of FC over 80 g of silica gel (mobile phases B and A): $R_f(H)=0.16$.

EXAMPLE 46

4(S)-Amino-3(S)-hydroxy-1(R),6,6-trimethyl-heptanedicarboxylic acid 1-(N-butyl)amide 7-[N-[2-(N-oxido-3-pyridyl)phenyl]]amide 31 mg of 4(S)-tert-butoxycarbonylamino-3(S)-hydroxy-1(R),6,6-trimethyl-heptanedicarboxylic acid 1-(N-butyl) amide 7-[N-[2-(N-oxido-3-pyridyl)phenyl]]amide are reacted described in Example 45) and the resulting crude product is purified by means of FC over 10 g of silica gel (mobile phase P). This gives the title compound: $R_f(S)=0.12$; $R_f(IV)=26.9$ min.

The starting material is prepared, for example, as follows:

a) 4(S)-Tert-butoxycarbonylamino-3(S)-hydroxy-1(R),6,6-trimethyl-heptanedicarboxylic acid 1-(N-butyl)amide 7-[N-[2-(N-oxido-3-pyridyl)phenyl]]amide 19 mg of meta-chloroperbenzoic acid are added to a solution of 30 mg of 4(S)-tert-butoxycarbonylamino-3(S)-hydroxy-1(R),6,6-trimethyl-heptanedicarboxylic acid 1-(N-butyl)amide 7-[2-(3-pyridyl)phenyl]]amide in 2 ml methylene chloride and the mixture is stirred overnight at room temperature. 5 mg of meta-chloroperbenzoic acid are again added and the mixture is stirred at room temperature until the reaction is complete. The reaction mixture is chromatographed directly, without further working up, over 10 g of silica gel (mobile phase M). The title compound is obtained: $R_f(P)=0.15$; FAB-MS: $(M+M)^+=585$.

EXAMPLE 47

5(S)-Formylamino-4(S)-hydroxy-2(R),7,7-trimethyl-8-[2(R,S)-methoxycarbonyl-3,4-dihydro-2H-1,4-benzothiazin-4-ylcarbonyl]-octanoic acid (N-butyl)amide 195 mg of 5(S)-amino-4(S)-hydroxy-2(R),7,7-trimethyl-8-[2(R,S)-methoxycarbonyl-3,4-dihydro-2H-1,4-benzothiazin-4-ylcarbonyl]-octanoic acid (N-butyl)amide (Example 18)) are reacted with 128 mg of 4-nitrophenyl formate in a manner analogous to that described in Example 17) and the product is purified over 30 g of silica gel (mobile phase M). The title compound is obtained as a yellowish-coloured solid: $R_f(N)=0.20$; FAB-MS: $(M+H)^+=536$.

EXAMPLE 48

5(S)-Amino-4(S)-hydroxy-2(R),7,7-trimethyl-8-(S,S-dioxo-3,4-dihydro-1H-2,4-benzothiazin-4-ylcarbonyl)-octanoic acid (N-butyl)amide Analogously to the processes described in Examples 21, 21a and 21b) for the corresponding reaction stages, the title compound is obtained starting from 228 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 120 mg of 3,4-dihydro-1H-2,4-benzothiazine via (4O,5N-isopropylidene)-5(S)-tert-butoxycarbonylamino-4(S)-hydroxy-2(R),7,7-trimethyl-8-(3,4-dihydro-1H-2,4-benzothiazin-4-ylcarbonyl)-octanoic acid (N-butyl)amide ($R_f(A)$=0.32) and 5(S)-tert-butoxycarbonylamino-4(S)-hydroxy-2(R),7,7-trimethyl-8-(S,S-dioxo-3,4-dihydro-1H-2,4-benzothiazin-4-ylcarbonyl]-octanoic acid (N-butyl)amide. When the reaction with p-toluenesulfonic acid hydrate in methanol as described in Example 21a) has ended, the reaction mixture is diluted with 2 ml of water and oxidized with 228 mg of Oxone and the product is isolated by extraction by customary processes; $R_f(K)$=0.51; $R_f(I)$=23.6 min), and purification by means of FC (10 g of silica gel, mobile phase O): $R_f(O)$=0.14; $R_f(I)$=17.3 min; FAB-MS: $(M+H)^+$=482.

The amine component employed as the starting material is prepared, for example, as follows:

a) 3,4-Dihydro-1H-2,4-benzothiazine 1.47 ml of trimethylsilyl trifluoromethanesulfonate are added dropwise to a solution of 1.0 g of N-tert-butoxycarbonyl-3,4-dihydro-1H-2,4-benzothiazine in 35 ml of methylene chloride at room temperature, and 1.41 ml of 2,6-lutidine is added. The reaction mixture is stirred at room temperature for 20 minutes and then diluted with 5 ml of methanol and concentrated. The crude product is purified by means of FC (30 g of silica gel, mobile phase G). This gives the pure title compound: $R_f(D)$=0.26; $R_f(I)$=19.5 min; anal. calc. for $C_8H_9NS$: C 63.54%, H 6.00%, N 9.26%; found C 63.22%. H 6.01%, N 8.99%.

b) N-Tert-butoxycarbonyl-3,4-dihydro-1H-2,4-benzothiazine 5.78 g of 2-acetylthiomethyl(N-tert-butoxycarbonyl)aniline are dissolved in 10 ml of tetrahydrofuran, and 5.72 g of potassium carbonate and 16.4 ml of a 35% formaldehyde solution are added at room temperature. The reaction mixture is stirred at 40°–50° C. for 3 h and then neutralized with potassium hydrogen sulfate solution. The intermediate is extracted with chloroform, and dried over sodium sulfate, 80 mg of p-toluenesulfonic acid hydrate are then added and the mixture is stirred at room temperature for 20 h. The reaction mixture is evaporated and the crude product is purified by means of FC (100 g of silica gel, mobile phase G): $R_f(D)$=0.45.

c) 2-Acetylthiomethyl(N-tert-butoxycarbonyl)aniline 38.6 ml of diisopropyl azocarboxylate are added to a solution of 51.4 g of triphenylphosphine in 50 ml of tetrahydrofuran at 0° C. After 30 min, a solution of 21.0 g of N-(tert-butoxycarbonyl)-2-(hydroxymethyl)aniline and 15 ml of thioacetic acid in 20 ml of tetrahydrouran is added dropwise. The reaction mixture is stirred at 0° C. for 2 h and then at room temperature for 22 h. The crude product is purified by means of FC (500 g of silica gel, mobile phase G): $R_f(3:1$ mixture of toluene and glacial acetic acid)=0.43; MS: $M^+$=281.

d) N-(Tert-butoxycarbonyl)-2-(hydroxymethyl)aniline 22.5 g of di-tert-butyldicarbonate and 21 ml of triethylamine are added to a solution of 12.3 g of 2-aminobenzyl alcohol in 100 ml of methylene chloride and the mixture is stirred at room temperature for 24 h. The reaction mixture is washed several times with 10% citric acid solution, saturated sodium bicarbonate solution and saturated sodium chloride solution and then concentrated. This gives the title compound: $R_f(A)$ 0.61.

EXAMPLE 49

5(S)-Amino-4(S)-hydroxy-2(R),7,7-trimethyl-8-(7-nitro-1,2,3,4-tetrahydroquinolin-1-ylcarbonyl)-octanoic acid (N-butyl)amide Analogously to the processes described in Examples 21, 21a and 21b) for the corresponding reaction stages, the title compound is obtained starting from 114 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 129 mg of 7-nitro-1,2,3,4-tetrahydroquinoline (A. P. Terent'ev et al. Khim. Geter. Soedin 12, 1663(1969)) analogously to the method described in 20b) via (4O,5N-isopropylidene)-5(S)-tert-butoxycarbonylamino-4(S)-hydroxy-2(R),7,7-trimethyl-8-(7-nitro-1,2,3,4-tetrahydroquinolin-1-ylcarbonyl)-octanoic acid (N-butyl)amide ($R_f(A)$=0.16; $R_f$(acetic acid)=0.55) and 5(S)-tert-butoxycarbonylamino-4(S)-hydroxy-2(R),7,7-trimethyl-8-(7-nitro-1,2,3,4-tetrahydroquinolin-1-ylcarbonyl]-octanoic acid (N-butyl)amide (purification over 10 g of silica gel, mobile phase A and ethyl acetate: $R_f(X)$=0.43): $R_f(W)$=0.63; $R_f(I)$=20.5 min; FAB-MS: $(M+H)^+$=477.

EXAMPLE 50

5(S)-Amino-4(S)-hydroxy-2(R),7,7-trimethyl-8-[3(R,S)-ethoxycarbonyl-7-nitro-1,2,3,4-tetrahydroquinolin-1-ylcarbonyl]-octanoic acid (N-butyl)amide Analogously to the processes described in Examples 21, 21a and 21b) for the corresponding reaction stages, the title compound is obtained starting from 183 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 125 mg of 3(R,S)-ethoxycarbonyl-7-nitro-1,2,3,4-tetrahydroquinoline via (4O,5N-isopropylidene)-5(S)-tert-butoxycarbonylamino-4(S)-hydroxy-2(R),7,7-trimethyl-8-[3(R,S)-ethoxycarbonyl-7-nitro-1,2,3,4-tetrahydroquinolin-1-yl-carbonyl]-octanoic acid (N-butyl)amide (purification over 20 g of silica gel, mobile phase A: $R_f(X)$=0.68; $R_f(I)$=31.6 min) and 5(S)-tert-butoxycarbonylamino-4(S)-hydroxy-2(R),7,7-trimethyl-8-[3(R,S)-ethoxycarbonyl-7-nitro-1,2,3,4-tetrahydroquinolin-1-ylcarbonyl]-octanoic acid (N-butyl)amide (purification over 10 g of silica gel, mobile phases A and G: $R_f(X)$=0.47; $R_f(I)$=24.9 min): $R_f(W)$=0.55; $R_f(I)$=21.3 min; FAB-MS: $(M+H)^+$=549.

The 3(R,S)-ethoxycarbonyl-7-nitro-1,2,3,4-tetrahydroquinoline employed is prepared analogously to the process of A. P. Terent'ev et al. Khim. Geter. Soedin 12,1663 (1969) starting from 246 mg of 3(R,S)-ethoxycarbonyl-1,2,3,4-tetrahydroquinoline (Example 31b): $R_f(A)$=0.57; $R_f(3:1$ mixture of toluene and ethyl acetate)= 0.49.

EXAMPLE 51

5(S)-Amino-4(S)-hydroxy-2(R),7,7-trimethyl-8-[2(R,S)-ethoxycarbonyl-2(R,S)-methyl-3,4-dihydro-2H-1,4-benzoxazin-4-ylcarbonyl]-octanoic acid (N-butyl)amide Analogously to the processes described in Examples 21, 21a and 21b) for the corresponding reaction stages, the title compound is obtained starting from 205 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 200 mg of 2(R,S)-ethoxycarbonyl-2(R,S)-methyl-3,4-dihydro-2H-1,4-benzoxazine via (4O,5N-isopropylidene)-5(S)-tert-butoxycarbonylamino-4(S)-hydroxy-2(R),7,7-trimethyl-8-[2(R,S)-ethoxycarbonyl-2(R,S)-methyl-3,4-dihydro-2H-1,4-benzoxazin-4-ylcarbonyl]-octanoic acid (N-butyl)amide ($R_f(A)$=0.24) and 5(S)-tert-butoxycarbonylamino-4(S)-hydroxy-2(R),7,7-trimethyl-8-[2(R,S)-ethoxycarbonyl-2(R,S)-methyl-3,4-dihydro-2H-1, 4-benzoxazin-4-ylcarbonyl]-octanoic acid (N-butyl)amide (purification over 10 g of silica gel, mobile phases A and G: $R_f(X)=0.50$; FAB-MS: $(M+H)^+=620$): $R_f(W)=0.25$; $R_f(I)=20.7/20.9$ min; FAB-MS: $(M+H)^+=520$.

The starting materials are prepared, for example, as follows:

a) 2(R,S)-Ethoxycarbonyl-2(R,S)-methyl-3,4-dihydro-2H-1,4-benzoxazine

The title compound is obtained analogously to Example 1r) starting from 800 mg of N-benzyloxycarbonyl-2(R,S)-ethoxycarbonyl-2(R,S)-methyl-3,4-dihydro-2H-1,4-benzoxazine. The crude product is purified by means of FC over 50 g of silica gel (mobile phase B). This gives the pure title compound: $R_f(A)=0.55$; MS: $M^+=221$.

b) N-Benzyloxycarbonyl-2(R,S)-ethoxycarbonyl-2(R,S)-methyl-3,4-dihydro-2H-1,4-benzoxazine A solution of 5.0 g of N-benzyloxycarbonyl-2(R,S)-ethoxycarbonyl-3,4-dihydro-2H-1,4-benzoxazine in 20 ml of tetrahydrofuran is added to a solution of 8.8 ml of a 2M lithium diisopropylamide solution in tetrahydrofuran at –20° C. After 20 min, 1.6 ml of methyl iodide are added dropwise and the reaction mixture is stirred at 0° C. for 4 h. After addition of 30 ml of a saturated ammonium chloride solution, the mixture is then extracted with ethyl acetate. The crude product is purified by means of FC over 200 g of silica gel (mobile phase E). This gives the pure title compound: $R_f(D)=0.25$; FAB-MS: $(M+H)^+=356$.

EXAMPLE 52

5(S)-Amino-4(S)-hydroxy-2(R),7,7-trimethyl-8-[3(R,S)-methylsulfonyl-1,2,3,4-tetrahydroquinolin-1-ylcarbonyl]-octanoic acid (N-butyl)amide 95 mg of (S)-tert-butoxycarbonylamino-4(S)-hydroxy-2(R),7,7-trimethyl-8-[3(R,S)-methylsulfonyl-1,2,3,4-tetrahydroquinolin-1-ylcarbonyl]-octanoic acid (N-butyl)amide are stirred in 2 ml of a 20% trifluoroacetic acid solution in methylene chloride at 0° C. for 2 h. Working up in a manner analogous to that described in Example 45) and purification of the crude product by FC over 10 g of silica gel (mobile phase M) gives the title compound as a diastereomer mixture: $R_f(S)=0.16/0.20$; $R_f(IV)=35.0/35.3$ min; FAB-MS: $(M+H)^+=510$.

The starting materials are prepared, for example, as follows:

a) 5(S)-Tert-butoxycarbonylamino-4(S)-hydroxy-2(R),7,7trimethyl-8-[3(R,S)-methylsulfonyl-1,2,3,4-tetrahydroquinolin-1-ylcarbonyl]-octanoic acid N(-butyl)amide The title compound is obtained starting from 170 mg of (4O,5N-isopropylidene)-5(S)-tert-butoxycarbonylamino-4(S)-hydroxy-2(R),7,7-trimethyl-8-[3(R,S)-methylsulfonyl-1,2,3,4-tetrahydroquinolin-1-ylcarbonyl]-octanoic acid (N-butyl)amide in an analogous manner to that in Example 21a) and is purified by FC over 25 g of silica gel with a mobile phase gradient of methylene chloride and methanol (from J to K). This gives the title compound: $R_f(P)=0.56$.

b) (4O,5N-Isopropylidene)-5(S)-tert-butoxycarbonylamino-4(S)-hydroxy-2(R),7,7-trimethyl-8-[3(R,S)-methylsulfonyl-1,2,3,4-tetrahydroquinolin-1-ylcarbonyl]-octanoic acid (N-butyl)amide The title compound is obtained in a manner analogous to that in Example 45b) by reaction of 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide, 0.06 ml of 1-chloro-N,N,2-trimethylpropenylamine, 140 mg of 3(R,S)-methylsulfonyl-1,2,3,4-tetrahydroquinoline and 4 mg of 4-DMAP, and subsequent purification of the crude product by means of FC over 80 g of silica gel with a mobile phase gradient of hexane and ethyl acetate (from B to A): $R_f(A)=0.15$.

c) 3(R,S)-Methylsulfonyl-1,2,3,4-tetrahydroquinoline

A solution of 6.5 g of 3-methylsulfonylquinoline in 200 ml of glacial acetic acid is hydrogenated in the presence of 690 mg of platinum oxide at 50° C. for 13 h. After the reaction mixture has been filtered over Celite® 545, the filtrate is concentrated and the crude product is purified by means of FC over 200 g of silica gel with a 99:1 mixture of methylene chloride and methanol as the mobile phase: $R_f(K)=0.45$; anal. calc. for $C_{10}H_{13}NO_2S$: C56.85%, H6.20%, N6.63%; found C56.95%, H6.17%, N6.77%.

d) 3-Methylsulfonylquinoline

A mixture of 28 mg of sodium tungstate dihydrate, 8 ml of water and 2 drops of glacial acetic acid is added to a solution of 6.1 g of 3-methylthioquinoline in 11 ml of dioxane. 7.1 ml of a 30% hydrogen peroxide solution are added dropwise at 65° C. in the course of 30 min. while stirring vigorously. The reaction mixture is then heated to 80° C. and stirred for a further 1 h. After cooling, the mixture is diluted with 100 ml of methylene chloride, the organic phase is separated off and the aqueous phase is extracted with methylene chloride.

After FC of the crude product over 150 g of silica gel with a mobile phase gradient of hexane and ethyl acetate (from D to A), the pure title compound is obtained: $R_f(A)=0.31$.

e) 3-Methylthioquinoline 5.0 g of sodium methane thiolate are added to a solution of 7.4 g of 3-bromoquinoline in 110 ml of dimethylformamide, while stirring, and the mixture is stirred at room temperature for 30 min. The reaction mixture is then concentrated, the residue is taken up in 100 ml of water and the mixture is extracted with methylene chloride. The organic phase is washed with saturated sodium chloride and added over sodium sulfate and the residue is purified by FC over 100 g of silica gel with a 1:2 mixture of diethyl ether and petroleum ether as the mobile phase. The pure title compound is obtained: mp 40° C.; $R_f(F)=0.24$; anal. calc. for $C_{10}H_9NS$: C68.53%, H5.18%, N7.99%; found C68.76%, H5.16%, N7.97%.

EXAMPLE 53

5(S)-Amino-4(S)-hydroxy-2(R),7,7-trimethyl-8-[3-methylsulfonyl-1,2,3,4-tetrahydroquinazolin-1-ylcarbonyl]-octanoic acid (N-butyl)amide In an analogous manner to that described in Examples 52, 52a and 52b) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 140 mg of 3-methylsulfonyl-1,2,3,4-tetrahydroquinazoline via (4O,5N-isopropylidene)-5(S)-tert-butoxycarbonylamino-4(S)-hydroxy-2(R),7,7-trimethyl-8-[3-methylsulfonyl-1,2,3,4-tetrahydroquinazolin-1 yl-carbonyl]-octanoic acid (N-butyl) amide ($R_f(A)=0.33$) and 5(S)-tert-butoxycarbonylamino-4(S)-hydroxy-2(R),7,7-trimethyl-8-[3-methylsulfonyl-1,2,3,4-tetrahydroquinazolin-1-yl-carbonyl]-octanoic acid (N-butyl)amide ($R_f(J)=0.37$): $R_f(S)=0.32$; $R_f(IV)=35.5$ min; FAB-MS: $(M+H)^+=511$.

The 3-methylsulfonyl-1,2,3,4-tetrahydroquinazoline employed as the starting material is prepared, for example, as follows:

0.17 ml of methanesulfonyl chloride is added to a mixture of 300 mg of 1,2,3,4-tetrahydroquinazoline (prepared by the method described by R. F. Smith et al. in J.Heterocycl. Chem.2 (1965)) and 0.47 ml of triethylamine in 14 ml of methylene chloride at 0° C., while stirring. After 5 min, saturated sodium chloride solution is added, the mixture is subsequently stirred briefly and, after drying over sodium sulfate, the organic phase is concentrated. Purification of the crude product by means of FC over 30 g of silica gel (mobile phase P) gives 3-methylsulfonyl-1,2,3,4-tetrahydroquinazoline: $R_f(K)=0.65$; IR(KBr): 3360(m), 1600(m), 1500(m), 1320(s), 1145(s), 770(s).

EXAMPLE 54

5(S)-Amino-4(S)-hydroxy-2(R),7,7-trimethyl-8-[3(R,S)-methylcarbonylamino-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 70 mg of 3-[N-tert-butoxycarbonyl-4(S)-(3-carboxy-2,2-dimethylpropyloxy-2, 2-dimethyl-1,3-oxazolidin-5(S)-yl]-2(R)-methyl-propionic acid (N-butyl)amide and 88 mg of 3(R,S)-methylcarbonylamino-1,2,3,4-tetrahydroquinoline via (4O, 5N-isopropylidene)-5(S)-tert-butoxycarbonylamino-4(S)-hydroxy-2(R),7,7-trimethyl-8-[3(R,S)-methylcarbonylamino-1,2,3,4-tetrahydroquinolin-1-ylcarbonyl]-octanoic acid (N-butyl)amide ($R_f(P)=0.55$) and 5(S)-tert-butoxycarbonylamino-4(S)-hydroxy-2(R),7,7-trimethyl-8-[3(R,S)-methylcarbonylamino-1,2,3,4-tetrahydroquinolin-1-ylcarbonyl]-octanoic acid (N-butyl) amide ($R_f(S)=0.24$) as a diastereomer mixture: $R_f(S)=0.10$; $R_f(IV)=33.5$ min; FAB-MS: $(M+H)^+=489$.

The 3(R,S)-methylcarbonylamino-1,2,3,4-tetrahydroquinoline employed as the starting material is prepared, for example, as follows:

5.6 ml of pyridine and 2.96 ml of acetyl chloride are added successively to a solution of 5.3 g of 3-aminoquinoline in 150 ml of methylene chloride at 0° C., while stirring. After 45 min at 0° C., the mixture is allowed to warm to room temperature and is subsequently stirred for a further 30 min, and the reaction mixture is then poured onto 150 ml of ice-water. After extraction of the alkaline aqueous phase with ethyl acetate, the combined organic phases are washed with 5% sodium bicarbonate solution and saturated sodium chloride solution and dried over sodium sulfate.

300 mg of the 3-(acetylamino)quinoline ($R_f(D)=0.43$) obtained by a single recrystallization from ethyl acetate/hexane are hydrogenated in 10 ml of ethanol in the presence of 60 mg of palladium-on-charcoal (10% of Pd) at 50° C. under normal pressure for 20 h. After the reaction mixture has been filtered over Celite® 545 and the crude product has been purified by chromatography over 25 g of silica gel (mobile phase P), 3(R,S)-methylcarbonylamino-1,2,3,4-tetrahydroquinoline is obtained: $R_f(P)=0.49$; MS: $(M)^+=190$.

EXAMPLE 55

4(S)-Amino-3(S)-hydroxy-1(R),6,6-trimethyl-heptanedicarboxylic acid 1-(N-butyl)amide 7-[N-(2carbamoylmethoxyphenyl)]amide Analogously to the processes described in Examples 21, 21a and 21b) for the corresponding reaction stages, the title compound is obtained starting from 120 mg of 3-[N-tert-butoxycarbonyl-4(S)-(3-carboxy-2,2-dimethylpropyloxy-2, 2-dimethyl-1,3-oxazolidin-5(S)-yl]-2(R)-methyl-propionic acid (N-butyl)amide and 83 mg of 2-(carbamoylmethoxy) aniline via (3O,4N-isopropylidene)4(S)-tert-butoxycarbonylamino-3(S)-hydroxy-1(R),6,6-trimethyl-heptanedicarboxylic acid 1-(N-butyl)amide 7-[N-(2-carbamoylmethoxyphenyl)]amide ($R_f(X)=0.33$) and 4(S)-tert-butoxycarbonylamino-3(S)-hydroxy-l(R),6,6-trimethyl-heptanedicarboxylic acid 1-(N-butyl)amide 7-[N-(2-carbamoylmethoxyphenyl)]amide ($R_f(X)=0.11$; $R_f(I)=21.5$ min): $R_f(W)=0.33$; $R_f(I)=15.7$ min; FAB-MS: $(M+H)^+=465$.

The 2-(carbamoylmethoxy)aniline employed as the starting material is prepared, for example, as follows:

8.0 g of potassium carbonate and 11.4 g of iodoacetamide are added to a solution of 4.0 g of 2-nitrophenol in 50 ml acetone. The reaction mixture is heated under reflux for 7 h and then concentrated. The residue is dissolved in chloroform and extracted with 0.05N of sodium hydroxide solution. Recyrstallization of the crude product from tetrahydrofuran gives 2-(carbamoylmethoxy)nitrobenzene of mp 190°–1° C.; $R_f(O)=0.55$.

2.0 g of 2-(carbamoylmethoxy)nitrobenzene are hydrogenated in the presence of 100 mg of palladium-on-charcoal (10% of Pd) in 50 ml of tetrahydrofuran at room temperature under normal pressure for 2 h. The reaction mixture is filtered over Hyflo® and concentrated. 2-(Carbamoylmethoxy)aniline is obtained as white crystals: mp 117° C.; $R_f(O)=0.36$; FAB-MS: $(M+H)^+=167$; anal. calc. for $C_8H_{10}N_2O_2$: C57.82%, H6.07%, N16.86%; found C57.71%, H6.04%, N16.87%.

EXAMPLE 56

4(S)-Amino-3(S)-hydroxy-1(R),6,6-trimethyl-heptanedicarboxylic acid 1-(N-butyl)amide 7-[N-(2carbamoylmethoxy-4-methoxyphenyl)]amide Analogously to the processes described in Examples 21, 21a and 21b) for the corresponding reaction stages, the title compound is obtained starting from 120 mg of 3-[N-tert-butoxycarbonyl-4(S)-(3-carboxy-2,2-dimethylpropyloxy-2, 2-dimethyl-1,3-oxazolidin-5(S)-yl]-2(R)-methyl-propionic acid (N-butyl)amide and 100 mg of 2-carbamoylmethoxy-4-methoxyaniline via (3O,4N-isopropylidene)4(S)-tert-butoxycarbonylamino-3(S)-hydroxy-1(R),6,6-trimethyl-heptanedicarboxylic acid 1-(N-butyl)amide 7-[N-(2-carbamoylmethoxy-4-methoxyphenyl)]amide ($R_f(X)=0.31$; $R_f(I)=25.4$ min) and 4(S)-tert-butoxycarbonylamino-3(S)-hydroxy-1(R),6,6-trimethyl-heptanedicarboxylic acid 1-(N-butyl)amide 7-[N-(2-carbamoylmethoxy-4methoxyphenyl)] amide ($R_f(X)=0.16$): $R_f(W)=0.57$; $R_f(I)=16.0$ min; FAB-MS: $(M+H)^+=495$.

The 2-carbamoylmethoxy-4-methoxyaniline employed as the starting material is prepared, for example, as follows:

Reaction of 0.84 g of 5-methoxy-2-nitrophenol, 1.66 g of potassium carbonate and 1.84 g of iodoacetamide by the process described in Example 55) gives 2-carbamoylmethoxy-4-methoxynitrobenzene: mp 185°–7° C.; $R_f(O)=0.58$.

930 mg of 2-carbamoylmethoxy-4-methoxynitrobenzene are hydrogenated in the presence of 300 mg of Raney nickel in 30 ml of methanol at room temperature under normal pressure for 12 h. The reaction mixture is filtered over Hyflo® and concentrated. Recrystallization of the crude product from methanol gives 2-carbamoylmethoxy-4-methoxyaniline of mp 139°–140° C.; $R_f(O)=0.25$.

EXAMPLE 57

4(S)-Amino-3(S)-hydroxy-1(R),6,6-trimethyl-heptanedicarboxylic acid 1-(N-butyl)amide 7-[N-(2-carbamoylmethoxy-5-methoxyphenyl)]amide Analogously to the processes described in Examples 21, 21a and 21b) for the corresponding reaction stages, the title compound is obtained starting from 120 mg of 3-[N-tert-butoxycarbonyl-4(S)-(3-carboxy-2,2-dimethylpropyloxy-2, 2-dimethyl-1,3-oxazolidin-5(S)-yl]-2(R)-methyl-propionic acid (N-butyl)amide and 100 mg of 2-carbamoylmethoxy-5-methoxyaniline via (3O,4N-isopropylidene)-4(S)-tert-butoxycarbonylamino-3(S)-hydroxy-1(R),6,6-trimethyl-heptanedicarboxylic acid 1-(N-butyl)amide 7-[N-(2-carbamoylmethoxy-5-methoxyphenyl)]amide ($R_f(X)$=0.35; $R_f(I)$=25.6 min) and 4(S)-tert-butoxycarbonylamino-3(S)-hydroxy-1(R),6,6-trimethyl-heptanedicarboxylic acid 1-(N-butyl)amide 7-[N-(2-carbamoylmethoxy-5methoxyphenyl)]amide ($R_f(X)$=0.11): $R_f(W)$=0.69; $R_f(I)$=16.3 min; FAB-MS: $(M+H)^+$=495.

The aniline derivative employed as the starting material is prepared, for example, as follows:

Reaction of 1.41 g of 4-methoxy-2-nitrophenol, 3.04 g potassium carbonate and 3.61 g of iodoacetamide analogously to the process described in Example 55) gives 2-carbamoylmethoxy-5-methoxynitrobenzene: mp 190°–1° C.; $R_f(O)$=0.58; FAB-MS: $(M+H)^+$=227; anal. calc. for $C_9H_{10}N_2O_5$: C47.79%, H4.46%, N12.38%; found C47.90%, H4.48%, N12.58%.

Starting from 1.13 g of 2-carbamoylmethoxy-5-methoxynitrobenzene, in an analogous manner to that described in Example 55), 2-carbamoylmethoxy-5-methoxyaniline is obtained: mp 121°–2° C.; $R_f(O)$=0.37; FAB-MS: $(M+H)^+$=197.

EXAMPLE 58

4(S)-Amino-3(S)-hydroxy-1(R),6,6-trimethyl-heptanedicarboxylic acid 1-(N-butyl)amide 7-[N-[2-carbamoylmethoxy-4-(methoxycarbonyl)phenyl]]amide Analogously to the processes described in Examples 21, 21a and 21b) for the corresponding reaction stages, the title compound is obtained starting from 120 mg of 3-[N-tert-butoxycarbonyl-4(S)-(3-carboxy-2,2-dimethylpropyloxy-2, 2-dimethyl-1,3-oxazolidin-5(S)-yl]-2(R)-methyl-propionic acid (N-butyl)amide and 100 mg of 2-carbamoylmethoxy-4-(methoxycarbonyl)aniline via (3O,4N-isopropylidene)-4(S)-tert-butoxycarbonylamino-3(S)-hydroxy-1(R),6,6-trimethyl-heptanedicarboxylic acid 1-(N-butyl)amide 7-[N-[2-carbamoylmethoxy-4-(methoxycarbonyl)phenyl]]amide ($R_f(X)$=0.35; $R_f(I)$=26.5 min) and 4(S)-tert-butoxycarbonylamino-3(S)-hydroxy-1(R),6,6-trimethyl-heptanedicarboxylic acid 1-(N-butyl)amide 7-[N-[2-carbamoylmethoxy-4-(methoxycarbonyl)phenyl]]amide ($R_f(X)$=0.09; $R_f(I)$=22.0 min): $R_f(W)$=0.70; $R_f(I)$=16.6 min; FAB-MS: $(M+H)^+$=523.

The aniline derivative employed as the starting material is prepared, for example, in an analogous manner to that described in Example 55) for the corresponding reaction stages:

Reaction of 1.08 g of 5-methoxycarbonyl-2-nitrophenol, 1.82 g of potassium carbonate and 2.02 g of iodoacetamide gives 2-carbamoylmethoxy-4-(methoxycarbonyl) nitrobenzene of mp 138°–9° C.; $R_f(O)$=0.63; FAB-MS: $(M+H)^+$255; anal. calc. for $C_{10}H_{10}N_2O_6$: C47.25%, H3.97%, N11.02%; found C47.08%, H4.04%, N10.79%. Starting from 1.16 g of 2-carbamoylmethoxy-4-(methoxycarbonyl)nitrobenzene, 2-carbamoylmethoxy-4-(methoxycarbonyl)aniline of mp 178°–80° C.; $R_f(O)$=0.37; MS: $M^+$=224; anal. calc. for $C_{10}H_{12}N_2O_4$: C53.57%, H5.39%, N12.49%; found C53.41%. H5.32%, N12.53%.

EXAMPLE 59

4(S)-Amino-3(S)-hydroxy-1(R),6,6-trimethyl-heptanedicarboxylic acid 1-(N-butyl)amide 7-[N-[2-carbamoylmethoxy-5-(methoxycarbonyl)phenyl]]amide Analogously to the processes described in Examples 21, 21a and 21b) for the corresponding reaction stages, the title compound is obtained starting from 120 mg of 3-[N-tert-butoxycarbonyl-4(S)-(3-carboxy-2,2-dimethylpropyloxy-2, 2-dimethyl-1,3-oxazolidin-5(S)-yl]-2(R)-methyl-propionic acid (N-butyl)amide and 100 mg of 2-carbamoylmethoxy-5-(methoxycarbonyl)aniline via (3O,4N-isopropylidene)-4(S)-tert-butoxycarbonylamino-3(S)-hydroxy-1(R),6,6-trimethyl-heptanedicarboxylic acid 1-(N-butyl)amide 7-[N-[2-carbamoylmethoxy-5-(methoxycarbonyl)phenyl]]amide (purification over 20 g of silica gel, mobile phase ethyl acetate: $R_f(X)$=0.26; $R_f(I)$=25.7 min) and 4(S)-tert-butoxycarbonylamino-3(S)-hydroxy-1(R),6,6trimethyl-heptanedicarboxylic acid 1-(N-butyl)amide 7-[N-[2-carbamoylmethoxy-5-(methoxycarbonyl)phenyl]]amide (purification over 10 g of silica gel, mobile phases ethyl acetate and S: $R_f(X)$=0.10; $R_f(I)$=21.5 min; FAB-MS: $(M+H)^+$=623): $R_f(W)$=0.68; $R_f(I)$=16.4 min.; FAB-MS: $(M+H)^+$=523.

The starting materials are prepared, for example, as follows:

a) 2-Carbamoylmethoxy-5-(methoxycarbonyl)aniline is obtained analogously to Example 56) starting from 1.0 g of 2-carbamoylmethoxy-5-(methoxycarbonyl) nitrobenzene: mp 181°–2° C.; $R_f(O)$=0.35; MS: $M^+$=224.

b) 2-Carbamoylmethoxy-5-(methoxycarbonyl)nitrobenzene is obtained analogously to Example 55) starting from 3.66 g of 4-methoxycarbonyl-2-nitrophenol, 6.91 g of potassium carbonate and 4.62 g of iodoacetamide: mp 185°–7° C.; $R_f(O)$=0.56.

EXAMPLE 60

5(S)-Amino-4(S)-hydroxy-2(S)-isopropyl-7,7-dimethyl-8-[3(R,S)-methylaminocarbonyl-1,2,3,4-tetrahydroquinolin-1-ylcarbonyl]-octanoic acid (N-butyl)amide In a manner analogous to that described in Examples 21, 21a) and 21b) for the corresponding reaction stages, the title compound is obtained starting from 300 mg of 3-[N-tert-butoxycarbonyl-4(S)-(3-carboxy-2,2-dimethylpropyloxy-2, 2-dimethyl-1,3-oxazolidin-5(S)-yl]-2(S)isopropyl-propionic acid (N-butyl)amide and 236 mg of 3(R,S)-methylaminocarbonyl-1,2,3,4-tetrahydroquinoline via (4O, 5N-isopropylidene)-5(S)-tert-butoxycarbonylamino-4(S)-hydroxy-2(S)-isopropyl-7,7-dimethyl-8-[3(R,S)-methylaminocarbonyl-1,2,3,4-tetrahydroquinolin-1-ylcarbonyl]-octanoic acid (N-butyl)amide (purification over 20 g of silica gel with mobile phase A: $R_f(I)$=29.6/29.9 min) and 5(S)-tert-butoxycarbonylamino-4(S)-hydroxy-2(S)-isopropyl-7,7dimethyl-8-[3(R,S)-methylaminocarbonyl-1,2,3,4-tetrahydroquinolin-1-yl-carbonyl]-octanoic acid (N-butyl)amide (purification, after extraction with ethyl acetate from sodium carbonate solution, by means of FC over silica gel (mobile phase H): $R_f(P)$=0.50) as a diastereomer mixture: $R_f(V)$=0.33; $R_f(I)$=19.1/19.3 min; FAB-MS: $(M+H)^+$=517.

The 3(R,S)-methylaminocarbonyl-1,2,3,4-tetrahydroquinoline employed as the starting material is obtained analogously to Example 1r via N-benzyloxycarbonyl-3(R,S)-methylaminocarbonyl-1,2,3, 4-tetrahydroquinoline, prepared from N-benzyloxycarbonyl-1,2,3,4-tetrahydroquinoline-3(R,S)-carboxylic acid and methylamine as described in Example 1a): $R_f(P)$=0.46.

EXAMPLE 61

5(S)-Amino-4(S)-hydroxy-2(R),7,7-trimethyl-8-[3(R,S)-methoxymethyl-1,2,3,4-tetrahydroquinolin-1-ylcarbonyl]-octanoic acid (N-butyl)amide Starting from 300 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 465 mg of 3(R,S)-methoxymethyl-1,2,3,4-tetrahydroquinoline and subsequent reaction of the (4O,5N-isopropylidene)-5(S)-tert-butoxycarbonylamino-4(S)-hydroxy-2(R),7,7-trimethyl-8-[3(R,S)-methoxymethyl-1,2,3,4-tetrahydroquinolin-1-ylcarbonyl]-octanoic acid (N-butyl)amide obtained (in a manner analogous to that described in Example 1a); $R_f(A)=0.38$), by the method described in Example 1), the title compound is obtained as a diastereomer mixture: $R_f(S)=0.31$; FAB-MS: $(M+H)^+=476$.

The amine component employed as the starting material is prepared, for example, as follows:

2.3 g of a potassium hydride suspension (20% in oil) are added to a solution of 2.6 g of 1-benzyl-3(R,S)-hydroxymethyl-1,2,3,4-tetrahydroquinoline in 30 ml of tetrahydrofuran at 0° C., while stirring, and 1.9 ml of methyliodide are then added. After 1 h, the reaction mixture is concentrated and the residue is purified over 160 g of silica gel with a 20:1 mixture of hexane and ethyl acetate. 1-Benzyl-3(R,S)-methoxymethyl-1,2,3,4-tetrahydroquinoline is obtained as a yellow solid: $R_f$(20:1 mixture of hexane and ethyl acetate)=0.32. A solution of 2.9 g of the product thus obtained in 30 ml of tetrahydrofuran is hydrogenated in the presence of 0.6 g of palladium-on-charcoal under the customary conditions. Purification of the crude product over 80 g of silica gel with methylene chloride as the eluting agent gives 3(R,S)-methoxymethyl-1,2,3,4-tetrahydroquinoline: $R_f$(methylene chloride)=0.32; $R_f(A)=0.56$.

EXAMPLE 62

5(S)-Formylamino-4(S)-hydroxy-2(R),7,7-trimethyl-8-[2(R,S)-methylaminocarbonyl-3,4-dihydro-2H-1,4-benzoxazin-4-ylcarbonyl]-octanoic acid (N-butyl)amide 140 mg of 5(S)-amino-4(S)-hydroxy-2(R),7,7-trimethyl-8-[2(R,S)-methylaminocarbonyl-3,4-dihydro-2H-1,4-benzoxazin-4-ylcarbonyl]-octanoic acid (N-butyl)amide (Example 28)) are reacted with 100 mg of 4-nitrophenyl formate in a manner analogous to that described in Example 17): $R_f(S)=0.33$; FAB-M S: $(M+H)^+=519$.

EXAMPLE 63

5(S)-Amino-4(S)-hydroxy-2(R),7,7-trimethyl-8-(3-acetyl-2,3-dihydro-1H-benzimidazo-1-ylcarbonyl)-octanoic acid N-butyl)amide In an analogous manner to that described in Examples 52, 52a and 52b) for the corresponding reaction stages, the title compound is obtained starting from 80 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 113 mg of 1-acetyl-2,3-dihydro-1H-benzimidazole, which is prepared by the method described by I. Butula in Liebigs Ann. Chem.718, 260 (1968) via (4O,5N-isopropylidene)-5(S)-tert-butoxycarbonylamino-4(S)-hydroxy-2(R),7,7-trimethyl-8-(3-acetyl-2,3-dihydro-1H-benzimidazo-1-ylcarbonyl)-octanoic acid (N-butyl)amide ($R_f(H)=0.46$) and 5(S)-tert-butoxycarbonylamino-4(S)-hydroxy-2(R),7,7-trimethyl-8-(3-acetyl-2,3-dihydro-1H-benzimidazo-1-ylcarbonyl)-octanoic acid (N-butyl)amide ($R_f(L)=0.20$): $R_f(S)=0.24$; $R_f(IV)=34.4$ min; FAB-MS: $(M+H)^+=461$.

EXAMPLE 64

5(S)-Amino-4(S)-hydroxy-2(R),7,7-trimethyl-8-[3(R,S)-ethylsulfonyl-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 80 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 178 mg of 3(R,S)-ethylsulfonyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)-ethylsulfonyl-1,2,3,4-tetrahydroquinolin-1-ylcarbonyl]-octanoic acid (N-butyl) amide (diastereomer mixture: $R_f(A)=0.09/0.14$) and 5(S)-tert-butoxycarbonylamino-4(S)-hydroxy-2(R),7,7-trimethyl-8-[3(R,S)-ethylsulfonyl-1,2,3,4-tetrahydroquinolin-1-ylcarbonyl]-octanoic acid (N-butyl) amide ($R_f(A)=0.08$) as a mixture of diastereomers: $R_f(S)=0.13/0.16$; $R_f(IV)=35.9/36.3$ min; FAB-MS: $(M+H)^+=524$.

The amine component employed as the starting material is prepared, for example, as follows:

a) 3(R,S)-Ethylsulfonyl-1,2,3,4-tetrahydroquinoline

A solution of 0.3 g of 3-ethylsulfonylquinoline in 15 ml of glacial acetic acid is hydrogenated in the presence of 30 mg of platinum oxide at 50° C. for 22 h. After working up analogously to Example 52c) and FC over 30 g of silica gel (mobile phase I), the pure title compound is obtained: mp 88°–90° C., $R_f(K)=0.51$; IR(KBr): 3380(s), 1590, 1500(m), 1270(s), 1130(s), 750(s); anal. calc. for $C_{11}H_{15}NO_2S$: C58.64%, H6.71%, N6.22%; found C58.95, 6.75, N6.21.

b) 3-Ethylsulfonylquinoline

Analogously to Example 52d), 1.3 ml of a 30% hydrogen peroxide solution are added to a mixture of 1.2 g of 3-ethylthioquinoline and 14 mg of sodium tungstate dihydrate in 6 ml of dioxane-water (2:1 mixture) and 1 drop of glacial acetic acid at 65° C. while stirring vigorously. The mixture is stirred at 80° C. for a further 1 h and, after cooling, is worked up in the customary manner. FC over 30 g of silica gel (mobile phase A) gives the pure title compound: $R_f(A)=0.34$; IR(KBr): 1305(s), 1150 and 1130(s); anal. calc. for $C_{11}H_{11}NO_2S$: C59.71%, H5.01%, N6.33%; found C59.82%, H5.03%, N6.49%.

c) 3-Ethylthioquinoline is prepared starting from 2.1 g of 3-bromoquinoline and 4.2 g of sodium ethanethiolate in 30 ml of dimethylformamide analogously to Example 52d) and is purified by means of FC over 30 g of silica gel with a 1:2 mixture of diethyl ether and petroleum ether as the mobile phase. This gives the title compound: $R_f(F)=0.31$.

EXAMPLE 65

5(S)-Amino-4(S)-hydroxy-2(R),7,7-trimethyl-8-[3(R,S)-methylcarbonyloxy-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 50 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 63 mg of 3(R,S)-methylcarbonyloxy-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methylcarbonyloxy-1,2,3,4-tetrahydroquinolin-1-yl-carbonyl]-octanoic acid (N-butyl)amide ($R_f(A)=0.30$) and 5(S)-tert-butoxycarbonylamino-4(S)-hydroxy-2(R),7,7-trimethyl-8-[3(R,S)-methylcarbonyloxy-1,2,3,4-tetrahydroquinolin-1-yl-carbonyl]-octanoic acid (N-butyl)amide ($R_f(A):0.07$) as a diastereomer mixture: $R_f(S)=0.29/0.31$; $R_f(IV)=18.6/18.9$ min; FAB-MS: $(M+H)^+=490$.

The 3(R,S)-methylcarbonyloxy-1,2,3,4-tetrahydroquinoline employed as the starting material is prepared, for example, as follows:

1.35 ml of acetyl chloride are added dropwise to a mixture of 2.5g of 3-hydroxyquinoline (prepared by the method described by Mills and Watson in J.Chem. Soc., 97, 753 (1910)), 8.6 ml of pyridine and 50 ml of methylene chloride, while cooling with ice. After the reaction mixture has been stirred at room temperature for 10 minutes, 50 ml of water are added. Customary working up and purification of the crude product by FC over 50 g of silica gel (mobile phase C) gives 3-methylcarbonyloxyquinoline: $R_f(A)$=0.55; IR ($CH_2Cl_2$): 1770(s) $cm^{-1}$.

2.80 g of the ester described above, dissolved in 280 ml of dioxane, are hydrogenated in the presence of 1.12 g of palladium-on-charcoal (10% of palladium) at 55° C. under normal pressure for 2 h. The reaction mixture is filtered over Celite '545 and concentrated. Purification of the residue by means of FC over 80 g of silica gel (mobile phase F) gives 3(R,S)-methylcarbonyloxy-1,2,3,4-tetrahydroquinoline: $R_f(A)$=0.65.

EXAMPLE 66

5(S)-Amino-4(S)-hydroxy-2(R),7,7-trimethyl-8-[2(R,S)-methoxycarbonyl-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 80 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 101 mg of 2(R,S)-methoxycarbonyl-1,2,3,4-tetrahydroquinoline via (4O,5N-isopropylidene)-5(S)-tert-butoxycarbonylamino-4(S)-hydroxy-2(R),7,7-trimethyl-8-[2(R,S)-methoxycarbonyl-1,2,3,4-tetrahydroquinolin-1-yl-carbonyl]-octanoic acid (N-butyl)amid ($R_f(A)$=0.35) and 5(S)-tert-butoxycarbonylamino-4(S)-hydroxy-2(R),7,7-trimethyl-8-[2(R,S)-methoxycarbonyl-1,2,3,4-tetrahydroquinolin-1-ylcarbonyl]-octanoic acid (N-butyl)amide ($R_f(P)$=0.53) as a diastereomer mixture: $R_f(S)$=0.23/0.30; $R_f(IV)$=38.1/39.3 min; FAB-MS: $(M+H)^+$=490.

The 2(R,S)-methoxycarbonyl-1,2,3,4-tetrahydroquinoline employed as the starting material is prepared, for example, as follows:

Reaction of 10.0 g of quinaldic acid with 5.4 ml of methyliodide by the method described in Example 97f) for 20 h at room temperature and purification of the crude product by FC over 80 g of silica gel (mobile phase C) gives methyl quinaldate as a white solid: $R_f(50:50:6$ mixture of hexane, ethyl acetate and glacial acetic acid)=0.65.

1.0 g of the abovementioned ester in 9 ml of ethanol is hydrogenated in the presence of 140 mg of platinum oxide at room temperature for 1 h. Purification of the crude product by FC over 60 g of silica gel (mobile phase P) gives 2(R,S)-methoxycarbonyl-1,2,3,4-tetrahydroquinoline: $R_f(A)$=0.80; MS: $(M)^+$=191.

EXAMPLE 67

5(S)-Amino-4(S)-hydroxy-2(R),7,7-trimethyl-8-[3(R,S)-methylaminocarbonyl-1,2,3,4-tetrahydroquinoxalin-1-ylcarbonyl}-octanoic acid (N-butyl)amide In an analogous manner to that described in Examples 52, 52a and 52b) for the corresponding reaction stages, the title compound is obtained starting from 32 mg of 5(S)-tert-butoxycarbonylamino-4(S)-hydroxy-2(R),7,7-trimethyl-8-[3(R,S)-methylaminocarbonyl-1,2,3,4-tetrahydroquinoxalin-1-ylcarbonyl]-octanoic acid (N-butyl) amide by reaction in 2 ml of 4N hydrochloric acid in dioxane (1 h at 0° C.) and FC purification over 10 g of silica gel (mobile phase P) as a diastereomer mixture:$R_f(S)$=0.07; $R_f(IV)$=31.7/32.0 min; FAB-MS: $(M+H)^+$=490.

The starting materials are prepared, for example, as follows:

a) 5(S)-Tert-butoxycarbonylamino-4(S)-hydroxy-2(R),7,7-trimethyl-8-[3(R,S)-methylaminocarbonyl-1,2,3,4-tetrahydroquinoxalin-1-ylcarbonyl]-octanoic acid (N-butyl) amide The title compound is obtained starting from 40 mg of (4O,5N-isopropylidene)-5(S)-tert-butoxycarbonylamino-4(S)-hydroxy-2(R),7,7-trimethyl-8-[3(R,S)-methylaminocarbonyl-1,2,3,4-tetrahydroquinoxalin-1-ylcarbonyl]-octanoic acid (N-butyl)amide analogously to Example 20a): $R_f(P)$=0.19; FAB-MS: $(M+H)^+$=590.

b) (4O,5N-Isopropylidene)-5(S)-tert-butoxycarbonylamino-4(S)-hydroxy-2(R),7,7-trimethyl-8-[3(R,S)-methylaminocarbonyl-1,2,3,4-tetrahydroquinoxalin-1-ylcarbonyl]-octanoic acid (N-butyl)amide The title compound is obtained starting from 237 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 268 mg of 2(R,S)-methylaminocarbonyl-1,2,3,4-tetrahydroquinoxaline analogously to Example 1a) and purification by means of FC over 30 g of silica gel with a 97:3:0.5 mixture of methylene chloride, methanol and concentrated ammonia as the mobile phase: $R_f(95:5:1$ mixture of methylene chloride, methanol and glacial acetic acid)=0.50; FAB-MS: $(M+H)^+$=630.

c) 2(R,S)-Methylaminocarbonyl-1,2,3,4-tetrahydroquinoxaline 0.33 g of 2-(methylaminocarbonyl)quinoxaline in 15 ml of ethanol is hydrogenated in the presence of 0.07 g of palladium-on-charcoal (10% of Pd) at room temperature for 6 h: $R_f(P)$=0.45.

d) 2-(Methylaminocarbonyl)quinoxaline is obtained starting from 0.5 g of 2-quinoxaloyl chloride by reaction with methylamine hydrochloride under customary reaction conditions: $R_f(P)$=0.69.

EXAMPLE 68

5(S)-Amino-4(S)-hydroxy-2(R),7,7-trimethyl-8-[4-acetyl-3(R,S)-methylaminocarbonyl-1,2,3,4-tetrahydroquinoxalin-1-ylcarbonyl]-octanoic acid (N-butyl)amide In an analogous manner to that described in Examples 52, 52a and 52b) for the corresponding reaction stages, the title compound is obtained starting from 38 mg of (4O,5N-Isopropylidene)-5(S)-tert-butoxycarbonylamino-4(S)-hydroxy-2(R),7,7-trimethyl-8-[4-acetyl-3(R,S)-methylaminocarbonyl-1,2,3,4-tetrahydroquinoxalin-1-ylcarbonyl]-octanoic acid (N-butyl)amide via 5(S)-tert-butoxycarbonylamino-4(S)-hydroxy-2(R),7,7-trimethyl-8-[4-acetyl-3(R,S)-methylaminocarbonyl-1,2,3,4-tetrahydroquinoxalin-1ylcarbonyl]-octanoic acid (N-butyl) amide ($R_f(P)$=0.39) as a mixture of diastereomers: $R_f(P)$=0.07; $R_f(IV)$=30.7/31.2 min; FAB-MS: $(M+H)^+$=532.

The starting material is prepared, for example, as follows:

40 mg of (4O,5N-isopropylidene)-5(S)-tert-butoxycarbonylamino-4(S)-hydroxy-2(R),7,7-trimethyl-8-[3(R,S)-methylaminocarbonyl-1,2,3,4-tetrahydroquinoxalin-1-ylcarbonyl]-octanoic acid (N-butyl) amide (Example 67b) are heated at 120° C. together with 0.09 ml of acetic anhydride for 1 h. The reaction mixture is then chromatographed directly over 50 g of silica gel with a 97:3:1 mixture of methylene chloride, methanol and con-

EXAMPLE 69

5(S)-Amino-4(S)-hydroxy-2(R),7,7-trimethyl-8-[3(R,S)-methylaminocarbonyl-1,2,3,4-tetrahydroquinolin-1-ylcarbonyl]-octanoic acid (N-butyl)amide In a manner analogous to that described in Examples 1) and 1a) for the corresponding reaction stages, the title compound is obtained starting from 300 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 570 mg of 3(R,S)-methylaminocarbonyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methylaminocarbonyl-1,2,3,4-tetrahydroquinolin-1-yl-carbonyl]-octanoic acid (N-butyl)amide ($R_f$(ethyl acetate)=0.36; $R_f$(N)=0.27), with purification over 80 g of silica gel (mobile phase S), as a diastereomer mixture: $R_f$(S)=0.21; FAB-MS: (M+H)$^+$=489.

The amine component employed is prepared starting from 1.2 g of 3(R,S)-methoxycarbonyl-1,2,3,4-tetrahydroquinoline, with reaction in 10 ml of a 3N methylamine solution in dimethylformamide at 50° C. for 30 h. Purification of the crude product, after concentration of the reaction mixture, by means of FC over silica gel (mobile phase N) gives 3(R,S)-methylaminocarbonyl-1,2,3,4-tetrahydroquinoline as a white solid: $R_f$(N)=0.25.

EXAMPLE 70

5(S)-Amino-4(S)-hydroxy-2(S)-isopropyl-7,7-dimethyl-8-[2(R,S)-methylaminocarbonyl-3,4-dihydro-2H-1,4-benzoxazin-4-ylcarbonyl]-octanoic acid (N-butyl)amide In a manner analogous to that described in Examples 21, 21a) and 21b) for the corresponding reaction stages, the title compound is obtained starting from 300 mg of 3-[N-tert-butoxycarbonyl-4(S)-(3-carboxy-2,2-dimethylpropyloxy-2,2-dimethyl-1,3-oxazolidin-5(S)-yl]-2(S)isopropyl-propionic acid (N-butyl)amide and 240 mg of 2(R,S)-methylaminocarbonyl-3,4-dihydro-2H-1,4-benzoxazine via (4O,5N-isopropylidene)-5(S)-tert-butoxycarbonylamino-4(S)-hydroxy-2(S)-isopropyl-7,7-dimethyl-8-[(R,S)-methylaminocarbonyl-3,4-dihydro-2H-1,4-benzoxazin-4-ylcarbonyl]-octanoic acid (N-butyl)amide ($R_f$(X)=0.45) and 5(S)-tert-butoxycarbonylamino-4(S)-hydroxy-2(S)-isopropyl-7,7-dimethyl-8-[2(R,S)-methylaminocarbonyl-3,4-dihydro-2H-1,4-benzoxazin-4-ylcarbonyl]-octanoic acid (N-butyl)amide ($R_f$(X)=0.28) as a diastereomer mixture: $R_f$(V)=0.55; $R_f$(I)=23.2 min; FAB-MS: (M+H)$^+$=519.

EXAMPLE 71

5(S)-Amino-4(S)-hydroxy-2(R),7,7-trimethyl-8-[2(R,S)-methoxyethylaminocarbonyl-3,4-dihydro-2H-1,4-benzoxazin-4-ylcarbonyl]-octanoic acid (N-butyl)amide In a manner analogous to that described in Examples 21, 21a) and 21b) for the corresponding reaction stages, the title compound is obtained starting from 205 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 237 mg of 2(R,S)-methoxyethylaminocarbonyl-3,4-dihydro-2H-1,4-benzoxazine via (4O,5N-isopropylidene)-5(S)-tert-butoxycarbonylamino-4(S)-hydroxy-2(R),7,7-trimethyl-8-[2(R,S)-methoxyethylaminocarbonyl-3,4-dihydro-2H-1,4-benzoxazin-4-ylcarbonyl]-octanoic acid (N-butyl)amide (analogously to Example 1a): $R_f$(A)=0.30) and 5(S)-tert-butoxycarbonylamino-4(S)-hydroxy-2(R),7,7-trimethyl-8-[2(R,S)-methoxyethylaminocarbonyl-3,4-dihydro-2H-1,4-benzoxazin-4-ylcarbonyl]-octanoic acid (N-butyl)amide ($R_f$(P)=0.53; FAB-MS: (M+H)$^+$=635) in a manner analogous to that described in Example 1), as a diastereomer mixture: $R_f$(V)=0.42; $R_f$(I)=18.0 min; FAB-MS: (M+H)$^+$=535.

The amine component employed as the starting material is prepared, for example, as follows:

5.3 ml of a 2M trimethylaluminium solution in hexane are added to a solution of 0.92 ml of 2-methoxyethylamine in 30 ml of methylene chloride at room temperature. The reaction mixture is stirred at 25° C. for 1 h, and a solution of 1.22 g of 2(R,S)-ethoxycarbonyl-3,4-dihydro-2H-1,4-benzoxazine in 20 ml of methylene chloride is then added dropwise in the course of 15 min. After the reaction mixture has been stirred at 40° C. for 16 h, water is added and it is extracted with chloroform. This gives 2(R,S)-methoxyethylaminocarbonyl-3,4-dihydro-2H-1,4-benzoxazine by recrystallization from ethyl acetate/hexane: $R_f$(P)=0.59.

EXAMPLE 72

5(S)-Amino-4(S)-hydroxy-2(R),7(S)-dimethyl-8-[2(R,S)-ethoxycarbonyl-3,4-dihydro-2H-1,4-benzoxazin-4-ylcarbonyl]-octanoic acid (N-butyl)amide 2 ml of a 25% solution of trifluoroacetic acid in methylene chloride are added to 40 mg of 5(S)-tert-butoxycarbonylamino-4(S)-hydroxy-2(R),7(S)-dimethyl-8-[2(R,S)-ethoxycarbonyl-3,4-dihydro-2H-1,4-benzoxazin-4-ylcarbonyl]-octanoic acid (N-butyl)amide, while cooling with ice. Stirring is continued at 0° C. When the reaction has ended (monitoring by TLC), 1 ml of toluene is added to the mixture, the solvent is rapidly evaporated off in vacuo and the oily residue is purified directly by means of FC over 10 g of silica gel (mobile phase P).

This gives the title compound as a diastereomer mixture: $R_f$(S)=0.27; $R_f$(IV)=35.0/35.2 min; FAB-MS: (M+H)$^+$=478.

The starting materials are prepared, for example, as follows:

a) 5(S)-Tert-butoxycarbonylamino-4(S)-hydroxy-2(R),7(S)-dimethyl-8-[2(R,S)-ethoxycarbonyl-3,4-dihydro-2H-1,4-benzoxazin-4-ylcarbonyl]-octanoic acid (N-butyl)amide The title compound is obtained in a manner analogous to that described in Example 21a) starting from 114 mg of (4O,5N-isopropylidene)-5(S)-tert-butoxycarbonylamino-4(S)-hydroxy-2(R),7(S)-dimethyl-8-[2(R,S)-ethoxycarbonyl-3,4-dihydro-2H-1,4-benzoxazin-4-ylcarbonyl]-octanoic acid (N-butyl)amide and is purified by means of FC over 25 g of silica gel (mobile phases A and B): $R_f$(A)=0.15; FAB-MS: (M+H)$^+$=578.

b) (4O,5N-Isopropylidene)-5(S)-tert-butoxycarbonylamino-4(S)-hydroxy-2(R),7(S)-dimethyl-8-[2(R,S)-ethoxycarbonyl-3,4-dihydro-2H-1,4-benzoxazin-4-ylcarbonyl]-octanoic acid (N-butyl)amide 0.07 ml of 1-chloro-N,N,2-trimethylpropenylamine is added to a solution of 90 mg of 3-[N-tert-butoxycarbonyl-4(S)-[3-carboxy-2(S)-methylpropyl]-2,2-dimethyl-1,3-oxazolidin-5(S)-yl]-2(R)-methyl-propionic acid (N-butyl) amide in 2 ml of methylene chloride at 0° C., under nitrogen, and the mixture is subsequently stirred for 30 min. 157 mg of 2(R,S)-ethoxycarbonyl-3,4-dihydro-2H-1,4-benzoxazine, dissolved in a little methylene chloride, and 4-DMAP are then added. After the mixture has warmed to room temperature, stirring is continued for a further 5 h and the reaction mixture is then chromatographed directly over 80 g of silica gel with an eluting agent gradient from E to A. This gives the pure title compound as a diastereomer mixture: $R_f(A)=0.30/0.40$.

c) 3-[N-Tert-butoxycarbonyl-4(S)-[3-carboxy-2(S)-methylpropyl]-2,2-dimethyl-1,3-oxazolidin-5(S)-yl]-2(R)-methyl-propionic acid (N-butyl)amide A solution of 311 mg of 3-[N-tert-butoxycarbonyl-4(S)-[4-hydroxy-2(S)-methylbutyl]-2,2-dimethyl-1,3-oxazolidin-5(S)-yl]-2-(R)-methyl-propionic acid (N-butyl)amide in a mixture of 4.8 ml of carbon tetrachloride and 4.8 ml of acetonitrile is added to a mixture of 928 mg of sodium metaperiodidate, 19 mg of ruthenium(III) chloride hydrate and 0.6 ml of water while stirring vigorously. After 1 h, the mixture is diluted with 30 ml of methylene chloride and 5 ml of isopropanol, and the aqueous phase is separated off and extracted with methylene chloride. The combined organic phase is concentrated, the residue is taken up in 10 ml of toluene and the mixture is concentrated again. The dark-coloured residue is purified by FC over 25 g of silica gel with a 50:50:1 mixture of hexane, ethyl acetate and glacial acetic acid: $R_f(B)=0.18$; FAB-MS: $(M+H)^+=443$.

d) 3-[N-Tert-butoxycarbonyl-4(S)-[4-hydroxy-2(S)-methylbutyl]-2,2-dimethyl-1,3-oxazolidin-5(S)-yl]-2(R)-methyl-propionic acid (N-butyl)amide 475 mg of 3-[N-tert-butoxycarbonyl-4(S)-[4-triisopropylsilyloxy-2(S)-methylbutyl]-2,2-dimethyl-1,3-oxazolidin-5(S)-yl]-2(R)-methyl-propionic acid (N-butyl) amide, dissolved in 12 ml of tetrahydrofuran, are stirred together with 1.63 ml of a 1M tetrabutylammonium fluoride solution in tetrahydrofuran at room temperature for 3 h. The organic phase is washed with saturated sodium chloride solution, added over sodium sulfate and concentrated. The crude product is purified by FC over 50 g of silica gel (mobile phase H). The title compound is obtained as the pure diastereomer: $R_f(H)=0.48$.

e) 3-[N-Tert-butoxycarbonyl-4(S)-4-triisopropylsilyloxy-2(S)-methylbutyl]-2,2-dimethyl-1,3-oxazolidin-5(S)-yl]-2(R)-methyl-propionic acid (N-butyl)amide The title compound is prepared in a manner analogous to that described in Example 1d), starting from 450 mg of 5(S)-tert-butoxycarbonylamino-4(S)-hydroxy-9-triisopropylsilyloxy-2(R),7(S)-dimethyl-nonanoic acid (N-butyl)amide: $R_f(A)=0.63$.

f) 5(S)-Tert-butoxycarbonylamino-4(S)-hydroxy-9-triisoproproylsilyloxy-2(R),7(S)-dimethyl-nonanoic acid (N-butyl)amide 550 mg of 5(S)-tert-butoxycarbonylamino-4(S)-hydroxy-7(S)-methyl-2-methylene-9-triisopropylsilyloxynonanoic acid (N-butyl)amide, dissolved in 30 ml of anhydrous methanol, are hydrogenated under argon at a pressure of 25 bar in the presence of 10 mg of bis[(S)-(−)-2,2'bis(diphenylphosphino)-1,1'-binaphthyl](trimethylamino) diruthenium tetrachloride until the reaction is complete. The reaction mixture is concentrated and the crude product thus obtained is purified over 25 g of silica gel (mobile phase A). This gives the title compound: $R_f(A)=0.34$.

g) 5(S)-Tert-butoxycarbonylamino-4(S)-hydroxy-7(S)-methyl-2-methylene-9-triisopropylsilyloxynonanoic acid (N-butyl)amide 23.9 ml of a 1.6M n-butyllithium solution in hexane are added to a solution of 2.7 g of methacrylic acid butylamide in 80 ml of tetrahydrofuran at −75° C. under argon in the course of 30 min. The reaction mixture is then stirred at 0° C. for 30 min. After cooling to −75° C., 29.0 ml of a 1.0M chlorotriisopropyloxytitanium solution in hexane is added dropwise to the clear solution in the course of 30 min, the dark-coloured reaction mixture is stirred at −75° C. for a further 15 min, and a solution of 3.1 g of 2(S)-tert-butoxycarbonylamino-4(S)-methyl-6-triisopropylsilyloxyhexanal in 18 ml of tetrahydrofuran is then added in the course of 10 min. After the mixture has been stirred at −75° C. for 1 h, 19 ml of saturated ammonium chloride solution are added dropwise and, after warming to room temperature, the white suspension is extracted with diethyl ether. The organic phase is washed with 25 ml of water and 25 ml of saturated sodium chloride solution, dried over sodium sulfate and concentrated. The crude product is purified by means of FC over 400 g of silica gel (mobile phase gradient from D to B), the stereoisomers being separated. This gives the title compound (diastereomer I): $R_f(A)=0.53$; and diastereomer II: $R_f(A)=0.45$.

h) 2(S)-Tert-butoxycarbonylamino-4(S)-methyl-6-triisopropylsilyloxyhexanal

A solution of 3.35 g methyl 2(S)-tert-butoxycarbonylamino-4(S)-methyl-6-triisopropylsilyloxyhexanoate in 44 ml of toluene is cooled to −75° C. under argon, and 12.9 ml of a 20% solution of diisobutylaluminium hydride in toluene are then added dropwise in the course of 30 min. The mixture is stirred at −75° C. for a further 45 min. The reaction is then quenched by rapid addition of 2.8 ml of methanol and the mixture is poured onto 50 ml of a half-saturated aqueous potassium sodium tartrate solution. The mixture is extracted with diethyl ether and the combined organic phases are dried over sodium sulfate and concentrated. The title compound $(R_f(E)=0.34)$ is further reacted directly as the crude product.

i) Methyl 2(S)-tert-butoxycarbonylamino-4(S)-methyl-6-triisopropylsilyloxyhexanoate 2.40 g of di-tert-butyl dicarbonate are added to a mixture of 2.63 g of methyl 2(S)-amino-4(S)-methyl-6-triisopropylsilyloxyhexanoate in 11 ml of dioxane and 5.5 ml of water at 0° C., while stirring. The mixture is then allowed to warm to room temperature and stirring is continued overnight. After the dioxane has been removed in vacuo, the aqueous phase which remains is brought to pH=2 by addition of 1M potassium hydrogen sulfate solution and extracted with ethyl acetate. The organic phase is washed with a 5% sodium bicarbonate solution and with saturated sodium chloride solution, dried over sodium sulfate and concentrated. The crude product is purified by FC over 400 g of silica gel (eluting agent gradient from J to L). This gives the title compound: $R_f(C)=0.63$.

j) Methyl 2(S)-amino-4(S)-methyl-6-triisopropylsilyloxyhexanoate 100 ml of 0.5N hydrochloric acid are added to a solution of 10.0 g of 3,6-dihydro-3(S)-[4-triisoproylsilyloxy-2(S)-methylbutyl]-6(R)-isopropyl-2,5-dimethoxypyrazine in 100 ml of tetrahydrofuran and the mixture is stirred at room temperature for 40 min. The reaction mixture is brought to pH 9 by addition of 1N sodium hydroxide solution and then extracted with methylene chloride. The combined organic phase is filtered through cotton wool and concentrated. The crude product is purified by FC over 900 g of silica gel with a 500:10:1 mixture of methylene chloride, methanol and 25% ammonia solution. In addition to the re-isolated starting material, this gives the title compound: $R_f$(methylene chloride-methanol-concentrated ammonia: (140:10:1))=0.34.

k) 3,6-Dihydro-3(S)-[4-triisopropylsilyloxy-2(S)-methylbutyl]-6-(R)-isopropyl-2,5-dimethoxypyrazine 34.1 ml of a 1.6M n-butyllithium solution in hexane are slowly added dropwise to a mixture of 10.2 ml of 2(R)-2, 5-dihydro3,6-dimethoxy-2-isopropylpyrazine in 15 ml of tetrahydrofuran at −75° C. to −65° C., under argon. The reaction mixture is then stirred at −75° C. for a further 30 min and subsequently added dropwise via a cannula to a solution, cooled to −75° C., of 16.6 g of 4-triisopropylsilyloxy-2(R)-methylbutylbromide in 70 ml of tetrahydrofuran. The reaction mixture is allowed to warm to −20° C., stirring is continued at this temperature for 2 h, and the mixture is finally brought to room temperature in the course of 1 h. After customary working up, the crude product is purified by FC over 900 g of silica gel (mobile phase J). This gives the title compound as the pure diastereomer: $R_f(G)=0.73$.

l) 4-Triisopropylsilyloxy-2(R)-methylbutyl bromide 15.4 ml of triisopropylsilyl triflate are added to a solution of 8.7 g of (R)-4-bromo-3-methylbutan-1-ol in 320 ml of methylene chloride at 0° C., and 6.6 ml of 2,6-lutidine are then added in the course of 30 min. The reaction mixture is subsequently poured onto 100 ml of ice-water and the aqueous phase is acidified by addition of 2N hydrochloric acid (pH 3). It is extracted with methylene chloride and the organic phase is washed with a 5% sodium bicarbonate solution and saturated sodium chloride solution and dried over sodium sulfate. After purification of the crude product by FC over 200 g of silica gel (mobile phase J), the title compound is obtained: $R_f(J)=0.48$.

m) (R)-4-Bromo-3-methylbutan-1-ol

The title compound is prepared starting from 18.8 g of ethyl (R)-4-bromo-3-methylbutyrate by reduction with dibutylaluminium hydride by the process described by Schmid and Barner in Helv. Chim. Acta, 62, 464 (1979), and is purified by means of FC over 200 g of silica gel with a mobile phase gradient of hexane and diethyl ether (from a 9:1 mixture to a 3:1 mixture): $R_f(C)=0.24$.

n) Ethyl (R)-4-brom-3-methylbutyrate

Starting from 11.7 g (R)-3-methyl-butyrolactone, which is prepared by the method described by Mattes et al. in J. Med. Chem., 30, 1948 (1987), the title compound is obtained by a process analogous to that described for the preparation of the 3(S)-enantiomer by Schmid and Bauer (Helv. Chim. Acta, 62, 464 (1979)), with subsequent purification by means of FC over 100 g of silica gel with a 9:1 mobile phase mixture of hexane and diethyl ether: $R_f(C)=0.77$.

EXAMPLE 73

5(S)-Formylamino-4(S)-hydroxy-2(R),7,7-trimethyl-8-[2 (R,S)-methylaminocarbonyl-3,4-dihydro-2H-1,4-benzothiazin-4-ylcarbonyl]-octanoic acid (N-butyl)amide Starting from 100 mg of 5(S)-amino-4(S)-hydroxy-2(R), 7,7-trimethyl-8-[2(R,S)-methylaminocarbonyl-3,4-dihydro-2H-1,4-benzothiazin-4-ylcarbonyl]-octanoic acid (N-butyl) amide (Example 27)), the title compound is obtained by the method described in Example 47), with subsequent purification by FC over 30 g of silica gel (mobile phase S), as a diastereomer mixture: $R_f(S)=0.24$; FAB-MS: $(M+H)^+=535$.

EXAMPLE 74

5(S)-Amino-2(R)-benzyl-4(S)-hydroxy-7,7-dimethyl-8-[3 (R)- or -3(S)-methoxycarbonylamino-1,2,3,4-tetrahydroquinolin-1-ylcarbonyl]-octanoic acid (N-butyl) amide In an analogous manner to that described in Examples 52, 52a and 52b) for the corresponding reaction stages, the title compound is obtained starting 80 mg of 3-[N-tert-butoxycarbonyl-4(S)(3-carboxy-2,2-dimethylpropyloxy-2, 2-dimethyl-1,3-oxazolidin-5(S)-yl]-2(R)-benzyl-propionic acid (N-butyl)amide and 77 mg of 3(R)- or 3(S)-methoxycarbonylamino-1,2,3,4-tetrahydroquinoline (stereoisomer II, Example 74h)) via (4O,5N-isopropylidene) -5(S)-tert-butoxycarbonylamino-2(R)-benzyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl)amide ($R_f(L)=0.27$; FAB-MS: $(M+H)^+=721$) and 5(S)-tert-butoxycarbonylamino-2(R)-benzyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl) amide ($R_f(L)=0.26$; FAB-MS: $(M+H)^+=681$) analogously to Example 92) as the pure diastereomer: $R_f(P)=0.39$; $R_f(IV)$ =41.8 min; FAB-MS: $(M+H)^+=581$.

The starting materials are prepared, for example, as follows:

a) 3-[N-Tert-butoxycarbonyl-4(S)-(3-carboxy-2,2-dimethylpropyloxy-2,2-dimethyl-1,3-oxazolidin-5(S)-yl]-2 (R)-benzyl-propionic acid (N-butyl)amide 576 mg of 3-[N-tert-butoxycarbonyl-4(S)-(4-benzyloxy-2,2-dimethylbutyloxy-2,2-dimethyl-1,3-oxazolidin-5(S)-yl] -2(R)-benzyl-propionic acid (N-butyl)amide in 10 ml of ethyl acetate are hydrogenated in the presence of palladium-on-charcoal (5% of Pd) and the crude product is purified over silica gel: $R_f$(2:1 mixture of ethyl acetate and hexane) =0.44; FAB-MS: $(M+H)^+=519$. Further reaction in a manner analogous to that described in Example 1b) gives the title compound: $R_f(P)=0.55$; FAB-MS: $(M+H)^+=533$.

b) 3-[N-Tert-butoxycarbonyl-4(S)-(4-benzyloxy-2,2-dimethylbutyloxy-2,2-dimethyl-1,3-oxazolidin-5(S)-yl-2 (R)-benzyl-propionic acid (N-butyl)amide A mixture of 580 mg of 2(R)-benzyl-9-benzyloxy-5(S)-tert-butoxycarbonylamino-4(S)-hydroxy-7,7-dimethyl-nonanoic acid (N-butyl)amide and 13 mg of p-toluenesulfonic acid in 3 ml of 2,2-dimethoxypropane and 6 ml of methylene chloride is stirred at room temperature for 2 h. Customary working up gives the title compound: $R_f(B)=0.60$; FAB-MS: $(M+H)^+=609$.

c) 2(R)-Benzyl-9-benzyloxy-5(S)-tert-butoxycarbonylamino-4(S)-hydroxy-7,7-dimethyl-nonanoic acid (N-butyl)amide A solution of 502 mg of 3(R)-benzyl-5(S)-[5-benzyloxy-1 (S)-tert-butoxycarbonylamino-3,3-dimethyl-pentyl]-2-oxo-tetrahydrofuran in 8.5 ml of butylamine is stirred at room temperature for 20 h and concentrated and the residue is purified by chromatography over silica gel (mobile phase A): $R_f(A)=0.47$; FAB-MS: $(M+H)^+=569$.

d) 3(R)-Benzyl-5(S)-[5-benzyloxy-1(S)-tert-butoxycarbonylamino-3,3-dimethyl-pentyl]-2-oxotetrahydrofuran A solution of 1.76 g of 5(S)-[5-benzyloxy-1(S)-tert-butoxycarbonylamino-3,3-dimethylpentyl]-2-oxo-tetrahydrofuran in 30 ml of tetrahydrofuran is added to a mixture of 9.14 ml of a 1M lithiumbis(trimethylsilyl)amide solution in tetrahydrofuran and 30 ml of tetrahydrofuran at −78° C. under argon and the mixture is stirred for 30 min. 0.63 ml of benzyl bromide in 30 ml of tetrahydrofuran are then added dropwise. After the mixture has been stirred at −78° C. for 3.5 h, the reaction is quenched by addition of 1.6 ml of propionic acid and the mixture is diluted with diethyl ether. The organic phase is washed with a 10% aqueous citric acid solution and a 1M sodium bicarbonate solution, dried over sodium sulfate and concentrated. Purification over silica gel (mobile phase D) gives the title compound: $R_f(D)=0.23$; FAB-MS: $(M+H)^+=496$.

e) 5(S)-[5-Benzyloxy-1(S)-tert-butoxycarbonylamino-3,3-dimethyl-pentyl]-2-oxotetrahydrofuran 5.52 g of the ethyl 9-benzyloxy-5(S)-tert-butoxycarbonylamino-4(R,S)-hydroxy-7,7-dimethyl-nonanoate obtained as the crude product are refluxed in 100 ml of toluene and 4 ml of glacial acetic acid at 110° C. under argon for 4.5 h. After the reaction mixture has cooled, it is diluted with ethyl acetate and worked up in the customary manner. The crude product is purified by chromatography over silica gel (mobile phase B), the two 5(S) and 5(R) stereoisomers being separated. This gives the pure title compound (diastereomer I) as a yellowish oil: $R_f(B)$=0.26; FAB-MS: $(M+H)^+$=406; and diastereomer II: $R_f(B)$=0.22.

f) Ethyl 9-benzyloxy-5(S)-tert-butoxycarbonylamino-4(R,S)-hydroxy-7,7-dimethyl-nonanoate A solution of 5.85 g of ethyl 9-benzyloxy-5(S)-tert-butoxycarbonylamino-4(R,S)-hydroxy-7,7-dimethyl-non-2-inoate in 100 ml of tetrahydrofuran is hydrogenated in the presence of 1.2 g of platinum-on-charcoal (5% of Pt; a further 1.2 g of catalyst are added after 24 h) at room temperature under normal pressure for 33 h. Filtration of the reaction mixture over Hyflo® and concentration of the filtrate gives the crude title compound as a yellow oil: $R_f(B)$=0.32; FAB-MS: $(M+H)^+$=452.

g) Ethyl 9-benzyloxy-5(S)-tert-butoxycarbonylamino-4(R,S)-hydroxy-7,7-dimethyl-non-2-inoate 22.2 ml of a 1.6M n-butyllithium solution in hexane are added to a solution of 5.1 ml of diisopropylamine in 40 ml of tetrahydrofuran at −78° C. under argon, while stirring. After 30 min, a solution, cooled to −78° C., of 2.5 ml of ethyl propiolate in 20 ml of tetrahydrofuran is added dropwise via a cannula. The yellow reaction solution is stirred at −78° C. for a further 1 h and 5.0 g of 6-benzyloxy-2(S)-tert-butoxycarbonylamino-4,4-dimethyl-hexanal (Example 390) in 30 ml of tetrahydrofuran are then added dropwise. After the mixture has been stirred for 4.5 h, the reaction is quenched by addition of saturated aqueous ammonium chloride solution and the reaction mixture is allowed to warm to room temperature and is worked up in the customary manner. The crude product is purified by FC over silica gel (eluting agent C). The title compound is obtained as a mixture of the 4(S) and 4(R) diastereomers in a ratio of about (5.4:1): $R_f(C)$=0.28; FAB-MS: $(M+H)^+$=448.

h) 3(R)- or 3(S)-Methoxycarbonylamino-1,2,3,4-tetrahydroquinoline

A solution of 6.54 g of 3-(methoxycarbonylamino) quinoline in 240 ml of ethanol is hydrogenated in the presence of 0.68 g of palladium-on-charcoal (10% of Pd) at 50° C. under normal pressure for 20 h. After customary working up, the crude product is chromatographed over 400 g of silica gel with an 8:1 mixture of methylene chloride and diethyl ether as the mobile phase. This gives 3(R,S)-methoxycarbonylamino-1,2,3,4-tetrahydroquinoline as a crystalline solid: $R_f(P)$=0.84; MS: $M^+$=206. 1.0 g of the product thus obtained is chromatographed over a Chiralcel$^R$ OD-Prep column (500×50 mm) with an 8:2 mixture of heptane and propanol as the eluting agent. The title compound is obtained in the form of the two pure stereoisomers as a crystalline solid: stereoisomer I: $[\alpha]^D{}^{RT}$=+28.7 (c=1; methylene chloride); stereoisomer II: $[\alpha]^D{}^{RT}$=−28.5 (c=1; methylene chloride).

i) 3-(Methoxycarbonylamino)quinoline 3.2 ml of methyl chloroformate am added dropwise to 5.0 g of 3-aminoquinoline in 30 ml of methylene chloride and 15 ml of pyridine at 0° C. in the course of 30 min. The mixture is subsequently stirred for a further 30 min and then worked up in the customary manner. The title compound is obtained as a crystalline solid: $R_f(H)$=0.41.

EXAMPLE 75

5(S)-Amino-2(R)-butyl-4(S)-hydroxy-7,7-dimethyl-8-[3(R)- or -3(S)-methoxycarbonylamino-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 81 mg of 3-[N-tert-butoxycarbonyl-4(S)(3-carboxy-2,2-dimethylpropyloxy-2,2-dimethyl-1,3-oxazolidin-5(S)-yl]-2(R)-butyl-propionic acid (N-butyl)amide and 83 mg of 3(R)- or 3(S)-methoxycarbonylamino-1,2,3,4-tetrahydroquinoline (stereoisomer II, Example 74h)) via (4O,5N-isopropylidene)-5(S)-tert-butoxycarbonylamino-2(R)-butyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl)amide ($R_f(L)$=0.32; FAB-MS: $(M+H)^+$=687) and 5(S)-tert-butoxycarbonylamino-2(R)-butyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl)amide ($R_f(L)$=0.15; FAB-MS: $(M+H)^+$=647), analogously to Example 92), as the pure diastereoisomer: $R_f(P)$=0.48; FAB-MS: $(M+H)^+$=547.

The starting materials are obtained, for example, as follows:

a) 3-[N-Tert-butoxycarbonyl-4(S)-(3-carboxy-2,2-dimethylpropyloxy-2,2-dimethyl-1,3-oxazolidin-5(S)-yl]-2(R)-butyl-propionic acid (N-butyl)amide The title compound is obtained in a manner analogous to that in Example 74a) starting from 338 mg of 3-[N-tert-butoxycarbonyl-4(S)(4-hydroxy-2,2-dimethylbutyloxy-2,2-dimethyl-1,3-oxazolidin-5(S)-yl]-2(R)-butyl-propionic acid (N-butyl)amide: $R_f(P)$=0.77; FAB-MS: $(M+H)^+$=499.

b) 3-[N-Tert-butoxycarbonyl-4(S)(4-hydroxy-2,2-dimethylbutyloxy-2,2-dimethyl-1,3-oxazolidin-5(S)-yl]-2(R)-butyl-propionic acid (N-butyl)amide Analogously to Examples 74b and 74c), starting from 455 mg of 3(R)-but-2-enyl-5(S)-[5-benzyloxy-1(S)-tert-butoxycarbonylamino-3,3-dimethyl-pentyl]-2-oxo-tetrahydrofuran das 3-[N-tert-butoxycarbonyl-4(S)(4-benzyloxy-2,2-dimethylbutyloxy-2,2-dimethyl-1,3-oxazolidin-5(S)-yl]-2(R)-but-2-enyl-propionic acid (N-butyl)amide is obtained (471 mg; $R_f(C)$=0.32; FAB-MS: $(M+H)^+$=573), and is then hydrogenated in 10 ml of ethyl acetate in the presence of palladium-on-charcoal (5% of Pd) at room temperature for 1 h to give the title compound: $R_f(A)$=0.32; FAB-MS: $(M+H)^+$=485.

c) 3(R)-But-2-enyl-5(S)-[5-benzyloxy-1(S)-tert-butoxycarbonylamino-3,3-dimethyl-pentyl]-2-oxo-tetrahydrofuran The title compound is obtained starting from 546 mg of 5(S)-[5-benzyloxy-1(S)-tert-butoxycarbonylamino-3,3-dimethyl-pentyl]-2-oxo-tetrahydrofuran and 0.17 ml of crotyl bromide by the process described in Example 74d): $R_f(D)$=0.32; FAB-MS: $(M+H)^+$=460.

EXAMPLE 76

5(S)-Amino-4(S)-hydroxy-2(R),7,7-trimethyl-8-[3(R,S)-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 150 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 181 mg of 3(R,S)-methoxymethylcarbonylamino-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methoxymethylcarbonylamino-1,2,3,4-tetrahydroquinolin-1-ylcarbonyl]-octanoic acid (N-butyl)amide ($R_f(P)$=0.58) and 5(S)-tert-butoxycarbonylamino-4

(S)-hydroxy-2(R),7,7-trimethyl-8-[3(R,S)-methoxymethylcarbonylamino-1,2,3,4-tetrahydroquinolin-1-ylcarbonyl]-octanoic acid (N-butyl)amide ($R_f(P)$=0.49), in a manner analogous to that described in Example 92), as a diastereomer mixture: $R_f(S)$=0.17; $R_f(V)$=14.7 min; FAB-MS: $(M+H)^+$=519.

3(R,S)-Methoxymethylcarbonylamino-1,2,3,4-tetrahydroquinoline is obtained from 3(R,S)-amino-1,2,3,4-tetrahydroquinoline by reaction with methoxyacetyl chloride analogously to Example 109b), as a crystalline solid: $R_f(P)$=0.63; MS: $M^+$=220.

EXAMPLE 77

5(S)-Amino-4(S)-hydroxy-2(R),7,7-trimethyl-8-[3-ethoxycarbonyl-1,2,3,4-tetrahydroquinazolin-1-ylcarbonyl]-octanoic acid (N-butyl)amide In an analogous manner to that described in Examples 52, 52a and 52b) for the corresponding reaction stages, the title compound is obtained starting from 90 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 163 mg of 3-ethoxycarbonyl-1,2,3,4-tetrahydroquinazoline via (4O,5N-isopropylidene)-5(S)-tert-butoxycarbonylamino-4(S)-hydroxy-2(R),7,7-trimethyl-8-(3-ethoxycarbonyl-1,2,3,4-tetrahydroquinazolin-1-ylcarbonyl)-octanoic acid (N-butyl)amide ($R_f(K)$=0.24) aud 5(S)-tert-butoxycarbonylamino-4(S)-hydroxy-2(R),7,7-trimethyl-8-(3-ethoxycarbonyl-1,2,3,4-tetrahydroquinazolin-1-ylcarbonyl)-octanoic acid (N-butyl)amide ($R_f(P)$=0.27): $R_f(S)$=0.19; $R_f(IV)$=38.0 min; FAB-MS: $(M+H)^+$=505.

The 3-ethoxycarbonyl-1,2,3,4-tetrahydroquinazoline employed as the starting material is prepared, for example, as follows: 0.35 ml of ethyl chloroformate is added to a mixture of 473 mg of 1,2,3,4-tetrahydroquinazoline (cf. Example 153)) and 1.03 ml of triethylamine in 30 ml methylene chloride at 0° C., while stirring. After 5 min, saturated aqueous sodium chloride solution is added and the reaction mixture is subsequently stirred briefly and worked up in the customary manner. This gives, after purification by means of FC over silica gel, 3-ethoxycarbonyl-1,2,3,4-tetrahydroquinazoline: $R_f(K)$=0.57; FAB-MS: $(M+H)^+$=207.

EXAMPLE 78

5(S)-Amino-4(S)-hydroxy-2(R),7,7-trimethyl-8-[3(R,S)-phenylcarbonyloxy-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 50 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 83 mg of 3(R,S)-phenylcarbonyloxy-1,2,3,4-tetrahydroquinoline via (4O,5N-isopropylidene)-5(S)-tert-butoxycarbonylamino-4(S)-hydroxy-2(R),7,7-trimethyl-8-[3(R,S)phenylcarbonyloxy-1,2,3,4-tetrahydroquinolin-1-yl-carbonyl]-octanoic acid (N-butyl)amide ($R_f(A)$=0.47) and 5(S)-tert-butoxycarbonylamino-(S)-hydroxy-2(R),7,7-trimethyl-8-[3(R,S)phenylcarbonyloxy-1,2,3,4-tetrahydroquinolin-1-ylcarbonyl]-octanoic acid (N-butyl)amide ($R_f(A)$=0.20) as a diastereomer mixture: $R_f(S)$=0.30; $R_f(V)$=28.1/28.6 min; FAB-MS: $(M+H)^+$=552.

The 3(R,S)-phenylcarbonyloxy-1,2,3,4-tetrahydroquinoline used as the starting material is prepared, for example, by the method described in J.Am. Chem. Soc., 66, 1168(1944): $R_f$(1:1 mixture of hexane-methylene chloride)=0.13; $R_f(A)$=0.80.

EXAMPLE 79

5(S)-Amino-4(S)-hydroxy-2(R),7,7-trimethyl-8-[2(R,S)-cyano-3,4-dihydro-2H-1,4-benzoxazin-4-ylcarbonyl]-octanoic acid (N-butyl)amide In an analogous manner to that described in Examples 52, 52a and 52b) for the corresponding reaction stages, the title compound is obtained starting from 65 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 68 mg of 2(R,S)-cyano-3,4-dihydro-2H1,4-benzoxazine, which is prepared by the process described by Bartsch and Schwarz in J. Heterocyclic Chem., 20, 45 (1983), via (4O,5N-isopropylidene)-5(S)-tert-butoxycarbonyl-amino-4(S)-hydroxy-2(R),7,7-trimethyl-8-[3(R,S)-cyano-3,4-dihydro-2H1,4-benzoxazin-4-yl-carbonyl]-octanic acid (N-butyl)amide ($R_f(A)$=0.47) and 5(S)-tert-butoxycarbonylamino-4(S)-hydroxy- 2(R),7,7-trimethyl-8-[3(R,S)-cyano-3,4-dihydro-2H1,4-benzoxazin-4-ylcarbonyl]-octanoic acid (N-butyl)amide ($R_f(A)$=0.16) as a diastereomer mixture: $R_f(S)$=0.34; $R_f(V)$=17.3 min; FAB-MS: $(M+H)^+$=459.

EXAMPLE 80

5(S)-Tert-butoxycarbonylamino-4(S)-hydroxy-2(R),7,7-trimethyl-8-[3(R,S)-methoxycarbonyl-3,4-dihydro-2H-1,4-benzoxazin-4-ylcarbonyl]-octanoic acid (N-butyl)amide 166 mg of (4O,5N-isopropylidene)-5(S)-tert-butoxycarbonylamino-4(S)-hydroxy-2(R),7,7-trimethyl-8-[3(R,S)-methoxycarbonyl-3,4-dihydro-2H-1,4-benzoxazin-4-ylcarbonyl]-octanoic acid (N-butyl)amide are stirred overnight in 3 ml of methanol in the presence of 5 mg of p-toluenesulfonic acid hydrate at room temperature. After the mixture has been concentrated, the crude product is purified over silica gel (mobile phase N): $R_f(N)$=0.30; FAB-MS: $(M+H)^+$=592.

The starting materials are prepared, for example, as follows:

a) (4O,5N-Isopropylidene)-5(S)-tert-butoxycarbonylamino-4(S)-hydroxy-2(R),7,7-trimethyl-8-[3(R,S)-methoxycarbonyl-3,4-dihydro-2H-1,4-benzoxazin-4-ylcarbonyl]-octanoic acid (N-butyl)amide The title compound is obtained starting from 120 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 203 mg of 3(R,S)-methoxycarbonyl-3,4-dihydro-2H-1,4-benzoxazine in a manner analogous to that in Example 1a), with purification over silica gel (mobile phase Y): $R_f(Y)$=0.64.

b) 3(R,S)-Methoxycarbonyl-3,4-dihydro-2H-1,4-benzoxazine 4.0 g of 3(R,S)-ethoxycarbonyl-3,4-dihydro-2H-1,4-benzoxazine (Example 20)) are stirred together with 0.8 g of magnesium powder in 100 ml of methanol at room temperature for 2 h. When the exothermic reaction has ended, the mixture is concentrated, the residue is taken up in methylene chloride and the organic phase is washed with 0.1N hydrochloric acid. After customary working up, the crude product is purified over 250 g of silica gel (mobile phase B): $R_f(B)$=0.26.

EXAMPLE 81

5(S)-Amino-4(S)-hydroxy-2(R),7,7-trimethyl-8-[3(R,S)-methoxycarbonyl-3,4-dihydro-2H-1,4-benzoxazin-4-ylcarbonyl]-octanoic acid (N-butyl)amide Starting from 78 mg of 5(S)-tert-butoxycarbonylamino-4(S)-hydroxy-2(R),7,7-trimethyl-8-3(R,S)-methoxycarbonyl-3,4-dihydro-2H-1,4-benzoxazin-4-ylcarbonyl]-octanoic acid (N-butyl)amide (Example 80)) in a manner analogous to that described in Example 1): $R_f(S)$ =0.37; FAB-MS: $(M+H)^+$=492.

EXAMPLE 82

5(S)-Amino-4(S)-hydroxy-2(R),7(R)dimethyl-8-[2(R,S)-ethoxycarbonyl-3,4-dihydro-2H1,4-benzoxazin-4-ylcarbonyl]-octanoic acid (N-butyl)amide Starting from 91 mg of 5(S)-tert-butoxycarbonylamino-4(S)-hydroxy-2(R),7(R)dimethyl-8-[2(R,S)-ethoxycarbonyl-3,4-dihydro-2H1,4-benzoxazin-4-ylcarbonyl]-octanoic acid (N-butyl)amide the title compound is obtained prepared in a manner analogous to that described in Example 72) as a diastereomer mixture: $R_f(S)$=0.26; $R_f(IV)$=35.2 min; FAB-MS: $(M+H)^+$=478.

The starting materials are prepared, for example, as follows:

a) 5(S)-Tert-butoxycarbonylamino-4(S)-hydroxy-2(R),7(R)-dimethyl-8-[2(R,S)-ethoxcarbonyl-3,4-dihydro-2H1,4-benzoxazin-4-ylcarbonyl]octanoic acid (N-butyl)amide The title compound is prepared in a manner analogous to that described in Example 72a) starting from 123 mg of (4O,5N-isopropylidene)-5(S)-tert-butoxycarbonylamino-4(S)-hydroxy-2(R),7(R)-dimethyl-8-[2(R,S)-ethoxycarbonyl-3,4-dihydro-2H1,4-benzoxazin-4-ylcarbonyl]-octanoic acid (N-butyl)amide: $R_f(A)$=0.12; FAB-MS: $(M+H)^+$=578.

b) 4O,5N-Isopropylidene)-5(S)-tert-butoxycarbonylamino-4(S)-hydroxy-2(R),7(R)-dimethyl-8-2(R,S)-ethoxycarbonyl-3,4-dihydro-2H1,4-benzoxazin-4-ylcarbonyl]-octanoic acid (N-butyl)amide The title compound is obtained in a manner analogous to that described in Example 72b) starting from 90 mg of 3-[N-tert-butoxycarbonyl-4(S)-[3-carboxy-2(R)-methylpropyl]-2,2-dimethyl-1,3-oxazolidin-5(S)-yl]-2(R)-methyl-propionic acid (N-butyl)amide as a diastereomer mixture: $R_f(A)$=0.31.

c) 3-[N-Tert-butoxycarbonyl-4(S)-[3-carboxy-2(R)-methylpropyl]-2,2-dimethyl-1,3-oxazolidin-5(S)-yl]-2(R)-methyl-propionic acid (N-butyl)amide In an analogous manner to that described in Example 72c), the title compound is prepared from 425 mg of 3-[N-tert-butoxycarbonyl-4(S)[4-hydroxy-2(R)-methylbutyl]-2,2-dimethyl-1,3-oxazolidin-5(S)-yl]-2-(R)-methyl-propionic acid (N-butyl)amide and purified by FC over 35 g of silica gel with a 50:50:1 mixture of hexane, ethyl acetate and glacial acetic acid as the mobile phase: $R_f(B)$=0.22.

d) 3-[N-Tert-butoxycarbonyl-4(S)-[4-hydroxy-2(R)-methylbutyl]-2,2-dimethyl-1,3-oxazolidin-5(S)-yl]-2-(R)-methyl-propionic acid (N-butyl)amide The title compound is prepared in a manner analogous to that described in Example 72d) starting from 694 mg of 3-[N-tert-butoxycarbonyl-4(S)-[4-triisopropylsilyloxy-2(R)-methylbutyl]-2,2-dimethyl-1,3-oxazolidin-5(S)-yl]-2-(R)-methyl-propionic acid (N-butyl)amide and the crude product is purified by FC over 60 g of silica gel (mobile phase A): $R_f(H)$=0.45.

e) 3-[N-Tert-butoxycarbonyl-4(S)-[4-triisopropylsilyloxy-2(R)-methylbutyl]-2,2-dimethyl-1,3-oxazolidin-5(S)-yl]-2-(R)-methyl-propionic acid (N-butyl)amide The title compound is prepared in a manner analogous to that described in Example 72e) starting from 800 mg of 5(S)tert-butoxycarbonylamino-4(S)-hydroxy-9-triisopropylsilyloxy-2(R),7(R)-dimethyl-nonanoic acid (N-butyl)amide: $R_f(A)$=0.69.

f) 5(S)-Tert-butoxycarbonylamino-4(S)-hydroxy-9-triisopropylsiloloxy-2(R),7(R)-dimethyl-nonanoic acid (N-butyl)amide The title compound is prepared in a manner analogous to that described in Example 72f) from 885 mg of 5(S)tert-butoxycarbonylamino-4(S)-hydroxy-7(R)-methyl-2-methylene-9-triisopropylsilyloxynonanoic acid (N-butyl) amide: $R_f(A)$=0.36.

g) 5(S)-Tert-butoxycarbonylamino-4(S)-hydroxy-7(R)-methyl-2-methylene-9-triisopropylsilyloxynonanoic acid (N-butyl)amide In a manner analogous to that described in Example 72g), the title compound is obtained starting from 3.2 g of 2(S)-tert-butoxycarbonylamino-4(R)-methyl-6-triisopropylsilyloxyhexanal ($R_f(D)$=0.36), which is prepared by processes analogous to those described in Examples 72h to 72n), starting from (S)-3-methylbutyrolactone, and is purified by FC over 400 g of silica gel (mobile phase gradient from E to B), the two stereoisomers being separated. This gives the title compound (diastereomer I): $R_f(A)$ =0.58; and diastereomer II: $R_f(A)$=0.47.

EXAMPLE 83

5(S)-Amino-4(S)-hydroxy-2(R),7,7-trimethyl-8-[3(R,S)-methoxy-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 50 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 54 mg of 3(R,S)-methoxy-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methoxy-1,2,3,4-tetrahydroquinolin-1-ylcarbonyl]-octanoic acid (N-butyl)amide ($R_f(A)$=0.38) and 5(S)-tert-butoxycarbonylamino-4(S)-hydroxy-2(R),7,7-trimethyl-8-[3(R,S)-methoxy-1,2,3,4-tetrahydroquinolin-1-ylcarbonyl]-octanoic acid (N-butyl)amide ($R_f(A)$=0.08; FAB-MS: $(M+H)^+$=562) as a diastereomer mixture: $R_f(S)$=0.24; $R_f(V)$ =16.6/17.5 min; FAB-MS: $(M+H)^+$=462.

The 3(R,S)-methoxy-1,2,3,4-tetrahydroquinoline employed as the starting material is prepared, for example, as follows:

1.05 g of anhydrous potassium carbonate and 0.48 ml of methyliodide are added to a solution of 1.0 g of 3-hydroxyquinoline in 8.5 ml of dimethylformamide and the reaction mixture is stirred at room temperature for 18 h. It is diluted with diethyl ether, the resulting suspension is filtered and the filtrate is concentrated. The crude product is purified by FC over 60 g of silica gel (mobile phase F) to give 3-methoxyquinoline: $R_f(A)$=0.53.

A solution of 0.34 g of 3-methoxyquinoline in 15 ml of ethanol is hydrogenated in the presence of 0.07 g of palladium-on-charcoal (10% of palladium) at 50° C. for 8 h and after customary working up, the crude product is purified by FC over silica gel (mobile phase K). This gives 3(R,S)-methoxy-1,2,3,4-tetrahydroquinoline: $R_f(A)$=0.61.

EXAMPLE 84

5(S)-Amino-4(S)-hydroxy-2(R),7,7-trimethyl-8-[2(R,S)-methoxymethyl-3,4-dihydro-2H1,4-benzothiazin-4-ylcarbonyl]-octanoic acid (N-butyl)amide In an analogous manner to that described in Examples 52, 52a and 52b) for the corresponding reaction stages, the title compound is obtained starting from 100 mg 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 107 mg of 2(R,S)-methoxymethyl-3,4-dihydro-2H1,4-benzothiazine via (4O,5N-isopropylidene)-5(S)-tert-butoxycarbonylamino-4(S)-hydroxy-2(R),7,7-trimethyl-8-[2(R,S)-methoxymethyl-3,4-dihydro-2H1,4-benzothiazin-4-ylcarbonyl]-octanoic acid (N-butyl)amide ($R_f(A)=0.41$) and 5(S)-tert-butoxycarbonylamino-4(S)-hydroxy-2(R),7,7-trimethyl-8-[2(R,S)-methoxymethyl-3,4-dihydro-2H1,4-benzothiazin-4-ylcarbonyl]-octanoic acid (N-butyl)amide ($R_f(K)=0.30$) as a diastereomer mixture: $R_f(S)=0.26/0.28$; $R_f(IV)=39.9/40.4$ min; FAB-MS: $(M+H)^+=494$.

The amine component employed above as the starting material is prepared, for example, as follows:

a) 2(R,S)-Methoxymethyl-3,4-dihydro-2H1,4-benzothiazine 3 ml of a 25% trifluoroacetic acid solution in methylene chloride are added to 435 mg of 4-tert-butoxycarbonyl-2(R,S)-methoxymethyl-3,4-dihydro-2H1,4-benzothiazine at 0° C. and the mixture is stirred for 3 h. The reaction mixture is concentrated and the residue is chromatographed over 30 g of silica gel with a 99:1 mixture of methylene chloride and methanol, This gives the title compound: $R_f$(99:1 mixture of methylene chloride/methanol)=0.67.

b) 4-Tert-butoxycarbonyl-2(R,S)-methoxymethyl-3,4-dihydro-2H1,4-benzothiazine 1.9 g of 4-tert-butoxycarbonyl-2(R,S)-hydroxymethyl-3,4-dihydro-2H1,4-benzothiazine are dissolved in 20 ml of tetrahydrofuran, and 1.5 g of a 20% potassium hydride suspension in oil are added at 0° C. 1.3 ml of methyl iodide are then added dropwise. The mixture is allowed to warm to room temperature and, when the reaction has ended, the mixture is poured onto water. After customary working up, the crude product is purified over 250 g of silica gel by means of FC (methylene chloride as the mobile phase): $R_f(D)=0.45$.

c) 4-Tert-butoxycarbonyl-2(R,S)-hydroxymethyl-3,4-dihydro-2H1,4-benzothiazine 2.3 g of di-tert-butyldicarbonate and 10 mg of 4-DMAP are added to 1.47 g of 2(R,S)-hydroxymethyl-3,4-dihydro-2H1,4-benzothiazine in 10 ml of tetrahydrofuran and the mixture is stirred for 17 h. The reaction mixture is concentrated and the residue is chromatographed directly over 150 g of silica gel (mobile phase D). This gives the title compound: $R_f(B)=0.52$.

d) 2(R,S)-Hydroxymethyl-3,4-dihydro-2H1,4-benzothiazine 1.6 g of 2(R,S)-ethoxycarbonyl-3,4-dihydro-2H1,4-benzothiazine are reacted with 1.06 g of lithium borohydride in 20 ml of tetrahydrofuran. After addition of 10 ml of methanol, the mixture is concentrated and the residue is purified by means of FC over 80 g of silica gel (mobile phase S). This gives the title compound: $R_f(S)=0.29$.

EXAMPLE 85

5(S)-Amino-4(S)-hydroxy-2(R),7,7-trimethyl-8-[3(R)- oder 3(S)-methoxycarbonylamino-1,2,3,4-tetrahydroquinolin-1-ylcarbonyl]-octanoic acid (N-butyl)amide The title compound is obtained starting from (4O,5N-isopropylidene)-5(S)-tert-butoxycarbonylamino-4(S)-hydroxy-2(R),7,7-trimethyl-8-[3(R)- oder 3(S)-methoxycarbonylamino-1,2,3,4-tetrahydroquinolin-1-ylcarbonyl]-octanoic acid (N-butyl)amide (diastereomer I) via 5(S)-tert-butoxycarbonylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide ($R_f(P)=0.34$) as the pure diastereomer: $R_f(S)=0.24$; $R_f(IV)=36.4$ min; FAB-MS: $(M+H)^+=505$.

The starting materials are obtained, for example, as follows:

a) (4O,5N-Isopropylidene)-5(S)-tert-butoxycarbonylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide The title compound is obtained starting from 50 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 68 mg of 3(R,S)-methoxycarbonylamino-1,2,3,4-tetrahydroquinoline with purification of the resulting crude product by means of FC over 25 g of silica gel (mobile phase gradient from B to A), the two 3(R) and 3(S) stereoisomers being separated. This gives the pure title compound (diastereomer I): $R_f(A)=0.19$; and diastereomer II: $R_f(A)=0.15$.

EXAMPLE 86

5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from (4O,5N-isopropylidene)-5(S)-tert-butoxycarbonylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide (diastereomer II; Example 85a)) via 5(S)-tert-butoxycarbonylamino-4(S)-hydroxy-2(R),7,7-trimethyl-8-[3(R)- oder 3(S)-methoxycarbonylamino-1,2,3,4-tetrahydroquinolin-1-ylcarbonyl]-octanoic acid (N-butyl)amide ($R_f(P)=0.32$) as the pure diastereomer: $R_f(S)=0.25$; $R_f(IV)=36.6$ min; FAB-MS: $(M+H)^+=505$.

EXAMPLE 87

5(S)-Amino-4(S)-hydroxy-2(R),7,7-trimethyl-8-[2(R,S)-allyloxymethyl-3,4-dihydro-2H-1,4-benzoxazin-4-ylcarbonyl]-octanoic acid (N-butyl)amide By methods analogous to those described in Examples 21, 21a and 21b), the title compound is obtained starting from 205 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 205 mg of 2(R,S)-allyloxymethyl-3,4-dihydro-2H-1,4-benzoxazine via (4O,5N-isopropylidene)-5(S)-tert-butoxycarbonylamino-4(S)-hydroxy-2(R),7,7-trimethyl-8-[2(R,S)-allyloxymethyl-3,4-dihydro-2H-1,4-benzoxazin-4-ylcarbonyl]-octanoic acid (N-butyl)amide ($R_f(A)=0.39$) and 5(S)-tert-butoxycarbonylamino-4(S)-hydroxy-2(R),7,7-trimethyl-8-[2(R,S)-allyloxymethyl-3,4-dihydro-2H-1,4-benzoxazin-4-ylcarbonyl]-octanoic acid (N-butyl)amide (purification over 10 g of silica gel, mobile phases A and ethyl acetate: $R_f(X)=0.50$; $R_f(I)=28.5$ min; FAB-MS: $(M+H)^+=604$) as a diastereomer mixture: $R_f(V)=0.38$; $R_f(I)=21.5/21.7$ min; FAB-MS: $(M+H)^+=504$.

The amine component is prepared, for example, as follows:

a) 2(R,S)-Allyloxymethyl-3,4-dihydro-2H-1,4-benzoxazine 0.8 ml of iododtrimethylsilane is added to a solution of 1.37 g of N-benzyloxycarbonyl-2(R,S)allyloxymethyl-3,4-dihydro-2H-1,4-benzoxazine in 25 ml of methylene chloride under argon. The reaction mixture is stirred at room temperature for 2 h, 10 ml of methanol are then added and the mixture is concentrated. The residue is extracted twice with 50 ml of a 10:1 mixture of hexane and diethyl ether and then dissolved in ethyl acetate, and the solution is washed with a 1N sodium carbonate solution and saturated sodium chloride solution. The crude product is purified by means of FC (100 g of silica gel, mobile phase D). This gives the pure title compound: $R_f(D)=0.17$.

b) N-Benzyloxycarbonyl-2(R,S)-allyloxymethyl-3,4-dihydro-2H-1,4-benzoxazine

The title compound is prepared starting from 3.0 g of N-benzyloxycarbonyl-2(R,S)-hydroxymethyl-3,4-dihydro-2H-1,4-benzoxazine, 2.75 g of sodium bis(trimethylsilyl)amide and 1.7 ml of 3-bromo-1-propene analogously to Example 61): $R_f(D)=0.32$; $R_f(3:1$ mixture of toluene and ethyl acetate)=0.61.

c) N-Benzyloxycarbonyl-2(R,S)-hydroxymethyl-3,4-dihydro-2H-1,4-benzoxazine

The title compound is obtained analogously to Example 84) starting from 50.0 g of N-benzyloxycarbonyl-2(R,S)-ethoxycarbonyl-3,4-dihydro-2H-1,4-benzoxazine and 5.4 g of lithiumborohydride analogously to Example 61): $R_f(3:1$ mixture of toluene and ethyl acetate)=0.26; $R_t(I)=23.8$ min; MS: $M^+=299$.

d) N-Benzyloxycarbonyl-2(R,S)-ethoxycarbonyl-3,4-dihydro-2H-1,4-benzoxazine

The title compound is obtained analogously to Example 1t) starting from 40.0 g of 2(R,S)-ethoxycarbonyl-3,4-dihydro-2H-1,4-benzoxazine, 39 ml of benzyl chloroformate and 22.3 g of sodium bicarbonate: $R_f(3:1$ mixture of toluene and ethyl acetate)=0.55; $R_t(I)=27.8$ min.

EXAMPLE 88

5(S)-Amino-4(S)-hydroxy-2(R),7,7-trimethyl-8-[2(R,S)-propyloxymethyl-3,4-dihydro-2H-1,4-benzoxazin-4-ylcarbonyl]-octanoic acid (N-butyl)amide Analogously to the methods described in Examples 21, 21a and 21b), the title compound is obtained starting from 205 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 291 mg of 2(R,S)-propyloxymethyl-3,4-dihydro-2H-1,4-benzoxazine via (4O,5N-isopropylidene)-5(S)-tert-butoxycarbonylamino-4(S)-hydroxy-2(R),7,7-trimethyl-8-[2(R,S)-propyloxymethyl-3,4-dihydro-2H-1,4-benzoxazin-4-ylcarbonyl]-octanoic acid (N-butyl)amide ($R_f(A)=0.38$; FAB-MS: $(M+H)^+=646$) and 5(S)-tert-butoxycarbonylamino-4(S)-hydroxy-2(R),7,7-trimethyl-8-[2(R,S)-propyloxymethyl-3,4-dihydro-2H-1,4-benzoxazin-4-ylcarbonyl]-octanoic acid (N-butyl)amide ($R_f(V)=0.58$; $R_t(I)=29.3$ min; FAB-MS: $(M+H)^+=606$) as a diastereomer mixture: $R_f(V)=0.29$; $R_t(I)=22.0/22.2$ min; FAB-MS: $(M+H)^+=506$.

The 2(R,S)-propyloxymethyl-3,4-dihydro-2H-1,4-benzoxazine employed is obtained analogously to Example 1r) starting from 1.8 g of N-benzyloxycarbonyl-2(R,S)-allyloxymethyl-3,4-dihydro-2H-1,4-benzoxazine (Example 87b) with purification of the crude product by means of FC (60 g of silica gel, mobile phase gradient from a 10:1 to a 3:1 mixture of toluene and ethyl acetate: $R_f(3:1$ mixture of toluene and ethyl acetate)=0.50; FAB-MS: $(M+H)^+=208$.

BEISPIEL 89

5(S)-Amino-4(S)-hydroxy-2(R),7,7-trimethyl-8-[2(R,S)-methoxymethyl-3,4-dihydro-2H-1,4-benzoxazin-4-ylcarbonyl]-octansäure(N-butyl)amid Analogously to the methods described in Examples 21, 21a and 21b), the title compound is obtained starting from 300 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 359 mg of 2(R,S)-methoxymethyl-3,4-dihydro-2H-1,4-benzoxazine via (4O,5N-isopropylidene)-5(S)-tert-butoxycarbonylamino-4(S)-hydroxy-2(R),7,7-trimethyl-8-[2(R,S)-methoxymethyl-3,4-dihydro-2H-1,4-benzoxazin-4-ylcarbonyl]-octanoic acid (N-butyl)amide ($R_f(A)=0.22$; $R_t(I)=31.3/31.6$ min) and 5(S)-tert-butoxycarbonylamino-4(S)-hydroxy-2(R),7,7-trimethyl-8-[2(R,S)-methoxymethyl-3,4-dihydro-2H-1,4-benzoxazin-4-ylcarbonyl]-octanoic acid (N-butyl)amide ($R_f(X)=0.31$; $R_t(I)=26.6$ min; FAB-MS: $(M+H)^+=578$) as a diastereomer mixture: $R_f(V)=0.33$; $R_t(I)=19.3/19.5$ min; FAB-MS: $(M+H)^+=478$.

The amine component is prepared, for example, as follows:

a) 2(R,S)-Methoxymethyl-3,4-dihydro-2H-1,4-benzoxazine is obtained analogously to Example 1r) starting from 1.7 g of N-benzyloxycarbonyl-2(R,S)-methoxymethyl-3,4-dihydro-H-1,4-benzoxazine: $R_f(3:1$ mixture of toluene and ethyl acetate)=0.47; $R_t(I)=12.9$ min; FAB-MS: $(M+H)^+=180$.

b) N-Benzyloxycarbonyl-2(R,S)-methoxymethyl-3,4-dihydro-2H-1,4-benzoxazine

The title compound is prepared analogously to Example 87b) starting from 3.0 g of N-benzyloxycarbonyl-2(R,S)-hydroxymethyl-3,4-dihydro-2H-1,4-benzoxazine, 2.4 g of sodium bis(trimethylsilyl)amide and 0.94 ml of methyliodide: $R_f(3:1$ mixture of toluene and ethyl acetate)=0.56; $R_t(I)=27.9$ min.

EXAMPLE 90

5(S)-Amino-4(S)-hydroxy-2(S)-isopropyl-7,7-dimethyl-8-[2(R)- or 2(S)-methylaminocarbonyl-3,4-dihydro-2H1,4-benzothiazin-4-ylcarbonyl]-octanoic acid (N-butyl)amide In an analogous manner to that described in Examples 52, 52a and 52b) for the corresponding reaction stages, the title compound is obtained starting from 100 mg of 3-[N-tert-butoxycarbonyl-4(S)-(3-carboxy-2,2-dimethylpropyl)-2,2-dimethyl-1,3-oxazolidin-5(S)-yl]-2(S)isopropyl-propionic acid (N-butyl)amide and 107 mg of 2(R)-or 2(S)-methylaminocarbonyl-3,4-dihydro-2H1,4-benzothiazine (stereoisomer I) via (4O,5N-isopropylidene)-5(S)-tert-butoxycarbonylamino-4(S)-hydroxy-2(S)-isopropyl-7,7-dimethyl-8-[2(R)- or 2(S)-methylaminocarbonyl-3,4-dihydro-2H1,4-benzothiazin-4-ylcarbonyl]-octanoic acid (N-butyl)amide ($R_f$(ethyl acetate)=0.64) and 5(S)-tert-butoxycarbonylamino-4(S)-hydroxy-2(S)-isopropyl-7,7-dimethyl-8-[2(R)- oder 2(S)-methylaminocarbonyl-3,4-dihydro-2H1,4-benzothiazin-4-yl-carbonyl]-octanoic acid (N-butyl)amide ($R_f(P)=0.50$) as the pure diastereomer: $R_f(S)=0.34$; $R_t(IV)=37.0$ min; FAB-MS: $(M+H)^+=535$.

The amine component employed as the starting material is prepared, for example, as follows:

0.2 g of 2(R,S)-Methylaminocarbonyl-3,4-dihydro-2H1,4-benzothiazine are chromatographed over cellulose triacetate (chromatography column 50×1000 mm) with a 95:5 mixture of ethanol and water as the eluting agent. Concentration of the stereoisomerically pure substance fractions gives 2(R)- or 2(S)-methylaminocarbonyl-3,4-dihydro-2H1,4-benzothiazine (stereoisomer I) as a yellowish oil: $[\alpha]^D=+8.3$ (c=1; methylene chloride); and 2(R)- or 2(S)-methylaminocarbonyl-3,4-dihydro-2H1,4-benzothiazine (stereoisomer II) as a yellowish oil: $[\alpha]^D=-9.1$ (c=1; methylene chloride).

EXAMPLE 91

5(S)-Amino-4(S)-hydroxy-2(S)-isopropyl-7,7-dimethyl-8-[2(R)- or 2(S)-methylaminocarbonyl-3,4-dihydro-2H1,4-benzothiazin-4-ylcarbonyl]-octanoic acid (N-butyl)amide In an analogous manner to that described in Examples 52, 52a and 52b) for the corresponding reaction stages, the title compound is obtained starting from 100 mg of 3-[N-tert-butoxycarbonyl-4(S)-(3-carboxy-2,2-dimethylpropyl)-2,2-dimethyl-1,3-oxazolidin-5(S)-yl]-2(S)isopropyl-propionic acid (N-butyl)amide and 107 mg of 2(R)- or 2(S)-methylaminocarbonyl-3,4-dihydro-2H1,4-benzothiazine (stereoisomer II; Example 90) via (4O,5N-isopropylidene)-5(S)-tert-butoxycarbonylamino-4(S)-hydroxy-2(S)-isopropyl-7,7-dimethyl-8-[2(R)- or 2(S)-methylaminocarbonyl-3,4-dihydro-2H1,4-benzothiazin-4-ylcarbonyl]-octanoic acid (N-butyl)amide ($R_f$(ethyl acetate) =0.60) and 5(S)-tert-butoxycarbonylamino-4(S)-hydroxy-2 (S)-isopropyl-7,7-dimethyl-8-[2(R)- or 2(S)-methylaminocarbonyl-3,4-dihydro-2H-1,4-benzothiazin-4-ylcarbonyl]-octanoic acid (N-butyl)amide ($R_f$(P)=0.58) as the pure diastereomer: $R_f$(S)=0.36; $R_f$(IV)=37.7 min; FAB-MS: (M+H)$^+$=535.

EXAMPLE 92

5(S)-Amino-4(S)-hydroxy-6-[1-[3(R,S)-methylaminocarbonyl-1,2,3,4-tetrahydroquinolin-1-ylcarbonylmethyl]cyclopropyl]-2(R)-methyl-hexanoic acid (N-butyl)amide 2 ml of 4N hydrochloric acid in dioxane are added to 116 mg of 5(S)-tert-butoxycarbonylamino-4(S)-hydroxy-6-[1-[3(R,S)-methylaminocarbonyl-1,2,3,4-tetrahydroquinolin-1-ylcarbonylmethyl]cyclopropyl]-2(R)-methyl-hexanoic acid (N-butyl)amide at 0° C. and the mixture is stirred for 2 h. 2 ml of toluene are added and the reaction mixture is concentrated. The oily residue is chromatographed over 10 g of silica gel (mobile phases K and L). This gives the title compound as a diastereomer mixture: $R_f$(P)=0.11; $R_f$(IV)= 32.6 min; FAB-MS: (M+H)$^+$=487.

The staring materials are prepared, for example, as follows:

a) 5(S)-Tert-butoxycarbonylamino-4(S)-hydroxy-6-[1-[3(R,S)-methylaminocarbonyl-1,2,3,4-tetrahydroquinolin-1-ylcarbonylmethyl]cyclopropyl]-2(R)-methyl-hexanoic acid (N-butyl)amide The title compound is prepared in a manner analogous to that described in Example 21a) starting from 180 mg of (4O,5N-isopropylidene)-5(S)-tert-butoxycarbonylamino-4 (S)-hydroxy-6-[1-[3(R,S)-methylaminocarbonyl-1,2,3,4-tetrahydroquinoline-1-yl-carbonylmethyl]cyclopropyl]-2 (R)-methyl-hexanoic acid (N-butyl)amide and is purified by means of FC over 25 g of silica gel (mobile phase J): $R_f$(P)=0.48.

b) (4O,5N-Isopropylidene)-5(S)-tert-butoxycarbonylamino-4(S)-hydroxy-6-[1-[3(R,S)-methylaminocarbonyl-1,2,3,4-tetrahydroquinolin-1-ylcarbonylmethyl]cyclopropyl]-2(R)-methyl-hexanoic acid (N-butyl)amide 100 mg of 3-[N-tert-butoxycarbonyl-4(S)-[1-(carboxymethyl)cyclopropylmethyl-]-2,2-dimethyl-1,3-oxazolidin-5(S)-yl]-2(R)-methyl-propionic acid (N-butyl) amide are reacted with 126 mg of 2(R,S)-methylaminocarbonyl-1,2,3,4-tetrahydroquinoline by a process analogous to that described in Example 72b) and the product is purified by means of FC over 30 g of silica gel with a 96:4 mixture of methylene chloride and methanol as the mobile phase. This gives the title compound: $R_f$(P)=0.54.

c) 3-[N-Tert-butoxycarbonyl-4(S)-[1-(carboxymethyl-cyclopropylmethyl]-2,2-dimethyl-1,3-oxazolidin-5(S)-yl]-2 (R)-methyl-propionic acid (N-butyl)amide A solution of 788 mg of 3-[N-tert-butoxycarbonyl-4(S)-[1-(2-hydroxyethyl)cyclopropylmethyl]-2,2-dimethyl-1,3-oxazolidin-5(S)-yl]-2-(R)-methyl-propionic acid (N-butyl) amide in 24 ml of a 1:1 mixture of carbon tetrachloride and acetonitrile is added to a mixture of 2.2 g of sodium metaperiodate, 47 mg of ruthenium(III) chloride hydrate and 24 ml of water and the reaction mixture is stirred vigorously for 1 h. After working up in a manner analogous to that described in Example 72c), the crude product is purified by means of FC over 80 g of silica gel with a 50:50:1 mixture of hexane, ethyl acetate and glacial acetic aicd as the mobile phase: $R_f$(1:2:0.1 mixture of hexane, ethyl acetate and glacial acetic acid)=0.66; FAB-MS: (M+H)$^+$=455.

d) 3-[N-Tert-butoxycarbonyl-4(S)-[1-(2-hydroxyethyl) cyclopropylmethyl]-2,2-dimethyl-1,3-oxazolidin-5(S)-yl]-2-(R)-methyl-propionic acid (N-butyl)amide The title compound is obtained by hydrogenation by a method analogous to that described in Example 39a) from 1.2 g of 3-[N-tert-butoxycarbonyl-4(S)-[1-(2-benzyloxyethyl)cyclopropylmethyl]-2,2-dimethyl-1,3-oxazolidin-5(S)-yl]-2-(R)-methyl-propionic acid (N-butyl) amide: $R_f$(A)=0.24.

e) 3-[N-Tert-butoxycarbonyl-4(S)-[1-(2-benzyloxyethyl) cyclopropylmethyl]-2,2-dimethyl-1,3-oxazolidin-5(S)-yl]-2-(R)-methyl-propionic acid (N-butyl)amide A solution of 3.1 g of 5(S)-tert-butoxycarbonylamino-6-[1-(2-benzyloxyethyl)cyclopropyl]-4(S)-hydroxy-2-methylenehexanoic acid (N-butyl)amide in 30 ml of absolute methanol is hydrogenated in the presence of 30 mg of bis[(S)-(−)-2,2'-bis(diphenylphosphino)-1,1'-binaphthyl]-(triethylamino)diruthenium tetrachloride in a manner analogous to that described in Example 72f) and the crude product is purified by means of FC over 100 g of silica gel (mobile phase A): $R_f$(A)=0.40; MS: M$^+$=491; anal. calc. for C68.54%, H9.45%, N5.71%; found C68.29%, H9.72%, N5.70%.

The 5(S)-tert-butoxycarbonylamino-6-[1-(2-benzyloxyethyl)cyclopropyl]-4(S)-hydroxy-2(R)-methyl-hexanoic acid (N-butyl)amide thus obtained is reacted with dimethoxypropane and p-toluenesulfonic acid hydrate in a manner analogous to that described in Example 1 d) and the product is purified by means of FC over 80 g of silica gel (mobile phase C). This gives the title compound as the pure diastereomer: $R_f$(A)=0.58, f) 5(S)-Tert-butoxycarbonylamino-6-[1-(2-benzyoxyethyl) cycopropyl]-4(S)-hydroxy-2-methylenehexanoic acid (N-butyl)amide Reaction of 6.5 g of 2(S)-tert-butoxycarbonylamino-3-[1-(2-benzyloxyethyl)cyclopropyl]-propanal in an analogous manner to that described in Example 1f) and subsequent purification of the crude product by means of FC over 500 g of silica gel (mobile phase from D to A), the two stereoisomers being separated, gives the pure title compound (diastereomer I): $R_f$(A)=0.52; and diastereomer II: $R_f$(A)=0.41.

g) 2(S)-Tert-butoxycarbonylamino-3-[1-(2-benzyloxyethyl) cyclopropyl]-propanal 7.0 g of 2(S)-tert-butoxycarbonylamino-3-[1-(2-benzyloxyethyl)cyclopropyl]-propan-1-ol are reacted by a process analogous to process 1g). Customary working up gives the title compound: $R_f$(A)=0.84.

h) 2(S)-Tert-butoxycarbonylamino-3-[1-(2-benzyloxyethyl) cyclopropyl]-propan-1-ol A mixture of 23.9 g of 3-tert-butoxycarbonyl-2,2-dimethyl-4(S)-[1-(2-benzyloxyethyl)cyclopropylmethyl]1, 3-oxazolidine, 0.67 g of p-toluenesulfonic acid hydrate and 100 ml of methanol is stirred at room temperature for 5 h. After the reaction mixture has been concentrated, diethyl ether is added. The organic phase is washed with saturated sodium bicarbonate solution and saturated sodium chloride solution and added over sodium sulfate. The crude product is purified by means of FC over 900 g of silica gel (mobile phase gradient from E to A): $R_f(C)=0.26$; anal. calc. for $C_{20}H_{31}NO_4$: C68.74%, H8.94%, N4.01%; found C68.44%, H8.93%, N4.09%.

i) 3-Tert-butoxycarbonyl-2,2-dimethyl-4(S)-[1-(2-benzyloxyethyl)cyclopropylmethyl]-1,3-oxazolidine 15.1 g of 3-tert-butoxycarbonyl-2,2-dimethyl-4(S)-[1-(2-hydroxyethyl)cyclopropylmethyl]-1,3-oxazolidine are dissolved in 50 ml of tetrahydrofuran, and 14.2 g of a potassium hydride suspension (20% in oil) are added at 0° C. The mixture is stirred at 0° C. for 1 h and 6.3 ml of benzyl bromide are then added dropwise, while stirring. After 90 min., 100 ml of water are slowly added to the reaction mixture and the aqueous phase is extracted with diethyl ether. This gives the title compound: $R_f(A)=0.8$; FAB-MS: $(M+H)^+=390$.

j) 3-Tert-butoxycarbonyl-2,2-dimethyl-4(S)-[1-(2-hydroxyethyl)cyclopropylmethyl]-1,3-oxazolidine 2.5 ml of diborane-dimethylsulfide complex are added to 18.0 g of 3-tert-butoxycarbonyl-2,2-dimethyl-4(S)-[(1-vinylcyclopropyl)methyl]-1,3-oxazolidine, dissolved in 300 ml of tetrahydrofuran at 0° C. in the course of 3 minutes and the mixture is then stirred for 3 h, while cooling with ice. 5 ml of water, 16 ml of 2N sodium hydroxide solution and 8.5 ml of a 30% hydrogen peroxide solution are added in succession and the mixture is subsequently stirred at room temperature for 1 h. It is then diluted with ice-cold potassium carbonate solution and the aqueous phase is extracted with ethyl acetate. Purification of the crude product is carried out over 900 g of silica gel (mobile phase B): $R_f(B)=0.25$; anal. calc. for $C_{16}H_{35}NO_4$: C 64.18%, H 9.76%, N 4.68%; found C 64.05%, H 9.76%, N 4.73%.

k) 3-Tert-butoxycarbonyl-2,2-dimethyl-4-(S)-[(1-vinylcyclopropyl)methyl]-1,3-oxazolidine 27.05 g of sodium-hexamethyldisilazane are added in portions to a suspension of 52.7 g of methyltriphenylphosphonium bromide in 470 ml of tetrahydrofuran in the course of 10 min. 20.9 g of 3-tert-butoxycarbonyl-2,2-dimethyl-4(S)-[(1-formylcyclopropyl)methyl]-1,3-oxazolidine are added dropwise to this mixture at 5° C. in the course of 10 min, and after warming to room temperature, the mixture is stirred for 1 h. The mixture is poured onto ice-water and the aqueous phase is extracted with methylene chloride. The title compound is purified by means of FC over 900 g of silica gel (mobile phase G): $R_f(G)=0.56$.

l) 3-Tert-butoxycarbonyl-2,2-dimethyl-4(S)-[(1-formylcyclopropyl)methyl]-1,3-oxazolidine 11.1 ml of dimethylsulfoxide in 150 ml of methylene chloride are added dropwise to a solution of 10.1 ml of oxalyl chloride in 130 ml of methylene chloride at −60° C. When the addition has ended, the mixture is subsequently stirred for a further 10 min, a solution of 22.3 g of 3-tert-butoxycarbonyl-2,2-dimethyl-4(S)-[(1-hydroxymethylcyclopropyl)methyl]-1,3-oxazolidine in 270 ml of methylene chloride is then added at −60° C. in the course of 20 min and the mixture is stirred for a further 30 min. 43.6 ml of triethylamine are then added at the same temperature and finally, after 30 min, 140 ml of a 20% potassium hydrogen sulfate solution are added to the reaction mixture. Customary working up gives the title compound as a crude product: $R_f(A)=0.73$.

m) 3-Tert-butoxycarbonyl-2,2-dimethyl-4(S)-[(1-hydroxymethylcyclopropyl)methyl]-1,3-oxazolidine 31.3 g of 3-tert-butoxycarbonyl-2,2-dimethyl-4(S)-[[(1-benzyloxymethyl)cyclopropyl)]methyl]-1,3-oxazolidine are dissolved in 300 ml of tetrahydrofuran and hydrogenated, with the addition of 3 g of palladium-on-charcoal (10% of Pd) at room temperature. The crude product is purified by means of FC over 900 g of silica gel (mobile phase A) (22.3 g of the title compound): $R_f(A)=0.32$.

n) 3-Tert-butoxycarbonyl-2,2-dimethyl-4(S)-[[(1-benzyloxymethyl)cyclopropyl]methyl]-1,3-oxazolidine A mixture of 31.4 g of 1-benzyloxymethyl-1-[2(S)-tert-butoxycarbonylamino-3-hydroxy-propan-1-yl]cyclopropane, 80 ml of 2-methoxypropene and 0.5 g of p-toluenesulfonic acid hydrate in 170 ml of methylene chloride is stirred at room temperature for 16 h. The mixture is concentrated and the residue is purified by means of FC over 900 g of silica gel (mobile phase G): $R_f(G)=0.23$.

o) 1-Benzyloxymethyl-1-[2(S)-tert-butoxycarbonylamino-3-hydroxypropan-1-yl]cyclopropane 4.3 g of lithium borohydride are added in portions to a solution of 30.9 g of 1-benzyloxymethyl-1-[2(S)-tert-butoxycarbonylamino-2-methoxycarbonyleth-1-yl]cyclopropane in 300 ml of tetrahydrofuran, while stirring. The mixture is stirred at room temperature for a further 2 h, 500 ml of methanol are then slowly added dropwise, the mixture is concentrated almost to dryness and the residue is taken up in methylene chloride. The organic phase is washed with 1N hydrochloric acid. Further customary working up gives the pure title compound: $R_f(B)=0.50$.

p) 1-Benzyloxymethyl-1-[2(S)-tert-butoxycarbonylamino-2-methoxycarbonyleth-1yl]cyclopropane 25.3 g of di-tert-butyl dicarbonate are added to a solution of 27.7 g of 1-benzyloxymethyl-1-[2(S)-amino-2-methoxycarbonyleth-1-yl]cyclopropane in 250 ml of tetrahydrofuran, while cooling with ice, and, after warming up, the mixture is stirred at room temperature for 4 h. The residue obtained after concentration of the reaction mixture is chromatographed over 900 g of silica gel (mobile phase D). This gives the pure title compound (34.8 g as a yellowish oil: $R_f(D)=0.33$.

q) 1-Benzyloxymethyl-1-[2(S)-amino-2-methoxycarbonyleth-1-yl]cyclopropane 105 ml of a 1.6M n-butyllithium solution in hexane are added to a solution of 32 ml of (2R)-(−)-2,5-dihydro-3,6-dimethoxy-2-isopropylpyrazine in 180 ml of tetrahydrofuran at −70° C. under argon. The mixture is stirred for 30 min and a solution of 39.1 g of 1-benzyloxymethyl-1-(bromomethyl)cyclopropane in 180 ml of tetrahydrofuran is then added dropwise at the same temperature. The reaction has ended after 2 h. The mixture is poured onto a 5N ammonium chloride solution and the aqueous phase is extracted with methylene chloride. The crude alkylation product thus obtained (38.04 g) is dissolved in 425 ml of acetonitrile, 425 ml of 1N hydrochloric acid are added and the mixture is stirred at room temperature for 2 h. It is then poured onto 500 ml of a 1N sodium bicarbonate solution and extracted with methylene chloride. The crude product is chromatographed over 900 g of silica gel (mobile phase N): $R_f(N)=0.28$.

r) 1-Benzyloxymethyl-1-(bromomethyl)cyclopropane 58.9 g of 1-benzyloxymethyl-1-(hydroxymethyl)cyclopropane and 88.5 g of triphenylphosphine are dissolved in 600 ml of methylene chloride, and 60 g of N-bromosuccinimide are added in portions at 0° C. The reaction mixture is stirred at room temperature for 16 h and concentrated and the residue is purified by means of FC over 3 kg of silica gel with a 1:1 mixture of methylene chloride and hexane as the eluting agent. This gives 68 g of the pure title compound: $R_f$(1:1 mixture from methylene chloride and hexane)=0.50.

s) 1-Benzyloxymethyl-1-(hydroxymethyl)cyclopropane 9.1 g of a sodium hydride suspension (60% in oil) and 29.7 g of benzyl bromide are added in succession to a solution of 23.2 g of 1,1-(bis-hydroxymethyl)cyclopropane (prepared by the method described in J. Org. Chem. 21, 1490 (1956)) in 250 ml of dimethylformamide, while stirring. After 2 h, the reaction mixture is concentrated and the residue is purified over 900 g of silica gel (mobile phase B): $R_f(B)$=0.33.

EXAMPLE 93

5(S)-Amino-4(S)-hydroxy-2(R),7,7-trimethyl-8-[3(R,S)-N, N-dimethylaminocarbonylamino-1,2,3,4-tetrahydroquinolin-1-ylcarbonyl]-octanoic acid (N-butyl) amide In an analogous manner to that described in Examples 52, 52a and 52b) for the corresponding reaction stages, the title compound is obtained starting from 100 mg of 3-[N-tert-butoxycarbonyl-4(S)-(3-carboxy-2,2-dimethylpropyloxy-2, 2-dimethyl-1,3-oxazolidin-5(S)-yl]-2(R)-methyl-propionic acid (N-butyl)amide and 144 mg of 3(R,S)-N,N-dimethylaminocarbonylamino-1,2,3,4-tetrahydroquinoline via (4O,5N-isopropylidene)-5(S)-tert-butoxycarbonylamino-4(S)-hydroxy-2(R),7,7-trimethyl-8-[3(R,S)N,N-dimethylaminocarbonylamino-1,2,3,4-tetrahydroquinolin-1-ylcarbonyl]-octanoic acid (N-butyl) amide [$R_f(L$, double migration zone)=0.42] and 5(S)-tert-butoxycarbonylamino-4(S)-hydroxy-2(R),7,7-trimethyl-8-[3(R,S)-N,N-dimethylaminocarbonylamino-1,2,3,4-tetrahydroquinolin-1-ylcarbonyl]-octanoic acid (N-butyl) amide [$R_f(L$, double migration zone)=0.37; FAB-MS: $(M+H)^+$=618) as a diastereomer mixture: $R_f(S)$=0.27; $R_f(V)$=17.8/18.1 min; FAB-MS: $(M+H)^+$=518.

The 3(R,S)-N,N-dimethylaminocarbonylamino-1,2,3,4-tetrahydroquinoline employed as the starting material is prepared, for example, as follows:

2.0 g of 3-aminoquinoline are added in portions to a solution of 1.65 ml of N,N-dimethylcarbamoyl chloride in 3.9 ml of pyridine and the reaction mixture is stirred at room temperature for 24 h. The reaction mixture is then poured onto 50 ml of ice-water. Customary working up and purification of the crude product by chromatography over 100 g of silica gel (mobile phase L) gives 3-(N,N-dimethylaminocarbonylamino)quinoline: $R_f(L)$=0.23; MS:M+=215.

1.4 g of the urea derivative described above, dissolved in 40 ml of ethanol, are hydrogenated in the presence of 0.28 g of palladium-on-charcoal (10% of palladium) at 50° C. for 40 h and, after renewed addition of 0.14 g of the catalyst, for a further 7 h. Customary working up and purification by FC over 170 g of silica gel with a 96:4 mixture of methylene chloride and methanol as the mobile phase gives 3(R,S)-N, N-dimethylaminocarbonylamino-1,2,3,4-tetrahydroquinoline: $R_f(L)$=0.36; MS: $(M)^+$=219.

EXAMPLE 94

5(S)-Amino-4(S)-hydroxy-2(S)-isopropyl-7,7-dimethyl-8-[2(R,S)-ethylaminocarbonyl-3,4-dihydro-2H-1,4-benzothiazin-4-ylcarbonyl]-octanoic acid (N-butyl)amide In an analogous manner to that described in Examples 52, 52a and 52b) for the corresponding reaction stages, the title compound is obtained starting from 80 mg of 3-[N-tert-butoxycarbonyl-4(S)-(3-carboxy-2,2-dimethylpropyloxy-2, 2-dimethyl-1,3-oxazolidin-5(S)-yl]-2(S)isopropylpropionic acid (N-butyl)amide and 100 mg of 2(R,S)-ethylaminocarbonyl-3,4-dihydro-2H-1,4-benzothiazine via (4O,5N-isopropylidene)-5(S)-tert-butoxycarbonylamino-4(S)-hydroxy-2(S)-isopropyl-7,7-dimethyl-8-[2(R,S)-ethylaminocarbonyl-3,4-dihydro-2H-1,4-benzothiazin-4-ylcarbonyl]-octanoic acid (N-butyl)amide ($R_f(L)$=0.40) and 5(S)-tert-butoxycarbonylamino-4(S)-hydroxy-2(S)-isopropyl-7,7dimethyl-8-[2(R,S)-ethylaminocarbonyl-3,4-dihydro-2H1,4-benzothiazin-4-ylcarbonyl]-octanoic acid (N-butyl)amide ($R_f(L)$=0.38; FAB-MS: $(M+H)^+$=649) as a diastereomer mixture: $R_f(S)$=0.30/0.27; $R_f(VI)$=38.9/39.5 min; FAB-MS: $(M+H)^+$=549. The 2(R,S)-ethylaminocarbonyl-3,4-dihydro-2H1,4-benzothiazine employed as the starting material is obtained starting from 2.0 g of 2(R,S)-methoxycarbonyl-3,4-dihydro-2H1,4-benzothiazine by reaction in 5 ml of a 2.3N ethylamine solution in dimethylformamide at 60° C. for 17 h and purification by means of FC over 80 g of silica gel (mobile phase A): $R_f(A)$=0.29.

EXAMPLE 95

5(S)-Amino-4(S)-hydroxy-2(R),7,7-trimethyl-8-[2(R,S)-methoxyethylaminocarbonyl-3,4-dihydro-2H1,4-benzothiazin-4-ylcarbonyl]-octanoic acid (N-butyl)amide In an analogous manner to that described in Examples 52, 52a and 52b) for the corresponding reaction stages, the title compound is obtained starting from 100 mg of 3-[N-tert-butoxycarbonyl-4(S)-(3-carboxy-2,2-dimethylpropyloxy-2, 2-dimethyl-1,3-oxazolidin-5(S)-yl]-2(R)-methyl-propionic acid (N-butyl)amide and 138 mg of 2(R,S)-methoxyethylaminocarbonyl-3,4-dihydro-2H1,4-benzothiazine via (4O,5N-isopropylidene)-5(S)-tert-butoxycarbonylamino-4(S)-hydroxy-2(R),7,7-trimethyl-8-[2(R,S)-methoxyethylaminocarbonyl-3,4-dihydro-2H1,4-benzothiazin-4-ylcarbonyl]-octanoic acid (N-butyl)amide ($R_f(K)$=0.38) and 5(S)-tert-butoxycarbonylamino-4(S)-hydroxy-2(R),7,7-trimethyl-8-[2(R,S)-methoxyethylaminocarbonyl-3,4-dihydro-2H1,4-benzothiazin-4-ylcarbonyl]-octanoic acid (N-butyl)amide ($R_f(K)$=0.23) as a diastereomer mixture: $R_f(P)$=0.45; $R_f(IV)$=36.0/36.4 min; FAB-MS: $(M+H)^+$=551.

The amine component employed as the starting material is prepared, for example, as follows:

839 mg of 2(R,S)-ethoxycarbonyl-3,4-dihydro-2H1,4-benzothiazine in 6.6 ml of a 6M 2-methoxyethylamine solution in dimethylformamide are stirred overnight at 50° C. The reaction mixture is concentrated and the residue is purified by FC over 25 g of silica gel with a 99:1:0.1 mixture of methylene chloride, methanol and ammonia (concentrated) as the mobile phase: $R_f(H)$=0.21.

EXAMPLE 96

5(S)-Amino-4(S)-hydroxy-2(S)-isopropyl-7,7-dimethyl-8-[3(R,S)-methoxymethyl-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 188 mg of 3-[N-tert-butoxycarbonyl-4(S)-(3-carboxy-2,2-dimethylpropyloxy-2, 2-dimethyl-1,3-oxazolidin-5(S)-yl]-2(S)isopropyl-propionic acid (N-butyl)amide and 206 mg of 3(R,S)-methoxymethyl-1,2,3,4-tetrahydroquinoline via (4O,5N-isopropylidene)-5(S)-tert-butoxycarbonylamino-4(S)-hydroxy-2(S)-isopropyl-7,7-dimethyl-8-[3(R,S)-methoxymethyl-1,2,3,4-tetrahydroquinolin-1-ylcarbonyl]-octanoic acid (N-butyl)amide ($R_f(A)$=0.54) and via 5(S)-tert-butoxycarbonylamino-4(S)-hydroxy-2(S)-isopropyl-7, 7-dimethyl-8-[3(R,S)-methoxymethyl-1,2,3,4- tetrahydroquinolin- 1-ylcarbonyl]-octanoic acid (N-butyl) amide ($R_f(A)$=0.20) as a diastereomer mixture: $R_f(S)$=0.29; $R_f(V)$=24.5 min; FAB-MS: (M+H)$^+$=504.

EXAMPLE 97

5(S)-Amino-4(S)-hydroxy-2(R),7,7-trimethyl-8-[3(R)-oder 3(S)-ethoxycarbonylindolin-1-ylcarbonyl]-octanoic acid (N-butyl)amide The title compound is prepared starting from 58 mg of 5(S)-tert-butoxycarbonylamino-4(S)-hydroxy-2(R),7,7-trimethyl-8-[3(R)- or 3(S)-ethoxycarbonylindolin-1-ylcarbonyl]-octanoic acid (N-butyl)amide analogously to Example 52) and is purified by FC over silica gel (mobile phase M): $R_f(S)$=0.13; $R_f(IV)$=39.5 min; FAB-MS: (M+H)$^+$=490.

The starting material are prepared, for example, as follows:

a) 5(S)-Tert-butoxycarbonylamino-4(S)-hydroxy-2(R),7,7-trimethyl-8-[3(R)- or -3(S)-ethoxycarbonylindolin-1-ylcarbonyl]-octanoic acid (N-butyl)amide The title compound is obtained starting from 73 mg of (4O,5N-isopropylidene)-5(S)-tert-butoxycarbonylamino-4(S)-hydroxy-2(R),7,7-trimethyl-8-[3(R)- or 3(S)-ethoxycarbonylindolin-1-ylcarbonyl]-octanoic acid (N-butyl)amide (diastereomer I) analogously to Example 20a) and is purified by FC over 25 g of silica gel (mobile phase J). This gives the title compound: $R_f(P)$=0.62.

b) (4O,5N-Isopropylidene)-5(S)-tert-butoxycarbonylamino-4(S)-hydroxy-2(R),7,7-trimethyl-8-[3(R)- or 3(S)-ethoxycarbonylindolin-1-ylcarbonyl]-octanoic acid (N-butyl)amide The title compound is prepared starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 126 mg of ethyl indoline-3(R,S)-carboxylate in an analogous manner to that described in Example 45b), and is purified by means of FC over 80 g of silica gel (mobile phase B), the two stereoisomers being separated. This gives the two pure diastereomers of the title compound: $R_f(A)$=0.48 for diastereomer I; $R_f(A)$=0.41 for diastereomer II.

c) Ethyl indoline-3-(R,S)-carboxylate 0.83 g of ethyl 1-(tert-butoxycarbonyl)indoline-3(R,S)-carboxylate is stirred in 5 ml of 4N hydrochloric acid in dioxane at 0° C. for 1 h. The reaction mixture is concentrated, the oily residue is taken up in methylene chloride and the mixture is washed with a little saturated sodium bicarbonate solution and saturated sodium chloride solution. After drying over sodium sulfate, the organic phase is evaporated and the residue is purified by means of FC over 80 g of silica gel (mobile phase B): $R_f(A)$=0.65; IR(chloroform): 1730(s).

d) Ethyl 1-(tert-butoxycarbonyl)indoline-3-(R,S)-carboxylate

A solution of 1.0 g of ethyl 1-(tert-butoxycarbonyl)indole-3-carboxylate in 20 ml of anhydrous ethanol is hydrogenated in the presence of 0.50 g of palladium-on-charcoal (5% of Pd) at 80° C. until the reaction has ended. After the reaction mixture has been filtered over Celite '545 and the filtrate has been concentrated, the oily residue is purified by means of FC over 15 g of silica gel with a 15:1 mixture of hexane and ethyl acetate as the mobile phase. This gives the title compound: $R_f(G)$=0.39; anal. calc. for $C_{16}H_{21}NO_4$: C65.96%, H7.27%, N4.81%; found C65.67%, H7.18%, N4.77%.

e) Ethyl 1-(tert-butoxycarbonyl)indole-3-carboxylate

A solution of 3.15 g of ethyl indole-3-carboxylate, 4.36 g of di-tert-butylcarbonate and 0.02 g of 4-DMAP in 30 ml of acetonitrile is stirred at room temperature for 15 min. The reaction mixture is then diluted with 200 ml of ethyl acetate. The organic phase is washed with dilute hydrochloric acid, water and saturated sodium chloride solution in succession, dried over sodium sulfate and concentrated. Purification by means of FC over 80 g of silica gel with a 15:1 mixture of hexane and ethyl acetate as the mobile phase gives 5.1 g of the title compound: $R_f(G)$=0.41.

f) Ethyl indole-3-carboxylate

A mixture of 3.23 g of indole-3-carboxylic acid in 85 ml of methanol and 8.5 ml of water is brought to pH=7 by addition of a 20% aqueous caesium carbonate solution and then evaporated in vacuo. The residue is twice taken up with in each case 30 ml of dimethylformamide and the mixture concentrated again. 30 ml of dimethylformamide are then added, 1.75 ml of iodoethane are subsequently added at room temperature and the mixture is stirred for 4 h. After concentration of the reaction mixture, the residue is purified over 30 g of silica gel (mobile phase D) by means of FC. This gives the title compound (3.15 g): $R_f(E)$=0.11.

EXAMPLE 98

5(S)-Amino-4(S)-hydroxy-2(R),7,7-trimethyl-8-[3(R)- or 3(S)-ethoxycarbonylindolin-1-ylcarbonl]-octanoic acid (N-butyl)amide The title compound is prepared starting from 41 mg of 5(S)-tert-butoxycarbonylamino-4(S)-hydroxy-2(R),7,7-trimethyl-8-[3(R)- or 3(S)-ethoxycarbonylindolin-1-ylcarbonyl]-octanoic acid (N-butyl)amide analogously to Example 97) and is purified by FC over silica gel (mobile phase M). This gives the title compound: $R_f(S)$=0.26; $R_f(IV)$=39.5 min; FAB-MS: (M+H)$^+$=490.

The starting material is prepared as follows:

a) 5(S)-Tert-butoxycarbonylamino-4(S)-hydroxy-2(R),7,7-trimethyl-8-[3(R)- or -3(S)-ethoxycarbonylindolin-1-ylcarbonyl]-octanoic acid (N-butyl)amide The title compound is obtained starting from 55 mg of (4O,5N-isopropylidene)-5(S)-tert-butoxycarbonylamino-4(S)-hydroxy-2(R),7,7-trimethyl-8-[3(R)- or 3(S)-ethoxycarbonylindolin-1-ylcarbonyl]-octanoic acid (N-butyl)amide (Example 97b), diastereomer II) in a manner analogous to that described in Example 97a) and is purified by FC over 25 g of silica gel (mobile phase J): $R_f(P)$=0.58.

EXAMPLE 99

5(S)-Amino-4(S)-hydroxy-2(R),7,7-trimethyl-8-[3(R)- or -3(S)-methylaminocarbonylamino-1,2,3,4-tetrahydroquinolin-1-ylcarbonyl]-octanoic acid (N-butyl) amide In an analogous manner to that described in Examples 52, 52a and 52b) for the corresponding reaction stages, the title compound is obtained starting from 40 mg of (4O,5N-isopropylidene)-5(S)-tert-butoxycarbonylamino-4(S)-hydroxy-2(R),7,7-trimethyl-8-[3(R)- or 3(S)-methylaminocarbonylamino-1,2,3,4-tetrahydroquinolin-1-ylcarbonyl]-octanoic acid (N-butyl)amide (diastereomer I) via 5(S)-tert-butoxycarbonylamino-4(S)-hydroxy-2(R),7,7-trimethyl-8-[3(R)- or 3(S)-methylaminocarbonylamino-1,2,3,4-tetrahydroquinolin-1-ylcarbonyl]-octanoic acid (N-butyl)amide ($R_f(P)$=0.49; FAB-MS: (M+H)$^+$=604) as the pure stereoisomer: $R_f(S)$=0.13; $R_f(IV)$=13.6 min; FAB-MS: (M+H)$^+$=504.

The starting materials are prepared, for example, as follows:

a) (4O,5N-Isopropylidene)-5(S)-tert-butoxycarbonylamino-4(S)-hydroxy-2(R),7,7-trimethyl-8-[3(R)- or -3(S)- methylaminocarbonylamino-1,2,3,4-tetrahydroquinolin-1-ylcarbonyl]-octanoic acid (N-butyl)amide Starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl) amide and 135 mg of 3(R,S)-methylaminocarbonylamino-1,2,3,4-tetrahydroquinoline, purification of the crude product by chromatography, the two 3(R)- and 3(S)-diastereomers being separated, gives the pure title compound (diastereomer I): $R_f(P)$=0.55; and diastereomer II: $R_f(P)$=0.50.

b) 3(R,S)-Methylaminocarbonylamino-1,2,3,4-tetrahydroquinoline 1.4 g of 3-(methylaminocarbonylamino)quinoline in 40 ml of ethanol are hydrogenated in a manner analogous to that described in Example 93). The crude product is purified over 200 g of silica gel with a 99:1:1 mixture of methylene chloride, methanol and glacial acetic acid as the mobile phase: $R_f(L)$=0.34; MS: $M^+$=205.

c) 3-(Methylaminocarbonylamino)quinoline 0.99 ml of methyl isocyanate is added to a solution of 2.0 g of 3-aminoquinoline in 15 ml of methylene chloride under argon and the mixture is heated under reflux for 2 h. A further 0.95 ml of methyl isocyanate is added and the reaction mixture is refluxed again for 2 h. The crude product is chromatographed over 100 g of silica gel (mobile phase gradient from L to P). This gives the title compound as a crystalline solid: $R_f(L)$=0.2; M+=201.

EXAMPLE 100

5(S)-Amino-4(S)-hydroxy-2(R),7,7-trimethyl-8-[3(R)- or 3(S)-methylaminocarbonylamino-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 40 mg of (4O,5N-isopropylidene)-5(S)-tert-butoxycarbonylamino-4(S)-hydroxy-2(R),7,7-trimethyl-8-[3(R)- or 3(S)-methylaminocarbonylamino-1,2,3,4-tetrahydroquinolin-1-ylcarbonyl]-octanoic acid (N-butyl)amide (diastereomer II; Example 99a)) via 5(S)-tert-butoxycarbonylamino-4(S)-hydroxy-2(R),7,7-trimethyl-8-[3(R)- or 3(S)-methylaminocarbonylamino-1,2,3,4-tetrahydroquinolin-1-ylcarbonyl]-octanoic acid (N-butyl)amide ($R_f$(95:5:1 mixture of methylene chloride, methanol and concentrated ammonia)=0.22; FAB-MS: $(M+H)^+$=604): $R_f(S)$=0.17; $R_f(IV)$=13.3 min; FAB-MS: $(M+H)^+$=504.

EXAMPLE 101

5(S)-Amino-4(S)-hydroxy-2(R),7,7-trimethyl-8-[3(R,S)-phenyl-1,2,3,4-tetrahydroquinolin-1-ylcarbonyl]-octanoic acid (N-butyl)amide In an analogous manner to that described in Examples 52, 52a and 52b) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 137 mg of 3(R,S)-phenyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)phenyl-1,2,3,4-tetrahydroquinolin-1-ylcarbonyl]-octanoic acid (N-butyl)amide ($R_f(A)$=0.57) and 5(S)-tert-butoxycarbonylamino-4(S)-hydroxy-2(R),7,7-trimethyl-8-[3(R,S)phenyl-1,2,3,4-tetrahydroquinolin-1-ylcarbonyl]-octanoic acid (N-butyl)amide ($R_f(P)$=0.59) as a diastereomer mixture: $R_f(S)$=0.28; $R_f(IV)$=32.0 min; FAB-MS: $(M+H)^+$=508.

The 3-(R,S)-phenyl-1,2,3,4-tetrahydroquinoline employed as the starting material is prepared by hydrogenation of 410 mg of 3-phenylquinoline, which is prepared by the method described by J. Stavennuiter et al. in Heterocycles, 26, 2711 (1987), dissolved in 10 ml of ethanol, in the presence of 100 mg of palladium-on-charcoal (10% of palladium) at 70° C. under normal pressure and subsequent purification of the crude product by means of FC over 30 g of silica gel with a 9:1 mixture of hexane and ethyl acetate as the mobile phase: mp. 84°–6° C.; $R_f(F)$=0.39; MS: M+=209.

EXAMPLE 102

5(S)-Amino-4(S)-hydroxy-2(R),7,7-trimethyl-8-[3(R,S)-methoxycarbonyl-4-oxo1,2,3,4-tetrahydroquinolin-1-ylcarbonyl]-octanoic acid (N-butyl)amide Analogously to the processes described in Examples 20, 20a and 20b) for the corresponding reaction stages, the title compound is obtained starting from 301 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 410 mg of 3(R,S)-methoxycarbonyl-4-oxo-1,2,3,4-tetrahydroquinoline (prepared in accordance with G. R. Proctor et al., J.Chem. Soc. Perkin Trans. I, 1803 (1972)) via (4O,5N-isopropylidene)-5(S)-tert-butoxycarbonylamino-4(S)-hydroxy-2(R),7,7-trimethyl-8-[3(R,S)-methoxycarbonyl-4-oxo-1,2,3,4-tetrahydroquinolin-1-ylcarbonyl]-octanoic acid (N-butyl)amide (analogously to Example 1a), with purification over 20 g of silica gel with a 1:3 mixture of ethyl acetate and toluene as the mobile phase: $R_f$(1:3 mixture of ethyl acetate and toluene)=0.15; $R_f(I)$=27.3 min) and 5(S)-tert-butoxycarbonylamino-4(S)-hydroxy-2(R),7,7-trimethyl-8-[3(R,S)-methoxycarbonyl-4-oxo-1,2,3,4-tetrahydroquinolin-1-ylcarbonyl]-octanoic acid (N-butyl)amide (purification over 10 g of silica gel with mobile phases A and ethyl acetate) as a diastereomer mixture: $R_f(V)$=0.35; $R_f(I)$=20.5/21.3 min; FAB-MS: $(M+H)^+$=504.

EXAMPLE 103

5(S)-Amino-4(S)-hydroxy-2(R),7,7-trimethyl-8-[3(R,S)allylaminocarbonyl-1,2,3,4-tetrahydroquinolin-1-ylcarbonyl]-octanoic acid (N-butyl)amide Analogously to the processes described in Examples 20, 20a and 20b) for the corresponding reaction stages, the title compound is obtained starting from 205 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 487 mg of 3(R,S)-allylaminocarbonyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)-allylaminocarbonyl-1,2,3,4-tetrahydroquinolin-1-yl-carbonyl]-octanoic acid (N-butyl)amide ($R_f(X)$=0.45; $R_f(I)$=29.1/29.5 min) and 5(S)-tert-butoxycarbonylamino-4(S)-hydroxy-2(R),7,7-trimethyl-8-[3(R,S)-allylaminocarbonyl-1,2,3,4-tetrahydroquinolin-1-ylcarbonyl]-octanoic acid (N-butyl)amide ($R_f(X)$=0.30; $R_f(I)$=25.2 min) as a diastereomer mixture: $R_f(V)$=0.28/0.34; $R_f(I)$=19.1/19.2 min; FAB-MS: $(M+H)^+$=515.

EXAMPLE 104

5(S)-Amino-4(S)-hydroxy-2(R),7,7-trimethyl-8-[3(R,S)-methoxycarbonylaminomethyl-1,2,3,4-tetrahydroquinolin-1-ylcarbonyl]-octanoic acid (N-butyl)amide Analogously to the processes described in Examples 20, 20a and 20b) for the corresponding reaction stages, the title compound is obtained starting from 600 mg of 3-[N-tert-butoxycarbonyl-4(S)-(3-carboxy-2,2-dimethylpropyloxy-2, 2-dimethyl-1,3-oxazolidin-5(S)-yl]-2(R)-methylpropionic acid (N-butyl)amide and 866 mg of 3(R,S)-methoxycarbonylaminomethyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methoxycarbonylaminomethyl-1,2,3,4-tetrahydroquinolin-1-ylcarbonyl]-octanoic acid (N-butyl)amide ($R_f(X)$=0.45) and 5(S)-tert-butoxycarbonylamino-4(S)-hydroxy-2(R),7,7-trimethyl-8-[3(R,S)-methoxycarbonylaminomethyl-1,2,3,4-tetrahydroquinolin-1-ylcarbonyl]-octanoic acid (N-butyl)amide ($R_f(X)$=0.25; $R_t(I)$=29.6 min; FAB-MS: $(M+H)^{+619}$) as a diastereomer mixture: $R_f(V)$=0.23; $R_t(I)$=21.9 min; FAB-MS: $(M+H)^+$= 519.

The amine component is prepared, for example, as follows:

a) 3(R,S)-Methoxycarbonylaminomethyl-1,2,3,4-tetrahydroquinoline

The title compound is prepared from 3.1 g of 3(R,S)-aminomethyl-1,2,3,4-tetrahydroquinoline and 2.2 ml methyl chloroformate in an analogous manner to that described in Example 54) (stirring for 2 h at 0° C.) and is purified by chromatography over silica gel with a 1:2 mixture of hexane and ethyl acetate as the mobile phase: $R_f(A)$=0.25; FAB-MS: $(M+H)^+$=221.

b) 3(R,S)-Aminomethyl-1,2,3,4-tetrahydroquinoline

A solution of 10 g of quinoline-3-carboxylic acid nitrile in 500 ml of ethanol is hydrogenated in the presence of 1.0 g of palladium-on-charcoal (10% of palladium) at 45° C. under normal pressure for 40 h: $R_f(A)$=0.61.

EXAMPLE 105

4(S)-Hydroxy-2(S)-isopropyl-5-(S)-methanesulfonylamino-7,7-dimethyl-8-[2(R)- or 2(S)-methylaminocarbonyl-3,4-dihydro-2H-1,4-benzothiazin-4-ylcarbonyl]-octanoic acid (N-butyl)amide 27 μl of triethylamine and 15 mg of methanesulfonic acid anhydride are added in succession to a solution of 5(S)-amino-4(S)-hydroxy-2(S)-isopropyl-7,7-dimethyl-8-[2(R)- or 2(S)-methylaminocarbonyl-3,4-dihydro-2H-1,4-benzothiazin-4-ylcarbonyl]-octanoic acid (N-butyl)amide (Example 90) in methylene chloride/dimethylformamide at 0° C. The reaction mixture is stirred overnight and then chromatographed directly over 10 g of silica gel (mobile phase P). This gives the title compound: $R_f(P)$=0.44; $R_t(IV)$=41.6 min; FAB-MS: $(M+H)^+$=613.

EXAMPLE 106

5(S)-Amino-4(S)-hydroxy-2(R),7,7-trimethyl-8-[3(R,S)-N, N-dimethylaminomethyl-1,2,3,4-tetrahydroquinolin-1-ylcarbonyl]-octanoic acid (N-butyl)amide Analogously to the processes described in Examples 20, 20a and 20b) for the corresponding reaction stages, the title compound is obtained starting from 151 mg of 3-[N-tert-butoxycarbonyl-4(S)-(3-carboxy-2,2-dimethylpropyloxy-2, 2-dimethyl-1,3-oxazolidin-5(S)-yl]-2(R)-methylpropionic acid (N-butyl)amide and 146 mg of 3(R,S)-N,N-dimethylaminomethyl-1,2,3,4-tetrahydroquinoline via (4O, 5N-isopropylidene)-5(S)-tert-butoxycarbonylamino-4(S)-hydroxy-2(R),7,7-trimethyl-8-[3(R,S)-N,N-dimethylaminomethyl-1,2,3,4-tetrahydroquinolin-1-ylcarbonyl]-octanoic acid (N-butyl)amide (analogously to Example 1a) with purification over 20 g of silica gel (mobile phase N): $R_f(N)$=0.39; FAB-MS: $(M+H)^+$=629) and 5(S)-tert-butoxycarbonylamino-4(S)-hydroxy-2(R),7,7-trimethyl-8-[3(R,S)-N,N-dimethylaminomethyl-1,2,3,4-tetrahydroquinolin-1-ylcarbonyl]-octanoic acid (N-butyl)amide (purification, after extraction with ethyl acetate from sodium carbonate solution, by means of FC over 10 g of silica gel (mobile phase J): $R_f(V)$=0.18 by the method described in Example 1) as a diastereomer mixture: $R_f(V)$ =0.06, $R_t(I)$=15.3 min; FAB-MS: $(M+H)^+$=489. The 3(R,S) -N,N-dimethylaminomethyl-1,2,3,4-tetrahydroquinoline employed as the starting material is obtained analogously to Example 1m) starting from 165 mg of (R,S)-N,N-dimethylaminocarbonyl-1,2,3,4-tetrahydroquinoline (Example 23c) and 80 mg of lithium aluminium hydride. Customary working up and purification of the crude product gives 3(R,S)-N,N-dimethylaminomethyl-1,2,3,4-tetrahydroquinoline: $R_f(O)$=0.20; MS: $M^+$=190.

EXAMPLE 107

5(S)-Amino-4(S)-hydroxy-2(R),7,7-trimethyl-8-[2(R,S)-methoxyiminomethyl-3,4-dihydro-2H-1,4-benzoxazin-4-ylcarbonyl]-octanoic acid (N-butyl)amide Analogously to the processes described in Examples 20, 20a and 20b) for the corresponding reaction stages, the title compound is obtained starting from 205 mg of 3-[N-tert-butoxycarbonyl-4(S)-(3-carboxy-2,2-dimethylpropyloxy-2, 2-dimethyl-1,3-oxazolidin-5(S)-yl]-2(R)-methylpropionic acid (N-butyl)amide and 220 mg of 2(R,S)-methoxyiminomethyl-3,4-dihydro-2H-1,4-benzoxazine via (4O,5N-isopropylidene)-5(S)-tert-butoxycarbonylamino-4 (S)-hydroxy-2(R),7,7-trimethyl-8-[2(R,S)-methoxyiminomethyl-3,4-dihydro-2H-1,4-benzoxazin-4-ylcarbonyl]-octanoic acid (N-butyl)amide (analogously to Example 1a): $R_f(A)$=0.44) and 5(S)-tert-butoxycarbonylamino-4(S)-hydroxy-2(R),7,7-trimethyl-8-[2(R,S)-methoxyiminomethyl-3,4-dihydro-2H-1,4-benzoxazin-4-ylcarbonyl]-octanoic acid (N-butyl)amide ($R_f$(V)=0.64; FAB-MS: $(M+H)^+$=591) in a manner analogous to that described in Example 1) as a diastereomer mixture: $R_f(V)$=0.25; $R_t(I)$=20.5/20.7 min; FAB-MS: $(M+H)^+$=491.

The amine component employed as the starting material is prepared, for example, as follows:

3.42 g of O-methylhydroxylamine hydrochloride are added to a solution of 600 mg of N-benzyloxycarbonyl-2 (R,S)-formyl-3,4-dihydro-2H-1,4-benzoxazine ($R_f$=0.31; prepared by means of Swern oxidation (Example 1g) from Example 87c) in 30 ml of pyridine and the reaction mixture is then stirred at room temperature for 36 h and subsequently concentrated. The crude product is dissolved in ethyl acetate and the solution is washed with a 1N sodium bicarbonate solution, water and saturated sodium chloride solution. N-Benzyloxycarbonyl-2(R,S)-methoxyiminomethyl-3,4-dihydro-2H-1,4-benzoxazine is obtained (540 mg): $R_f(A)$= 0.61. A further reaction analogously to Example 87a) and purification of the crude product by means of FC over 50 g of silica gel (mobile phase N) gives 2(R,S)-methoxyiminomethyl-3,4-dihydro-2H-1,4-benzoxazine: $R_f(A)$=0.51.

EXAMPLE 108

5(S)-Amino-4(S)-hydroxy-2(R),7,7-trimethyl-8-[3(R,S)-carbamoyl-3,4-dihydro-2H-1,4-benzoxazin-4-ylcarbonyl]-octanoic acid (N-butyl)amide In an analogous manner to that described in Examples 92, 52a and 52b) for the corresponding reaction stages, the title compound is obtained starting from 70 mg of 3-[N-tert-butoxycarbonyl-4(S)-(3-carboxy-2,2-dimethylpropyl)-2,2- dimethyl-1,3-oxazolidin-5(S)-yl]-2(R)-methyl-propionic acid (N-butyl)amide and 82 mg of 3(R,S)-carbamoyl-3,4-dihydro-2H-1,4-benzoxazine via (4O,5N-isopropylidene)-5(S)-tert-butoxycarbonylamino-4(S)-hydroxy-2(R),7,7-trimethyl-8-[3(R,S)-carbamoyl-3,4-dihydro-2H-1,4-benzoxazin-4-ylcarbonyl]-octanoic acid (N-butyl)amide ($R_f$(P)=0.47) and 5(S)-tert-butoxycarbonylamino-4(S)-hydroxy-2(R),7,7-trimethyl-8-[3(R,S)-carbamoyl-3,4-dihydro-2H-1,4-benzoxazin-4-ylcarbonyl]-octanoic acid (N-butyl)amide ($R_f$(P)=0.38) in a manner analogous to that described in Example 52) as a diastereomer mixture: $R_f$(S) =0.12/0.10; $R_f$(IV)=32.2/33.6 min; FAB-MS: (M+H)$^+$=477.

The amine component employed as the starting material is prepared, for example, as follows:

1.20 g of 3(R,S)-ethoxycarbonyl-3,4-dihydro-2H-1,4-benzoxazine (obtained as a by-product in the preparation of 2(R,S)-ethoxycarbonyl-3,4-dihydro-2H-1,4-benzoxazine; Example 16a)) are dissolved in 20 ml of a 6N ammonia solution in methanol and the solution is kept in a bomb tube at 50° C. for 60 h. Concentration and purification of the crude product by means of FC over 180 g of silica gel (mobile phase O) gives 3(R,S)-carbamoyl-3,4-dihydro-2H-1,4-benzoxazine: $R_f$(T)=0.26.

EXAMPLE 109

5(S)-Amino-4(S)-hydroxy-2(R),7,7-trimethyl-8-[3(R)-oder 3(S)-ethoxycarbonylamino-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 125 mg of (4O,5N-isopropylidene)-5(S)-tert-butoxycarbonylamino-4(S)-hydroxy-2(R),7,7-trimethyl-8-[3(R)- or 3(S)-ethoxycarbonylamino-1,2,3,4-tetrahydroquinolin-1-ylcarbonyl]-octanoic acid (N-butyl)amide (diastereomer I) via 5(S)-tert-butoxycarbonylamino-4(S)-hydroxy-2(R),7,7-trimethyl-8-[3(R)- or 3(S)-ethoxycarbonylamino-1,2,3,4-tetrahydroquinolin-1-ylcarbonyl]-octanoic acid (N-butyl) amide ($R_f$(P)=0.43) as the pure stereoisomer: $R_f$(S)=0.21; $R_f$(IV)=37.6 min; FAB-MS: (M+H)$^+$=519.

The starting materials are prepared, for example, as follows:

a) (4O,5N-Isopropylidene)-5(S)-tert-butoxycarbonylamino-4(S)-hydroxy-2(R),7,7-trimethyl-8-[3(R)- or 3(S)-ethoxycarbonylamino-1,2,3,4-tetrahydroquinolin-1-ylcarbonyl]-octanoic acid (N-butyl)amide The title compound is obtained starting from 200 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 289 mg of 2(R, S)-ethoxycarbonylamino-1,2,3,4-tetrahydroquinoline with FC over 25 g of silica gel (mobile phase gradient from C to A), the two 3(R)- and 3(S)-stereoisomers being separated. This gives the pure title compound (diastereomer I): $R_f$(A) =0.28; and diastereomer II: $R_f$(A)=0.20.

b) 3(R,S)Ethoxycarbonylamino-1,2,3,4-tetrahydroquinoline 10 ml of a 10% sodium hydroxide solution and 0.34 ml of ethyl chloroformate are added in succession to a solution of 0.5 g of 3(R,S)-amino-1,2,3,4-tetrahydroquinoline in 6 ml of toluene, while stirring vigorously, and when the addition has ended, the mixture is stirred for a further 5 min. Customary working up and chromatography of the crude product over 25 g of silica gel with methylene chloride as the mobile phase gives the title compound: $R_f$(P)=0.78; MS: M$^+$=220.

c) 3(R,S)-Amino-1,2,3,4-tetrahydroquinoline

The solution of 35 g of 3-aminoquinoline in 330 ml of ethanol is hydrogenated in the presence of a total of 27 g of Raney nickel at 55° C. under a pressure of 90 bar for 44 h. After customary working up, the crude product is purified over 900 g of silica gel (mobile phase S): $R_f$(S)=0.40; MS: M$^+$=148.

EXAMPLE 110

5(S)-Amino-4(S)-hydroxy-2(R),7,7-trimethyl-8-[3(R)- or 3(S)-ethoxycarbonylamino-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 150 mg of (4O,5N-isopropylidene)-5(S)-tert-butoxycarbonylamino-4(S)-hydroxy-2(R),7,7-trimethyl-8-[3(R)- or 3(S)-ethoxycarbonylamino-1,2,3,4-tetrahydroquinolin-1-ylcarbonyl]-octanoic acid (N-butyl)amide (diastereomer II, Example 109a) via 5(S)-tert-butoxycarbonylamino-4(S)-hydroxy-2(R),7,7-trimethyl-8-[3(R)- or 3(S)-ethoxycarbonylamino-1,2,3,4-tetrahydroquinolin-1-ylcarbonyl]-octanoic acid (N-butyl)amide ($R_f$(P)=0.45) as the pure stereoisomer: $R_f$(S)=0.18; $R_f$(IV)=37.4 min; FAB-MS: (M+H)$^+$=519.

EXAMPLE 111

5(S)-Amino-4(S)-hydroxy-2(R),7,7-trimethyl-8-[3(R)- or 3(S)-propyloxycarbonylamino-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 118 mg of (4O,5N-isopropylidene)-5(S)-tert-butoxycarbonylamino-4(S)-hydroxy-2(R),7,7-trimethyl-8-[3(R)- or 3(S) propyloxycarbonylamino-1,2,3,4-tetrahydroquinolin-1-ylcarbonyl]-octanoic acid (N-butyl)amide (diastereomer I) via 5(S)-tert-butoxycarbonylamino-4(S)-hydroxy-2(R),7,7-trimethyl-8-[3(R)- or 3(S)propyloxycarbonylamino-1,2,3,4-tetrahydroquinolin-1ylcarbonyl]-octanoic acid (N-butyl) amide ($R_f$(P)=0.44) as the pure stereoisomer: $R_f$(S)=0.29; $R_f$(IV)=39.7 min; FAB-MS: (M+H)$^+$=533.

The starting materials are prepared, for example, as follows:

a) (4O,5N-Isopropylidene)-5(S)-tert-butoxycarbonylamino-4(S)-hydroxy-2(R),7,7-trimethyl-8-[3(R)- or 3(S)-propyloxycarbonylamino-1,2,3,4-tetrahydroquinolin-1-ylcarbonyl]-octanoic acid (N-butyl)amide The title compound is obtained starting from 150 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 231 mg of 3(R,S)-propyloxycarbonylamino-1,2,3,4-tetrahydroquinoline with chromatographic separation of the two 3(R)- and 3(S)-stereoisomers over 25 g of silica gel (mobile phase gradient from C to A). This gives the title compound (diastereomer I): $R_f$(A)=0.37; and diastereomer II: $R_f$(A)=0.30.

b) 3(R,S)-Propyloxycarbonylamino-1,2,3,4-tetrahydroquinoline

Analogously to the method described in Example 108b) from 3(R,S)-amino-1,2,3,4-tetrahydroquinoline and propyl-chloroformate: $R_f$(P)=0.84; MS: M$^+$=234.

EXAMPLE 112

5(S)-Amino-4(S)-hydroxy-2(R),7,7-trimethyl-8-[3(R)- or 3(S)-propyloxycarbonylamino-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 94 mg of (4O,5N-isopropylidene)-5(S)-tert-butoxycarbonylamino-4(S)-hydroxy-2(R),7,7-trimethyl-8-[3(R)- or 3(S) propyloxycarbonylamino-1,2,3,4-tetrahydroquinolin-1-ylcarbonyl]-octanoic acid (N-butyl)amide (diastereomer II; Example 111a)) via 5(S)-tert-butoxycarbonylamino-4(S)-hydroxy-2(R),7,7-trimethyl-8-[3(R)- or 3(S) propyloxycarbonylamino-1,2,3,4-tetrahydroquinolin-1-ylcarbonyl]-octanoic acid (N-butyl)amide ($R_f(P)$=0.40) as the pure stereoisomer: $R_f(S)$=0.27; $R_t$=(IV)=39.8 min; FAB-MS: (M+H)$^+$=533.

EXAMPLE 113

5(S)-Amino-4(S)-hydroxy-2(R),7,7-trimethyl-8-[2(R,S)-(dioxolan-2-yl)-3,4-dihydro-2H-1,4-benzoxazin-4-ylcarbonyl]-octanoic acid (N-butyl)amide In a manner analogous to that described in Examples 21a and 21b), the title compound is obtained starting from 205 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 207 mg of 2(R,S)-(dioxolan-2-yl)-3,4-dihydro-2H-1,4-benzoxazine via (4O,5N-isopropylidene)-5(S)-tert-butoxycarbonylamino-4(S)-hydroxy-2(R),7,7-trimethyl-8-[2(R,S)-(dioxolan2-yl)-3, 4-dihydro-2H-1,4-benzoxazin-4-ylcarbonyl]-octanoic acid (N-butyl)amide ($R_f(A)$=0.22), with subsequent reaction with iodo-trimethylislane, in a manner analogous to that described in Example 87a), as a diastereomer mixture: $R_f(V)$=0.27; $R_t(I)$=23.1/23.3 min; FAB-MS: (M+H)$^+$=506.

The 2(R,S)-(dioxolan2-yl)-3,4-dihydro-2H-1,4-benzoxazine employed as the starting material is prepared by reaction of 500 mg of N-benzyloxycarbonyl-2(R,S)-formyl-3,4-dihydro-2H-1,4-benzoxazine (Example 107) with 0.28 ml of ethylene glycol in 25 ml of toluene under reflux, with azeotropic removal of water, overnight in the presence of 25 mg of p-toluenesulfonic acid hydrate. After customary working up and FC of the crude product over silica gel with a 6:1 mixture of toluene and ethyl acetate, N-benzyloxycarbonyl-2(R,S)-(dioxolan2-yl)-3,4-dihydro-2H-1,4-benzoxazine is obtained ($R_f$(3:1 mixture of toluene and ethyl acetate)=0.52). Subsequent hydrogenolysis analogously to Example 1r) gives 2(R,S)-(dioxolan2-yl)-3,4-dihydro-2H-1,4-benzoxazine: $R_f(P)$=0.74; FAB-MS: (M+H)$^+$=208.

EXAMPLE 114

5(S)-Amino-4(S)-hydroxy-2,2,7,7-tetramethyl-8-[3(R)- or 3(S)-methoxycarbonylamino-1,2,3,4-tetrahydroquinolin-1-ylcarbonyl]-octanoic acid (N-butyl)amide Starting from 92 mg of 3-[N-tert-butoxycarbonyl-4(S)-(3-carboxy-2,2-dimethylpropyloxy-2,2-dimethyl-1,3-oxazolidin-5(S)-yl]-2,2-dimethyl-propionic acid (N-butyl)amide and 109 mg of 3(R)- or 3(S)-methoxycarbonylamino-1,2,3,4-tetrahydroquinoline (stereoisomer II, Example 74h)), the title compound is obtained via (4O,5N-isopropylidene)-5(S)-tert-butoxycarbonylamino-4(S)-hydroxy-2,2,7,7-tetramethyl-8-[3(R)- or 3(S)-methoxycarbonylamino-1,2,3,4-tetrahydroquinolin-1-ylcarbonyl]-octanoic acid (N-butyl)amide ($R_f(L)$=0.31; FAB-MS: M+H)$^+$=659) and 5(S)-tert-butoxycarbonylamino-4(S)-hydroxy-2,2,7,7-tetramethyl-8-[3(R)- or 3(S)-methoxycarbonylamino-1,2,3,4-tetrahydroquinolin-1-ylcarbonyl]-octanoic acid (N-butyl)amide ($R_f(L)$=0.20; FAB-MS: (M+H)$^+$=619) analogously to Example 92) as the pure diastereomer: $R_f(P)$=0.43; $R_f(IV)$=35.3 min; FAB-MS: (M+H)$^+$=519.

The starting materials are obtained, for example, as follows:

a) 3-[N-Tert-butoxycarbonyl-4(S)-(3-carboxy-2,2-dimethylpropyloxy-2,2-dimethyl-1,3-oxazolidin-5(S)-yl]-2,2-dimethyl-propionic acid (N-butyl)amide The title compound is obtained in a manner analogous to that in Example 74a) starting from 204 mg of 3-[N-tert-butoxycarbonyl-4(S)-(4-hydroxy-2,2-dimethylbutyloxy-2,2-dimethyl-1,3-oxazolidin-5(S)-yl]-2,2-dimethyl-propionic acid (N-butyl)amide: $R_f(L)$=0.15; FAB-MS: (M+H)$^+$=471.

b) 3-[N-Tert-butoxycarbonyl-4(S)-(4-hydroxy-2,2-dimethylbutyloxy-2,2-dimethyl-1,3-oxazolidin-5(S)-yl]-2,2-dimethyl-propionic acid (N-butyl)amide Analogously to Examples 74b and 74c), starting from 398 mg of 5(S)-[5-benzyloxy-1(S)-tert-butoxycarbonylamino-3,3-dimethyl-pentyl]-3,3-dimethyl-2-oxo-tetrahydrofuran, 3-[N-tert-butoxycarbonyl-4(S)-(4-benzyloxy-2,2-dimethylbutyloxy-2,2-dimethyl-1,3-oxazolidin-5(S)-yl]-2,2-dimethyl-propionic acid (N-butyl)amide is obtained (309 mg; $R_f(B)$=0.41; FAB-MS: (M+H)$^+$=547), and is subsequently hydrogenated in 5 ml of ethyl acetate in the presence of palladium-on-charcoal (5% of Pd) at room temperature for 2 h to give the title compound: $R_f(L)$=0.33; FAB-MS: (M+H)$^+$=457.

c) 5(S)-[5-Benzyloxy-1(S)-tert-butoxycarbonylamino-3,3-dimethyl-pentyl]-3,3-dimethyl-2-oxo-tetrahydrofuran The title compound is obtained starting from 518 mg of 5(S)-[5-benzyloxy-1(S)-tert-butoxy-carbonylamino-3,3-dimethyl-pentyl]-2-oxo-tetrahydrofuran and 0.18 ml of methyl iodide by a process analogous to that described in Example 74d). After stirring at −78° C. for 3 h, the reaction mixture is allowed to warm to 0° C., stirring is continued for a further 2 h and the mixture is worked up by customary processes. This gives the title compound: $R_f(D)$=0.30; FAB-MS: (M+H)$^+$=434.

EXAMPLE 115

5(S)-Amino-4(S)-hydroxy-2(R),7,7-trimethyl-8-[3(R,S)-(2-oxo-oxazolidin3-yl)-1,2,3,4-tetrahydroquinolin-1-ylcarbonyl]-octanoic acid (N-butyl)amide The title compound is obtained in a manner analogous to that described in Examples 92, 52a) and 52b), starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 144 mg of 3(R,S)-(2-oxo-oxazolidin-3-yl)-1,2,3,4-tetrahydroquinoline via (4O,5N-isopropylidene)-5(S)-tert-butoxycarbonylamino-4(S)-hydroxy-2(R),7,7-trimethyl-8-[3(R,S)-(2-oxo-oxazolidin-3-yl)-1,2,3,4-tetrahydroquinolin-1-ylcarbonyl]-octanoic acid (N-butyl)amide ($R_f(P)$=0.57) and 5(S)-tert-butoxycarbonylamino-4(S)-hydroxy-2(R),7,7-trimethyl-8-[3(R,S)-(2-oxo-oxazolidin-3-yl)-1,2,3,4-tetrahydroquinolin-1-ylcarbonyl]-octanoic acid (N-butyl)amide ($R_f(P)$=0.48) as a diastereomer mixture: $R_f(P)$=0.15; $R_t(V)$=15.7 min; FAB-MS: (M+H)$^+$=517.

The amine component employed is prepared, for example, as follows:

26.0 g of 3-bromoquinoline and 4.35 g of 2-oxazolidinone in 200 ml of xylene are heated under reflux in the presence of 7.4 g of potassium acetate and 4.8 g of copper powder for 9 h, analogously to the process of B.Renger in Synthesis (1985) 856. After the mixture has been worked up, the crude product is purified over silica gel with a 500:10:1 mixture of methylene chloride, methanol and concentrated ammonia as the mobile phase, to give 3-(quinolin-3-yl)-2-oxazolidinone as a crystalline solid: $R_f$(500:10:1 mixture of methylene chloride, methanol and concentrated ammonia)=0.39; FAB-MS: (M+H)⁺=215. Hydrogenation of 0.67 g of the resulting product in 10 ml of ethanol in the presence of 0.1 g of palladium-on-charcoal (10% of palladium) at 50° C. in the course of 20 h and FC over 80 g of silica get (mobile phase N) gives 3(R,S)-(2-oxo-oxazolidin-3-yl)-1,2,3,4-tetrahydroquinoline as a white solid: R$_f$(N)=0.61; MS: M⁺=218.

EXAMPLE 116

5(S)-Amino-4(S)-hydroxy-2(R),7,7-trimethyl-8-[3(R,S)-methoxymethoxymethyl-1,2,3,4-tetrahydroquinolin-1-ylcarbonyl]-octanoic acid (N-butyl)amide In a manner analogous to that described in Examples 21, 21a) and 21b) for the corresponding reaction stages, the title compound is obtained starting from 600 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 815 mg of 3(R,S)-methoxymethoxymethyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methoxymethoxymethyl-1,2,3,4-tetrahydroquinolin-1-ylcarbonyl]-octanoic acid (N-butyl)amide (R$_f$(A)=0.14; FAB-MS: (M+H)⁺=646) and 5(S)-tert-butoxycarbonylamino-4(S)-hydroxy-2(R),7,7-trimethyl-8-[3(R,S)-methoxymethoxymethyl-1,2,3,4-tetrahydroquinolin-1-ylcarbonyl]-octanoic acid (N-butyl) amide (R$_f$(X)=0.36; FAB-MS: (M+H)⁺=606) as a diastereomer mixture: R$_f$(X)=0.40; R$_t$(I)=23.5 min; FAB-MS: (M+H)⁺=506.

The 3(R,S)-methoxymethoxymethyl-1,2,3,4-tetrahydroquinoline employed as the starting material is prepared in a manner analogous to that described in Example 105) for the amine component, starting from N-benzyloxycarbonyl-3(R,S)-hydroxymethyl-1,2,3,4-tetrahydroquinoline: R$_f$(A)=0.44; FAB-MS: (M+H)⁺=208.

EXAMPLE 117

5(S)-Amino-4(S)-hydroxy-2(R),7,7-trimethyl-8-[3(R,S)-allyloxymethyl-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 134 mg of 3(R,S)-allyloxymethyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)-allyloxymethyl-1,2,3,4-tetrahydroquinolin-1-ylcarbonyl]-octanoic acid (N-butyl)amide (R$_f$(A)=0.48) and 5(S)-tert-butoxycarbonylamino-4(S)-hydroxy-2(R),7,7-trimethyl-8-[3(R,S)-allyloxymethyl-1,2,3,4-tetrahydroquinolin-1-ylcarbonyl]-octanoic acid (N-butyl)amide (R$_f$(A)=0.24) as a diastereomer mixture: R$_f$(S)=0.25; R$_t$(IV)=42.3 min; FAB-MS: (M+H)⁺=502.

The amine component employed is obtained, for example, as follows:

0.5 g of a potassium hydride suspension (20% in oil) is added to a solution of 0.6 g of 1-tert-butoxycarbonyl-3(R,S)-hydroxymethyl-1,2,3,4-tetrahydroquinoline in 7 ml of tetrahydrofuran at 0° C., the mixture is stirred for 30 min and 0.58 ml of allyl bromide is then added. After the mixture has been stirred at 0° C. for 45 min, it is worked up in the customary manner and the crude product is purified over 50 g of silica gel (mobile phase F). 1-Tert-butoxycarbonyl-3(R,S)-allyloxymethyl-1,2,3,4-tetrahydroquinoline is obtained as a colourless oil (R$_f$(F)=0.40), which is then reacted analogously to Example 20a). Purification by means of FC over 50 g of silica gel with methylene chloride as the mobile phase gives 3(R,S)-allyloxymethyl-1,2,3,4-tetrahydroquinoline: R$_f$(F)=0.40; MS: M⁺=203.

EXAMPLE 118

5(S)-Amino-4(S)-hydroxy-2(R),7,7-trimethyl-8-[3(R,S)-methoxyethoxymethyl-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 100 mg 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 146 mg of 3(R,S)-methoxyethoxymethyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methoxyethoxymethyl-1,2,3,4-tetrahydroquinolin-1-ylcarbonyl]-octanoic acid (N-butyl)amide (R$_f$(A)=0.22) and 5(S)-tert-butoxycarbonylamino-4(S)-hydroxy-2(R),7,7-trimethyl-8-[3(R,S)-methoxyethoxymethyl-1,2,3,4-tetrahydroquinolin-1-ylcarbonyl]-octanoic acid (N-butyl) amide (R$_f$(H)=0.12): R$_f$(S)=0.22; R$_t$(IV)=38.6 min; FAB-MS: (M+H)⁺=520.

The amine component employed is obtained, for example, as follows:

Reaction of 0.6 g of 1-tert-butoxycarbonyl-3(R,S)-hydroxymethyl-1,2,3,4-tetrahydroquinoline by a process analogous to that described in Example 117) with 0.64 ml of 2-bromomethyl methyl ether at room temperature for 5 h and customary working up gives 1-tert-butoxycarbonyl-3(R,S)-methoxyethoxymethyl-1,2,3,4-tetrahydroquinoline (R$_f$(A)=0.67), which is reacted as described in Example 117) for the corresponding reaction stage to give 3(R,S)-methoxyethoxymethyl-1,2,3,4-tetrahydroquinoline: R$_f$(A)=0.53; MS: M⁺=221.

EXAMPLE 119

5(S)-Amino-4(S)-hydroxy-2(R),7,7-trimethyl-8-[3(R,S)-(2-oxopyrrolidin-1-yl)-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 142 mg of 3(R,S)-(2-oxopyrrolidin-1-yl)-1,2,3,4-tetrahydroquinoline via (4O,5N-isopropylidene)-5(S)-tert-butoxycarbonylamino-4(S)-hydroxy-2(R),7,7-trimethyl-8-[3(R,S)-(2-oxopyrrolidin-1-yl)-1,2,3,4-tetrahydroquinolin-1-yl-carbonyl]-octanoic acid (N-butyl)amide (R$_f$(L)=0.31) and 5(S)-tert-butoxycarbonylamino- 4(S)-hydroxy-2(R),7,7-trimethyl-8-[3(R,S)-(2-oxopyrrolidin-1-yl)-1,2,3,4-tetrahydroquinolin-1-ylcarbonyl]-octanoic acid (N-butyl)amid (R$_f$(L)=0.23) as a diastereomer mixture: R$_f$(S)=0.24; R$_t$(IV)=35.4 min; FAB-MS: (M+H)⁺=515.

The amine component employed is prepared, for example, as follows:

A mixture of 4.26 g of 2-pyrrolidone, 26.0 g of 3-bromoquinoline, 7.4 g of potassium acetate and 4.8 g of copper powder in 200 ml of xylene is heated under reflux for 12 h in a manner analogous to that in Example 115). After the mixture has been worked up, the crude product is purified over 250 g of silica gel (mobile phase K). This gives 1-(quinolin-3-yl)-2-oxopyrrolidine as a crystalline solid: $R_f(L)$=0.32.

A solution of 1.0 g of the product thus obtained in 20 ml of ethanol is hydrogenated in the presence of 0.2 g of palladium-on-charcoal (10% of palladium) at 50° C. over 22 h. After customary working up, the crude product is purified by means of FC over 30 g of silica gel (mobile phase K) to give crystalline 3(R,S)-(2-oxopyrrolidin-1-yl)-1,2,3,4-tetrahydroquinoline: $R_f(K)$=0.36; MS: $M^+$=216.

EXAMPLE 120

5(S)-Amino-4(S)-hydroxy-6-[1-[2(R)-oder 2(S)-methylaminocarbonyl-3,4-dihydro-2H-1,4-benzothiazin-4-ylcarbonylmethyl]-cyclopropyl]-2(R)-methyl-hexanoic acid (N-butyl)amide In an analogous manner to that described in Examples 92, 52a and 52b) for the corresponding reaction stages, the title compound is obtained starting from 100 mg of 3-[N-tert-butoxycarbonyl-4(S)-[1-(carboxymethyl)cyclopropylmethyl]-2,2-dimethyl-1,3-oxazolidin-5(S)-yl]-2(R)-methyl-propionic acid (N-butyl)amide and 137 mg of 2(R)- or 2(S)-methylaminocarbonyl-3,4-dihydro-2H-1,4-benzothiazine (stereoisomer I; Example 90) via (4O,5N-isopropylidene)-5(S)-tert-butoxycarbonylamino-4(S)-hydroxy-6-[1-[2(R)- or 2(S)-methylaminocarbonyl-3,4-dihydro-2H-1,4-benzothiazin-4-ylcarbonylmethyl]-cyclopropyl]-2(R)-methyl-hexanoic acid (N-butyl)amide ($R_f(P)$=0.54) and 5(S)-tert-butoxycarbonylamino-4(S)-hydroxy6-[1-[2(R)- or 2(S)-methylaminocarbonyl-3,4-dihydro-2H-1,4-benzothiazin-4-ylcarbonylmethyl]-cyclopropyl]-2(R)-methyl-hexanoic acid (N-butyl)amide ($R_f(P)$=0.41) as the pure stereoisomer: $R_f(P)$=0.11; $R_f(IV)$=33.3 min; FAB-MS: $(M+H)^+$=505.

EXAMPLE 121

5(S)-Amino-4(S)-hydroxy-6-[1-[3(R)- or 3(S)-methoxycarbonylamino-1,2,3,4-tetrahydroquinolin-1-ylcarbonylmethyl]-cyclopropyl]-2(R)-methyl-hexanoic acid (N-butyl)amide In an analogous manner to that described in Examples 92, 52a and 52b) for the corresponding reaction stages, the title compound is obtained starting from 100 mg of 3-[N-tert-butoxycarbonyl-4(S)-[1-(carboxymethyl)cyclopropylmethyl]-2,2-dimethyl-1,3-oxazolidin-5(S)-yl]-2(R)-methyl-propionic acid (N-butyl)amide and 113 mg of 3(R)- or 3(S)-methoxycarbonylamino-1,2,3,4-tetrahydroquinoline (stereoisomere I in Example 74h) via (4O,5N-isopropylidene)-5(S)-tert-butoxycarbonylamino-4(S)-hydroxy-6-[1-[3(R)- or 3(S)-methoxycarbonylamino-1,2,3,4-tetrahydroquinolin-1-ylcarbonylmethyl]-cyclopropyl]-2(R)-methyl-hexanoic acid (N-butyl)amide ($R_f(P)$=0.57) and 5(S)-tert-butoxycarbonylamino-4(S)-hydroxy6-[1-[3(R)- or 3(S)-methoxycarbonylamino-1,2,3,4-tetrahydroquinolin-1-yl-carbonylmethyl]cyclopropyl]-2(R)-methyl-hexanoic acid (N-butyl)amide ($R_f(P)$=0.51) as the pure stereoisomer: $R_f(S)$=0.20; FAB-MS: $(M+H)^+$=503.

EXAMPLE 122

5(S)-Amino-4(S)-hydroxy-6-[1-[3(R)- or 3(S)-methoxycarbonylamino-1,2,3,4-tetrahydroquinolin-1-ylcarbonylmethyl]-cyclopropyl]-2-(R)-methyl-hexanoic acid (N-butyl)amide In an analogous manner to that described in Examples 92, 52a and 52b) for the corresponding reaction stages, the title compound is obtained starting from 100 mg of 3-[N-tert-butoxycarbonyl-4(S)-[1-(carboxymethyl)cyclopropylmethyl]-2,2-dimethyl-1,3-oxazolidin-5(S)-yl]-2(R)-methyl-propionic acid (N-butyl)amide and 3(R)- or 3(S)-methoxycarbonylamino-1,2,3,4-tetrahydroquinoline (stereoisomer II in Example 74h) via (4O,5N-isopropylidene)-5(S)-tert-butoxycarbonylamino-4(S)-hydroxy-6-[1-[3(R)- or 3(S)-methoxycarbonylamino-1,2,3,4-tetrahydroquinolin-1-ylcarbonylmethyl]-cyclopropyl]-2-(R)-methyl-hexanoic acid (N-butyl)amide ($R_f(P)$=0.60) and 5(S)-tert-butoxycarbonylamino-4(S)-hydroxy-6-[1-[3(R)- or 3(S)-methoxycarbonylamino-1,2,3,4-tetrahydroquinolin-1-ylcarbonylmethyl]-cyclopropyl]-2(R)-methyl-hexanoic acid (N-butyl)amide ($R_f(P)$=0.50) as the pure stereoisomer: $R_f(S)$=0.19; $R_f(IV)$=35.1 min; FAB-MS: $(M+H)^+$=503.

EXAMPLE 123

5(S)-Amino-4(S)-hydroxy-2(R),7,7-trimethyl-8-[3(R,S)-methoxyethoxy-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 136 mg of 3(R,S)-methoxyethoxy-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methoxyethoxy-1,2,3,4-tetrahydroquinolin-1-ylcarbonyl]octanoic acid (N-butyl)amide ($R_f(P)$=0.44) and 5(S)-tert-butoxycarbonylamino-4(S)-hydroxy-2(R),7,7-trimethyl-8-[3(R,S)-methoxyethoxy-1,2,3,4-tetrahydroquinolin-1-ylcarbonyl]-octanoic acid (N-butyl)amide ($R_f(L)$=0.28) as a diastereomer mixture: $R_f(S)$=0.32; $R_f(IV)$=37.4/38.0 min; FAB-MS: $(M+H)^+$=506.

The amine component employed is prepared, for example, as follows:

0.75 g of a potassium hydride suspension (20% in oil) is added to a solution of 0.5 g of 3-hydroxyquinoline in 10 ml of tetrahydrofuran, while cooling with ice, and the mixture is stirred for 1 h. 1.25 ml of 2-bromomethyl methyl ether, dissolved in 10 ml of dimethylformamide, are then added and the mixture is allowed to warm to room temperature and is finally stirred at 60° C. for 1 h. After customary working up, the 3-(Methoxyethoxy)quinoline thus obtained is purified by means of FC over 80 g of silica gel (mobile phase B): $R_f$(97:3:0.5 mixture of methylene chloride, methanol and concentrated ammonia)=0.31. 1.0 g of the quinoline derivative mentioned in 10 ml of ethanol is hydrogenated in the presence of 0.1 g of palladium-on-charcoal (10% of Pd) at 50° C. for 4 h. FC over 50 g of silica gel with a 100:1 mixture of methylene chloride and methanol as the eluting agent gives 3(R,S)-methoxyethoxy-1,2,3,4-tetrahydroquinoline: $R_f$(97:3:0.5 mixture of methylene chloride, methanol and concentrated ammonia)=0.49; MS: $M^+$=207.

EXAMPLE 124

5(S)-Amino-4(S)-hydroxy-2(R),7,7-trimethyl-8-[3(R,S)-propyloxy-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 100 mg of 3-[N-tert-butoxycarbonyl-4(S)-(3-carboxy-2,2-dimethylpropyloxy-2, 2-dimethyl-1,3-oxazolidin-5(S)-yl]-2(R)-methyl-propionic acid (N-butyl)amide and 126 mg of 3(R,S)-propyloxy-1,2,3,4-tetrahydroquinoline via (4O,5N-isopropylidene)-5(S)-tert-butoxycarbonylamino-4(S)-hydroxy-2(R),7,7-trimethyl-8-[3(R,S)-propyloxy-1,2,3,4-tetrahydroquinolin-1-ylcarbonyl]-octanoic acid (N-butyl)amide ($R_f(P)$=0.83) and 5(S)-tert-butoxycarbonylamino-4(S)-hydroxy-2(R),7,7-trimethyl-8-[3(R,S)-propyloxy-1,2,3,4-tetrahydroquinolin-1-ylcarbonyl]-octanoic acid (N-butyl)amide ($R_f(P)$=0.57) as a diastereomer mixture: $R_f(S)$=0.33; $R_f(IV)$=42.2/42.6 min; FAB-MS: $(M+H)^+$=490.

The 3(R,S)-propyloxy-1,2,3,4-tetrahydroquinoline employed is obtained by the process described under Example 123) via 3-propyloxyquinoline ($R_f(A)$=0.58; MS: $(M+H)^+$=187): $R_f$(methylene chloride)=0.35; MS: $M^+$=191.

EXAMPLE 125

5(S)-Amino-4(S)-hydroxy-2(S)-isopropyl-7,7-dimethyl-8-[3(R)- or -3(S)-methoxycarbonylamino-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 80 mg of 3-[N-tert-butoxycarbonyl-4(S)-(3-carboxy-2,2-dimethylpropyloxy-2,2-dimethyl-1,3-oxazolidin-5(S)-yl]-2(S)isopropyl-propionic acid (N-butyl)amide and 85 mg of 3(R)- or 3(S)-methoxycarbonylamino-1,2,3,4-tetrahydroquinoline (stereoisomer II, Example 74h) via (4O,5N-isopropylidene)-5(S)-tert-butoxycarbonylamino-4(S)-hydroxy-2(S)-isopropyl-7,7-dimethyl-8-[3(R)- or 3(S)-methoxycarbonylamino-1,2,3,4-tetrahydroquinolin-1-ylcarbonyl]octanoic acid (N-butyl)amide ($R_f(P)$=0.67) and 5(S)-tert-butoxycarbonylamino-4(S)-hydroxy-2(S)-isopropyl-7,7-dimethyl-8-[3(R)- or 3(S)-methoxycarbonylamino-1,2,3,4-tetrahydroquinolin-1-ylcarbonyl]-octanoic acid (N-butyl)amide ($R_f(P)$=0.59) as the pure stereoisomer: $R_f(S)$=0.23; $R_f(IV)$=38.5 min; FAB-MS: $(M+H)^+$=533.

EXAMPLE 126

5(S)-Amino-4(S)-hydroxy-2(R),7,7-trimethyl-8-[3(R,S)-methoxymethyloxy-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 127 mg of 3(R,S)-methoxymethyloxy-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methoxymethyloxy-1,2,3,4-tetrahydroquinolin-1-ylcarbonyl]-octanoic acid (N-butyl)amide ($R_f(A)$=0.30) and 5(S)-tert-butoxycarbonylamino-4(S)-hydroxy-2(R),7,7-trimethyl-8-[3(R,S)-methoxymethyloxy-1,2,3,4-tetrahydroquinolin-1-yl-carbonyl]-octanoic acid (N-butyl)amide ($R_f(L)$=0.29; FAB-MS: $(M+H)^+$=592) by reaction in 6 ml of 50% trifluoro acetic acid in methylene chloride at 0° C. for 15 min, as a diastereomer mixture: $R_f(S)$=0.36; $R_f(IV)$=38.0/38.4 min; FAB-MS: $(M+H)^+$=492.

The 3(R,S)-methoxymethyloxy-1,2,3,4-tetrahydroquinoline employed is obtained by the processes described under Example 123) starting from 0.7 g of 3-hydroxyquinoline and 1.09 ml of methoxymethyl chloride via 3-(methoxymethyloxy)quinoline ($R_f(A)$=0.46): $R_f(P)$=0.84; MS: $M^+$=193.

EXAMPLE 127

5(S)-Amino-4(S)-hydroxy-2(R),7,7-trimethyl-8-[3(R,S)-cyclopropylcarbonylamino-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 178 mg of 3(R,S)-cyclopropylcarbonylamino-1,2,3,4-tetrahydroquinoline via (4O,5N-isopropylidene)-5(S)-tert-butoxycarbonylamino-4(S)-hydroxy-2(R),7,7-trimethyl-8-[3(R,S)-cyclopropylcarbonylamino- 1,2,3,4-tetrahydroquinolin-1-ylcarbonyl]-octanoic acid (N-butyl)amide ($R_f(P)$=0.51) and 5(S)-tert-butoxycarbonylamino-4(S)-hydroxy-2(R),7,7-trimethyl-8-[3(R,S)-cyclopropylcarbonylamino-1,2,3,4-tetrahydroquinolin-1-ylcarbonyl]-octanoic acid (N-butyl) amide ($R_f(P)$=0.37) as a diastereomer mixture: $R_f(S)$=0.13; $R_f(V)$=16.6/17.0 min; FAB-MS: $(M+H)^+$=515.

3(R,S)-Cyclopropylcarbonylamino-1,2,3,4-tetrahydroquinoline is obtained by reaction of 1.0 g of 3-amino-1,2,3,4-tetrahydroquinoline in a mixture of 11 ml of toluene and 3.2 ml of a 10% aqueous sodium hydroxide solution with 0.65 ml of cyclopropanecarboxylic acid chloride analogously to Example 109b), as a white solid: $R_f(P)$ =0.61; MS: $M^+$=216.

EXAMPLE 128

5(S)-Amino-4(S)-hydroxy-2(R),7,7-trimethyl-8-[3(R)- or 3(S)-allyloxycarbonylamino-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 64 mg of (4O,5N-isopropylidene)-5(S)-tert-butoxycarbonylamino-4(S)-hydroxy-2(R),7,7-trimethyl-8-[3(R,S)-allyloxycarbonylamino-1,2,3,4-tetrahydroquinolin-1-ylcarbonyl]-octanoic acid (N-butyl)amide (diastereomer I) via 5(S)-tert-butoxycarbonylamino-4(S)-hydroxy-2(R),7,7-trimethyl-8-[3(R)- or 3(S)-allyloxycarbonylamino-1,2,3,4-tetrahydroquinolin-1-ylcarbonyl]octanoic acid (N-butyl) amide ($R_f(P)$=0.50) as the pure stereoisomer: $R_f(S)$=0.25; $R_f(IV)$=39.9 min; FAB-MS: $(M+H)^+$=531.

The starting materials are prepared, for example, as follows:

a) (4O,5N-Isopropylidene)-5(S)-tert-butoxycarbonylamino-4(S)-hydroxy-2(R),7,7-trimethyl-8-[3(R)- or 3(S)-allyloxycarbonylamino-1,2,3,4-tetrahydroquinolin-1-ylcarbonyl]-octanoic acid (N-butyl)amide The title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 127 mg of 3(R,S)-allyloxycarbonylamino-1,2,3,4-tetrahydroquinoline with FC over 25 g of silica gel (mobile phase C), the 3(R) and 3(S) stereoisomers being separated. This gives the title compound (diastereomer I): $R_f(A)$=0.46; and diastereomer II: $R_f(A)$=0.34.

b) 3(R,S)-Allyloxycarbonylamino-1,2,3,4-tetrahydroquinoline

In a manner analogous to that described in Example 109b) from 1.0 g of 1.0 g of 3(R,S)-amino-1,2,3,4- tetrahydroquinoline and 0.75 ml of allylchloroformate: $R_f(P)$ =0.81; MS: $M^+$=232.

EXAMPLE 129

5(S)-Amino-4(S)-hydroxy-2(R),7,7-trimethyl-8-[3(R)- or 3(S)-allyloxycarbonylamino-1,2,3,4-tetrahydroquinolin-1-ylcarbonyl]-octanoic acid (N-butyl)amide In an analogous manner to that described in Examples 92, 52a and 52b) for the corresponding reaction stages, the title compound is obtained starting from 45 mg of (4O,5N-isopropylidene)-5(S)-tert-butoxycarbonylamino-4(S)-hydroxy-2(R),7,7-trimethyl-8-[3(R)- or 3(S)-allyloxycarbonylamino-1,2,3,4-tetrahydroquinolin-1-ylcarbonyl]-octanoic acid (N-butyl)amide (diastereomer II; Example 128a)) via 5(S)-tert-butoxycarbonylamino-4(S)-hydroxy-2(R),7,7-trimethyl-8-[3(R)- or 3(S)-allyloxycarbonylamino-1,2,3,4-tetrahydroquinolin-1-ylcarbonyl]-octanoic acid (N-butyl)amide ($R_f(P)$=0.53) as the pure stereoisomer: $R_f(S)$=0.22; $R_f(IV)$=39.7 min; FAB-MS: $(M+H)^+$=531.

EXAMPLE 130

4(S)-Amino-3(S)-hydroxy-1(R),6,6-trimethyl-heptanedicarboxylic acid 1-(N-butyl)amide-7-(N-phenyl,-N-phenethyl)amide In an analogous manner to that described in Examples 92, 52a and 52b) for the corresponding reaction stages, the title compound is obtained starting from 100 mg of 3-[N-tert-butoxycarbonyl-4(S)-(3-carboxy-2,2-dimethylpropyloxy-2,2-dimethyl-1,3-oxazolidin-5(S)-yl]-2(R)-methyl-propionic acid (N-butyl)amide and 130 mg of N-phenethylaniline via (3O,4N-isopropylidene)-4(S)-tert-butoxycarbonylamino-3(S)-hydroxy-1(R),6,6-trimethyl-heptanedicarboxylic acid 7-(N-butyl)amide 7-(N-phenyl,-N-phenethyl)amide ($R_f(K)$= 0.40) and 4(S)-tert-butoxycarbonylamino-3(S)-hydroxy-1(R),6,6-trimethyl-heptanedicarboxylic acid 7-(N-butyl)amide 7-(N-phenyl,-N-phenethyl)amide ($R_f(L)$=0.43): $R_f(S)$ =0.20; $R_f(V)$=29.3 min; FAB-MS: $(M+H)^+$=496.

EXAMPLE 131

5(S)-Amino-4(S)-hydroxy-2(R),7,7-trimethyl-8-[3(R,S)-methylaminocarbonyloxy-1,2,3,4-tetrahydroquinolin-1-ylcarbonyl]octanoic acid (N-butyl)amide In an analogous manner to that described in Examples 92, 52a and 52b) for the corresponding reaction stages, the title compound is obtained starting from 100 mg of 3-[N-tert-butoxycarbonyl- 4(S)-(3-carboxy-2,2-dimethylpropyl)-2,2-dimethyl-1,3-oxazolidin-5(S)-yl]-2(R)-methyl-propionic acid (N-butyl)amide and 136 mg of 3(R,S)-methylaminocarbonyloxy-1,2,3,4-tetrahydroquinoline via (4O,5N-isopropylidene)-5(S)-tert-butoxycarbonylamino-4 (S)-hydroxy-2(R),7,7-trimethyl-8-[3(R,S)-methylaminocarbonyloxy-1,2,3,4-tetrahydroquinolin-1-ylcarbonyl]-octanoic acid (N-butyl)amide ($R_f(K)$=0.23) and 5(S)-tert-butoxycarbonylamino-4(S)-hydroxy-2(R),7,7-trimethyl-8-[3(R,S)-methylaminocarbonyloxy-1,2,3,4-tetrahydroquinolin-1-ylcarbonyl]-octanoic acid (N-butyl) amide ($R_f(L)$=0.26) as a diastereomer mixture: $R_f(S)$=0.27; $R_f(V)$=13.0/13.4 min; FAB-MS: $(M+H)^+$=505.

The amine component employed is obtained, for example, as follows:

0.98 ml of methyl isocyanate is added to a suspension of 1.0 g of 3-hydroxyquinoline in 8 ml of methylene chloride and the reaction mixture is heated under reflux for 5 h. Purification by chromatography over 50 g silica gel (mobile phase J) gives 3-(methylaminocarbonyloxy)quinoline as a solid: $R_f(L)$=0.26.

1.17 g of the carbamate mentioned, dissolved in 30 ml of ethanol, are hydrogenated in the presence of 0.24 g of palladium-on-charcoal (10% of Pd) at 40° C. for 17 h. Purification by chromatography over silica gel (mobile phase C and I) gives 3(R,S)-methylaminocarbonyloxy-1,2,3,4-tetrahydroquinoline as a solid: $R_f(P)$=0.72; MS: $M^+$=206.

EXAMPLE 132

5(S)-Amino-4(S)-hydroxy-2(R),7,7-trimethyl-8-[2(R)- or -2(S)-methoxymethyloxymethyl-3,4-dihydro-2H-1,4-benzoxazin-4-ylcarbonyl]-octanoic acid (N-butyl)amide Starting from 500 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl) amide and 314 mg of 2(R)- or 2(S)-methoxymethoxymethyl-3,4-dihydro-2H-1,4-benzoxazine via (4O,5N-isopropylidene)-5(S)-tert-butoxycarbonylamino-4(S)-hydroxy-2(R),7,7-trimethyl-8-[2(R)- or 2(S)-methoxymethoxymethyl-3,4-dihydro-2H-1,4-benzoxazin-4-ylcarbonyl]-octanoic acid (N-butyl)amide (analogously to Example 1a); $R_f(A)$=0.25; $R_f(VI)$=34.4 min) and 5(S)-tert- butoxycarbonylamino-4(S)-hydroxy-2(R),7,7-trimethyl-8-[2(R,S)-methoxymethoxymethyl-3,4-dihydro-2H-1,4-benzoxazin-4-ylcarbonyl]-octanoic acid (N-butyl)amide ($R_f(X)$=0.38; FAB-MS: $(M+H)^+$=608) in a manner analogous to that described in Example 1), as the pure diastereomer: $R_f(V)$=0.38; $R_f(VI)$=22.5 min; FAB-MS: $(M+H)^+$=508.

The amine component employed as the starting material is prepared, for example, as follows: 4.4 ml of diisopropylethylamine and then 1.8 ml of chloromethyl methyl ether are added dropwise to a solution of 2.5 g of enantiomerically pure N-benzyloxycarbonyl-[2(R)- or 2(S)-hydroxymethyl]-3,4-dihydro-2H-1,4-benzoxazine ($[\alpha]_D$=+28.8 (c=1.0 in $CHCl_3$)), obtained by separation of the racemate (Example 87c) by column chromatography over Chiracel OD (hexane/ isopropanol 80:20), in 10 ml of methylene chloride under argon. The reaction mixture is stirred at room temperature for 4 h and then concentrated. The crude product is purified by means of FC over 100 g of silica gel (mobile phase D) to give N-benzyloxycarbonyl-[2(R)- or 2(S)-methoxymethoxymethyl]-3,4-dihydro-2H-1,4-benzoxazine: $R_f(A)$=0.56. Further reaction analogously to Example 1r) gives 2(R)- or 2(S)-methoxymethoxymethyl-3,4-dihydro-2H-1,4-benzoxazine: $R_f(A)$=0.35; $R_f(I)$=13.8 min; $[\alpha]_D$=+31.7 (c=1.0 in $CHCl_3$).

EXAMPLE 133

5(S)-Amino-4(S)-hydroxy-2(R),7,7-trimethyl-8-[2(R)- or 2(S)-methoxymethyloxymethyl-3,4-dihydro-2H-1,4-benzoxazin-4-ylcarbonyl]-octanoic acid (N-butyl)amide:

Starting from 500 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl) amide and 314 mg of 2(R)- or 2(S)-methoxymethoxymethyl-3,4-dihydro-2H-1,4-benzoxazine via (4O,5N-isopropylidene)-5(S)-tert-butoxycarbonylamino-4(S)-hydroxy-2(R),7,7-trimethyl-8-[2(R)- or 2(S)-methoxymethoxymethyl-3,4-dihydro-2H-1,4-benzoxazin-4-ylcarbonyl]-octanoic acid (N-butyl)amide (analogously to Example 1a); $R_f(A)$=0.25; $R_f(VI)$=35.3 min) and 5(S)-tert-butoxycarbonylamino-4(S)-hydroxy-2(R),7,7-trimethyl-8-[2(R,S)-methoxymethoxymethyl-3,4-dihydro- 2H-1,4-benzoxazin-4-ylcarbonyl]-octanoic acid (N-butyl) amide (R$_f$(X)=0.38; FAB-MS: (M+H)$^+$=608) in a manner analogous to that described in Example 1) as the pure diastereomer: R$_f$(V)=0.39; R$_f$(VI)=23.2 min; FAB-MS: (M+H)$^+$=508.

The amine component employed as the starting material is prepared, for example, as follows:

4.4 ml of diisopropylethylamine and then 1.8 ml of chloromethyl methyl ether are added dropwise to a solution of 2.5 g of N-benzyloxycarbonyl-[2(R)- or 2(S)-hydroxymethyl]-3,4-dihydro-2H-1,4-benzoxazine (Example 87c), ([α]$_D$=−28.8 (c=1.0 in CHCl$_3$)) in 10 ml of methylene chloride under argon. The reaction mixture is stirred at room temperature for 4 h and then concentrated. The crude product is purified by means of FC over 100 g of silica gel (mobile phase D) to give N-benzyloxycarbonyl-[2(R)- or 2(S)-methoxymethoxymethyl]-3,4-dihydro-2H-1,4-benzoxazine (2.5 g): R$_f$(A)=0.56. Further reaction analogously to Example 1r) gives 2(R)- or 2(S)-methoxymethoxymethyl-3,4-dihydro-2H-1,4-benzoxazine: R$_f$(A)=0.35; R$_f$(I)=13.8 min; [α]$_D$=−32.8 (c=1.0 in CHCl$_3$).

EXAMPLE 134

5(S)-Amino-4(S)-hydroxy-2(R),7,7-trimethyl-8-[3(R,S) (methylaminocarbonyl)indolin-1-ylcarbonyl]-octanoic acid (N-butyl)amide Analogously to the processes described in Examples 92, 20a and 20b) for the corresponding reaction stages, the title compound is obtained starting from 150 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 87 mg of indoline-3(R,S) carboxylic acid (N-methyl)amide via (4O,5N-isopropylidene)-5(S)-tert-butoxycarbonylamino-4(S)-hydroxy-2(R),7,7-trimethyl-8-[3(R,S) (methylaminocarbonyl)indolin-1-ylcarbonyl]-octanoic acid (N-butyl)amide (R$_f$(P)=0.58) and 5(S)-tert-butoxycarbonylamino-4(S)-hydroxy-2(R),7,7-trimethyl-8-[3(R,S)-(methylaminocarbonyl)indolin-1-ylcarbonyl]-octanoic acid (N-butyl)amide (R$_f$(P)=0.44) R$_f$(S)=0.07; R$_f$(VI)=31.4/31.8 min; FAB-MS: (M+H)$^+$=475.

The amine component employed as the starting material is prepared, for example, as follows:

a) Indoline-3(R,S)-carboxylic acid (N-methyl)amide 3 ml of a 25% solution of trifluoroacetic acid in methylene chloride are added to a solution of 216 mg of 1-(tert-butoxycarbonyl)indoline-3(R,S)-carboxylic acid (N-methyl) amide in 1 ml of methylene chloride at 0° C., while stirring. After 90 min, the mixture is allowed to warm to room temperature and stirring is continued for 2 h. Concentration of the mixture and purification of the crude product over 50 g of silica gel (mobile phase K) gives the title compound: R$_f$(P)=0.52.

b) 1-(Tert-butoxycarbonyl)indolin-3(R,S)-carboxylic acid (N-methyl)amide 0.35 ml of 1-chloro-N,N,2-trimethylpropenylamine is added to a solution of 0.59 g of 1-(tert-butoxycarbonyl) indoline-3(R,S)carboxylic acid in methylene chloride at 0° C. After 30 min, 0.93 ml of triethylamine, 0.23 g of methylamine hydrochloride and 4-DMAP, as a catalyst, are added and the mixture is stirred at room temperature for 3 h. The reaction mixture is then chromatographed directly over 80 g of silica gel (mobile phase J). This gives the title compound: R$_f$(P)=0.65.

c) 1-(Tert-butoxycarbonyl)indoline-3(R,S)-carboxylic acid

A mixture of 0.7 g of ethyl 1-(tert-butoxycarbonyl) indoline-3(R,S)-carboxylate (Example 97d) in 18 ml of methanol/water (1:1) and 2.9 ml of a 1N sodium hydroxide solution is stirred at 50° C. for 3 h. After the methanol has been removed in vacuo, the aqueous phase is brought to pH 2 and extracted with ethyl acetate. Customary further working up gives the title compound as a white solid: R$_f$(hexane/ethyl acetate/glacial acetic acid (75:25:1))=0.23.

EXAMPLE 135

5(S)-Amino-4(S)-hydroxy-2(R),7,7-trimethyl-8-[3(R,S)-formylamino-1,2,3,4-tetrahydroquinolin-1-ylcarbonyl]-octanoic acid (N-butyl)amide Analogously to the processes described in Examples 92, 20a and 20b) for the corresponding reaction condition stages, the title compound is obtained starting from 100 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 115 mg of 3(R,S)-formylamino-1,2,3,4-tetrahydroquinoline via (4O,5N-isopropylidene)-5(S)-tert-butoxycarbonylamino-4(S)-hydroxy-2(R),7,7-trimethyl-8-[3(R,S)-formylamino-1,2,3,4-tetrahydroquinolin-1-ylcarbonyl]-octanoic acid (N-butyl) amide (R$_f$(K)=0.07) and 5(S)-tert-butoxycarbonylamino-4 (S)-hydroxy-2(R),7,7-trimethyl-8-[3(R,S)-formylamino-1, 2,3,4-tetrahydroquinolin-1-ylcarbonyl]-octanoic acid (N-butyl)amide (R$_f$(N)=0.23): R$_f$(S)=0.05; R$_f$(V)=10.9 min; FAB-MS: (M+H)$^+$=475.

The amine component employed as the starting material is prepared, for example, as follows:

A solution of 0.50 g of 3(R,S)-amino-1,2,3,4-tetrahydroquinoline and 0.62 g of 4-nitrophenyl formate in 10 ml of methylene chloride is stirred at room temperature for 1 h and then concentrated. Chromatography over 65 g of silica gel (mobile phase J) gives a white solid: R$_f$(P)=0.57.

EXAMPLE 136

5(S)-Amino-4(S)-hydroxy-2(R),7,7-trimethyl-8-[3(R,S)-ethylcarbonylamino-1,2,3,4-tetrahydroquinolin-1-ylcarbonyl]-octanoic acid (N-butyl)amide Analogously to the processes described in Examples 92, 20a and 20b) for the corresponding reaction stages, the title compound is obtained starting from 100 mg of 3-[N-tert-butoxycarbonyl- 4(S)-(3-carboxy-2,2-dimethylpropyl)-2,2-dimethyl-1,3-oxazolidin-5(S)-yl]-2(R)-methyl-propionic acid (N-butyl)amide and 134 mg of 3(R,S)-ethylcarbonylamino-1,2,3,4-tetrahydroquinoline via (4O, 5N-isopropylidene)-5(S)-tert-butoxycarbonylamino-4(S)-hydroxy-2(R),7,7-trimethyl-8-[3(R,S)-ethylcarbonylamino-1,2,3,4-tetrahydroquinolin-1-ylcarbonyl]-octanoic acid (N-butyl)amide (R$_f$(K)=0.23) and 5(S)-tert-butoxycarbonylamino-4(S)-hydroxy-2(R),7,7-trimethyl-8-[3(R,S)-ethylcarbonylamino-1,2,3,4-tetrahydroquinolin-1-ylcarbonyl]-octanoic acid (N-butyl)amide (R$_f$(N)=0.22); R$_f$(S)=0.17; R$_f$(V)=14.1/14.4 min; FAB-MS: (M+H)$^+$=503.

EXAMPLE 137

5(S)-Amino-4(S)-hydroxy-2(R),7,7-trimethyl-8-[3(R,S)-pentyl-1,2,3,4-tetrahydroquinolin-1-ylcarbonyl]-octanoic acid (N-butyl)amide Starting from 230 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl) amide and 284 mg 3(R,S)-pentyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)-pentyl-1,2,3,4-tetrahydroquinolin-1-ylcarbonyl]- octanoic acid (N-butyl)amide (analogously to Example 1a); $R_f(A)$=0.44) and 5(S)-tert-butoxycarbonylamino-4(S)-hydroxy-2(R),7,7-trimethyl-8-[3(R,S)-pentyl-1,2,3,4-tetrahydroquinolin-1-ylcarbonyl]-octanoic acid (N-butyl) amide ($R_f(X)$=0.47; FAB-MS: $(M+H)^+$=602) in a manner analogous to that described in Example 1), as a diastereomer mixture: $R_f(V)$=0.33; $R_f(VI)$=30.1 min; FAB-MS: $(M+H)^+$=502.

The amine component is prepared, for example, as follows:

a) 3(R,S)-Pentyl-1,2,3,4-tetrahydroquinoline

The title compound is prepared in a manner analogous to that described in Example 1r) starting from 1.33 g of N-benzyloxycarbonyl-[3(R,S)-penten-1-yl]-1,2,3,4-tetrahydroquinoline: $R_f(A)$=0.68.

b) N-Benzyloxycarbonyl-[3(R,S)-penten-1-yl]-1,2,3,4-tetrahydroquinoline 2.0 g of sodium bis(trimethylsilyl)amide are added to a suspension of 3.0 g of n-butyltriphenylphosphonium bromide in 40 ml of tetrahydrofuran and the mixture is stirred at 35° C. for 30 min. Thereafter, a solution of 1.48 g of N-benzyloxycarbonyl-3(R,S)-formyl-1,2,3,4-tetrahydroquinoline in 10 ml of tetrahydrofuran is added dropwise and the mixture is stirred at 25° C. for 2 h. The crude product is purified by means of FC over 100 g of silica gel (mobile phase F): $R_f(D)$=0.50; MS(EI): $M^+$=335.

c) N-Benzyloxycarbonyl-3(R,S)-formyl-1,2,3,4-tetrahydroquinoline

The title compound is obtained by means of Swern oxidation analogously to Example 1g) starting from 7.0 g of N-benzyloxycarbonyl-3(R,S)-hydroxymethyl-1,2,3,4-tetrahydroquinoline: $R_f(A)$=0.42.

d) N-Benzyloxycarbonyl-3(R,S)-hydroxymethyl-1,2,3,4-tetrahydroquinoline 14.0 g of N-benzyloxycarbonyl-3(R,S)-carboxy-1,2,3,4-tetrahydroquinoline are stirred in 400 ml of tetrahydrofuran with 9.0 ml of 10M borane-dimethylsulfide complex at 25° C. for 16 h. The reaction mixture is diluted several times with methanol and evaporated. The crude product is recrystallized from ethyl acetate/hexane: mp 62°-4° C.; $R_f(X)$=0.50; FAB-MS: $(M+H)^+$=298; anal. calc. for $C_{18}H_{19}NO_3$: C 72.71%, H 6.44%, N 4.71%; found C 72.84%, H 6.35%, N 4.75%.

EXAMPLE 138

5(S)-Amino-4(S)-hydroxy-2(R),7,7-trimethyl-8-[3(R,S)-methoxyethyl-1,2,3,4-tetrahydroquinolin-1-ylcarbonyl]-octanoic acid (N-butyl)amide Starting from 230 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 287 mg of 3(R,S)-methoxyethyl-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methoxyethyl-1,2,3,4-tetrahydroquinolin-1-ylcarbonyl]-octanoic acid (N-butyl)amide (analogously to Example 1a); $R_f(A)$=0.17; $R_f(VI)$=35.8 min) and 5(S)-tert-butoxycarbonylamino-4(S)-hydroxy-2(R),7,7-trimethyl-8-[3(R,S)-methoxyethyl-1,2,3,4-tetrahydroquinolin-1-ylcarbonyl]-octanoic acid (N-butyl)amide ($R_f(V)$=0.81; $R_f(VI)$=31.0 min) in a manner analogous to that described in Example 1) as a diastereomer mixture: $R_f(V)$=0.44; $R_f(VI)$=23.6 min; FAB-MS: $(M+H)^+$=490.

The amine component is prepared, for example, as follows:

a) 3(R,S)-Methoxyethyl-1,2,3,4-tetrahydroquinoline

The title compound is prepared in a manner analogous to that described in Example 1r) starting from 2.3 g of N-benzyloxycarbonyl-3(R,S)-(1-methoxyethen-2-yl)-1,2,3,4-tetrahydroquinoline: $R_f(A)$=0.40; FAB-MS: $(M+H)^+$=192.

b) N-Benzyloxycarbonyl-3(R,S)-(1-methoxyethen-2-yl)-1,2,3,4-tetrahydroquinoline

The title compound is prepared in a manner analogous to that described in Example 137b) starting from 4.8 g of N-benzyloxycarbonyl-3(R,S)-formyl-1,2,3,4-tetrahydroquinoline, 7.2 g of methoxymethyl-triphenylphosphonium chloride and 5.4 g of sodium-bis(trimethylsilyl)amide: $R_f(A)$=0.67.

EXAMPLE 139

5(S)-Formylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide Starting from 80 mg of 5(S)-amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide (Example 86), the title compound is obtained by the method described in Example 47), with purification by FC over 10 g of silica gel (mobile phase gradient from J to K): $R_f(P)$=0.46; $R_f(VI)$=36.6 min; FAB-MS: $(M+H)^+$=533.

EXAMPLE 140

5(S)-Acetamido-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide A mixture of 80 mg of 5(S)-amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide (Example 86) and 13.9 µl of acetic anhydride in 2 ml of methylene chloride is stirred overnight at room temperature and then chromatographed directly over 10 g of silica gel (mobile phase gradient J to L). This gives the title compound as an amorphous solid: $R_f(P)$=0.42; $R_f(VI)$=37.5 min; FAB-MS: $(M+H)^+$=547.

EXAMPLE 141

5(S)-Amino-2(R)-ethyl-4(S)-hydroxy-7,7-dimethyl-8-[3(R)- or -3(S)-methoxycarbonylamino-1,2,3,4-tetrahydroquinolin-1-ylcarbonyl]-octanoic acid (N-butyl)amide Starting from 82 mg of 3-[N-tert-butoxycarbonyl-4(S)-(3-carboxy-2,2-dimethyl-propyl)-2,2-dimethyl-1,3-oxazolidin-5(S)-yl]-2(R)-ethyl-propionic acid (N-butyl)amide and 91 mg of 3(R)- or 3(S)-methoxycarbonylamino-1,2,3,4-tetrahydroquinoline (stereoisomer II, Example 74h) via (4O,5N-isopropylidene)-5(S)-tert-butoxycarbonylamino-2(R)-ethyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl)amide ($R_f(L)$=0.24; FAB-MS:$(M+H)^+$=659) and 5(S)-tert-butoxycarbonylamino-2(R)-ethyl-4(S)-hydroxy-7,7-dimethyl-8-[3(R)- or 3(S)-methoxy-carbonylamino-1,2,3,4-tetrahydroquinolin-1-ylcarbonyl]-octanoic acid (N-butyl)amide ($R_f(L)$=0.23; FAB-MS:$(M+H)^+$=619) analogously to Example 92) as the pure diastereomer: $R_f(P)$=0.23; $R_f(IV)$=38.8 min; FAB-MS:$(M+H)^+$=519.

The starting materials were prepared as follows:

a) 3-[N-Tert-butoxycarbonyl-4(S)-(3-carboxy-2,2-dimethylpropyl)-2,2-dimethyl-1,3-oxazolidin-5(S)-yl]-2(R)-ethyl-propionic acid (N-butyl)amide Starting from 200 mg of 3(R)-ethyl-5(S)-[5-benzyloxy-1(S)-tert-butoxy- carbonylamino-3,3-dimethyl-pentyl]-2-oxo-tetrahydrofuran via 2(R)-ethyl-9-benzyloxy-5(S)-tert-butoxycarbonylamino-4(S)-hydroxy-7,7-dimethyl-nonanoic acid (N-butyl)amide ($R_f(A)$=0.28; FAB-MS: $(M+H)^+$=507), 3-[N-tert-butoxycarbonyl-4(S)-(4-benzyloxy-2,2-dimethylbutyl)-2,2-dimethyl-1,3-oxazolidin-5(S)-yl]-2(R)-ethyl-propionic acid (N-butyl)amide ($R_f(B)$=0.46; FAB-MS: $(M+H)^+$=547) and 3-[N-tert-butoxycarbonyl-4(S)-(2,2-dimethyl-4-hydroxybutyl)-2,2-dimethyl-1,3-oxazolidin-5(S)-yl]-2(R)-ethyl-propionic acid (N-butyl)amide ($R_f(A)$=0.24; FAB-MS: MS:$(M+H)^+$=457) in a manner analogous to that described in Examples 74a,74b and 74c), as the pure diastereomer: $R_f(P)$=0.58; FAB-MS:$(M+H)^+$=471.

b) 3(R)-Ethyl-5(S)-[5-benzyloxy-1(S)-tert-butoxycarbonylamino-3,3-dimethyl-pentyl]-2-oxotetrahydrofuran A solution of 496 mg of 5(S)-[5-benzyloxy-1(S)-tert-butoxycarbonyl-amino-3,3-dimethylpentyl]-2-oxotetrahydrofuran (Example 74e)) and 0.44 ml of hexamethylphosphoric acid triamide in 15 ml of tetrahydrofuran is added to a solution of 2.48 mmol of lithium diisopropylamide in 10 ml of tetrahydrofuran at −78 C. under argon and the mixture is stirred for 30 min. 0.10 ml of ethyl iodide in 10 ml of tetrahydrofuran is then added dropwise. After the mixture has been stirred at −78 C. for 8.5 h, the reaction is quenched by addition of 0.45 ml of propionic acid and the mixture is worked up analogously to Example 74d). Purification over silica gel (mobile phase D) gives the title compound: $R_f(D)$=0.28; FAB-MS:$(M+H)^+$=434.

EXAMPLE 142

5(S)-Amino-4(S)-hydroxy-2(R)-(2-methyl)propyl-7,7-dimethyl-8-[3(R)- or 3(S)-methoxycarbonylamino-1,2,3,4-tetrahydroquinolin-1-yl-carbonyl]-octanoic acid (N-butyl)amide Starting from 80 mg of 3-[N-tert-butoxycarbonyl-4(S)-(3-carboxy-2,2-dimethylpropyl)-2,2-dimethyl-1,3-oxazolidin-5(S)-yl]-2(R)-(2-methyl)propyl-propionic acid (N-butyl)amide and 85 mg of 3(R)- or 3(S)-methoxycarbonylamino-1,2,3,4-tetrahydroquinoline (stereoisomer II, Example 74h) via (4O,5N-isopropylidene)-5(S)-tert-butoxycarbonylamino-2(R)-(2-methyl)propyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl)amide ($R_f(L)$=0.38; FAB-MS: $(M+H)^+$=687) and 5(S)-tert-butoxycarbonylamino-2(R)-(2-methyl)propyl-4(S)-hydroxy-7,7-dimethyl-8-[3(R)- or 3(S)-methoxycarbonylamino-1,2,3,4-tetrahydroquinolin-1-yl-carbonyl]-octanoic acid (N-butyl)amide ($R_f(L)$=0.21; FAB-MS:$(M+H)^+$=647) analogously to Example 92) as the pure diastereomer: $R_f(P)$=0.17; $R_f(IV)$=37.2 min; FAB-MS:$(M+H)^+$=547.

The starting materials were prepared as follows:

a) 3-[N-Tert-butoxycarbonyl-4(S)-(3-carboxy-2,2-dimethylpropyl)-2,2-dimethyl-1,3-oxazolidin-5(S)-yl]-2(R)-(2-methyl)propyl-propionic acid (N-butyl)amide starting from 207 mg of 3(R)-[(2-methyl)propen-3-yl]-5(S)-[5-benzyloxy-1(S)-tert-butoxycarbonylamino-3,3-dimethyl-pentyl]-2-oxotetrahydrofuran via 2(R)-[(2-methyl)propen-3-yl]-9-benzyloxy-5(S)-tert-butoxycarbonylamino-4(S)-hydroxy-7,7-dimethyl-nonanoic acid (N-butyl)amide ($R_f(A)$ =0.38; FAB-MS:$(M+H)^+$=533), 3-[N-tert-butoxy-carbonyl-4(S)-(4-benzyloxy-2,2-dimethylbutyl)-2,2-dimethyl-1,3-oxazolidin-5(S)-yl]-2(R)-[(2-methyl)propen-3-yl]-propionic acid (N-butyl)amide ($R_f(B)$=0.48; FAB-MS:$(M+H)^+$=573) and 3-[N-tert-butoxycarbonyl-4(S)-(2,2-dimethyl-4-hydroxybutyloxy-2,2-dimethyl-1,3-oxazolidin-5(S)-yl]-2(R)-(2-methyl)propyl-propionic acid (N-butyl) amide ($R_f(A)$=0.35; FAB-MS:$(M+H)^+$=485) in a manner analogous to that described in Examples 74a,74b and 74c), as the pure diastereomer: $R_f(P)$=0.65; FAB-MS:$(M+H)^+$=499.

b) 3(R)-[(2-Methyl)propen-3-yl]-5(S)-[5-benzyloxy-1(S)-tert-butoxy carbonylamino-3,3-dimethyl-pentyl]-2-oxo-tetrahydrofuran A solution of 480 mg of 5(S)-[5-benzyloxy-1(S)-tert-butoxycarbonyl-amino-3,3-dimethylpentyl]-2-oxotetrahydrofuran in 15 ml of tetrahydrofuran is added to a mixture of 2.4 ml of a 1M lithium bis(trimethylsilyl)amide solution and 10 ml of tetrahydrofuran at −78° C. under argon and the mixture is stirred for 30 min. 0.13 ml of 3-bromo-2-methylpropene in 10 ml of tetrahydrofuran is then added dropwise. After the mixture has been stirred at −78° C. for 6 h, the reaction is quenched by addition of 0.44 ml of propionic acid and the mixture is worked up analogously to Example 74d). Purification over silica gel (mobile phase D) gives the title compound: $R_f(D)$=0.34; FAB-MS:$(M+H)^+$=460.

EXAMPLE 143

5(S)-Amino-4(S)-hydroxy-2(R)-(2-methyl)propyl-7,7-dimethyl-8-[3(R)- or 3(S)-methoxycarbonylamino-1,2,3,4-tetrahydroquinolin-1-ylcarbonyl]-octanoic acid (N-methyl)amide Starting from 57 mg of 3-[N-tert-butoxycarbonyl-4(S)-(3-carboxy-2,2-dimethylpropyloxy-2,2-dimethyl-1,3-oxazolidin-5(S)-yl]-2(R)-(2-methyl)propyl-propionic acid (N-methyl)amide and 64 mg 3(R)- or 3(S)-methoxycarbonylamino-1,2,3,4-tetrahydroquinoline (stereoisomer II, Example 74h) via (4O,5N-isopropylidene)-5(S)-tert-butoxycarbonylamino-2(R)(2-methyl)propyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-methyl)amide ($R_f(L)$=0.25; FAB-MS:$(M+H)^+$=645) and 5(S)-tert-butoxycarbonylamino-2(R)-(2-methyl)propyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-methyl)amide ($R_f(L)$=0.12; FAB-MS:$(M+H)^+$=605) analogously to Example 92) as the pure diastereomer: $R_f(P)$=0.07; $R_f(IV)$=42.8 min; FAB-MS:$(M+H)^+$=505.

The starting materials were prepared as follows:

a) 3-[N-Tert-butoxycarbonyl-4(S)-(3-carboxy-2,2-dimethylpropyl)-2,2-dimethyl-1,3-oxazolidin-5(S)-yl]-2(R)-(2-methyl)propyl-propionic acid (N-methyl)amide starting from 156 mg of 2(R)-[(2-methyl)propen-3-yl]-9-benzyloxy-5(S)-tert-butoxycarbonylamino-4(S)-hydroxy-7,7-dimethyl-nonanoic acid (N-methyl)amide ($R_f(L)$=0.33; FAB-MS: $(M+H)^+$=491) via 3-[N-tert-butoxy-carbonyl-4(S)-(4-benzyloxy-2,2-dimethylbutyl)-2,2-dimethyl-1,3-oxazolidin-5(S)-yl]-2(R)-[(2-methyl)propen-3-yl]-propionic acid (N-methyl)amide ($R_f(L)$=0.48; FAB-MS: $(M+H)^+$=531) and 3-[N-tert-butoxycarbonyl-4(S)-(2,2-dimethyl-4-hydroxybutyloxy-2,2-dimethyl-1,3-oxazolidin-5(S)-yl]-2(R)-(2-methyl)propyl-propionic acid (N-methyl) amide ($R_f(P)$=0.48; FAB-MS:$(M+H)^+$=443) in a manner analogous to that described in Examples 74a and 74b), as the pure diastereomer: $R_f(P)$=0.59; FAB-MS: $(M+H)^+$=457.

b) 2(R)-[(2-Methyl)propen-3-yl]-9-benzyloxy-5(S)-tert-butoxycarbonyl-amino-4(S)-hydroxy-7,7-dimethyl-nonanoic acid (N-methyl)amide 10 ml of methylamine are introduced into a solution of 194 mg of 3(R)-[(2-methyl)propen-3-yl]-5(S)-[5-benzyloxy-1(S)-tert-butoxycarbonyl-amino-3,3-dimethyl-pentyl]-2-oxotetrahydrofuran (Example 142b)) in 4 ml of tetrahydrofuran at 0° C. and a condensation reaction is carried out. The solution is stirred at room temperature for 24 h and concentrated and the residue is purified by chromatography over silica gel (mobile phase L): $R_f(L)=0.33$; FAB-MS:$(M+H)^+=491$.

EXAMPLE 144

5(S)-Amino-2(R)-benzyl-4(S)-hydroxy-7,7-dimethyl-8-[3(R)- or -3(S)-methoxycarbonylamino-1,2,3,4-tetrahydroquinolin-1-ylcarbonyl]-octanoic acid (N-methyl)amide Starting from 80 mg of 3-[N-tert-butoxycarbonyl-4(S)-(3-carboxy-2,2-dimethylpropyl)-2,2-dimethyl-1,3-oxazolidin-5(S)-yl]-2(R)-benzylpropionic acid (N-methyl)amide and 84 mg of 3(R)- or 3(S)-methoxy-carbonylamino-1,2,3,4-tetrahydroquinoline (stereoisomer II, Example 74h) via (4O,5N-isopropylidene)-5(S)-tert-butoxycarbonylamino-2(R)-benzyl-4(S)-hydroxy-7,7-dimethyl-8-[3(R)- or 3(S)-methoxycarbonylamino-1,2,3,4-tetrahydroquinolin-1-yl-carbonyl]octanoic acid (N-methyl)amide ($R_f(L)=0.35$; FAB-MS:$(M+H)^+=679$) and 5(S)-tert-butoxycarbonylamino-2(R)-benzyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-methyl)amide ($R_f(L)=0.24$; FAB-MS:$(M+H)^+=639$) analogously to Example 92) as the pure diastereomer: $R_f(P)=0.15$; $R_f(IV)=37.0$ min; FAB-MS:$(M+H)^+=539$.

The starting materials were prepared as follows:

a) 3-[N-Tert-butoxycarbonyl-4(S)-(3-carboxy-2,2-dimethylpropyl)-2,2-dimethyl-1,3-oxazolidin-5(S)-yl]-2(R)-benzyl-propionic acid (N-methyl)amide starting from 505 mg of 2(R)-benzyl-9-benzyloxy-5(S)-tert-butoxycarbonyl-amino-4(S)-hydroxy-7,7-dimethyl-nonanoic acid (N-methyl)amide via 3-[N-tert-butoxycarbonyl-4(S)-(4-benzyloxy-2,2-dimethylbutyloxy-2,2-dimethyl-1,3-oxazolidin-5(S)-yl]-2(R)-benzyl-propionic acid (N-methyl)amide ($R_f(A)=0.43$; FAB-MS:$(M+H)^+=567$) and 3-[N-tert-butoxycarbonyl-4(S)-(2,2-dimethyl-4-hydroxybutyloxy-2,2-dimethyl-1,3-oxazolidin-5(S)-yl]-2(R)-benzylpropionic acid (N-methyl)amide ($R_f(B)=0.14$; FAB-MS:$(M+H)^+=477$) in a manner analogous to that described in Examples 74a,74b and 74c), as the pure diastereomer: $R_f(L)=0.17$; FAB-MS:$(M+H)^+=491$.

b) 2(R)-Benzyl-9-benzyloxy-5(S)-tert-butoxycarbonylamino-4(S)-hydroxy-7,7-dimethylnonanoic acid (N-methyl)amide 8 ml of methylamine are passed into a solution of 476 mg of 3(R)-benzyl-5(S)-[5-benzyloxy-1(S)-tert-butoxycarbonylamino-3,3-dimethyl-pentyl]-2-oxotetrahydrofuran (Example 74d)) in 4 ml of tetrahydrofuran at 0° C. and a condensation reaction is carried out. The solution is stirred at room temperature for 30 h and concentrated and the residue is further reacted without chromatography: $R_f(L)=0.48$; FAB-MS:$(M+H)^+=527$.

EXAMPLE 145

5(S)-Amino-4(S)-hydroxy-2(S)-isopropyl-7,7-dimethyl-8-[2(R)- or -2(S)-methoxymethoxymethyl-3,4-dihydro-2H-1,4-benzoxazin-4-ylcarbonyl]-octanoic acid (N-butyl)amide Analogously to the processes described in Examples 20, 20a and 20b) for the corresponding reaction stages, the title compound is obtained starting from 300 mg of 3-[N-tert-butoxycarbonyl-4(S)-(3-carboxy-2,2-dimethylpropyl)-2,2-dimethyl-1,3-oxazolidin-5(S)-yl]-2(S)isopropyl-propionic acid (N-butyl)amide and 195 mg of 2(R)- or 2(S)-methoxymethoxymethyl-3,4-dihydro-2H-1,4-benzoxazine (Example 132) via (4O,5N-isopropylidene)-5(S)-tert-butoxycarbonylamino-4(S)-hydroxy-2(S)-isopropyl-7,7-dimethyl-8-[2(R)- or 2(S)-methoxymethoxymethyl-3,4-dihydro-2H-1,4-benzoxazin-4-ylcarbonyl]-octanoic acid (N-butyl)amide ($R_f(A)=0.36$; $R_f(VI)=38.4$ min) and 5(S)-tert-butoxycarbonylamino-4(S)-hydroxy-2(S)-isopropyl-7,7-dimethyl-8-[2(R)- or 2(S)-methoxymethoxymethyl-3,4-dihydro-2H-1,4-benzoxazin-4-ylcarbonyl]-octanoic acid (N-butyl)amide ($R_f(X)=0.53$; $R_f(VI)=32.1$ min; FAB-MS: $[M+H]^+=636$) as the pure diastereomer: $R_f(V)=0.33$; $R_f(VI)=26.2$ min; FAB-MS: $[M+H]^+=536$.

EXAMPLE 146

5(S)-Amino-4(S)-hydroxy-2(R),7,7-trimethyl-8-[3(R,S)-methoxypropyl-1,2,3,4-tetrahydroquinolin-1-ylcarbonyl]-octanoic acid (N-butyl)amide Starting from 200 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 90 mg of 3(R,S)-methoxypropyl-1,2,3,4-tetrahydroquinoline via (4O,5N-isopropylidene)-5(S)-tertbutoxycarbonylamino-4(S)-hydroxy-2(R),7,7-trimethyl-8-[3(R,S)-methoxypropyl-1,2,3,4-tetrahydroquinolin-1-ylcarbonyl]-octanoic acid (N-butyl)amide (analogously to Example 1a); $R_f(X)=0.57$; $R_f(VI)=34.3$ min) and 5(S)-tert-butoxycarbonylamino-4(S)-hydroxy-2(R),7,7-trimethyl-8-[3(R,S)-methoxpropyl-1,2,3,4-tetrahydroquinolin-1-ylcarbonyl]-octanoic acid (N-butyl)amide ($R_f(X)=0.37$; $R_f(VI)=30.3$ min; FAB-MS: $(M+H)^+=604$) in a manner analogous to that described in Example 1), as the diastereomer mixture: $R_f(V)=0.42$; $R_f(VI)=23.0$ min; FAB-MS: $(M+H)^+=504$.

The amine component is prepared, for example, as follows: a) 3(R,S)-Methoxypropyl-1,2,3,4-tetrahydroquinoline The title compound is prepared in a manner analogous to that described in Example 1r) starting from 0.32 g of N-benzyloxycarbonyl-3(R,S)-(1-methoxyprop-2-en-3-yl)-1,2,3,4-tetrahydroquinoline: $R_f(A)=0.50$.

b) N-Benzyloxycarbonyl-3(R,S)-(1-methoxyprop-2-en-3-yl)-1,2,3,4-tetrahydroquinoline The title compound is prepared in a manner analogous to that described in Example 137b) starting from 1.50 g of N-benzyloxycarbonyl-3(R,S)-formyl-1,2,3,4-tetrahydroquinoline, 3.1 g of methoxyethyl-triphenylphosphonium bromide and 2.0 g of sodium bis (trimethylsilyl)amide: $R_f(A)=0.55$.

EXAMPLE 147

5(S)-Amino-4(S)-hydroxy-2(R),7,7-trimethyl-8-[3(R,S)-methoxycarbonylamino-2,3,4,5-tetrahydro-1H-benz[6,7-b]azepin-1-ylcarbonyl]-octanoic acid (N-butyl)amide Analogously to the processes described in Examples 92, 20a and 20b) for the corresponding reaction stages, the title compound is obtained starting from 100 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 120 mg of 3(R,S)-methoxycarbonylamino-2,3,4,5tetrahydro-1H-benz[6,7-b]azepine via (4O,5N-isopropylidene)-5(S)-tert-butoxycarbonylamino-4(S)-hydroxy-2(R),7,7-trimethyl-8-[3(R,S)-methoxycarbonylamino-2,3,4,5-tetrahydro-1H-benz[6,7-b]azepin-1-ylcarbonyl]-octanoic acid (N-butyl)

amide (R$_f$(P)=0.58) and 5(S)-tert-butoxycarbonylamino-4 (S)-hydroxy-2(R),7,7-trimethyl-8-[3(R,S)-methoxycarbonylamino-2,3,4,5-tetrahydro-1H-benz[6,7-b]azepin-1-ylcarbonyl]-octanoic acid (N-butyl)amide (R$_f$(P)=0.39; FAB-MS: (M+H)$^+$=619): R$_f$(S)=0.14; R$_t$(VI)=37.6 min; FAB-MS: (M+H)$^+$=519.

The amine component employed as the starting material is prepared, for example, as follows:

1.1 ml of a 10% aqueous sodium hydroxide solution are first added to a suspension of 0.40 g of 3(R,S)-amino-2,3,4,5-tetrahydro-1H-benz[6,7-b]azepine in 6 ml of toluene, and a solution of 200 μl of methyl chloroformate in 1.5 ml of toluene is then added dropwise, with vigorous stirring. After 15 min, the organic phase is separated off, dried over sodium sulfate and concentrated. Chromatography over 50 g of silica gel (mobile phase 1 gives a white solid: R$_f$(L)=0.67; R$_f$(methylene chloride)=0.19.

EXAMPLE 148

5(S)-Amino-4(S)-hydroxy-2(R),7,7-trimethyl-8-[3(R,S)-methoxycarbonyl-(N-methyl)amino-1,2,3,4-tetrahydroquinolin-1-ylcarbonyl]-octanoic acid (N-butyl)amide Analogously to the processes described in Examples 92, 20a and 20b) for the corresponding reaction stages, the title compound is obtained starting from 84 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl)amide and 95 mg of 3(R,S)-methoxycarbonyl-(N-methyl)amino-1,2,3,4-tetrahydroquinoline via (4O,5N-isopropylidene)-5(S)-tert-butoxycarbonylamino-4(S)-hydroxy-2(R),7,7-trimethyl-8-[3(R,S)-methoxycarbonyl-(N-methyl)amino-1,2,3,4-tetrahydroquinolin-1-ylcarbonyl]-octanioc acid (N-butyl)amide (R$_f$(P)=0.61) and 5(S)-tert-butoxycarbonylamino-4(S)-hydroxy-2(R),7,7-trimethyl-8-[3(R,S)-methoxycarbonyl-(N-methyl)amino-1,2,3,4-tetrahydroquinolin-1-ylcarbonyl]-octanoic acid (N-butyl)amide (R$_f$(P)=0.61) and 5(S)-tert-butoxycarbonylamino-4(S)-hydroxy-2(R),7,7-trimethyl-8-[3(R,S)-methoxycarbonyl-(N-methyl)amino-1,2,3,4-tetrahydroquinolin-1ylcarbonyl]-octanoic acid (N-butyl)amide (R$_f$(P)=0.46): R$_f$(S)=0.14; R$_t$(V)=19.9 min; FAB-MS: (M+H)$^+$=519.

The amine component employed as the starting material is prepared, for example, as follows:

a) 3(R,S)-Methoxycarbonyl-(N-methyl)amino-1,2,3,4-tetrahydroquinoline

In a manner analogous to that described in Example 134a), 110 mg of 1-(tert-butoxycarbonyl)-3(R,S)-methoxycarbonyl-(N-methyl)amino-1,2,3,4-tetrahydroquinoline are reacted and the crude product is purified over 10 g of silica gel (mobile phase J): R$_f$(L)=0.68; MS(EI): (M)$^+$=220.

b) 1-(Tert-butoxycarbonyl)-3(R,S)-methoxycarbonyl-(N-methyl)amino-1,2,3,4-tetrahydroquinoline 44 mg of sodium hydride (80% dispersion in oil) are added to 0.30 g of 1-(tert-butoxycarbonyl)-3(R,S)-(methoxycarbonyl)amino-1,2,3,4-tetrahydroquinoline, dissolved in 10 ml of tetrahydrofuran, at 0° C., while stirring. After 30 min, 120 μl of methyl iodide are added and the mixture is stirred at room temperature for 4 h. After cautious concentration, the residue is chromatographed directly over 50 g of silica gel with a (20:1) mixture of methylene chloride and diethyl ether as the eluent. This gives the title compound: R$_f$(methylene chloride/diethyl ether (10:1))=0.57.

c) 1-(Tert-butoxycarbonyl)-3(R,S)(methoxycarbonyl)amino-1,2,3,4-tetrahydroquinoline 1.38 g of di-tert-butyl carbonate are added to 1.0 g of 3(R,S)-(methoxycarbonyl)amino-1,2,3,4-tetrahydroquinoline, dissolved in 7 ml of dioxane and 3.5 ml of water, at 0° C. The mixture is stirred at room temperature for 24 h and a further 1.4 g of di-tert-butyl carbonate are then added. When the reaction has ended (48 h in total), the mixture is concentrated to remove the dioxane and the aqueous phase is extracted with methylene chloride. Purification of the crude product over 100 g of silica gel (mobile phase gradient F to A) gives, in addition to re-isolated starting material, the title compound: R$_f$(P)=0.34.

EXAMPLE 149

5(S)-Formylamino-4(S)-hydroxy-2(S)-isopropyl-7,7-dimethyl-8-[2(R)- or -2(S)-methoxymethoxymethyl-3,4-dihydro-2H-1,4-benzoxazin-4-ylcarbonyl]-octanoic acid N-butyl)amide Analogously to the process described in Example 47), the title compound is obtained starting from 50 mg of 5(S)-amino-4(S)-hydroxy-2(S)-isopropyl-7,7-dimethyl-8-[2(R)- or 2(S)-methoxymethoxymethyl-3,4-dihydro-2H-1,4-benzoxazin-4-ylcarbonyl]-octanoic acid (N-butyl)amide (Example 145), with subsequent purification by FC over 10 g of silica gel (mobile phase J): R$_f$(P)=0.45; R$_t$(VI)=27.7; FAB-MS: (M+H)$^+$=564.

EXAMPLE 150

5(S)-Amino-4(S)-hydroxy-2(S)-isopropyl-7,7-dimethyl-8-[3(R)- or -3(S)-methoxycarbonylamino-1,2,3,4-tetrahydroquinolin-1-ylcarbonyl]-octanoic acid (N-butyl)amide Starting from 80 mg of 3-[N-tert-butoxycarbonyl-4(S)-(3-carboxy-2,2-dimethylpropyl)-2,2-dimethyl-1,3-oxazolidin-5(S)-yl]-2(S)-isopropyl-propionic acid (N-butyl)amide and 85 mg of 3(R)- or 3(S)-methoxycarbonylamino-1,2,3,4-tetrahydroquinoline (stereoisomer I, Example 74h), the title compound is obtained in an analogous manner to that described in Example 125) as the pure stereoisomer: R$_f$(S)=0.18; R$_t$(IV)=38.6 min; FAB-MS: (M+H)$^+$=533.

EXAMPLE 151

5(S)-Amino-4(S)-hydroxy-2(R),7,7-trimethyl-8-[2(R,S)-methoxyethyl-3,4-dihydro-2H-1,4-benzoxazin-4-ylcarbonyl]-octanoic acid (N-butyl)amide Starting from 230 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl) amide and 193 mg of 2(R,S)-methoxyethyl-3,4-dihydro-2H-1,4-benzoxazine, the title compound is obtained via (4O,5N-isopropylidene)-5(S)-tert-butoxycarbonylamino-4(S)-hydroxy-2(R),7,7-trimethyl-8-[2(R,S)-methoxyethyl-3,4-dihydro-2H-1,4-benzoxazin-4-ylcarbonyl]-octanoic acid (N-butyl)amide (analogously to Example 1a); R$_f$(A)=0.19; R$_t$(VI)=36.6/36.9 min) and 5(S)-tert-butoxycarbonylamino-4(S)-hydroxy-2(R),7,7-trimethyl-8-[2(R,S)-methoxyethyl-3,4-dihydro-2H-1,4-benzoxazin-4-ylcarbonyl]-octanoic acid (N-butyl)amide (R$_f$(X)=0.36; R$_t$(VI)=30.6 min; FAB-MS: (M+H)$^+$=592) in a manner analogous to that described in Example 1) as a diastereomer mixture:R$_f$(V)=0.32; R$_t$(VI)=23.7/24.1 min; FAB-MS: (M+H)$^+$=492.

The amine component is prepared, for example, as follows:

a) 2(R,S)-Methoxyethyl-3,4-dihydro-2H-1,4-benzoxazine

The title compound is prepared in a manner analogous to that described in Example 1r) starting from 1.45 g of N-benzyloxycarbonyl-2(R,S)-(1-methoxyethen-2-yl)-3,4-dihydro-2H-1,4-benzoxazine and is purified by means of FC over 100 g of silica gel (mobile phase B): R$_f$(A)=0.30; FAB-MS: (M+H)$^+$=194.

b) N-Benzyloxycarbonyl-2(R,S)-(1-methoxyethen-2-yl)-3,4-dihydro-2H-1,4-benzoxazine The title compound is prepared analogously to the process described in Example 138b) starting from 1.25 g of N-benzyloxycarbonyl-2(R,S)-formyl-3,4-dihydro-2H-1,4-benzoxazine (Example 107), 7.2 g of methoxymethyl-triphenylphosphonium chloride and 1.57 g of potassium bis(trimethylsilyl)amide: R$_f$(A)=0.49 und 0.54.

EXAMPLE 152

5(S)-Amino-4(S)-hydroxy-2(S)-isopropyl-7,7-dimethyl-8-[2(R)- or -2(S)-methoxyethyl-3,4-dihydro-2H-1,4-benzoxazin-4-ylcarbonyl]-octanoic acid (N-butyl)amide Analogously to the processes described in Examples 20, 20a and 20b) for the corresponding reaction stages, the title compound is obtained starting from 300 mg of 3-[N-tert-butoxycarbonyl-4(S)-(3-carboxy-2,2-dimethylpropyl)-2,2-dimethyl-1,3-oxazolidin-5(S)-yl]-2(S)isopropyl-propionic acid (N-butyl)amide and 150 mg of 2(R)- or 2(S)-methoxyethyl-3,4-dihydro-2H-1,4-benzoxazine via (4O,5N-isopropylidene)-5(S)-tert-butoxycarbonylamino-4(S)-hydroxy-2(S)-isopropyl-7,7-dimethyl-8-[2(R)- or 2(S)-methoxyethyl-3,4-dihydro-2H-1,4-benzoxazin-4-ylcarbonyl]-octanoic acid (N-butyl)amide (R$_f$(A)=0.41); R$_f$(VI)=37.8 min) and 5(S)-tert-butoxycarbonylamino-4(S)-hydroxy-2(S)-isopropyl-7,7-dimethyl-8-[2(R)- oder 2(S)-methoxyethyl-3,4-dihydro-2H-1,4-benzoxazin-4-ylcarbonyl]-octanoic [sic] (N-butyl)amide (R$_f$(A)=0.13; R$_f$(X)=0.47; R$_f$(VI)=33.9 min; FAB-MS: [M+H]$^+$=620) as the pure diastereomer: R$_f$(V)=0.34; R$_f$(VI)=25.3 min; FAB-MS: [M+H]$^+$=520.

The amine component employed as the starting material is prepared, for example, as follows:

The racemate 2(R,S)-methoxyethyl-3,4-dihydro-2H-1,4-benzoxazine (Example 151a) is separated by means of preparative separation on a Chiracel OD column (5×50 cm, mobile phase hexane/isopropanol (975:25)) into the pure enantiomers 2(R)- and 2(S)-methoxyethyl-3,4-dihydro-2H-1,4-benzoxazine; enantiomer eluting first: [α]$_D$=+10.4 (c=1.0 in CHCl$_3$); second enantiomer: [α]$_D$=−10.5 (c=1.0 in CHCl$_3$).

EXAMPLE 153

5(S)-Amino-4(S)-hydroxy-2(R),7,7-trimethyl-8-[3butyl-2,3-dihydro-4(H)-quinazolinon-1-ylcarbony]-octanoic acid (N-butyl)amide Analogously to the processes described in Examples 92, 20a and 20b) for the corresponding reaction stages, the title compound is obtained starting from 100 mg of 3-[N-tert-butoxycarbonyl-4(S)-(3-carboxy-2,2-dimethylpropyl)-2,2-dimethyl-1,3-oxazolidin-5(S)-yl]-2(R)-methylpropionic acid (N-butyl)amide and 134 mg of 3-butyl-2,3-dihydro-4(H)-quinazolinone via (4O,5N-isopropylidene)-5(S)-tert-butoxycarbonylamino-4(S)-hydroxy-2(R),7,7-trimethyl-8-[3-butyl-2,3-dihydro-4(H)-quinazolinon-1-ylcarbonyl]-octanoic acid (N-butyl)amide and 5(S)-tert-butoxycarbonylamino-4(S)-hydroxy-2(R),7,7-trimethyl-8-[3-butyl-2,3-dihydro-4(H)-quinazolinon-1-ylcarbonyl]-octanoic acid (N-butyl)amide (R$_f$(N)=0.19; FAB-MS: (M+H)$^+$=603): R$_f$(O)=0.27; FAB-MS: (M+H)$^+$=503.

The amine component employed as the starting material is prepared by a process analogous to those described in J. Med. Chem. 11 (1968) 1136 and in Synthesis (1982) 266.

EXAMPLE 154

5(S)-Amino-4(S)-hydroxy-2(R),7,7-trimethyl-8-[3(R,S)-(2-carbamoyl)ethyl-1,2,3,4-tetrahydroquinolin-1-ylcarbonyl]-octanoic acid (N-butyl)amide Starting from 230 mg of 3-[N-tert-butoxycarbonyl-4(S)-(3-carboxy-2,2-dimethylpropyl)-2,2-dimethyl-1,3-oxazolidin-5(S)-yl]-2(R)-methyl-propionic acid (N-butyl) amide and 205 mg of 3(R,S)-(2-carbamoyl)ethyl-1,2,3,4-tetrahydroquinoline, the title compound is obtained via (4O,5N-isopropylidene)-5(S)-tert-butoxycarbonylamino-4(S)-hydroxy-2(R),7,7-trimethyl-8-[3(R,S)-(2-carbamoyl)ethyl-1,2,3,4-tetrahydroquinolin-1-ylcarbonyl]-octanoic acid (N-butyl)amide (analogously to Example 1a); R$_f$(X)= 0.08; R$_f$(V)=0.56; R$_f$(VI)=30.8 min) and 5(S)-tert-butoxycarbonylamino-4(S)-hydroxy-2(R),7,7-trimethyl-8-[3(R,S)-(2-carbamoyl)ethyl-1,2,3,4-tetrahydroquinolin-1-ylcarbonyl]-octanoic acid (N-butyl)amide (R$_f$(P)=0.32; R$_f$(VI)=26.8 min; FAB-MS: (M+H)$^+$=603) in a manner analogous to Example 1) as a diastereomer mixture: R$_f$(V) =0.21; R$_f$(VI)=20.3 min; FAB-MS: (M+H)$^+$=503.

The amine component is prepared, for example, as follows:

a) 3(R,S)-(2-Carbamoyl)ethyl-1,2,3,4-tetrahydroquinoline

The title compound is prepared in a manner analogous to that described in Example 1r) starting from 825 mg of N-benzyloxycarbonyl-3(R,S)-[(2-carbamoyl)ethen-1-yl]-1,2,3,4-tetrahydroquinoline and is purified by means of FC over 30 g of silica gel (mobile phase H): FAB-MS: (M+H)$^+$=205.

b) N-Benzyloxycarbonyl-3(R,S)-[(2-carbamoyl)ethen-1-yl]-1,2,3,4-tetrahydroquinoline The reaction of 1.48 g of N-benzyloxycarbonyl-2(R,S)-formyl-3,4-dihydro-2H-1,4-benzoxazine (Example 107) with 2.15 ml of trimethylsilyl-diethylphosphonoacetate and 0.3 g of sodium hydride (80% dispersion in oil) gives, after customary working up, 1.7 g of N-benzyloxycarbonyl-3(R,S)-[(2-carboxy)ethen-1-yl]-1,2,3,4-tetrahydroquinoline. The title compound is obtained therefrom in a manner analogous to that described in Example 1a): R$_f$(X)=0.47.

EXAMPLE 155

5(S)-Formylamino-4(S)-hydroxy-2(S)-isopropyl-7,7-dimethyl-8-[3(R)- or 3(S)-methoxycarbonylamino-1,2,3,4-tetrahydroquinolin-1-ylcarbonyl]-octanoic acid (N-butyl)amide Starting from 35 mg of 5(S)-amino-4(S)-hydroxy-2(S)-isopropyl-7,7-dimethyl-8-[3(R)- or 3(S)-methoxycarbonylamino-1,2,3,4-tetrahydroquinolin-1-ylcarbonyl]-octanoic acid (N-butyl)amide (Example 125), the title compound is obtained by the method described in Example 47), with purification by FC over 10 g of silica gel (mobile phase K): R$_f$(O)=0.52; R$_f$(IV)=40.9 min; FAB-MS: (M+H)$^+$=561.

EXAMPLE 156

5(S)-Amino-2(R)-but-2-enyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl)amide 54 mg of 5(S)-tert-butoxycarbonylamino-2(R)-but-2-enyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl)amide are dissolved in 1 ml of methylene chloride, and 0.16 ml of trifluoroacetic acid is added at 0° C. under argon. After 2.5 h at 0° C. and 2 h at room temperature, the reaction mixture is worked up and purified in a manner analogous to that in Example 45) (mobile phase P): $R_f(P)=0.29$; $R_f(IV)=39.0$ min; FAB-MS: $(M+H)^+=545$.

The starting materials are prepared, for example, as follows:

a)-5(S)-Tert-butoxycarbonylamino-2(R)-but-2-enyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl)amide Starting from 87 mg of 3-[N-tert-butoxycarbonyl-4(S)-(3-carboxy-2,2-dimethylpropyl)-2,2-dimethyl-1,3-oxazolidin-5(S)-yl]-2(R)-but-2-enyl-propionic acid (N-butyl)amide and 91 mg of 3(R)- or 3(S)-methoxycarbonylamino-1,2,3,4-tetrahydroquinoline (stereoisomer II, Example 74h) via (4O,5N-isopropylidene)-5(S)-tert-butoxycarbonylamino-2(R)-but-2-enyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl)amide $(R_f(L)=0.20$; FAB-MS: $(M+H)^+=685)$ analogously to Example 92): $(R_f(P)=0.42$; FAB-MS: $(M+H)^+=645)$.

b)3-[N-Tert-butoxycarbonyl-4(S)-(3-carboxy-2,2-dimethylpropyl)-2,2-dimethyl-1,3-oxazolidin-5(S)-yl]-2(R)-but-2-enyl-propionic acid (N-butyl)amide A solution of 809 mg of pyridinium dichromate in 2 ml of N,N-dimethylformamide is added dropwise via a cannula to a solution of 290 mg of 3-[N-tert-butoxycarbonyl-4(S)-(4-hydroxy-2,2-dimethylbutyl)-2,2-dimethyl-1,3-oxazolidin-5(S)-yl]-2(R)-but-2-enyl-propionic acid (N-butyl)amide in 2 ml of N,N-dimethylformamide at room temperature under argon. After 23 h, a further 238 mg of pyridinium dichromate are added. After a total of 29 h, the reaction mixture is poured into water, extracted with diethyl ether (3 times), dried ($Na_2SO_4$) and concentrated. Purification over silica gel (mobile phase P) gives the title compound: $R_f(P)=0.48$; FAB-MS: $(M+H)^+=497$.

c) 3-[N-Tert-butoxycarbonyl-4(S)-(4-hydroxy-2,2-dimethylbutyl)-2,2-dimethyl-1,3-oxazolidin-5(S)-yl]-2(R)-but-2-enyl-propionic acid (N-butyl)amide 474 mg of 3-[N-tert-butoxycarbonyl-4(S)-(4-tert-butyl-diphenylsilyloxy-2,2-dimethylbutyl)-2,2-dimethyl-1,3-oxazolidin-5(S)-yl]-2(R)-but-2-enyl-propionic acid (N-butyl)amide are dissolved in 5 ml of tetrahydrofuran, and 1.2 ml of a 1M tetrabutylammonium fluoride solution in tetrahydrofuran are added at room temperature under argon. After 4 h, the reaction mixture is diluted with diethyl ether, washed with water and brine, dried ($Na_2SO_4$) and concentrated. Purification over silica gel (mobile phase A) gives the title compound: $R_f(A)=0.40$; FAB-MS: $(M+H)^+=483$.

d) 3-[N-Tert-butoxycarbonyl-4(S)-(4-Tert-butyl-diphenylsilyloxy-2,2-dimethylbutyl)-2,2-dimethyl-1,3-oxazolidin-5(S)-yl]-2(R)-but-2-enyl-propionic acid (N-butyl)amide Starting from 472 mg of 3(R)-but-2-enyl-5(S)-[5-tert-butyl-diphenylsilyloxy-1(S)-tert-butoxycarbonylamino-3,3-dimethyl-pentyl]-2-oxo-tetrahydrofuran via 2(R)-but-2-enyl-9-tert-butyldiphenylsilyloxy-5(S)-tert-butoxycarbonylamino-4(S)-hydroxy-7,7-dimethyl-nonanoic acid (N-butyl)amide $(R_f(A)=0.64$; FAB-MS: $(M+H)^+=681)$ analogously to Examples 74b and 74c): $R_f(B)=0.71$; FAB-MS: $(M+H)^+=721$.

e) 3(R)-But-2-enyl-5(S)-[5-tert-butyl-diphenylsilyloxy-1(S)-tert-butoxycarbonylamino-3,3-dimethyl-pentyl]-2-oxo-tetrahydrofuran 4.6 ml of a 1M lithium bis-(trimethylsilyl)amide solution in tetrahydrofuran and 0.26 ml of crotyl bromide (89%, 5.7:1 E:Z) are added to 1.22 g of 5(S)-[5-tert-butyl-diphenylsilyloxy-1(S)-tert-butoxycarbonylamino-3,3-dimethyl-pentyl]-2-oxo-tetrahydrofuran analogously to Example 74d). Working up after 5 h and subsequent purification by means of FC over silica gel (mobile phase C) gives the title compound, of uniform (R) configuration on C-3, as a 2E/2Z isomer mixture which cannot be separated: $(R_f(C)=0.62$; FAB-MS: $(M+H)^+=608)$.

f)-5(S)-[5-Tert-butyl-diphenylsilyloxy-1(S)-tert-butoxycarbonylamino-3,3-dimethyl-pentyl]-2-oxo-tetrahydrofuran 1.37 g of 5(S)-[benzyloxy-1(S)-tert-butoxycarbonylamino-3,3-dimethyl-pentyl]-2-oxotetrahydrofuran are hydrogenated analogously to Example 74a) and the product is purified by means of FC over silica gel (mobile phase B): $R_f(B)=0.14$; FAB-MS: $(M+H)^+=316$. 825 mg of 5(S)-[hydroxy-1(S)-tert-butoxycarbonylamino-3,3-dimethyl-pentyl]-2-oxotetrahydrofuran are dissolved in 10 ml of N,N-dimethylformamide, and 0.75 ml of tert-butyl-diphenylsilylchloride and 392 mg of imidazole are added at room temperature under argon. After 3 h, the reaction mixture is diluted with water, extracted with pentane (2 times), dried ($Na_2SO_4$) and concentrated. Purification over silica gel (mobile phase D) gives the title compound: $R_f(D)=0.27$; FAB-MS: $(M+H)^+=554$.

EXAMPLE 157

5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-(2-morpholin-4-yl-ethyl)amide dihydrochloride 58 mg of 5(S)-tert-butoxycarbonylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-(2-morpholin-4-yl-ethyl)amide are stirred in 3 ml of 4N hydrochloric acid in dioxane at 0° C. for 3 h. The reaction mixture is concentrated, 2 ml of 4N hydrochloric acid in dioxane are added again and the mixture is subsequently stirred at 0° C. for 3 h. Lyophilization and drying under a high vacuum gives the title compound: $R_f(S)=0.15$; $R_t(VI)=8.8$ min; FAB-MS: $(M+H)^+=562$.

The starting material is prepared, for example, as follows:
a) 5(S)-Tert-butoxycarbonylamino-4(S)-hydroxy-2(R),7,7-dimethyl-8-[3(R)- or 3(S)-methoxycarbonylamino-1,2,3,4-tetrahydroquinolin-1-ylcarbonyl]-octanoic acid N-(2-morpholin-4-yl-ethyl) amide 50 mg of methyl {1-[5(S)-tert-butoxycarbonylamino-3,3-dimethyl-5(S)-(4R)-methyl-5-oxotetrahydrofuran-2(S)-yl)-pentanoyl]-1,2,3,4-tetrahydroquinolin-3(R or S)-yl}-carbamate are stirred in N-(2-aminoethyl)-morpholine (1 ml) at 80° C. overnight. The reaction mixture is concentrated and the residue is purified by means of FC over silica gel (methylene chloride/methanol 92.5:7.5). The title compound is obtained as a yellowish oil: $R_f(P)=0.30$; $R_t(VI)=12.6$ min; FAB-MS: $(M+H)^+=662$.

b) Methyl {1-[5(S)-tert-butoxycarbonylamino-3,3-dimethyl-5(S)-(4R)-methyl-5-oxotetrahydrofuran-2(S)-yl)-pentanoyl]-1,2,3,4-tetrahydroquinolin-3(R or S)-yl}-carbamate A total of 142 mg of para-toluenesulfonic acid hydrate are added in portions to a solution of 5(S)-tert-butoxycarbonylamino-4(S)-hydroxy-2(R),7,7-trimethyl-8-[3(R) or 3(S)-methoxycarbonylamino-1,2,3,4-tetrahydroquinolin-1-ylcarbonyl]-octanoic acid (N-butyl) amide (300 mg) in 6 ml of toluene/methylene chloride (1:2) at room temperature in the course of 72 h while stirring. The white suspension is subsequently stirred for a further 24 h, pyridine (20 μl) is added and the mixture is chromatographed directly over silica gel (30 g, mobile phase J). The title compound is obtained as a white solid substance: $R_f(P)=0.68$; FAB-MS: $(M+H)^+=532$.

EXAMPLE 158

5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-[2-(1-acetyl)piperidin-4-yl)-ethyl]amide hydrochloride acetyl-piperidine 55 mg of 5(S)-tert-butoxycarbonylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-[2-(1-acetylpiperidin-4-yl)-ethyl]amide are reacted in 2 ml of 4N hydrochloric acid in dioxane at 0° C. in a manner analogous to that described in Example 159). After lyophilization, the residue is treated with 2 ml of anhydrous diethyl ether, the solvent is removed and the product is dried under a high vacuum. The title compound is obtained as a solid: $R_f(S)=0.25$; $R_t(VI)=10.5$ min; FAB-MS: $(M+H)^+=602$.

The starting material is prepared, for example, as follows:
a) 5(S)-Tert-butoxycarbonylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-[2-(1-acetylpiperidin-4-yl)-ethyl]amide A mixture of 50 mg of methyl {1-[5(S)-tert-butoxycarbonylamino-3,3-dimethyl-5(S)-(4(R)-methyl-5-oxo-tetrahydrofuran-2(S)-yl)-pentanoyl]-1,2,3,4-tetrahydroquinoline-3(R or S)-yl}carbamate, 1-acetyl-4-(2-aminoethyl)-piperidine (48 mg) and 2-hydroxy-pyridine (9 mg) in 2 ml of triethylamine is stirred in an inert atmosphere at 80° C. for 20 h. After cooling, 20 ml of a sodium hydrogensulfate solution is added to the reaction mixture and the mixture is extracted with methylene chloride (3×20 ml). The combined organic phases are dried over magnesium sulfate and concentrated. Purification of the crude product by means of FC (30 g of silica gel, methylene chloride/methanol 92.5:7.5) gives the title compound as a yellowish oil: $R_f(P)=0.50$; $R_t(VI)=14.9$ min; FAB-MS: $(M+H)^+=702$.

EXAMPLE 159

5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-(2-morpholin-4-yl-2-oxoethyl) amide hydrochloride 51 mg of 5(S)-tert-butoxycarbonylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-(2-morpholin-4-yl-2-oxo-ethyl)amide are stirred in 2 ml of 4N hydrochloric acid in dioxane at 0° C. for 3 h. The reaction mixture is lyophilized under a high vacuum and dried to constant weight at room temperature. The residue is treated with 2 ml of anhydrous diethyl ether, the solvent is removed and the product is dried under a high vacuum. The title compound is obtained as a white solid: $R_f(S)=0.44$; $R_f(P)=0.56$; $R_t(VI)=11.3$ min; FAB-MS: $(M+H)^+=576$.

The starting material is prepared, for example, as follows:
a) 5(S)-Tert-butoxycarbonylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-(2-morpholin-4-yl-2-oxoethyl)amide By reaction of 50 mg of methyl {1-[5(S)-tert-butoxycarbonylamino-3,3-dimethyl-5(S)-(4(R)-methyl-5-oxo-tetrahydrofuran-2(S)-yl)-pentanoyl]-1,2,3,4-tetrahydroquinoline-3(R or S)-yl}-carbamate and 41 mg of 2-amino-1-morpholin-4-yl-ethanone in the presence of 2-hydroxypyridine (9 mg), in a manner analogous to that described in Example 158a), and subsequent FC purification (30 g of silica gel, methylene chloride/methanol 92.5:7.5), the title compound is obtained as a yellow oil: $R_f(P)=0.39$; $R_t(VI)=14.0$ min; FAB-MS: $(M+H)^+=676$.

EXAMPLE 160

5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-(2-carbamoyl-2-methylpropyl) amide hydrochloride 65 mg of 5(S)-tert-butoxycarbonylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-(2-carbamoyl-2-methyl-propyl)amide are reacted in 2 ml of 4N hydrochloric acid in dioxane at 0° C. in a manner analogous to that described in Example 159). Lyophilization and drying under a high vacuum gives the title compound as a white solid: $R_f(S)=0.09$; $R_t(VI)=9.87$ min; FAB-MS: $(M+H)^+=548$.

The 5(S)-tert-butoxycarbonylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid N-(2-carbamoyl-2-methyl-propyl)amide employed as the starting material is obtained in a manner analogous to that described in Example 158a) from 50 mg of methyl {1-[5(S)-tert-butoxycarbonylamino-3,3-dimethyl-5(S)-(4(R)-methyl-5-oxo-tetrahydrofuran-2(S)-yl)-pentanoyl]-1,2,3,4-tetrahydroquinolin-3(R or S)-yl}-carbamate, 33 mg of 3-amino-2,2-dimethyl-propionamide and 9 mg of 2-hydroxy-pyridine in triethylamine (2 ml), with FC purification of the crude product, as a pale yellow oil: $R_f(P)=0.13$; $R_t(VI)=13.9$ min; FAB-MS: $(M+H)^+=648$.

EXAMPLE 161

Tablets each comprising 50 mg of active ingredient, for example 5(S)-amino-4(S)-hydroxy-2(R),7,7-trimethyl-8-[3(R,S)-methoxycarbonyl-1,2,3,4-tetrahydroquinolin-1-ylcarbonyl]-octanoic acid (N-butyl)amide or a salt thereof, can be produced as follows:

| Composition (10000 Tablets) | |
| --- | --- |
| Active ingredient | 500.0 g |
| Lactose | 500.0 g |
| Potato starch | 352.0 g |
| Gelatin | 8.0 g |
| Talc | 60.0 g |
| Magnesium stearate | 10.0 g |
| Silicon dioxide (highly disperse) | 20.0 g |
| Ethanol | q.s. |

The active ingredient is mixed with the lactose and 292 g of potato starch and the mixture is moistened with an ethanolic solution of the gelatin and granulated through a sieve. After drying, the remainder of the potato starch, the magnesium stearate, the talc and the silicon dioxide are admixed and the mixture is pressed into tablets each of 145.0 mg weight and 50.0 mg active ingredient content, which, if desired, can be provided with dividing grooves for finer adjustment of the dosage.

EXAMPLE 162

Gelatin solution

A sterile-filtered aqueous solution, with 20% of cyclodextrins as solubilizing agents, of one of the compounds of the Formula I mentioned in the preceding examples, for example 5(S)-amino-4(S)-hydroxy-2(R),7,7-trimethyl-8-[3 (R,S)-methoxycarbonyl-1,2,3,4-tetrahydroquinolin-1-ylcarbonyl]-octanoic acid (N-butyl)amide or a salt thereof, as the active ingredient is mixed with a sterile gelatin solution, which contains phenol as a preservative, under aseptic conditions and while heating, such that 1.0 ml of solution has the following composition:

| Active ingredient | 3.0 mg |
|---|---|
| Gelatin | 150.0 mg |
| Phenol | 4.7 mg |
| distilled water with 20% cyclodextrins as solubilizing agents | 1.0 ml |

EXAMPLE 163

Sterile dry substance for injection 5 mg of one of the compounds of the formula I mentioned in the preceding examples; for example 5(S)-amino-4(S)-hydroxy-2(R),7,7-trimethyl-8-[3(R,S)-methoxycarbonyl-1,2,3,4-tetrahydroquinolin-1-ylcarbonyl]-octanoic acid (N-butyl)amide or a salt thereof, are dissolved as the active ingredient in 1 ml of an aqueous solution containing 20 mg of mannitol and 20% of cyclodextrins as solubilizing agents. The solution is subjected to sterile filtration and is introduced into a 2 ml ampoule under asceptic conditions, frozen and lyophilized. Before use, the lyophilizate is dissolved in 1 ml of distilled water or 1 ml of physiological saline solution. The solution is used intramuscularly or intraveneously. This formulation can also be introduced into two-chamber injection ampoules.

EXAMPLE 164

Nasal spray 500 mg of finely ground (<5.0 μm) powder of one of the compounds of the Formula I mentioned in the preceding examples, for example 5(S)-amino-4(S)-hydroxy-2(R),7,7-trimethyl-8-[3(R,S)-methoxycarbonyl-1,2,3,4-tetrahydroquinolin-1-ylcarbonyl]-octanoic acid (N-butyl) amide or a salt thereof, are suspended as the active ingredient in a mixture of 3.5 ml of "Myglyol 812" and 0,08 g of benzyl alcohol. This suspension is introduced into a container with a metering valve. 5.0 g of "Freon 12" are introduced under pressure into a container through the valve. The "Freon" is dissolved in the Myglyol/benzyl alcohol mixture by shaking. This spray container contains about 100 individual doses, which can be adminsitered individually.

EXAMPLE 165

Film-coated tablets

To produce 10 000 tablets each comprising 100 mg of active ingredient, for example 5(S)-amino-4(S)-hydroxy-2 (R),7,7-trimethyl-8-[3(R,S)-methoxycarbonyl-1,2,3,4-tetrahydroquinolin-1-ylcarbonyl]-octanoic acid (N-butyl) amide or a salt thereof, the following constituents are processed:

| Active ingredient | 1000 g |
|---|---|
| Maize starch | 680 g |
| Colloidal silicic acid | 200 g |
| Magnesium stearate | 20 g |
| Stearic acid | 50 g |
| Sodium carboxymethylstarch | 250 g |
| Water | quantum satis |

A mixture of one of the compounds of the formula I mentioned in the preceding examples, as the active ingredient, 50 g of maize starch and the colloidal silicic acid, is processed with starch mucilage from 250 g of maize starch and 2.2 kg of demineralized water to give a moist composition. This is passed through a sieve of 3 mm mesh size and dried at 45° in a fluidized bed dryer for 30 min. The dried granules are forced through a sieve of 1 mm mesh size, mixed with a previously sieved mixture (1 mm sieve) of 330 g of maize starch, the magnesium stearate, the stearic acid and the sodium carboxymethylstarch and the mixture is pressed to slightly domed tablets.

EXAMPLE 166

Pharmaceutical Preparations comprising a compound according to one of Examples 1 to 160 can furthermore be produced in a manner analogous to that described in Examples 161 to 165

We claim:

1. A compound of the formula I

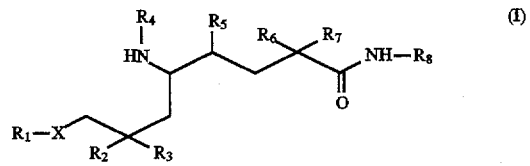

in which $R_1$ heterocyclyl which is bonded via a ring nitrogen atom and has 4 to 8 ring atoms and zero, 1 or 2 fused-on aryl and/or cycloalkyl radicals, it being possible for the heterocyclyl mentioned to contain, in addition to the ring nitrogen atom via which it is bonded, further ring heteroatoms chosen from the group consisting of oxygen, nitrogen, nitrogen substituted by lower alkyl, lower alkanoyl, lower alkanesulfonyl or lower alkoxycarbonyl, sulfur and sulfur linked with 1 or 2 oxygen atoms, X is a carbonyl or methylene group, $R_2$ and $R_3$ independently of one another are hydrogen or lower alkyl or, together with the carbon atom with which they are bonded, are a cycloalkylidene radical, $R_4$ is hydrogen, lower alkyl, lower alkanoyl or lower alkoxycarbonyl, $R_5$ is hydroxyl, lower alkanoyloxy or lower alkoxycarbonyloxy, $R_6$ is hydrogen, lower alkyl, lower alkenyl, lower alkynyl, cycloalkyl, cycloalkyl-lower alkyl, aryl-lower alkyl or heteroaryl-lower alkyl having 5 to 7 ring atoms in the heteroaryl ring and $R_7$ is hydrogen or lower alkyl, or $R_6$ and $R_7$, together with the carbon atom with which they are bonded, are a cycloalkylidene radical and $R_8$ denotes an aliphatic, cycloaliphatic-aliphatic or heteroarylaliphatic radical, or a salt thereof.

2. A compound according to claim 1 of the formula I, in which $R_1$ is 5- to 8-membered heterocyclyl which is bonded via a ring nitrogen atom, may be fused with 1 or 2 fused-on phenyl or cycloalkyl radicals and can contain 1 or 2 further ring heteroatoms chosen from oxygen, nitrogen and free or oxidized sulfur, X is a carbonyl or methylene group, $R_2$ and $R_3$ independently of one another are hydrogen or lower alkyl or, together with the carbon atom with which they are bonded, are 3- to 8-membered cycloalkylidene, $R_4$ is hydrogen, lower alkyl, lower alkanoyl or lower alkoxycarbonyl, $R_5$ is hydroxyl, lower alkanoyloxy or lower alkoxycarbonyloxy, $R_6$ is hydrogen, lower alkyl, 3- to 8-membered cycloalkyl, 3- to 8-membered cycloalkyl-lower alkyl, lower alkenyl, lower alkynyl, phenyl which is unsubstituted or substituted as defined below, indenyl, naphthyl, phenyl- or naphthyl-lower alkyl which are unsubstituted or substituted in the phenyl or naphthyl part as defined below, pyridyl-lower alkyl or imidazolyl-lower alkyl, $R_7$ is hydrogen or lower alkyl or $R_6$ and $R_7$, together with the carbon atom with which they are bonded, are 3- to 8-membered cycloalkylidene and $R_8$ is lower alkyl, lower alkoxy-lower alkyl, amino-lower alkyl, N-lower alkylamino-lower alkyl, N,N-di-lower alkylamino-lower alkyl, N,N-lower alkylenamino-lower alkyl N,N-(aza-lower alkylenamino)-lower alkyl, N,N-(oxa-lower alkylenamino)-lower alkyl, N,N-(thia-lower alkylenamino)-lower alkyl or heteroaryl-lower alkyl having 5 to 7 ring atoms in the heteroaryl ring, which contains a ring nitrogen atom and can contain a further ring heteroatom chosen from oxygen, sulfur and nitrogen, in which phenyl, naphthyl, and phenyl and naphthyl radicals as a constituent of naphthylamino, N-phenyl- or N-naphthyl-N-(lower alkoxy-lower alkyl)-amino, N-phenyl- or N-naphthyl-N-lower alkyl-amino, indenyl, phenyl- or naphthyl-lower alkyl and N-phenyl-N-(phenyl-lower alkyl)-amino can be mono- or polysubstituted, for example mono- or disubstituted, by lower alkyl, hydroxyl, lower alkoxy, carbamoyl-lower alkoxy, N-lower alkylcarbamoyl-lower alkoxy, N-lower alkylcarbamoyl, N,N-di-lower alkylcarbamoyl-lower alkoxy, amino, N-lower alkyl- or N,N-di-lower alkylamino, carboxyl, lower alkoxycarbonyl, carbamoyl, sulfamoyl, lower alkanesulfonyl, halogen, nitro, phenyl, 5- or 6-membered heteroaryl containing, as the heteroatom, 1 nitrogen, sulfur or oxygen atom, 2N atoms, 1N atom and 1S atom or 1N atom and 1O atom, such as pyridyl, and/or by cyano, and radicals $R_1$ can be N-substituted by lower alkyl, lower alkanoyl, lower alkoxycarbonyl or lower alkanesulfonyl, S-mono- or S,S-disubstituted by oxy and/or mono- or di-C-substituted by lower alkyl, hydroxy-lower alkyl, lower alkoxy-lower alkyl, lower alkenyloxy-lower alkyl, naphthoxy-lower alkyl, phenyloxy-lower alkyl, phenyl-lower alkoxy-lower alkyl, lower alkanoyloxy-lower alkyl, benzoyloxy-lower alkyl, lower alkoxycarbonyloxy-lower alkyl, phenyloxycarbonyloxy-lower alkyl, phenyl-lower alkoxycarbonyloxy-lower alkyl, amino-lower alkyl, N-lower alkylamino-lower alkyl, N,N-di-lower alkylamino-lower alkyl, carbamoyl-lower alkyl, lower alkanoylamino-lower alkyl, benzoylamino-lower alkyl, lower alkoxycarbonylamino-lower alkyl, lower alkoxycarbonyl-lower alkyl, lower alkoxy-lower alkoxy-lower alkyl, lower alkylthio-lower alkoxy-lower alkyl, N-lower alkoxyimino-lower alkyl, cycloalkoxy-lower alkyl, cycloalkyl-lower alkoxy-lower alkyl, lower alkenyl, lower alkenyloxy, lower alkoxy-lower alkenyl, lower alkynyl, lower alkynyloxy, lower alkanoyl, oxo, hydroxyl, lower alkoxy, carbamoyl-lower alkoxy, N-lower alkylcarbamoyl-lower alkoxy, N-lower alkylcarbamoyloxy, N,N-di-lower alkylcarbamoyloxy, lower alkoxy-lower alkoxy, lower alkylthio-lower alkoxy, lower alkanoyloxy, benzoyloxy, N-lower alkylcarbamoyl, amino, N-lower alkylamino, N,N-di-lower alkylamino, lower alkanoylamino, benzoylamino, cycloalkylcarbonylamino, cycloalkyl-lower alkanoylamino, lower alkoxy-carbonyl-lower alkylamino, lower alkenyloxycarbonylamino, lower alkoxy-lower alkoxy-carbonylamino, lower alkoxy-lower alkanoylamino, N-lower alkylcarbamoylamino, N,N-di-lower alkylcarbamoylamino, N-lower alkanoyl-N-lower alkyl-amino, lower alkoxycarbonyl-amino, N-lower alkoxycarbonyl-N-lower alkyl-amino, N,N-lower alkylenamino, N,N-(1-oxo-lower alkylen) amino, N,N-(1-oxo2-oxa-lower alkylen)amino, carboxyl, lower alkoxycarbonyl, phenyl-lower alkoxycarbonyl, phenyloxycarbonyl, pyrrolidinylcarbonyl, piperidinylcarbonyl, piperazinylcarbonyl, morpholinylcarbonyl, thiomorpholinylcarbonyl, S,S-dioxothiomorpholin-4-ylcarbonyl, cyano, carbamoyl, N,N-di-lower alkylcarbamoyl, N-lower alkenylcarbamoyl, N-cycloalkylcarbamoyl, N-cycloalkyl-lower alkylcarbamoyl, N-hydroxy-lower alkylcarbamoyl, N-lower alkoxy-lower alkylcarbamoyl, N-carboxy-lower alkylcarbamoyl, carbamoyl-lower alkylcarbamoyl, lower alkoxycarbonyl-lower alkylcarbamoyl, phenyl, dioxolan-2-yl, oxazol-2-yl, oxazolin-2-yl, oxazolidin-2-yl, nitro, sulfamoyl, lower alkanesulfonyl, phosphono, lower alkanephosphono, di-lower alkylphosphono and/or halogen or a pharmaceutically acceptable salt thereof.

3. A compound according to claim 1 of the formula I, in which $R_1$ is 5- or 6-membered N,N-(1-oxo-lower alkylene)amino or N,N-(1-oxo2-oxa-lower alkylene)-amino, $C_1$–$C_7$-alkanoyl, oxo, nitro, $C_1$–$C_4$-alkanesulfonyl and/or halogen, indolin-1-yl, isoindolin-2-yl, 2,3-dihydrobenzimidazol-1-yl, 1,2,3,4-tetrahydroquinol-1-yl, 1,2,3,4-tetrahydroisoquinol-2-yl, 1,2,3,4-tetrahydro-1,3-benzodiazin-1-yl, 1,2,3,4-tetrahydro-1,4-benzodiazin-1-yl, 3,4-dihydro-2H-1,4-benzoxazin-4-yl, which may be S,S-dioxidized, 3,4-dihydro-2H-1,3-benzthiazin-1-yl, 3,4,5,6,7,8-hexahydro-2H, 1,4-benzoxazin-4-yl, 3,4,5,6,7,8-hexahydro-2H-1,4-benzthiazin-4-yl, 2,3,4,5-tetrahydro-1H-1-benz[6,7-b]azepin-1-yl or 5,6-dihydrophenanthridin-5-yl, X is a carbonyl group, $R_2$ and $R_3$ independently of one another are hydrogen or $C_1$–$C_4$-alkyl, or, together with the carbon atom with which they are bonded, are 3- to 8-membered cycloalkylidene, $R_4$ is hydrogen or $C_1$–$C_4$ alkanoyl, $R_5$ is hydroxyl, $R_6$ is hydrogen, $C_1$–$C_4$ alkyl, 3- to 8-membered cycloalkyl or phenyl-$C_1$–$C_4$ alkyl and $R_7$ is hydrogen, and $R_6$ and $R_7$, together with the carbon atom with which they are bonded, are 3- to 8-membered cycloalkylidene, and $R_8$ is $C_1$–$C_7$-alkyl, $C_1$–$C_4$-alkoxy-$C_1$–$C_4$-alkyl, amino-$C_1$–$C_4$-alkyl, N-$C_1$–$C_4$-alkylamino-$C_1$–$C_4$-alkyl, alkyl, N,N-di-$C_1$–$C_4$-alkylamino-$C_1$–$C_4$-alkyl, 5- or 6-membered N,N-lower alkylenamino-$C_1$–$C_4$-alkyl and N,N-(aza)-, N,N-(oxa)- or N,N-(thia)lower alkyleneamino-$C_1$–$C_4$-alkyl, carbamoyl-$C_1$–$C_4$-alkyl, N-$C_1$–$C_4$-alkylcarbamoyl, N,N-di-$C_1$–$C_4$-alkylcarbamoyl, cyano-$C_1$–$C_4$-alkyl or pyridyl-$C_1$–$C_4$-alkyl, or a pharmaceutically acceptable salt thereof.

4. A compound according to claim 1 of the formula 1, in which $R_1$ is a group of the formula Ia

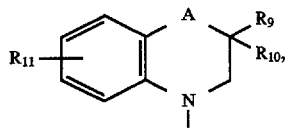

in which

A is a direct bond, methylene, ethylene, imino, oxy or thio, $R_9$ is $C_1$–$C_4$-alkoxy-$C_1$–$C_4$-alkyl, $C_3$–$C_5$-alkenyloxy-$C_1$–$C_4$-alkyl, $C_1$–$C_4$-alkoxy-$C_1$–$C_4$-alkoxy-$C_1$–$C_4$-alkyl, $C_1$–$C_4$-alkoxycarbonylamino-$C_1$–$C_4$-alkyl, $C_1$–$C_4$-alkoxyimino-$C_1$–$C_4$-alkyl, phenyl, $C_1$–$C_4$-alkoxycarbonyl, cyano, carbamoyl, N-$C_1$–$C_4$-alkylcarbamoyl, $C_1$–$C_4$-alkoxy-$C_1$–$C_4$-alkylcarbamoyl, $C_1$–$C_4$-alkoxy, $C_1$–$C_4$-alkoxy-$C_1$–$C_4$-alkoxy, $C_1$–$C_7$-alkanoyloxy, benzoyloxy, N-$C_1$–$C_4$-alkylcarbamoylamino, $C_1$–$C_4$-alkanoylamino, $C_1$–$C_7$-alkoxycarbonylamino, 3- to 3- to 6-membered cycloalkylcarbonylamino, $C_1$–$C_4$-alkoxy-$C_1$–$C_4$-alkanoylamino, or 5- or 6- membered N,N-(1-oxo-lower alkylene)amino or N,N-(1-oxo-2-oxa-lower alkylene)amino or is N-$C_1$–$C_4$-alkylcarbamoylamino $R_{10}$ is hydrogen or $C_1$–$C_4$-alkyl, X is a carbonyl group, $R_2$ and $R_3$ independently of one another are hydrogen or $C_1$–$C_4$-alkyl, or together with the carbon atom with which they are bonded, are 3- to 8-membered cycloalkylidene, $R_4$ is hydrogen or $C_1$–$C_4$-alkanoyl, $R_5$ is hydroxyl, $R_6$ is hydrogen, $C_1$–$C_4$-alkyl, 3- to 8-membered cycloalkyl or phenyl-$C_1$–$C_4$-alkyl $R_7$ is hydrogen and $R_8$ is $C_1$–$C_7$-alkyl, $C_1$–$C_4$-alkoxy-$C_1$–$C_4$-alkyl, amino-$C_1$–$C_4$-alkyl, N-$C_1$–$C_4$-alkylamino-$C_1$–$C_4$-alkyl, N,N-di-$C_1$–$C_4$-alkylamino-$C_1$–$C_4$-alkyl, 5- or 6-membered N,N-lower alkyleneamino-$C_1$–$C_4$-alkyl or N,N-(aza)-, N,N-(oxa)- or N,N-(thia) lower alkyleneamino-$C_1$–$C_4$-alkyl or pyridyl-$C_1$–$C_4$-alkyl, or a pharmaceutically acceptable salt thereof.

5. A compound according to claim 1 of the formula Ic

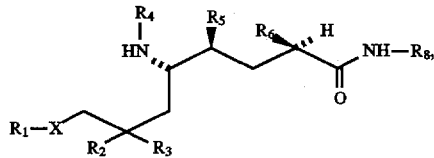

in which $R_1$, $R_2$, $R_3$, $R_4$, $R_5$, $R_6$, $R_7$, $R_8$, $R_9$, and $R_{10}$ are as defined in claim 1, or a pharmaceutically acceptable salt thereof.

6. A compound according to claim 1 of the formula Id

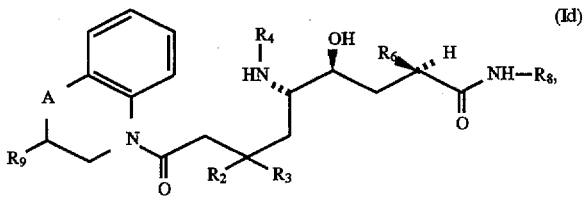

in which

A is a direct bond, methylene, oxy or thio, $R_2$ and $R_3$ are $C_1$–$C_4$-alkyl, $R_4$ is hydrogen or $C_1$–$C_4$-alkanoyl, $R_6$ is $C_1$–$C_4$-alkyl or phenyl-$C_1$–$C_4$-alkyl, $R_8$ is $C_1$–$C_7$-alkyl and $R_9$ is $C_1$–$C_4$-alkoxycarbonylamino, $C_1$–$C_4$-alkoxy-$C_1$–$C_4$-alkoxy-$C_1$–$C_4$-alkyl, $C_1$–$C_4$-alkoxy-$C_1$–$C_4$-alkyl or N-$C_1$–$C_4$-alkylcarbamoyl, or a salt thereof.

7. A compound according to claim 1 being 5(S)-Amino-4(S)-hydroxy-2(S)-isopropyl-7,7-dimethyl-8-[2(R)- or -2(S)-methoxymethoxymethyl-3,4-dihydro-2H-1,4-benzoxazin-4-ylcarbonyl]-octanoic acid (N-butyl)amide or a salt thereof.

8. A compound according to claim 1 being 5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid-N-(2-morpholin-4-yl-ethyl)amide or a salt thereof.

9. A compound according to claim 1 being 5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid-N-[2-(1-acetyl)-piperidin-4-yl)-ethyl]amide or a salt thereof.

10. A compound according to claim 1 being 5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid-N-(2-morpholin-4-yl-2-oxo-ethyl)amide or a salt thereof.

11. A compound according to claim 1 being 5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid-N-(2-carbamoyl-2-methyl-propyl)amide or a salt thereof.

12. A compound according to claim 1 being

5(S)-Amino-4(S)-hydroxy-2(R),7,7-trimethyl-8-(1,2,3,4-tetrahydroisoquinolin-2-ylcarbonyl)octanoic acid (N-butyl)amide;

5(S)-Amino-4(S)-hydroxy-2(R),7,7-trimethyl-8-[3(R)- or 3(S)-ethoxycarbonylpiperidin-1-ylcarbonyl]-octanoic acid (N-butyl)amide;

5(S)-Amino-4(S)-hydroxy-2(R),7,7-trimethyl-9-(1,2,3,4-tetrahydroquinolin-1-yl)-nonanoic acid (N-butyl)amide;

5(S)-Amino-4(S)-hydroxy-2(R),7,7-trimethyl-8-[3(R,S)-carboxy-1,2,3,4-tetrahydroquinolin-1-ylcarbonyl]-octanoic acid (N-butyl)amide;

5(S)-Amino-4(S)-hydroxy-2(R),7,7-trimethyl-8-[2(R,S)-ethoxycarbonyl-3,4-dihydro-2H-1,4-benzoxazin-4-ylcarbonyl]-octanoic acid (N-butyl)amide, or a salt thereof.

5(S)-Formylamino-4(S)-hydroxy-2(R),7,7-trimethyl-8-[2(R,S)-ethoxycarbonyl-4-dihydro-2H-1,4-benzoxazin-4-ylcarbonyl]-octanoic acid (N-butyl)amide;

5(S)-Amino-4(S)-hydroxy-2(R),7,7-trimethyl-8-[2(R,S)-methoxycarbonyl-3,4-dihydro-2H-1,4-benzthiazin-4-ylcarbonyl]-octanoic acid (N-butyl)amide;

5(S)-Amino-4(S)-hydroxy-2(R),7,7-trimethyl-8-[3(R,S)-ethoxycarbonyl-3,4-dihydro-2H-1,4-benzoxazin-4-ylcarbonyl]-octanoic acid (N-butyl)amide;

5(S)-Amino-4(S)-hydroxy-2(R),7,7-trimethyl-8-[3(R,S)-tert-butoxycarbonyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R)-or 3(S)-methoxycarbonyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-dimethylaminocarbonyl-1,2,3,4-tetrahydroquinolin-1-ylcarbonyl]-octanoic acid (N-butyl)amide;

5(S)-Amino-4(S)-hydroxy-2(R),7,7-trimethyl-8-[2(R,S)-butylaminocarbonyl-3,4-dihydro-2H-1,4-benzoxazin-4-ylcarbonyl]-octanoic acid (N-butyl)amide;5(S)-Amino-4(S)-hydroxy-2(R),7,7-trimethyl-8-[3(R,S)-butylaminocarbonyl-1,2,3,4-tetrahydroquinolin-1-ylcarbonyl]-octanoic acid (N-butyl)amide or a salt thereof.

5(S)-Amino-4(S)-hydroxy-2(R),7,7-trimethyl-8-[3(R,S)-morpholinocarbonyl-1,2,3,4-tetrahydroquinolin-1-ylcarbonyl]-octanoic acid (N-butyl)amide;

5(S)-Amino-4(S)-hydroxy-2(R),7,7-trimethyl-8-[2(R,S)-methylaminocarbonyl-3,4-dihydro-2H-1,4-benzothiazin-4ylcarbonyl]-octanoic acid (N-butyl) amide;

5(S)-Amino-4(S)-hydroxy-2(R),7,7-trimethyl-8-[2(R,S)-methylaminocarbonyl-3,4-dihydro-2H-1,4-benzoxazin-4-ylcarbonyl]-octanoic acid (N-butyl) amide;

5(S)-Amino-4(S)-hydroxy-2(R),7,7-trimethyl-8-[3(R,S)-acetyl-1,2,3,4-tetrahydroquinolin-4-ylcarbonyl]-octanoic acid (N-butyl)amide;

5(S)-Amino-4(S)-hydroxy-2(R),7,7-trimethyl-8-[2(R,S)-glycinylcarbonyl-3,4-dihydro-2H-1,4-benzoxazin-4-ylcarbonyl]-octanoic acid (N-butyl)amide;

5(S)-Amino-4(S)-hydroxy-2(R),7,7-trimethyl-8-[3(R,S)-ethoxycarbonyl-1,2,3,4-tetrahydroquinolin-1-ylcarbonyl]-octanoic acid (N-butyl)amide or a salt thereof 5(S)-Amino-4(S)-hydroxy-2(R),7,7-trimethyl-8-[3(R,S)-isopropoxycarbonyl-1,2,3,4-tetrahydroquinolin-1-ylcarbonyl]-octanoic acid (N-butyl)amide;

5(S)-Amino-4(S)-hydroxy-2(R),7,7-trimethyl-8-(6-bromo-1,2,3,4-tetrahydroquinolin-1-ylcarbonyl)-octanoic acid (N-butyl)amide;

5(S)-Amino-4(S)-hydroxy-2(R),7,7-trimethyl-8-[6-bromo-3(R,S)-ethoxycarbonyl-1,2,3,4-tetrahydroquinolin-1-ylcarbonyl]-octanoic acid (N-butyl)amide;

5(S)-Amino-4(S)-hydroxy-7,7-dimethyl-8-[2(R,S)-methoxycarbonyl-3,4-dihydro-2H-1,4-benzothiazin-4-ylcarbonyl]-octanoic acid (N-butyl)amide;

5(S)-Amino-4(S)-hydroxy-2(R),7,7-trimethyl-8-[3,3-bis-(methoxycarbonyl)-1,2,3,4-tetrahydroquinolin-1-ylcarbonyl]-octanoic acid (N-butyl)amide;

5(S)-Amino-4(S)-hydroxy-2(R,S)-isopropyl-7,7-dimethyl-8-[2(R,S)-methoxycarbonyl-3,4-dihydro-2H-1,4-benzothiazin-4-ylcarbonyl]-octanoic acid (N-butyl)amide;

5(S)-Tert-butoxycarbonylamino-4(S)-hydroxy-2(S)-isopropyl-7,7-dimethyl-8-[2(R,S)-methylaminocarbonyl-3,4-dihydro-2H-1,4-benzothiazin-4-ylcarbonyl]-octanoic acid (N-butyl) amide;

5(S)-Amino-4(S)-hydroxy-2(S)-isopropyl-7,7-dimethyl-8-[2(R,S)-methylaminocarbonyl-3,4-dihydro-2H-1,4-benzothiazin-4-yloctanoic acid (N-butyl)amide;

5(S)-Amino-4(S)-hydroxy-2(R,S)-isopropyl-7,7-dimethyl-8-(1,2,3,4-tetrahydroquinolin-1-ylcarbonyl)-octanoic acid (N-butyl)amide;

5(S)-Amino-4(S)-hydroxy-2(R,S)-isopropyl-7,7-dimethyl-8-[2(R,S)-carbamoyl-3,4-dihydro-2H-1,4-benzothiazin-4-ylcarbonyl]-octanoic acid (N-butyl) amide;

5(S)-Amino-4(S)-hydroxy-2(R),7,7-trimethyl-8-[2(R,S)-methoxycarbonyl-3,4-dihydro-2H-1,4-benzoxazin-4-ylcarbonyl]-octanoic acid (N-butyl)amide;

5(S)-Amino-4(S)-hydroxy-2(R),7,7-trimethyl-8-[3(R,S)-hydroxymethyl-1,2,3,4-tetrahydroquinolin-1ylcarbonyl]-octanoic acid (N-butyl)amide;

5(S)-Formylamino-4(S)-hydroxy-2(R),7,7-trimethyl-8-[2(R,S)-methoxycarbonyl-3,4-dihydro-2H-1,4-benzothiazin-4-ylcarbonyl]-octanoic acid (N-butyl) amide;

5(S)-Amino-4(S)-hydroxy-2(R),7,7-trimethyl-8-(S,S-dioxo-3,4-dihydro-1H-2,4-benzothiazin-4-ylcarbonyl)-octanoic acid (N-butyl)amide;

5(S)-Amino-4(S)-hydroxy-2(R),7,7-trimethyl-8-(7-nitro-1,2,3,4-tetrahydroquinolin-1-ylcarbonyl)-octanoic acid (N-butyl)amide;

5(S)-Amino-4(S)-hydroxy-2(R),7,7-trimethyl-8-[3(R,S)-ethoxycarbonyl-7-nitro-1,2,3,4-tetrahydroquinolin-1-ylcarbonyl]-octanoic acid (N-butyl)amide;

5(S)-Amino-4(S)-hydroxy-2(R),7,7-trimethyl-8-[2(R,S)-ethoxycarbonyl-2(R,S)-methyl-3,4-dihydro-2H-1,4-benzoxazin-4-ylcarbonyl]-octanoic acid (N-butyl) amide;

5(S)-Amino-4(S)-hydroxy-2(R),7,7-trimethyl-8-[3(R,S)-methylsulfonyl-1,2,3,4-tetrahydroquinolin-1-ylcarbonyl]-octanoic acid (N-butyl)amide;

5(S)-Amino-4(S)-hydroxy-2(R),7,7-trimethyl-8-[3-methylsulfonyl-1,2,3,4-tetrahydroquinazolin-1-ylcarbonyl]-octanoic acid (N-butyl)amide;

5(S)-Amino-4(S)-hydroxy-2(R),7,7-trimethyl-8-[3(R,S)-methylcarbonylamino-1,2,3,4-tetrahydroquinolin-1-ylcarbonyl]-octanoic acid (N-butyl)amide;

5(S)-Amino-4(S)-hydroxy-2(S)-isopropyl-7,7-dimethyl-8-[3(R,S)-methylaminocarbonyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methoxymethyl-1,2,3,4-tetrahydroquinolin-1-ylcarbonyl]-octanoic acid (N-butyl)amide;

5(S)-Formylamino-4(S)-hydroxy-2(R),7,7-trimethyl-8-[2(R,S)-methylaminocarbonyl-3,4-dihydro-2H-1,4-benzoxazin-4-ylcarbonyl]-octanoic acid (N-butyl) amide;

5(S)-Amino-4(S)-hydroxy-2(R),7,7-trimethyl-8-(3-acetyl-2,3-dihydro-1H-benzimidazo-1-ylcarbonyl)-octanoic acid (N-butyl)amide;

5(S)-Amino-4(S)-hydroxy-2(R),7,7-trimethyl-8-[3(R,S)-ethylsulfonyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methylcarbonyloxy-1,2,3,4-tetrahydroquinolin-1-ylcarbonyl]-octanoic acid (N-butyl)amide;

5(S)-Amino-4(S)-hydroxy-2(R),7,7-trimethyl-8-[2(R,S)-methoxycarbonyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methylaminocarbonyl-1,2,3,4-tetrahydroquinoxalin-1-ylcarbonyl]-octanoic acid (N-butyl)amide;

5(S)-Amino-4(S)-hydroxy-2(R),7,7-trimethyl-8-[4-acetyl-3(R,S)-methylaminocarbonyl-1,2,3,4-tetrahydroquinoxalin-1-ylcarbonyl]-octanoic acid (N-butyl)amide;

5(S)-Amino-4(S)-hydroxy-2(R),7,7-trimethyl-8-[3(R,S)-methylaminocarbonyl-1,2,3,4-tetrahydroquinolin-1-ylcarbonyl]-octanoic acid (N-butyl)amide;

5(S)-Amino-4(S)-hydroxy-2(S)-isopropyl-7,7-dimethyl-8-[2(R,S)-methylaminocarbonyl-3,4-dihydro-2H-1,4-benzoxazin-4-ylcarbonyl]-octanoic acid (N-butyl)amide;5(S)-Amino-4(S)-hydroxy-2(R),7,7-trimethyl-8-[2(R,S)-methoxyethylaminocarbonyl-3,4-dihydro-2H-1,4-benzoxazin-4-ylcarbonyl]-octanoic acid(N-butyl)amide;

5(S)-Amino-4(S)-hydroxy-2(R),7(S)-dimethyl-8-[2(R,S)-ethoxycarbonyl-3,4-dihydro-2H1,4-benzoxazin-4-ylcarbonyl]-octanoic acid (N-butyl)amide;

5(S)-Formylamino-4(S)-hydroxy-2(R),7,7-trimethyl-8-[2(R,S)-methylaminocarbonyl-3,4-dihydro-2H-1,4-benzothiazin-4-ylcarbonyl]-octanoic acid(N-butyl)amide;

5(S)-Amino-2(R)-benzyl-4(S)-hydroxy-7,7-dimethyl-8-[3(R)- or -3(S)-methoxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-1,2,3,4-tetrahydroquinolin-1-ylcarbonyl]-octanoic acid (N-butyl)amide;

5(S)-Amino-4(S)-hydroxy-2(R),7,7-trimethyl-8-[3-ethoxycarbonyl-1,2,3,4-tetrahydroquinazolin-1-ylcarbonyl]-octanoic acid (N-butyl)amide;

5(S)-Amino-4(S)-hydroxy-2(R),7,7-trimethyl-8-[3(R,S)-phenylcarbonyloxy-1,2,3,4-tetrahydroquinolin-1-ylcarbonyl]-octanoic acid (N-butyl)amide;

5(S)-Amino-4(S)-hydroxy-2(R),7,7-trimethyl-8-[2(R,S)-cyano-3,4-dihydro-2H1,4-benzoxazin-4--ylcarbonyl]-octanoic acid (N-butyl)amide;

5(S)-Tert-butoxycarbonylamino-4(S)-hydroxy-2(R),7,7-trimethyl-8-[3(R,S)-methoxycarbonyl-3,4-dihydro-2H-1,4-benzoxazin-4-ylcarbonyl]-octanoic acid (N-butyl)amide;

5(S)-Amino-4(S)-hydroxy-2(R),7,7-trimethyl-8-[3(R,S)-methoxycarbonyl-3,4-dihydro-2H-1,4-benzoxazin-4-ylcarbonyl]-octanoic acid (N-butyl)amide;

5(S)-Amino-4(S)-hydroxy-2(R),7(R)-dimethyl-8-[2(R,S)-ethoxycarbonyl-3,4-dihydro-2H1,4-benzoxazin-4-ylcarbonyl]-octanoic acid (N-butyl)amide;

5(S)-Amino-4(S)-hydroxy-2(R),7,7-trimethyl-8-[3(R,S)-methoxy-1,2,3,4-tetrahydroquinolin-1-ylcarbonyl]-octanoic acid (N-butyl)amide;

5(S)-Amino-4(S)-hydroxy-2(R),7,7-trimethyl-8-[2(R,S)-methoxymethyl-3,4-dihydro-2H1,4-benzothiazin-4-ylcarbonyl]-octanoic acid (N-butyl)amide;

5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[2(R,S)-allyloxymethyl-3,4-dihydro-2H-1,4-benzoxazin-4-ylcarbonyl]-octanoic acid (N-butyl)amide;

5(S)-Amino-4(S)-hydroxy-2(R),7,7-trimethyl-8-[2(R,S)-propyloxymethyl-3,4-dihydro-2H-1,4-benzoxazin-4-ylcarbonyl]-octanoic acid (N-butyl)amide;

5(S)-Amino-4(S)-hydroxy-2(R),7,7-trimethyl-8-[2(R,S)-methoxymethyl-3,4-dihydro-2H-1,4-benzoxazin-4-ylcarbonyl]-octanoic acid (N-butyl)amide;

5(S)-Amino-4(S)-hydroxy-2(S)-isopropyl-7,7-dimethyl-8-[2(R)- or 2(S)-methylaminocarbonyl-3,4-dihydro-2H1,4-benzothiazin-4-ylcarbonyl]-octanoic acid (N-butyl)amide;

5(S)-Amino-4(S)-hydroxy-2(S)-isopropyl-7,7-dimethyl-8-[2(R)- or 2(S)-methylaminocarbonyl-3,4-dihydro-2H1,4-benzothiazin-4-ylcarbonyl]-octanoic acid (N-butyl)amide;

5(S)-Amino-4(S)-hydroxy-6-[1-[3(R,S)-methylaminocarbonyl-1,2,3,4-tetrahydroquinolin-1-ylcarbonylmethyl]cyclopropyl]-2(R)-methyl-hexanoic acid (N-butyl)amide;5(S)-Amino-4(S)hydroxy-2(R),7,7-trimethyl-8-[3(R,S)-N,N-dimethylaminocarbonylamino-1,2,3,4-tetrahydroquinolin-1-ylcarbonyl]-octanoic acid (N-butyl)amide;

5(S)-Amino-4(S)-hydroxy-2(S)-isopropyl-7,7-dimethyl-8-[2(R,S)-ethylaminocarbonyl-3,4-dihydro-2H1,4-benzothiazin-4-ylcarbonyl]-octanoic acid (N-butyl)amide;

5(S)-Amino-4(S)-hydroxy-2(R),7,7-trimethyl-8-[2(R,S)-methoxyethylaminocarbonyl-3,4-dihydro-2H1,4-benzothiazin-4-ylcarbonyl]-octanoic acid (N-butyl)amide;

5(S)-Amino-4(S)-hydroxy-2(S)-isopropyl-7,7-dimethyl-8-[3(R,S)-methoxymethyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R)- or 3(S)-ethoxycarbonylindolin-1-ylcarbonyl]-octanoic acid (N-butyl)amide;

5(S)-Amino-4(S)-hydroxy-2(R),7,7-trimethyl-8-[3(R)- or 3(S)-ethoxycarbonylindolin-1-ylcarbonyl]-octanoic acid (N-butyl)amide;

5(S)-Amino-4(S)-hydroxy-2(R),7,7-trimethyl-8-[3(R)- or -3(S)-methylaminocarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-phenyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methoxycarbonyl-4-oxo-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methoxycarbonylaminomethyl-1,2,3,4-tetrahydroquinolin-1-ylcarbonyl]-octanoic acid (N-butyl)amide;4(S)-Hydroxy-2(S)-isopropyl-5-(S)-methanesulfonylamino-7,7-dimethyl-8-[2(R)- or 2(S)-methylaminocarbonyl-3,4-dihydro-2H-1,4-benzthiazin-4-ylcarbonyl]-octanoic acid (N-butyl)amide;

5(S)-Amino-4(S)-hydroxy-2(R),7,7-trimethyl-8-[3(R,S)-N,N-dimethylaminomethyl-1,2,3,4- tetrahydroquinolin-1-ylcarbonyl]-octanoic acid (N-butyl)amide;

5(S)-Amino-4(S)-hydroxy-2(R),7,7-trimethyl-8-[2(R,S)-methoxyiminomethyl-3,4-dihydro-2H-1,4-benzoxazin-4-ylcarbonyl]-octanoic acid (N-butyl)amide;

5(S)-Amino-4(S)-hydroxy-2(R),7,7-trimethyl-8-[3(R,S)-carbamoyl-3,4-dihydro-2H-1,4-benzoxazin-4-ylcarbonyl]-octanoic acid (N-butyl)amide;

5(S)-Amino-4(S)-hydroxy-2(R),7,7-trimethyl-8-[3(R)- or 3(S)-ethoxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R)- or 3(S)-ethoxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R)- or 3(S)-propyloxycarbonylamino-1,2,3,4-tetrahydroquinolin-1-ylcarbonyl]-octanoic acid(N-butyl)amide;

5(S)-Amino-4(S)-hydroxy-2(R),7,7-trimethyl-8-[3(R)- or 3(S)-propyloxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[2(R,S)-(dioxolan2-yl)-3,4-dihydro-2H-1,4-benzoxazin-4-ylcarbonyl]-octanoic acid (N-butyl)amide;

5(S)-Amino-4(S)-hydroxy-2,2,7,7-tetramethyl-8-[3(R)- or 3(S)-methoxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-(2-oxo-oxazolidin-3-yl)-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methoxymethoxymethyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-allyloxymethyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methoxyethoxymethyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-(2-oxopyrrolidin-1-yl)-1,2,3,4-tetrahydroquinolin-1-ylcarbonyl]-octanoic acid (N-butyl)amide;

5(S)-Amino-4(S)-hydroxy-6-[1-[2(R)- or 2(S)-methylaminocarbonyl-3,4-dihydro-2H-1,4-benzothiazin-4-ylcarbonylmethyl]-cyclopropyl]-2(R)-methyl-hexanoic acid (N-butyl)amide;

5(S)-Amino-4(S)-hydroxy-6-[1-[3(R)- or 3(S)-methoxycarbonylamino-1,2,3,4-tetrahydroquinolin-1-ylcarbonylmethyl]-cyclopropyl]-2(R)-methyl-hexanoic acid (N-butyl)amide;

5(S)-Amino-4(S)-hydroxy-6-[1-[3(R)- or 3(S)-methoxycarbonylamino-1,2,3,4-tetrahydroquinolin-1-ylcarbonylmethyl]-cyclopropyl]-2-(R)-methyl-hexanoic acid (N-butyl)amide;

5(S)-Amino-4(S)-hydroxy-2(R),7,7-trimethyl-8-[3(R,S)-methoxyethoxy-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-propyloxy-1,2,3,4-tetrahydroquinolin-1-ylcarbonyl]-octanoic acid (N-butyl)amide;

5(S)-Amino-4(S)-hydroxy-2(S)-isopropyl-7,7-dimethyl-8-[3(R)- or 3(S)-methoxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methoxymethyloxy-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-cyclopropylcarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R)- or 3(S)-allyloxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methylaminocarbonyloxy-1,2,3,4-tetrahydroquinolin-1-ylcarbonyl]-octanoic acid (N-butyl)amide;

5(S)-Amino-4(S)-hydroxy-2(R),7,7-trimethyl-8-[2(R)- or -2(S)-methoxymethyloxymethyl-3,4-dihydro-2H-1,4-benzoxazin-4-ylcarbonyl]-octanoic acid (N-butyl)amide;

5(S)-Amino-4(S)-hydroxy-2(R),7,7-trimethyl-8-[3(R,S)-(methylaminocarbonyl)indolin-1-ylcarbonyl]-octanoic acid (N-butyl)amide;

5(S)-Amino-4(S)-hydroxy-2(R),7,7-trimethyl-8-[3(R,S)-formylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-ethylcarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-pentyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methoxyethyl-1,2,3,4-tetrahydroquinolin-1-ylcarbonyl]-octanoic acid (N-butyl)amide;

5(S)-Formylamino-4(S)-hydroxy-2(R),7,7-trimethyl-8-[3(R)- or 3(S)-methoxycarbonylamino-1,2,3,4-tetrahydroquinolin-1-ylcarbonyl]-octanoic acid (N-butyl)amide;

5(S)-Acetamido-4(S)-hydroxy-2(R),7,7-trimethyl-8-[3(R)- or 3(S)-methyoxycarbonylamino-1,2,3,4-tetrahydroquinolin-1-ylcarbonyl]-octanoic acid (N-butyl)amide;

5(S)-Amino-2(R)-ethyl-4(S)-hydroxy-7,7-dimethyl-8-[3(R)- or -3(S)-methyoxycarbonylamino-1,2,3,4-tetrahydroquinolin-1-ylcarbonyl]-octanoic acid (N-butyl)amide;

5(S)-Amino-4(S)-hydroxy-2(R)-(2-methyl)propyl-7,7-dimethyl-8-[3(R)- or 3(S)-methyoxycarbonylamino-1,2,3,4-tetrahydroquinolin-1-yl-carbonyl]-octanoic acid (N-butyl)amide;

5(S)-Amino-4(S)-hydroxy-2(R)-(2-methyl)propyl-7,7-dimethyl-8-[3(R)- or 3(S)-methyoxycarbonylamino-1,2,3,4-tetrahydroquinolin-1-ylcarbonyl]-octanoic acid (N-methyl)amide;

5(S)-Amino-2(R)-benzyl-4(S)-hydroxy-7,7-dimethyl-8-[3(R)- or -3(S)-methyoxycarbonylamino-1,2,3,4-tetrahydroquinolin-1-ylcarbonyl]-octanoic acid (N-methyl)amide;

5(S)-Amino-4(S)-hydroxy-2(R),7,7-trimethyl-8-[3(R,S)-methoxypropyl-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methoxycarbonylamino-2,3,4,5-tetrahydro-1H-benz[6,7-b]azepin-1-ylcarbonyl]-octanoic acid (N-butyl)amide;

5(S)-Amino-4(S)-hydroxy-2(R),7,7-trimethyl-8-[3(R,S)-methoxycarbonyl-(N-methyl)amino-1,2,3,4-tetrahydroquinolin-1-ylcarbonyl]-octanoic acid (N-butyl)amide;

5(S)-Formylamino-4(S)-hydroxy-2(S)-isopropyl-7,7-dimethyl-8-[2(R)- or -2(S)-methoxymethoxymethyl-3,4-dihydro-2H-1,4-benzoxazin-4-ylcarbonyl]-octanoic acid(N-butyl)amide;

5(S)-Amino-4(S)-hydroxy-2(S)-isopropyl-7,7-dimethyl-8-[3(R)- or -3(S)-methoxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[2(R,S)-methoxyethyl-3,4-dihydro-2H-1,4-benzoxazin-4-ylcarbonyl]-octanoic acid (N-butyl)amide;

5(S)-Amino-4(S)-hydroxy-2(S)-isopropyl-7,7-dimethyl-8-[2(R)- or -2(S)-methoxyethyl-3,4-dihydro-2H-1,4-benzoxazin-4-ylcarbonyl]-octanoic acid (N-butyl)amide;

5(S)-Amino-4(S)-hydroxy-2(R),7,7-trimethyl-8-[3-butyl-2,3-dihydro-4(H)-quinazolinon-1-ylcarbonyl]-octanoic acid (N-butyl)amide;

5(S)-Amino-4(S)-hydroxy-2(R),7,7-trimethyl-8-[3(R,S)-(2-carbamoyl)ethyl-1,2,3,4-tetrahydroquinolin-1-ylcarbonyl]-octanoic acid (N-butyl)amide;

5(S)-Formylamino-4(S)-hydroxy-2(S)-isopropyl-7,7-dimethyl-8-[3(R)- or 3(S)-methoxycarbonylamino-1,2,3,4-tetrahydroquinolin-1-ylcarbonyl]-octanoic acid (N-butyl)amide;

5(S)-Amino-2(R)-but-2-enyl-4(S)-hydroxy-7,7-dimethyl-8-[3(R)- or 3(S)-methoxycarbonylamino-1,2,3,4-tetrahydroquinolin-1-ylcarbonyl]-octanoic acid (N-butyl)amide;

5(S)-Amino-4(S)-hydroxy-2(R),7,7-trimethyl-8-[3(R,S)-methoxycarbonyl-1,2,3,4-tetrahydroquinolin-1-ylcarbonyl]-octanoic acid (N-butyl)amide;

5(S)-Amino-4(S)-hydroxy-2(R),7,7-trimethyl-8-(1,2,3,4-tetrahydroquinolin-1-ylcarbonyl)octanoic acid (N-butyl)amide;

5(S)-Amino-4(S)-hydroxy-2(R),7,7-trimethyl-8-(2,3-dihydroindol-1-ylcarbonyl)-octanoic acid (N-butyl)amide;

or, in each case, a pharmaceutically acceptable salt thereof.

13. A pharmaceutical preparation comprising a therapeutically effective amount of a compound according to claim 1 in the free form or in a pharmaceutically acceptable salt form, in admixture to pharmaceutical excipients.

14. A method for the treatment of high blood pressure, which comprises administering a therapeutically effective amount of a compound according to claim 1 or a pharmaceutically acceptable salt thereof to a warm-blooded animal in need of treatment.

* * * * *